(12) United States Patent
Guichou et al.

(10) Patent No.: US 10,995,089 B2
(45) Date of Patent: May 4, 2021

(54) ZAINDOLE DERIVATIVES AND THEIR USE AS ERK KINASE INHIBITORS

(71) Applicants: AGV Discovery ENSCM, Montpellier (FR); Institut National de la Sante et de la Recherche Medicale (INSERM), Paris (FR); Centre National de la Recherche Scientifique (CNRS), Paris (FR); Universite de Montpellier, Montpellier (FR)

(72) Inventors: Jean-François Guichou, Uchaud (FR); Cédric Bories, Jacou (FR); Clément Geoffroy, Vergeze (FR); Charline Duquenne, Saint Bres (FR); Muriel Gelin, Clapiers (FR); Gilles Labesse, Montpellier (FR); Yannick Bessin, Montpellier (FR); Loic Mathieu, Montpellier (FR)

(73) Assignees: AGV DISCOVERY, Clapiers (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/777,386

(22) PCT Filed: Nov. 17, 2016

(86) PCT No.: PCT/EP2016/078080
§ 371 (c)(1),
(2) Date: May 18, 2018

(87) PCT Pub. No.: WO2017/085230
PCT Pub. Date: May 26, 2017

(65) Prior Publication Data
US 2020/0283432 A1 Sep. 10, 2020

(30) Foreign Application Priority Data
Nov. 18, 2015 (EP) .................................. 15306835

(51) Int. Cl.
*C07D 471/04* (2006.01)
*A61P 35/00* (2006.01)
*C07D 519/00* (2006.01)
*C07F 9/6561* (2006.01)
*C07D 491/048* (2006.01)
*C07D 491/107* (2006.01)
*C07D 491/113* (2006.01)

(52) U.S. Cl.
CPC ............ *C07D 471/04* (2013.01); *A61P 35/00* (2018.01); *C07D 491/048* (2013.01); *C07D 491/107* (2013.01); *C07D 491/113* (2013.01); *C07D 519/00* (2013.01); *C07F 9/6561* (2013.01)

(58) Field of Classification Search
CPC .............. C07D 471/04; C07D 491/113; C07D 491/107; C07D 491/048; C07D 519/00; C07F 9/6561; A61P 35/00
See application file for complete search history.

(56) References Cited

U.S. PATENT DOCUMENTS

| 8,697,697 B2 | 4/2014 | Fairfax et al. |
| 9,695,200 B2 * | 7/2017 | Jacobsen ................. A61P 29/00 |
| 2006/0106041 A1 | 5/2006 | Kuo et al. |
| 2006/0106069 A1 | 5/2006 | Martinez-Botella et al. |
| 2007/0043068 A1 | 2/2007 | Arnold et al. |
| 2014/0011806 A1 | 1/2014 | Fairfax et al. |

FOREIGN PATENT DOCUMENTS

| GB | 2515785 A | 1/2015 |
| WO | 2005/028475 A2 | 3/2005 |
| WO | 2008/005457 A2 | 1/2008 |

(Continued)

OTHER PUBLICATIONS

Bodai et al., "A novel target for Huntington's disease: ERK at the crossroads of signaling", Bioessays, 2011, vol. 34, No. 2, pp. 142-148.
Caunt et al., "MEK1 and MEK2 inhibitors and cancer therapy: the long and winding road", Nature Reviews: Cancer, Oct. 2015, vol. 15, No. 10, pp. 577-592.
Cheung et al., "Emerging Role for Erk as a Key Regulator of Neuronal Apoptosis", Science's STKE, 2004. (5 pages).
Davies et al., "Mutations of the BRAF gene in human cancer", Letters to Nature, Jun. 27, 2002, vol. 417, pp. 494-954.
Downward, Julian, "Targeting Ras Signalling Pathways in Cancer Therapy", Nature Reviews: Cancer, Jan. 2003, vol. 3, pp. 11-22.
Garnett et al., "Guilty as charged: B-Raf is a human oncogene", Cancer Cell, Oct. 2004, vol. 6, pp. 313-319.

(Continued)

Primary Examiner — Laura L Stockton
(74) Attorney, Agent, or Firm — Buchanan Ingersoll & Rooney PC

(57) ABSTRACT

The present invention concerns a compound of formula (I): H or one of its pharmaceutically acceptable salts, especially for use as inhibitors of the ERK kinase activity in particular ERK2 activity, it also concerns prodrugs of these compounds.

(I)

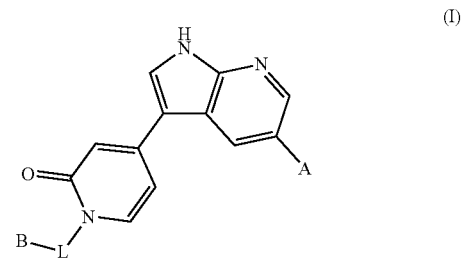

15 Claims, 1 Drawing Sheet

(56) References Cited

FOREIGN PATENT DOCUMENTS

| WO | 2008/011557 A2 | 1/2008 |
|----|----|----|
| WO | 2008/076805 A2 | 6/2008 |
| WO | WO 2012/094313 | 7/2012 |
| WO | 2013/022766 A1 | 2/2013 |
| WO | 2014/023367 A1 | 2/2014 |
| WO | WO 2014/060395 | 4/2014 |

OTHER PUBLICATIONS

Lito et al., "Tumor adaptation and resistance to RAF inhibitors," Nature Medicine, Nov. 2013, vol. 19, No. 11, pp. 1401-1409.

Little et al., "Mechanisms of acquired resistance to ERK1/2 pathway inhibitors", Oncogene, 2012, pp. 1-9.

Thalhamer et al., "MAPKs and their relevance to arthritis and inflammation", Rheumatology, 2008, vol. 47, pp. 409-414.

\* cited by examiner

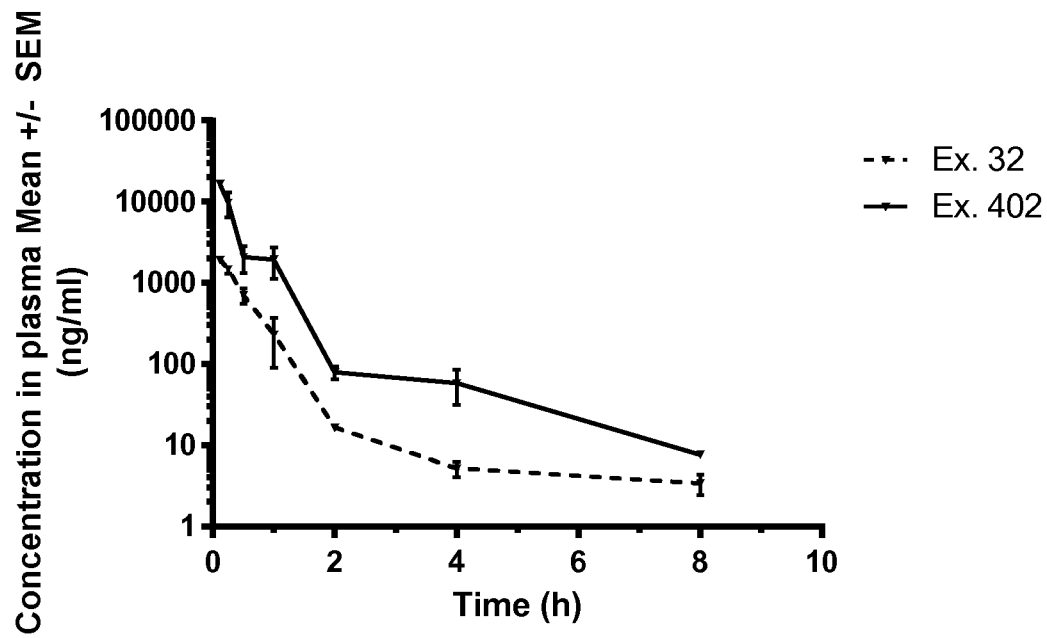
Figure 1: Pharmacokinetics profile of a parent drug (example 32) and corresponding prodrug (compound 402) after an intraveinous dose of 2mg/kg
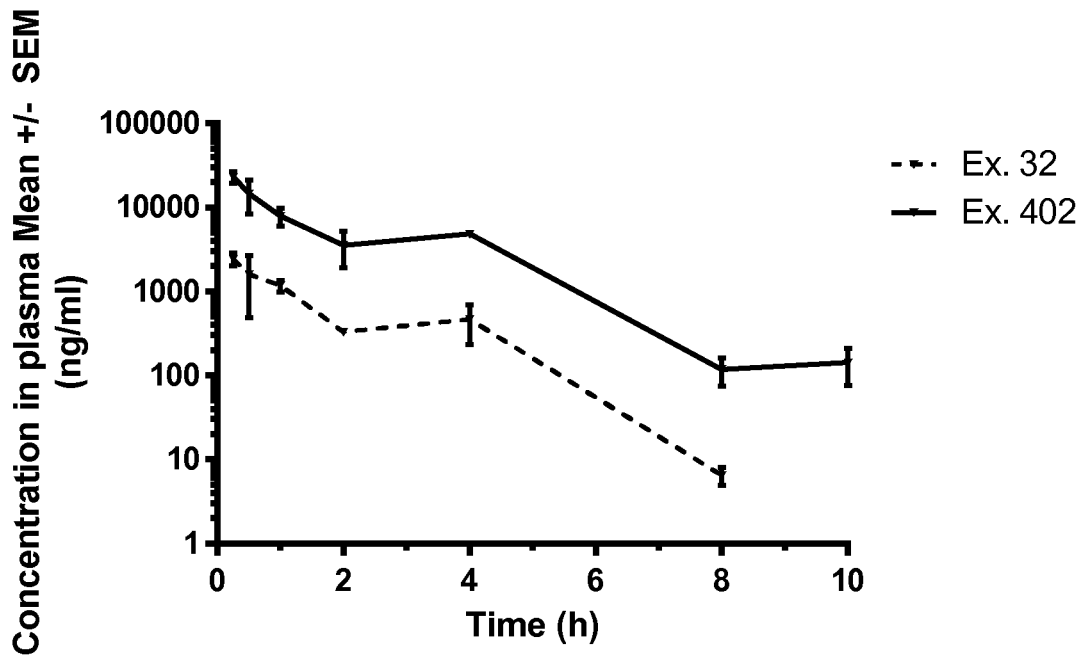
Figure 2: Pharmacokinetics profile of parent drug (example 32) and corresponding prodrug (compound 402) after an oral dose of 20 mg/kg

ZAINDOLE DERIVATIVES AND THEIR USE AS ERK KINASE INHIBITORS

CROSS-REFERENCE TO RELATED APPLICATIONS

This application is a U.S. National Stage Application pursuant to 35 U.S.C. § 371 of International Patent Application PCT/EP2016/078080, filed on Nov. 17, 2016, and published as WO 2017/085230 on May 26, 2017, which claims priority to European Patent Application 15306835.8, filed on Nov. 18, 2015, all of which are incorporated herein by reference in their entireties for all purposes.

FIELD OF THE INVENTION

The present invention relates to azaindole derivatives which are inhibitors of ERK kinases (ERK1 and ERK2), to the process for the preparation thereof and to the therapeutic use thereof.

BACKGROUND OF THE INVENTION

ERK protein belongs to the RAS/RAF/MEK/ERK pathway which plays a major role in cell cycle, proliferation, growth and survival. RAS/RAF/MEK/ERK pathway is activated by growth factors through their receptor tyrosine kinase that allows activation of GTPases RAS. In its turn, RAS activates RAF proteins. Then, RAF activates MEK, which activates ERK. Finally, this enables phosphorylation of many substrates that have key roles in metabolism, protein synthesis, cell proliferation and survival. RAF mutations lead specifically to an over-activation of this RAS/RAF/MEK/ERK pathway and are responsible for 7% of all human cancers (Davies et al., Nature. 2002; Garnett et al., Cancer Cell. 2004). Indeed, RAF mutations are frequently observed in melanomas (27-70%), thyroid cancers (36-53%), colorectal cancers (5-22%) and ovarian cancers (30%). Likewise, RAS mutations occur in almost 30% of cancers and are present in pancreatic (90%), lung (35%), colorectal (45%) and liver (30%) cancers (Downward, Nat Rev Cancer. 2003). Thus, proteins of RAS/RAF/MEK/ERK pathway represent targets of interest for cancers treatment. Indeed, pharmaceutical companies focused on upstream kinases (RAF, MEK). However, resistances ultimately appear after current treatment with RAF and MEK inhibitors (Lito et al., Nat Med. 2013; Caunt et al., Nat Rev Cancer. 2015). Moreover, most resistances to MEK or RAF inhibitors induce ERK reactivation, through different mechanisms such as MEK mutation, B-RAF amplification, C-RAF mutation . . . (Little et al., Oncogene. 2013). Furthermore, RAF or MEK inhibition suppresses ERK negative feedback that restores upward signaling and finally ERK activity (Lito et al., Nat Med. 2013). In light of the resistance phenomena that emerged after current treatment with RAF and MEK inhibitors, it is essential to develop new therapeutic options.

Except for its key role in hyperproliferative diseases, ERK signaling has also been described as implied in neurodegenerative disorders such as in Parkinson's, Alzheimer's and Huntington's diseases (Cheung et al., Sci STKE. 2004; Bodai et al., Bioessays. 2012) and in inflammation such as in the pathogenesis of Rheumatoid Arthritis (Thalhamer et al., Rheumatology. 2008).

Thus, the present invention relates to ERK inhibitors development to treat a broad spectrum of diseases.

Some ERK inhibitors are already described in the prior art. Thus, U.S. Pat. No. 8,697,697 B2 describes substituted pyrazole derivatives as inhibitors of ERK2 kinase activity.

Pyrrolo[2,3-b]pyrazine derivatives are also reported as ERK inhibitors in an international patent application WO 2014/060395 A1.

However, there remains a need for efficient compounds that are able to selectively inhibit ERK1 and/or ERK2 kinases.

The present invention is precisely directed to novel compounds for use as inhibitors of the ERK kinases activity.

The compounds of the present invention are novel azaindole derivatives with at least an enhanced anti-proliferative activity.

The compounds according to the invention are also characterized by their low toxicity.

A first subject of the invention concerns the compounds corresponding to the general formula (I)

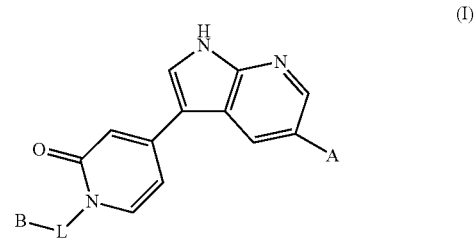

(I)

wherein:

A represents a 6- to 10-membered aryl group; a 5- to 12-membered heteroaryl group or a 4- to 12-membered heterocyclic group, A being optionally substituted with one or more substituents chosen among halogen atoms, hydroxyl, $(C_1-C_6)$alkyl, cyano, oxo, carbonyl; tert-butyloxycarbonyl, 1,3-dioxolanyl, 1,4-dioxolanyl, $(C_1-C_6)$alkoxy, —$COOR_1$, —$CONR_1R_2$ and $NR_1R_2$, with said $(C_1-C_6)$alkyl being itself optionally substituted with a hydroxyl, $NR_1R_2$, $(C_1-C_6)$alkoxy, or —$S(C_1-C_6)$alkyl group, and said 4- to 12-membered heterocyclic group optionally comprising two fused cycles wherein the two cycles share at least two atoms;

L represents a linker chosen among linear or branched $(C_1-C_6)$alkylene group, preferably $(C_1-C_3)$alkylene, said alkylene group being optionally substituted with at least one halogen, hydroxyl, $(C_1-C_6)$alkoxy, —COOR1 or $NR_1R_2$ groups;

B represents a 6- to 10-membered aryl or a 5- to 12-membered heteroaryl group with B being optionally substituted with one or more substituents chosen among halogen atoms, trifluoromethyl (—$CF_3$), trifluoromethoxy (—$OCF_3$), hydroxyl, $(C_1-C_6)$alkyl, $(C_1-C_6)$alkoxy, —$CONR_1R_2$, $NR_1R_2$, hydroxy$(C_1-C_6)$alkyl, hydroxy$(C_1-C_6)$alkoxy, $(C_1-C_6)$alkoxy$(C_1-C_6)$alkyl, $(C_1-C_6)$alkoxy$(C_1-C_6)$alkoxy and $(C_1-C_6)$alkyl $NR_1R_2$ groups;

with two adjacent carbon atoms of said aryl group being optionally substituted by two oxygen atoms linked together by a $(C_1-C_6)$alkylene group, $R_1$ and $R_2$ represent, independently of each other, a hydrogen atom, a $(C_1-C_6)$alkyl group, a $(C_1-C_6)$alkoxy group, a hydroxy$(C_1-C_6)$alkyl group or a hydroxy$(C_1-C_6)$alkoxy group, or one of their pharmaceutically acceptable salts.

After extensive searching of the ERK crystalline structure and structural screening tests, the inventors have identified that these azaindole derivatives of formula (I) selectively target the active sites of the ERK kinases, and act as effective inhibitors of ERK kinases activity as demonstrated in the following examples.

In the meaning of the present invention, a "kinase inhibitor" is intended to mean a compound that reduces or suppresses the activity of the targeted kinase, as compared with said activity determined without said inhibitor.

Within the meaning of the invention, the term "prevent" or "prevention" with respect to an event is intended to mean the decrease of a risk of occurrence of said event.

As will be seen below, these compounds have utility in the treatment of conditions or diseases in which modification of the activity of ERK would have a positive therapeutic outcome, in particular cancers.

Another subject concerns processes for preparing the compounds of general formula (I).

Another subject concerns the compounds of general formula (I) for their use especially in medicaments or in pharmaceuticals compositions.

A further subject concerns the compounds according to the invention for use as inhibitors of the ERK kinases activity, particularly for use as inhibitors of the ERK1 and/or ERK2 kinases activity.

The present invention also deals with prodrugs P of compounds of general formula (I).

In the context of the present invention, the following abbreviations and empirical formulae are used:

Abbreviations

In the context of the present invention, the following abbreviations and empirical formulae are used:

$BH_3$ Borane
Boc tert-butyloxycarbonyl
C18 column Reversed-phase C18 column
$Cs_2CO_3$ Cesiumcarbonate
DIEA N,N-Diisopropylethylamine
DMF Dimethylformamide
DMSO Dimethylsulfoxide
° C. Degree Celsius
DCM Dichloromethane
ee Enantiomeric Excess
g gram(s)
h hour(s)
$H_2$ Hydrogen
HCl Hydrochloric acid
HPLC High performance liquid chromatography
LC/MS Liquid chromatography/mass spectrometry
LiHMDS Lithium bis(trimethylsilyl)amide
M Mole(s) per liter
MeOH Methanol
mg Milligram(s)
MH+ Pseudo-molecular ion (positive ion mode in mass spectrometry)
MHz Megahertz
μl Microliter(s)
ml Milliliter(s)
mmol Millimole(s)
mol Mole(s)
$NaBH_3CN$ Sodium cyanoborohydride
$Na_2CO_3$ Sodium carbonate
$NaHCO_3$ Sodium hydrogen carbonate
$NH_4Cl$ Ammonium chloride
NMR Nuclear Magnetic Resonance
$PdCl_2(PPh_3)_2$ Bis(triphenylphosphine)palladium(II) dichloride
$Pd(dba)_2$ Bis(dibenzylideneacetone)palladium(0)
$Pd(dba)_3$ Tris(dibenzylideneacetone)palladium(0)
$Pd(PtBu_3)_2$ Bis(tri-tert-butylphosphine) palladium(0)
tBuONa Sodium tert-butoxide
THF Tetrahydrofuran
Ts Tosyl
RuPhos 2-Dicyclohexylphosphino-2',6'-diisopropoxybiphenyl
RuPhosPd G2Chloro(2-dicyclohexylphosphino-2',6'-diisopropoxy-1,1'-bi-phenyl)[2-(2'-amino-1,1'-biphenyl)]palladium(II)
TBAF Tetrabutylammonium fluoride
Xantphos 4,5-Bis(diphenylphosphino)-9,9-dimethylxanthene Other features, properties and advantages of the invention will emerge more clearly from the description and examples that follow.

COMPOUNDS OF THE INVENTION

As above identified, the compounds according to the invention correspond to general formula (I):

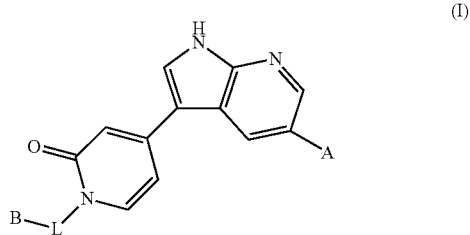

(I)

wherein:

A represents a 6- to 10-membered aryl group; a 5- to 12-membered heteroaryl group or a 4- to 12-membered heterocyclic group, A being optionally substituted with one or more substituents chosen among halogen atoms, hydroxyl, $(C_1\text{-}C_6)$alkyl, cyano, oxo, carbonyl; tert-butyloxycarbonyl, 1,3-dioxolanyl, 1,4-dioxolanyl, $(C_1\text{-}C_6)$alkoxy, —$COOR_1$, —$CONR_1R_2$ and $NR_1R_2$, with said $(C_1\text{-}C_6)$alkyl being itself optionally substituted with a hydroxyl, $NR_1R_2$, $(C_1\text{-}C_6)$alkoxy, or —$S(C_1\text{-}C_6)$alkyl group, and said 4- to 12-membered heterocyclic group optionally comprising two fused cycles wherein the two cycles share at least two atoms;

L represents a linker chosen among linear or branched $(C_1\text{-}C_6)$alkylene group, preferably $(C_1\text{-}C_3)$alkylene group, said alkylene group being optionally substituted with at least one halogen atom, hydroxyl, $(C_1\text{-}C_6)$alkoxy, —$COOR_1$ or $NR_1R_2$ groups;

B represents a 6- to 10-membered aryl, preferably phenyl, or a 5- to 12-membered heteroaryl group, with B being optionally substituted with one or more substituents chosen among halogen atoms, trifluoromethyl (—$CF_3$), trifluoromethoxy (—$OCF_3$), hydroxyl, $(C_1\text{-}C_6)$alkyl, $(C_1\text{-}C_6)$alkoxy, —$CONR_1R_2$, $NR_1R_2$, hydroxy$(C_1\text{-}C_6)$alkyl, hydroxy$(C_1\text{-}C_6)$alkoxy, $(C_1\text{-}C_6)$alkoxy$(C_1\text{-}C_6)$alkyl, $(C_1\text{-}C_6)$alkoxy$(C_1\text{-}C_6)$alkoxy and $(C_1\text{-}C_6)$alkyl $NR_1R_2$ groups;

with two adjacent carbon atoms of said aryl group being optionally substituted by two oxygen atoms linked together by a $(C_1\text{-}C_6)$alkylene, preferably $(C_1\text{-}C_3)$alkylene group, and R$_1$ and R$_2$ representing, independently of each other, a hydrogen atom, a (C$_1$-C$_6$)alkyl group, a (C$_1$-C$_6$)alkoxy group, a hydroxy(C$_1$-C$_6$)alkyl group, or a hydroxy(C$_1$-C$_6$)alkoxy group, or one of their pharmaceutically acceptable salts.

According to a particular embodiment, the compounds according to the invention correspond to general formula (I) wherein:

A represents a 6- to 10-membered aryl group; a 5- to 12-membered heteroaryl group or a 4- to 12-membered heterocyclic group, A being optionally substituted with one or more substituents chosen among halogen atoms, hydroxyl, (C$_1$-C$_6$)alkyl, cyano, carbonyl; tert-butyloxycarbonyl, 1,3-dioxolanyl, 1,4-dioxolanyl, (C$_1$-C$_6$)alkoxy, —COOR$_1$, —CONR$_1$R$_2$ and NR$_1$R$_2$, with said (C$_1$-C$_6$)alkyl being itself optionally substituted with a hydroxyl, NR$_1$R$_2$, (C$_1$-C$_6$)alkoxy, or —S(C$_1$-C$_6$)alkyl group, and said 4- to 12-membered heterocyclic group optionally comprising two fused cycles wherein the two cycles share at least two atoms;

L represents a linker chosen among linear or branched (C$_1$-C$_6$)alkylene group, preferably (C$_1$-C$_3$)alkylene group, said alkylene group being optionally substituted with at least one halogen atom, hydroxyl, (C$_1$-C$_6$)alkoxy, —COOR$_1$ or NR$_1$R$_2$ groups;

B represents a 6- to 10-membered aryl, preferably phenyl, or a 5- to 12-membered heteroaryl group, with B being optionally substituted with one or more substituents chosen among halogen atoms, trifluoromethyl (—CF$_3$), hydroxyl, (C$_1$-C$_6$)alkyl, (C$_1$-C$_6$)alkoxy, —CONR$_1$R$_2$, NR$_1$R$_2$, hydroxy(C$_1$-C$_6$)alkyl, (C$_1$-C$_6$)alkoxy(C$_1$-C$_6$)alkoxy and (C$_1$-C$_6$)alkyl NR$_1$R$_2$ groups;

with two adjacent carbon atoms of said aryl group being optionally substituted by two oxygen atoms linked together by a (C$_1$-C$_6$)alkylene, preferably (C$_1$-C$_3$)alkylene group, and R$_1$ and R$_2$ representing, independently of each other, a hydrogen atom, a (C$_1$-C$_6$)alkyl group, a (C$_1$-C$_6$)alkoxy group, a hydroxy(C$_1$-C$_6$)alkyl group, or a hydroxy(C$_1$-C$_6$)alkoxy group, or one of their pharmaceutically acceptable salts.

The compounds of the invention may be prepared according to methods well-known by the skilled artisan, as illustrated in the examples that follow.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may also exist in the form of bases or of acid-addition salts. These salts may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more molecules of water or with a solvent. Such hydrates and solvates also form part of the invention.

In the context of the present invention, the following definitions apply:

a halogen atom: a fluorine, a chlorine, a bromine or an iodine atom. The halogen atoms may be more particularly chosen among chlorine and fluorine atoms.

C$_t$-C$_z$: a carbon-based chain possibly containing from t to z carbon atoms in which t and z may take values from 1 to 10; for example, C$_1$-C$_3$ is a carbon-based chain possibly containing from 1 to 3 carbon atoms.

an alkyl: a linear or branched saturated aliphatic group, in particular comprising form 1 to 6 carbon atoms. Examples that may be mentioned include methyl, ethyl, n-propyl, isopropyl, butyl, isobutyl, tert-butyl, pentyl, etc. . . .

an alkoxy: a radical —O-alkyl in which the alkyl group is as defined previously.

4- to 12-membered heterocyclic group: a monocyclic saturated ring containing at least one heteroatom. Examples of 4- to 12-membered heterocyclic group that may be mentioned include azetidinyl, pyrrolidinyl, piperidinyl, morpholinyl, thiomorpholinyl, piperazinyl, 2-oxa-6-azaspiro[3.3]heptanyl and also fused bicycle like morpholinyl fused with oxetanyl or oxolanyl group.

an aryl: a monocyclic or bicyclic aromatic group containing between 5 and 10 carbon atoms, in particular between 6 to 10 carbon atoms. By way of examples of an aryl group, mention may be made of phenyl or naphthyl group. Preferably, the aryl group is phenyl.

a heteroaryl: a 5- to 12-membered monocyclic or bicyclic aromatic group containing from 1 to 5 heteroatoms chosen from O, S and N. Examples of monocyclic heteroaryls that may be mentioned include imidazolyl, pyrazolyl, thiazolyl, oxazolyl, isothiazolyl, isoxazolyl, furyl, thienyl, oxadiazolyl, thiadiazolyl, triazolyl, tetrazolyl, pyridinyl, pyrazinyl, pyrimidinyl, pyridazinyl and triazinyl. Examples of bicyclic heteroaryls that may be mentioned include indolyl, isoindolyl, benzofuryl, benzothiophenyl, benzoxazolyl, benzimidazolyl, indazolyl, benzothienyl, isobenzofuryl, isobenzothiazolyl, pyrrolo[2,3-c]pyridyl, pyrrolo[2,3-b]pyridyl, pyrrolo[3,2-b]pyridyl, pyrrolo[3,2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridyl, imidazo[4,5-c]pyridyl, pyrazolo[2,3-a]pyridyl, pyrazolo[2,3-a]pyrimidinyl, pyrazolo[2,3-a]pyrazinyl, thiazolo[5,4-b]pyridyl, thiazolo[5,4-c]pyridyl, thiazolo[4,5-c]pyridyl, thiazolo[4,5-b]pyridyl, oxazolo[5,4-b]pyridyl, oxazolo[5,4-c]pyridyl, oxazolo[4,5-c]pyridyl, oxazolo[4,5-b]pyridyl, isothiazolo[5,4-b]pyridyl, isothiazolo[5,4-c]pyridyl, isothiazolo[4,5-c]pyridyl, isothiazolo[4,5-b]pyridyl, isoxazolo[5,4-b]pyridyl, isoxazolo[5,4-c]pyridyl, isoxazolo[4,5-c]pyridyl and isoxazolo[4,5-b]pyridyl.

The heteroaryl groups may be more preferably chosen among naphtyl, quinolinyl, indolyl, pyridinyl, pyrazinyl and thiazolyl groups.

According to one embodiment, L represents a linker chosen among linear or branched (C$_1$-C$_6$)alkylene, preferably linear or branched (C$_1$-C$_3$)alkylene, said alkylene group being optionally substituted with one group chosen from a hydroxyl group and (C$_1$-C$_6$)alkoxy group.

As L group that may be specially mentioned are methylene and ethylene groups, optionally substituted with one group chosen from hydroxyl and (C$_1$-C$_6$)alkoxy group.

As already explained, B represents a 6- to 10-membered aryl, preferably a phenyl group, or a 5- to 12-membered heteroaryl group, preferably a 5-6-membered heteroaryl group and more preferably a group chosen from thiazolyl, pyridinyl, naphtyl, quinolinyl, isoquinolinyl, and indolyl, with said aryl or heteroaryl being optionally substituted with one or more substituents chosen among halogen atoms, trifluoromethyl, hydroxyl, $(C_1-C_6)$alkyl, $(C_1-C_6)$alkoxy, —$CONR_1R_2$, $NR_1R_2$, hydroxy$(C_1-C_6)$alkyl, $(C_1-C_6)$alkoxy $(C_1-C_6)$alkoxy and $(C_1-C_6)$alkyl $NR_1R_2$ groups.

According to one embodiment variant, B represents a 6- to 10-membered aryl group, preferably a phenyl group, optionally substituted with one or two substituents chosen among trifluoromethyl, trifluoromethoxy, hydroxyl, $(C_1-C_6)$ alkyl, $(C_1-C_6)$alkoxy, hydroxy$(C_1-C_6)$alkyl, $(C_1-C_6)$ alkoxy$(C_1-C_6)$alkyl, $(C_1-C_6)$alkoxy$(C_1-C_6)$alkoxy groups or halogen atoms.

According to another one embodiment variant, B represents an aryl wherein two adjacent carbon atoms are substituted by two oxygen atoms linked together by a $(C_1-C_6)$ alkylene group.

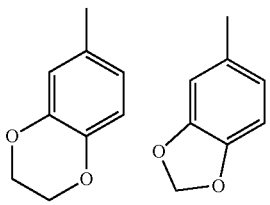

may be specifically mentioned.

According to a preferred embodiment, B is a phenyl group bearing two substituents chosen from the following couples: two halogen atoms, an halogen atom and a group hydroxyl, an halogen atom and a group $(C_1-C_6)$alkoxy$(C_1-C_6)$alkoxy.

According to another preferred embodiment, B is a phenyl group substituted by one or two halogen atoms, particularly this embodiment corresponds to formulae IIa et IIb:

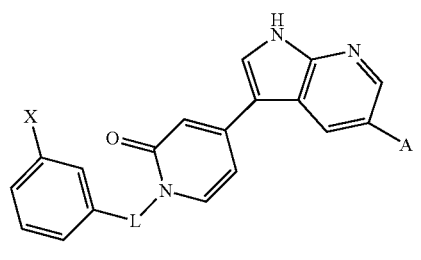

IIa

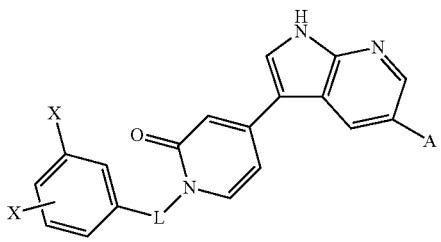

IIb

Wherein X denotes a halogen atom, L and A having the meaning previously defined.

As already explained, A represents a 6- to 10-membered aryl, preferably a phenyl group; a 5- to 12-membered heteroaryl group, preferably a 5-6-membered heteroaryl group and more preferably a group chosen from pyridinyl, thiophenyl, pyrazolyl; or a 4- to 12-membered heterocyclic group, preferably a 5- to 7-membered heterocyclic group and more preferably chosen from tetrahydropyranyl, pyrrolidinyl, piperidinyl, morpholinyl, thiomorpholinyl, piperazinyl or 2-oxa-6-azaspiro[3.3]heptanyl group, that is a compound of formula:

or a group 1, 4 dioxenyl:

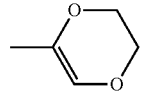

Advantageously A is a morpholinyl group or a 1,4-oxazepanyl group.

Advantageously A is substituted with one or more substituents chosen among a hydroxyl, $(C_1-C_6)$alkyl, cyano, oxo, carbonyl, boc, 1,3-dioxolanyl, 1,4-dioxolanyl, $(C_1-C_6)$ alkoxy, —$COOR_1$, —$CONR_1R_2$ and $NR_1R_2$ groups or halogen atoms, preferably a fluorine atom, said alkyl, being itself optionally substituted with at least one hydroxyl, $NR_1R_2$, $(C_1-C_6)$alkoxy or —$S(C_1-C_6)$alkyl groups.

According to one embodiment variant, A is a 4- to 12-membered heterocyclic group optionally comprising two fused cycles wherein the two cycles share at least two, preferably 2, 3 or 4 atoms.

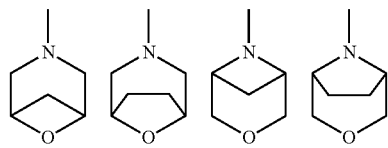

1,4-Oxazepanyl;

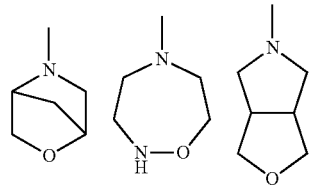

may be specifically mentioned

According to a first embodiment variant, A is a 4- to 7-membered heterocyclic group optionally substituted with one or more substituents chosen among halogen atoms, hydroxyl, $(C_1-C_6)$alkyl, cyano, oxo, carbonyl, boc, 1,3-dioxolanyl, 1,4-dioxolanyl, $(C_1-C_6)$alkoxy, —$COOR_1$, —$CONR_1R_2$ and $NR_1R_2$, said alkyl group being optionally substituted by with a hydroxyl, $NR_1R_2$, $(C_1-C_6)$alkoxy or —$S(C_1-C_6)$alkyl group.

According to a second embodiment variant, A is a morpholinyl group optionally substituted with one or two substituents chosen among hydroxyl, $(C_1-C_6)$alkyl, cyano, carbonyl, 1,3-dioxolanyl, 1,4-dioxolanyl, $(C_1-C_6)$alkoxy, —$COOR_1$, —$CONR_1R_2$, and $NR_1R_2$, said alkyl group being optionally substituted by with a hydroxyl, $NR_1R_2$, or $(C_1-C_6)$alkoxy groups or a morpholinyl group fused with an oxetanyl or oxolanyl group.

A may also be a 1,4-oxazepanyl group optionally substituted with one or two substituents chosen among hydroxyl, $(C_1$-$C_6)$alkyl, cyano, carbonyl, 1,3-dioxolanyl, 1,4-dioxolanyl, $(C_1$-$C_6)$alkoxy, —COOR$_1$, —CONR$_1$R$_2$, and NR$_1$R$_2$, said alkyl group being optionally substituted by with a hydroxyl, NR$_1$R$_2$, or $(C_1$-$C_6)$alkoxy group.

When A is a non-substituted morpholinyl group, the compounds correspond to formula III:

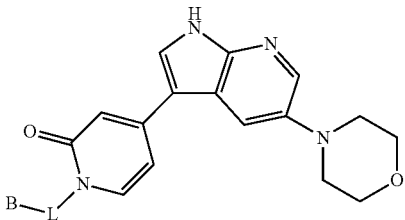

Wherein L and B have the meaning previously defined.

Among the compounds of formula (I) mention may be made especially of the following compounds 1: 1-(3-Chlorobenzyl)-4-[5-(4-fluorophenyl)-1H-pyrrolo[2,3-b]pyridin-3-yl]-1H-pyridin-2-one;
2: 1-(3-Chlorobenzyl)-4-[5-(4-hydroxymethylphenyl)-1H-pyrrolo[2,3-b]pyridin-3-yl]-1H-pyridin-2-one;
3: 4-{3-[1-(3-Chlorobenzyl)-2-oxo-1,2-dihydropyridin-4-yl]-1H-pyrrolo[2,3-b]pyridin-5-yl}-N-methylbenzamide;
4: 1-(3-Chlorobenzyl)-4-[5-(6-fluoropyridin-3-yl)-1H-pyrrolo[2,3-b]pyridin-3-yl]-1H-pyridin-2-one;
5: 1-(3-Chlorobenzyl)-4-[5-thiophen-3-yl-1H-pyrrolo[2,3-b]pyridin-3-yl]-1H-pyridin-2-one;
6: 1-(3-Chlorobenzyl)-4-[5-(5-chlorothiophen-2-yl)-1H-pyrrolo[2,3-b]pyridin-3-yl]-1H-pyridin-2-one;
7: 1-(3-Chlorobenzyl)-4-[5-(1H-pyrazol-4-yl)-1H-pyrrolo[2,3-b]pyridin-3-yl]-1H-pyridin-2-one;
8: 1-(3-Chlorobenzyl)-4-[5-(5-methyl-1H-pyrazol-4-yl)-1H-pyrrolo[2,3-b]pyridin-3-yl]-1H-pyridin-2-one;
9: 1-(3-Chlorobenzyl)-4-(5-piperidin-1-yl-1H-pyrrolo[2,3-b]pyridin-3-yl)-1H-pyridin-2-one;
10: 1-(3-Chlorobenzyl)-4-(5-(4-cyanopiperidin-1-yl)-1H-pyrrolo[2,3-b]pyridin-3-yl)-1H-pyridin-2-one;
11: 1-(3-Chlorobenzyl)-4-[5-(4-hydroxymethylpiperidin-1-yl)-1H-pyrrolo[2,3-b]pyridin-3-yl]-1H-pyridin-2-one;
12: 1-(3-Chlorobenzyl)-4-[5-(1,4-dioxa-8-azaspiro[4.5]dec-8-yl)-1H-pyrrolo[2,3-]pyridin-3-yl]-1H-pyridin-2-one;
13: 1-(3-Chlorobenzyl)-4-[5-(4-oxopiperidin-1-yl)-1H-pyrrolo[2,3-b]pyridin-3-yl]-1H-pyridin-2-one;
14: 1-(3-Chlorobenzyl)-4-[5-(4-hydroxypiperidin-1-yl)-1H-pyrrolo[2,3-b]pyridin-3-yl]-1H-pyridin-2-one;
15: 1-(3-Chlorobenzyl)-4-[5-(4-methoxyaminopiperidin-1-yl)-1H-pyrrolo[2,3-b]pyridin-3-yl]-1H-pyridin-2-one;
16: 1-(3-Chlorobenzyl)-4-(5-pyrrolidin-1-yl-1H-pyrrolo[2,3-b]pyridin-3-yl)-1H-pyridin-2-one
17: 1-(3-Chlorobenzyl)-4-(5-morpholin-4-yl-1H-pyrrolo[2,3-b]pyridin-3-yl)-1H-pyridin-2-one
18: 1-(3-Chlorobenzyl)-4-[5-(3-methylmorpholin-4-yl)-1H-pyrrolo[2,3-b]pyridin-3-yl]-1H-pyridin-2-one;
19: 1-(3-Chlorobenzyl)-4-[5-(2-methylmorpholin-4-yl)-1H-pyrrolo[2,3-b]pyridin-3-yl]-1H-pyridin-2-one;
20: 4-(3-(1-(3-Chlorobenzyl)-2-oxo-1,2-dihydropyridin-4-yl)-1H-pyrrolo[2,3-b]pyridin-5-yl)-N-methylmorpholine-2-carboxamide;
21: Tert-butyl 4-(3-(1-(3-chlorobenzyl)-2-oxo-1,2-dihydropyridin-4-yl)-1H-pyrrolo[2,3-b]pyridin-5-yl)piperazine-1-carboxylate;
22: 1-(3-Chlorobenzyl)-4-(5-(piperazin-1-yl)-1H-pyrrolo[2,3-b]pyridin-3-yl)pyridin-2(1H)-one;
23: 4-(3-(1-(3-Chlorobenzyl)-2-oxo-1,2-dihydropyridin-4-yl)-1H-pyrrolo[2,3-b]pyridin-5-yl)-N-ethylpiperazine-1-carboxamide;
24: 4-(3-(1-(3-Chlorobenzyl)-2-oxo-1,2-dihydropyridin-4-yl)-1H-pyrrolo[2,3-b]pyridin-5-yl)-N-(2-hydroxyethyl)piperazine-1-carboxamide;
25: 1-Benzyl-4-(5-morpholino-1H-pyrrolo[2,3-b]pyridin-3-yl)pyridin-2(1H)-one
26: 1-(4-Bromobenzyl)-4-(5-morpholino-1H-pyrrolo[2,3-b]pyridin-3-yl)pyridin-2(1H)-one;
27: 1-(3-Iodobenzyl)-4-(5-morpholino-1H-pyrrolo[2,3-b]pyridin-3-yl)pyridin-2(1H)-one;
28: 4-(5-Morpholino-1H-pyrrolo[2,3-b]pyridin-3-yl)-1-(3-(trifluoromethyl)benzyl)pyridin-2(1H)-one;
29: 1-(3-Methoxybenzyl)-4-(5-morpholino-1H-pyrrolo[2,3-b]pyridin-3-yl)pyridin-2(1H)-one;
30: 1-(4-Chloro-3-fluorobenzyl)-4-(5-morpholino-1H-pyrrolo[2,3-b]pyridin-3-yl)pyridin-2(1H)-one;
31: 1-(3-Chloro-4-fluorobenzyl)-4-(5-morpholino-1H-pyrrolo[2,3-b]pyridin-3-yl)pyridin-2(1H)-one;
32: 1-(3-Chloro-2-fluorobenzyl)-4-(5-morpholino-1H-pyrrolo[2,3-b]pyridin-3-yl)pyridin-2(1H)-one;
33: 1-(3,4-Dichlorobenzyl)-4-(5-morpholino-1H-pyrrolo[2,3-b]pyridin-3-yl)pyridin-2(1H)-one;
34: 1-(2,4-Dichlorobenzyl)-4-(5-morpholino-1H-pyrrolo[2,3-b]pyridin-3-yl)pyridin-2(1H)-one;
35: 1-(5-Chloro-2-hydroxybenzyl)-4-(5-morpholino-1H-pyrrolo[2,3-b]pyridin-3-yl)pyridin-2(1H)-one;
36: 1-(5-Chloro-3-hydroxybenzyl)-4-(5-morpholino-1H-pyrrolo[2,3-b]pyridin-3-yl)pyridin-2(1H)-one;
37: 1-(5-Chloro-2-(2-methoxyethoxy)benzyl)-4-(5-morpholino-1H-pyrrolo[2,3-b]pyridin-3-yl)pyridin-2(1H)-one;
38: 1-(3-Chloro-5-(2-methoxyethoxy)benzyl)-4-(5-morpholino-1H-pyrrolo[2,3-b]pyridin-3-yl)pyridin-2(1H)-one;
39: 4-(5-Morpholino-1H-pyrrolo[2,3-b]pyridin-3-yl)-1-(pyridin-3-ylmethyl)pyridin-2(1H)-one;
40: 1-((6-Chloropyridin-3-yl)methyl)-4-(5-morpholino-1H-pyrrolo[2,3-b]pyridin-3-yl)pyridin-2(1H)-one;
41: 1-((6-Chloropyridin-2-yl)methyl)-4-(5-morpholino-1H-pyrrolo[2,3-b]pyridin-3-yl)pyridin-2(1H)-one;
42: 1-(1-(3-Chlorophenyl)-2-hydroxyethyl)-4-(5-morpholino-1H-pyrrolo[2,3-b]pyridin-3-yl)pyridin-2(1H)-one;
43: 2-(3-Chlorophenyl)-2-(4-(5-morpholino-1H-pyrrolo[2,3-b]pyridin-3-yl)-2-oxopyridin-1(2H)-yl)acetic acid;
44: 1-(2-(3-Chlorophenyl)-2-hydroxyethyl)-4-(5-morpholino-1H-pyrrolo[2,3-b]pyridin-3-yl)pyridin-2(1H)-one;
210: 1-(4-Chlorobenzyl)-4-(5-morpholino-1H-pyrrolo[2,3-b]pyridin-3-yl)pyridin-2(1H)-one;
211: 1-(3-Bromobenzyl)-4-(5-morpholino-1H-pyrrolo[2,3-b]pyridin-3-yl)pyridin-2(1H)-one;
212: 1-(3-Bromo-4-fluorobenzyl)-4-(5-morpholino-1H-pyrrolo[2,3-b]pyridin-3-yl)pyridin-2(1H)-one;
213: 1-(3-Bromo-5-fluorobenzyl)-4-(5-morpholino-1H-pyrrolo[2,3-b]pyridin-3-yl)pyridin-2(1H)-one;
214: 1-(3-Bromo-2-fluorobenzyl)-4-(5-morpholino-1H-pyrrolo[2,3-b]pyridin-3-yl)pyridin-2(1H)-one;
215: 1-(4-Iodobenzyl)-4-(5-morpholino-1H-pyrrolo[2,3-b]pyridin-3-yl)pyridin-2(1H)-one;
216: 1-(4-Fluoro-3-iodobenzyl)-4-(5-morpholino-1H-pyrrolo[2,3-b]pyridin-3-yl)pyridin-2(1H)-one;

217: 1-(2-Fluoro-3-iodobenzyl)-4-(5-morpholino-1H-pyrrolo[2,3-b]pyridin-3-yl)pyridin-2(1H)-one;
218: 1-(3-Fluoro-5-iodobenzyl)-4-(5-morpholino-1H-pyrrolo[2,3-b]pyridin-3-yl)pyridin-2(1H)-one;
219: 1-(3-Chloro-5-iodobenzyl)-4-(5-morpholino-1H-pyrrolo[2,3-b]pyridin-3-yl)pyridin-2(1H)-one;
220: 1-(4-Chloro-3-iodobenzyl)-4-(5-morpholino-1H-pyrrolo[2,3-b]pyridin-3-yl)pyridin-2(1H)-one;
226: 1-(2-Chloro-3-fluorobenzyl)-4-(5-morpholino-1H-pyrrolo[2,3-b]pyridin-3-yl)pyridin-2(1H)-one;
227: 1-(3-Chloro-5-fluorobenzyl)-4-(5-morpholino-1H-pyrrolo[2,3-b]pyridin-3-yl)pyridin-2(1H)-one;
228: 1-(5-Chloro-2-fluorobenzyl)-4-(5-morpholino-1H-pyrrolo[2,3-b]pyridin-3-yl)pyridin-2(1H)-one;
230: 1-(3-Fluoro-4-(trifluoromethyl)benzyl)-4-(5-morpholino-1H-pyrrolo[2,3-b]pyridin-3-yl)pyridin-2(1H)-one;
231: 1-(2-Fluoro-3-(trifluoromethyl)benzyl)-4-(5-morpholino-1H-pyrrolo[2,3-b]pyridin-3-yl)pyridin-2(1H)-one;
232: 1-(3-Chloro-4-(trifluoromethyl)benzyl)-4-(5-morpholino-1H-pyrrolo[2,3-b]pyridin-3-yl)pyridin-2(1H)-one;
238: 1-(3-Chloro-5-methylbenzyl)-4-(5-morpholino-1H-pyrrolo[2,3-b]pyridin-3-yl)pyridin-2(1H)-one;
241: 1-(3-Chloro-5-(methoxymethyl)benzyl)-4-(5-morpholino-1H-pyrrolo[2,3-b]pyridin-3-yl)pyridin-2(1H)-one
303: 1-(1-(3-Chlorophenyl)ethyl)-4-(5-morpholino-1H-pyrrolo[2,3-b]pyridin-3-yl)pyridin-2(1H)-one;
305: 1-(1-(3-Chlorophenyl)-2-methoxyethyl)-4-(5-morpholino-1H-pyrrolo[2,3-b]pyridin-3-yl)pyridin-2(1H)-one;
308: 1-(1-(3,4-Dichlorophenyl)ethyl)-4-(5-morpholino-1H-pyrrolo[2,3-b]pyridin-3-yl)pyridin-2(1H)-one or one of their pharmaceutically acceptable salts.

Another subject of the present invention is directed to the prodrugs of compounds of formula (I) and their pharmaceutically acceptable salts.

Particularly the present invention is directed to the prodrugs (P)

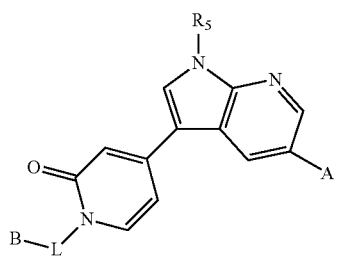

(P)

wherein $R_5$ represents a group chosen among —$CH_2$—O—$COR_6$ and —$CR_6R_7$—O—$PO_3R_8R_9$, with $R_6$, $R_7$, $R_8$ and $R_9$, identical or different, being chosen among H and ($C_1$-$C_6$) alkyl groups, A, B, L having the definitions mentioned above, more particularly A represents a 6- to 10-membered aryl group; a 5- to 12-membered heteroaryl group or a 4- to 12-membered heterocyclic group, A being preferably a non-substituted morpholinyl group, A being optionally substituted with one or more substituents chosen among halogen atoms, hydroxyl, ($C_1$-$C_6$)alkyl, cyano, oxo, carbonyl, tert-butyloxycarbonyl, 1,3-dioxolanyl, 1,4-dioxolanyl, ($C_1$-$C_6$)alkoxy, —$COOR_1$, —$CONR_1R_2$ and $NR_1R_2$, with said ($C_1$-$C_6$)alkyl being itself optionally substituted with a hydroxyl, $NR_1R_2$, ($C_1$-$C_6$)alkoxy, or —S($C_1$-$C_6$)alkyl group, and said 4- to 12-membered heterocyclic group optionally comprising two fused cycles wherein the two cycles share at least two atoms;

L represents a linker chosen among linear or branched ($C_1$-$C_6$)alkylene group, said alkylene group being optionally substituted with at least one halogen, hydroxyl, ($C_1$-$C_6$)alkoxy, —$COOR_1$ or $NR_1R_2$ groups;

B represents a 6- to 10-membered aryl or a 5- to 12-membered heteroaryl group with B being optionally substituted with one or more substituents chosen among halogen atoms, trifluoromethyl, trifluoromethoxy, hydroxyl, ($C_1$-$C_6$)alkyl, ($C_1$-$C_6$)alkoxy, —$CONR_1R_2$, $NR_1R_2$, hydroxy($C_1$-$C_6$)alkyl, hydroxy($C_1$-$C_6$)alkoxy, ($C_1$-$C_6$)alkoxy($C_1$-$C_6$)alkyl, ($C_1$-$C_6$)alkoxy($C_1$-$C_6$)alkoxy and ($C_1$-$C_6$)alkyl $NR_1R_2$ groups;

with two adjacent carbon atoms of said 6- to 10-membered aryl group being optionally substituted by two oxygen atoms linked together by a ($C_1$-$C_6$)alkylene group, $R_1$ and $R_2$ represent, independently of each other, a hydrogen atom, a ($C_1$-$C_6$)alkyl group, a ($C_1$-$C_6$)alkoxy group, a hydroxy($C_1$-$C_6$)alkyl group or a hydroxy($C_1$-$C_6$)alkoxy group, or one of their pharmaceutically acceptable salts.

The prodrugs P may also be in the form of bases or of acid-addition salts particularly with an alkali metal such as Na or with amino acids such as lysine or valine.

Depending on the medium, the salts of these prodrugs may be mono-salts or di-salts.

According to a general meaning, a prodrug is a compound that, after administration, is metabolized (i.e. converted within the body) into a pharmaceutically active drug.

The prodrugs according to the invention advantageously present a gain in terms of solubility and bioavailability.

Among the prodrugs P mention may be made especially of the following compounds:

400: (3-(1-(3-Chloro-2-fluorobenzyl)-2-oxo-1,2-dihydropyridin-4-yl)-5-morpholino-1H-pyrrolo[2,3-b]pyridin-1-yl)methyl isobutyrate;
401: (3-(1-(3-Chloro-2-fluorobenzyl)-2-oxo-1,2-dihydropyridin-4-yl)-5-morpholino-1H-pyrrolo[2,3-b]pyridin-1-yl)methyl pivalate;
402: (3-(1-(3-Chloro-2-fluorobenzyl)-2-oxo-1,2-dihydropyridin-4-yl)-5-morpholino-1H-pyrrolo[2,3-b]pyridin-1-yl)methyl dihydrogen phosphate;
403: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl dihydrogen phosphate;
404: (3-(1-(3-Chlorobenzyl)-2-oxo-1,2-dihydropyridin-4-yl)-5-morpholino-1H-pyrrolo[2,3-b]pyridin-1-yl)methyl dihydrogen phosphate;
405: (3-(1-(3-Bromobenzyl)-2-oxo-1,2-dihydropyridin-4-yl)-5-morpholino-1H-pyrrolo[2,3-b]pyridin-1-yl)methyl dihydrogen phosphate;
406: (3-(1-(3-Bromo-5-fluorobenzyl)-2-oxo-1,2-dihydropyridin-4-yl)-5-morpholino-1H-pyrrolo[2,3-b]pyridin-1-yl)methyl dihydrogen phosphate;
407: (3-(1-(3-Bromo-2-fluorobenzyl)-2-oxo-1,2-dihydropyridin-4-yl)-5-morpholino-1H-pyrrolo[2,3-b]pyridin-1-yl)methyl dihydrogen phosphate
408: (3-(1-(3-Chloro-5-fluorobenzyl)-2-oxo-1,2-dihydropyridin-4-yl)-5-morpholino-1H-pyrrolo[2,3-b]pyridin-1-yl)methyl dihydrogen phosphate;

409: (3-(1-(3-Fluoro-5-iodobenzyl)-2-oxo-1,2-dihydropyridin-4-yl)-5-morpholino-1H-pyrrolo[2,3-b]pyridin-1-yl) methyl dihydrogen phosphate,
415: (3-(1-(4-Chlorobenzyl)-2-oxo-1,2-dihydropyridin-4-yl)-5-morpholino-1H-pyrrolo[2,3-b]pyridin-1-yl)methyl dihydrogen phosphate;
416: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl sodium hydrogen phosphate
417: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl disodium phosphate;
or one of their pharmaceutically acceptable salts.

Among the prodrugs P, mention may also be made of the alkylated forms of compounds 400-417:
402 a: Di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate;
403 a Di-tert-butyl(3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl phosphate
404 a: Di-tert-butyl(3-(1-(3-chlorobenzyl)-2-oxo-1,2-dihydropyridin-4-yl)-5-morpholino-1H-pyrrolo[2,3-b]pyridin-1-yl)methyl phosphate
405 a: Di-tert-butyl(3-(1-(3-bromobenzyl)-2-oxo-1,2-dihydropyridin-4-yl)-5-morpholino-1H-pyrrolo[2,3-b]pyridin-1-yl)methyl phosphate
406 a: Di-tert-butyl(3-(1-(3-bromo-5-fluorobenzyl)-2-oxo-1,2-dihydropyridin-4-yl)-5-morpholino-1H-pyrrolo[2,3-b]pyridin-1-yl)methyl phosphate
407 a Di-tert-butyl(3-(1-(3-bromo-2-fluorobenzyl)-2-oxo-1,2-dihydropyridin-4-yl)-5-morpholino-1H-pyrrolo[2,3-b]pyridin-1-yl)methyl phosphate
408 a: Di-tert-butyl(3-(1-(3-chloro-5-fluorobenzyl)-2-oxo-1,2-dihydropyridin-4-yl)-5-morpholino-1H-pyrrolo[2,3-b]pyridin-1-yl)methyl phosphate
409 a: Di-tert-butyl(3-(1-(3-fluoro-5-iodobenzyl)-2-oxo-1,2-dihydropyridin-4-yl)-5-morpholino-1H-pyrrolo[2,3-b]pyridin-1-yl)methyl phosphate
415 a Di-tert-butyl(3-(1-(4-chlorobenzyl)-2-oxo-1,2-dihydropyridin-4-yl)-5-morpholino-1H-pyrrolo[2,3-b]pyridin-1-yl)methyl phosphate,
or one of their pharmaceutically acceptable salts.

Processes

The present invention also concerns a process for preparing compounds of general formula (I) wherein A represents a 6- to 10-membered aryl or a 5- to 12-membered heteroaryl group, said aryl or heteroaryl being substituted or non-substituted, L and B being as defined in the present text, wherein the following steps are carried out in that order, starting from a 5-bromo-7-azaindole:
a) Iodinating said 5-bromo-7-azaindole for obtaining a 5-bromo-3-iodo-7-azaindole,
b) Protecting the nitrogen atom of the pyrrolyl moiety of the azaindole,
c) earring out a first Suzuki coupling reaction of the compound obtained at step b) with a 2-oxo-1,2-dihydropyridin-4-ylboronic acid or ester derivative at a temperature within the range from 50 to 100° C. preferably from 70° C. to 80° C.;
d) earring out a second Suzuki coupling reaction of the compound obtained at step c) with an aryl or heteroarylboronic acid under microwave irradiation at a temperature within the range from 120 to 180° C., preferably 150° C.

Specifically, in accordance with the invention, the compounds of general formula (I) can be prepared according to the process illustrated by the general scheme 1 and 2, below:

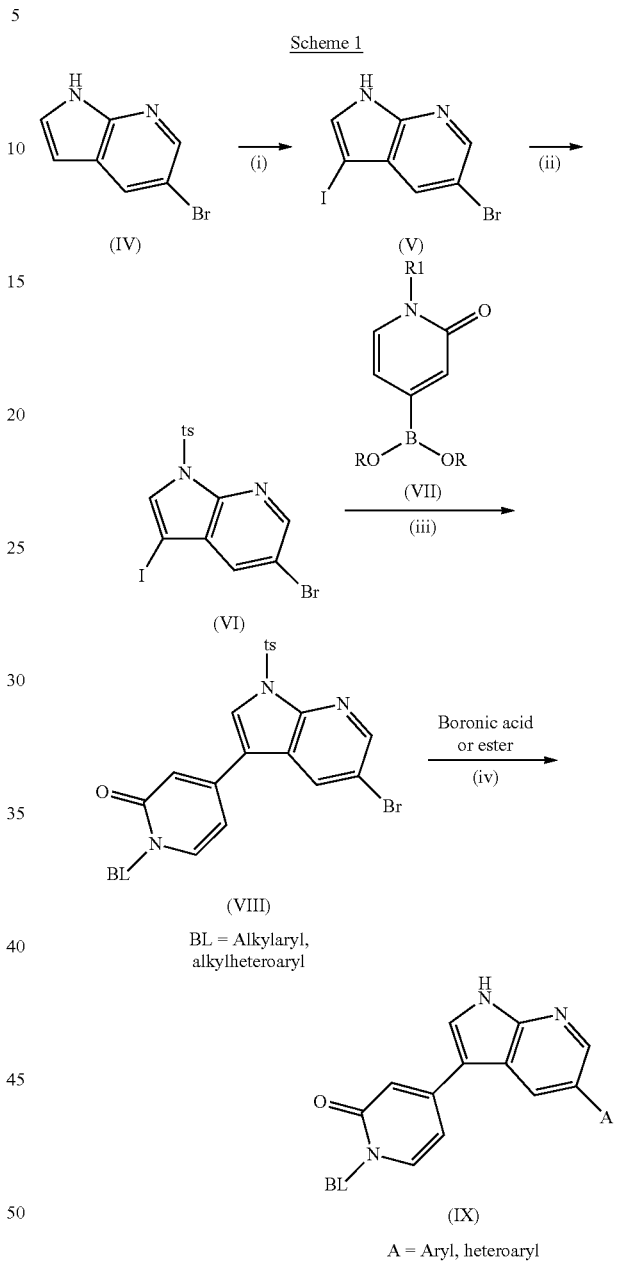

Scheme 1

BL = Alkylaryl, alkylheteroaryl

A = Aryl, heteroaryl

5-Bromo-3-iodo-7-azaindole V is obtained from compound IV by iodination with N-iodosuccinimide (NIS) (step i). Iodination is performed in a solvent as acetone or THF, at room temperature. Compound V is then protected with a tosyl group in step ii, and the obtained compound VI is introduced in a Suzuki coupling in step iii. The coupling is performed at 70-80° C., in presence of a 2-oxo-1,2-dihydropyridin-4-ylboronic acid or ester derivative and a catalytic amount of palladium, in a solvent as a mixture of acetonitrile and aqueous $Na_2CO_3$. Compounds of formula VII are commercially available or prepared by a N-alkylation, starting from 4-(4,4,5,5-tetramethyl-1,3,2-dioxaborolan-2-yl)pyridin-2(1H)-one, an alkyl bromide and a base (as $Cs_2CO_3$ or $Na_2CO_3$) in anhydrous DMF. Suzuki coupling gives protected compound of formula VIII which is introduced a second time in a Suzuki coupling, but this time under microwaves irradiation at 150° C., in presence of aryl or heteroarylboronic acid, a catalytic amount of palladium in a mixture of acetonitrile and aqueous Na$_2$CO$_3$ (step iv). Aryl or heteroarylboronic acids used in this step are commercially available. Protecting group is also removed during this step, to give final expected compounds of formula IX.

The present invention also concerns a process for preparing compounds of general formula (I) wherein A represents 4- to 7-membered heterocyclic group, substituted or non-substituted, L and B being as defined in the present text, wherein the following steps are carried out in that order, starting from a 5-bromo-7-azaindole:

a) earring out a Buchwald-Hartwig coupling with a compound comprising a 4- to 7-membered heterocyclic group on said 5-bromo-7-azaindole for obtaining a 5-substitued 7-azaindole, b) iodinating the 5-substitued 7-azaindole for obtaining a 5-substitued-3-iodo-7-azaindole, c) protecting the nitrogen atom of the pyrrolyl moiety of the azaindole, d) earring out a Suzuki coupling reaction of the compound obtained at step b) with a 2-oxo-1,2-dihydropyridin-4-ylboronic acid or ester derivative at a temperature within the range from 50 to 100° C. preferably from 70° C. to 80° C., e) optionally performing a microwave irradiation at a temperature within the range from 120 to180° C., preferably 150° C.

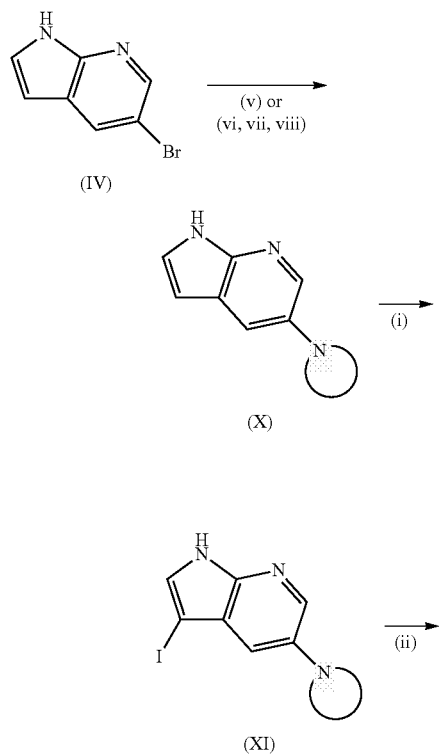

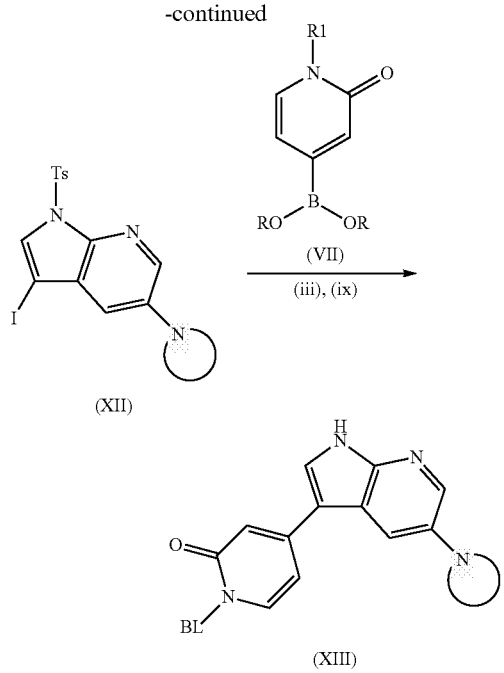

Examples of formula XIII can be prepared according to scheme 2. Synthesis starts from 5-bromo-7-azaindole IV which is substituted with a saturated 5- or 6-membered heterocycle via a Buchwald-Hartwig coupling (step v). Reaction occurs at 60° C. in presence of RuPhos Pd 2$^{nd}$ generation, its ligand RuPhos and LiHMDS to give derivatives of formula X.

In some cases, most frequently when the saturated heterocycle to introduce presents several free H bonds, the substrate IV need first to be protected with a 2-trimethylsilylethoxymethyl protecting group (step vi). This group will permit the Buchwald-Hartwig reaction to occur with the heterocycle, a catalytic amount of Pd(dba)$_2$, xantphos and sodium tert-butoxide in toluene at 110° C. (step vii). Protecting group is then removed with ethylenediamine and TBAF in step viii to give intermediates of formula X.

Synthesis continues by a iodination with NIS (as step i in scheme 1), followed by a protection with TsCl (as step ii in scheme 1), and then a Suzuki reaction to introduce a substituted 2-oxo-1,2-dihydropyridin-4-yl moiety. This last step is performed at 70° C. during 1 to 2 h (as step iii in scheme 1) and then during a few minutes e.g from 5 to 15 minutes at 150° C. under microwaves irradiation to directly obtained unprotected compounds of formula XIII.

Applications

As specified previously and clearly illustrated by the following examples, the compounds according to the present invention are useful as inhibitors of the ERK kinases activity.

According to a first aspect, the compounds of the invention are used as inhibitors of the ERK2 kinase activity.

More specifically the compounds of the invention are used for preventing and/or inhibiting and/or treating a disease or a condition mediated by ERK kinases activity, in particular by ERK2 kinase activity.

The present invention therefore provides a method for preventing and/or treating a disease or a condition mediated by ERK kinases activity, comprising at least a step of administering to an individual in need thereof at least an effective amount of at least one compound in accordance with the invention.

According to one embodiment, the disease or the condition may be chosen among cancers and metastases.

More specifically, the disease or the condition may be chosen among glioblastomas, multiple myelomas, carcinomas, leukemia, in particular myeloid (AML), lymphocytic, myelocytic, myelogenous (CML) or lymphoblastic leukemias, myelodysplastic syndromes, Kaposi's sarcomas, cutaneous angiosarcomas, solid tumours, lymphomas, in particular non-hodgkin's lymphomas, melanomas, in particular malignant melanomas, bladder cancers, breast cancers, gastric cancers, colon cancers, colorectal cancers, endometrial cancers, lung cancers, including non-small-cell cancers, pancreatic cancers, prostate cancers, rectal cancers, kidney cancers, head and neck cancers, liver cancers, ovarian cancers, in particular serous ovarian cancers, seminoma cancers, cancers of the respiratory tract and chest, thyroid cancers, in particular papillary or follicular thyroid cancers, or other tumours expressing ERK.

According to another embodiment, the disease or condition may be chosen among a neoplastic disorder, an allergy disorder, an inflammatory disorder, an autoimmune disorder, a Plasmodium related disease, a mast cell associated disease, a graft-versus-host disease, a metabolic syndrome, a CNS related disorder, a neurodegenerative disorder, a pain condition, a substance abuse disorder, a prion disease, a heart disease, a fibrotic disease, idiopathic arterial hypertension (IPAH), or primary pulmonary hypertension (PPH).

According to yet another embodiment, the compounds of the invention may be used for preventing and/or inhibiting and/or treating the Human Immunodeficiency Virus (HIV).

The compounds of the present invention may be used alone or combined with chemotherapeutic agents or radiotherapeutic regimen.

Thus, according to one embodiment, a method of the invention may comprise the step of administering a compound of formula (I) in accordance with the invention, separately, sequentially or simultaneously with a chemotherapeutic agent. As examples of chemotherapeutic agents that may be suitable for the invention, one may mention chemotherapeutic agents chosen from alkylating agents, intercalating agents, antimicrotubule agents, antimitotics, antimetabolites, antiproliferative agents, antibiotics, immunomodulatory agents, anti-inflammatories, kinases inhibitors, anti-angiogenic agents, antivascular agents, oestrogenic and androgenic hormones.

A radiotherapeutic regimen may be administered by exposing an individual in need thereof to a source of ionizing radiation such as X-ray, gamma-ray or beta-ray.

According to another of its aspects, the present invention relates to a pharmaceutical composition comprising at least one compound according to the invention or a pharmaceutically acceptable salt thereof, and at least one pharmaceutically acceptable excipient.

The compounds according to the invention may be used for the preparation of medicaments, in particular of medicaments for inhibiting the activity of ERK kinases.

Thus, according to yet another of its aspects, the present invention relates to a medicament comprising at least one compound according to the invention, or a pharmaceutically acceptable salt thereof.

The term "pharmaceutically acceptable" means that which is useful in preparing a pharmaceutical composition that is generally safe, non-toxic, and neither biologically nor otherwise undesirable and includes what is acceptable for veterinary as well as human pharmaceutical use.

The pharmaceutical compositions may contain more particularly an effective dose of at least one compound according to the invention.

An "effective dose" means an amount sufficient to induce a positive modification in the condition to be regulated or treated, but low enough to avoid serious side effects. An effective amount may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

A compound of formula (I) according to the invention may be administered in an effective dose by any of the accepted modes of administration in the art.

In one embodiment, a compound of the invention may be used in a composition intended to be administrated by oral, nasal, sublingual, aural, ophthalmic, topical, rectal, vaginal, urethral, or parenteral injection route.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, ointments, gels, creams, sticks, lotions, pastes, soft and hard gelatine capsules, suppositories, sterile injectable solutions, sterile packages powders and the like.

According to one embodiment, a pharmaceutical composition of the invention may be intended to be administered separately, sequentially or simultaneously with an agent useful for the prevention and/or the treatment of a disease condition, in particular a cancer condition, said agent being different from the compound of formula (I) of the invention.

The applications also include a novel kit-of-parts that is suitable for use in the treatment of cancers.

A kit-of-part according to the invention may comprise (i) a compound of formula (I) according to the invention, and (ii) at least one agent useful for the prevention and/or the treatment of a cancer condition, said agent being different from said compound of formula (I). An agent useful for the prevention and/or treatment of a cancer condition may be a chemotherapeutic agent or a radiotherapeutic agent.

The present invention will be better understood by referring to the following examples which are provided for illustrative purpose only and should not be interpreted as limiting in any manner the instant invention.

Equipment and Analytical Methods Used for the Syntheses of Examples
Microwaves Irradiation:
  Apparatus: CEM Discover with Synergy Software.
  Method: 10 or 30 mL sealed tube, power 50 W, high stirring, and irradiation time 15 or 30 min.
Flash Chromatography:
  Apparatus: Biotage SP with auto-collector and UV detection (2 wavelengths).
  Normal phase columns: 10, 25 or 120 g Biotage external dry load cartridge kit, packed with Sigma-Aldrich 40-63 µm silica gel.
  Reverse phase column: 30 g Biotage SNAP Cartridges, KP-C18-HS.
Liquid Chromatography:
  Apparatus: Waters alliance 2695 HPLC system with autosampler and Waters 2996 diode array detector.
  Analytical Method:
    Column: Macherey-Nagel Nucleoshell RP18 plus (5 µm, 4 mm×100 mm).
    Column temperature: 40° C.
    Solvents: A ($H_2O$ 99.9%, $H_2CO_2$ 0.1%); B ($CH_3CN$ 99.9%, $H_2CO_2$ 0.1%).
    Flow rate: 1 mL/min.
    Gradient (A/B v/v): 90/10 (t=0 min), 90/10 (t=1 min), 0/100 (t=7 min), 0/100 (t=10 min).
    Detection: 210-400 nm range.
Mass Spectrometer:
  Apparatus: Waters Micromass ZQ (simple quad).
  Mass detection method: Electrospray positive mode (ESI+), mass range: 50-800 uma.
NMR Spectrometer:
  Apparatus: Bruker 300 MHz.
  Methods: 1H NMR spectra performed in DMSO-d6 using DMSO-d5 as internal reference, chemical shifts expressed in parts per million (ppm), signals expressed as follows: s=singlet, d=doublet, t=triplet, q=quadruplet, sept=septuplet, dd=double doublet, dt=double triplet, m=multiplet or large singlet, br=broad, H=proton.
  $^{31}P$ NMR spectra performed in DMSO-d6, chemical shifts expressed in parts per million (ppm), signals expressed as follows: s=singlet.

Example 1: 1-(3-Chlorobenzyl)-4-[5-(4-fluorophenyl)-1H-pyrrolo[2,3-b]pyridin-3-yl]-1H-pyridin-2-one Step 1: 5-Bromo-3-iodo-1H-pyrrolo[2,3-b]pyridine

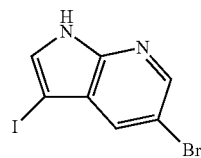 [SMILES: Brc1cnc2[nH]cc(I)c2c1]

6.28 g (27.9 mmol) of N-iodosuccinimide are added portionwise to a solution of 5 g (25.4 mmol) of 5-bromo-1H-pyrrolo[2,3-b]pyridine in 100 ml of acetone. The mixture is stirred for 1 hour at ambient temperature then cooled to 0° C. The precipitate is filtered off, rinsed with a small amount of cold acetone and dried under vacuum for several hours to give 7.18 g of a white solid. The compound is used in the next step without further purification.
Yield: 88%.
$^1$H NMR (DMSO-d6, 300 MHz): δ 12.34 (br s, 1H); 8.31 (d, J=2.1 Hz, 1H); 7.86 (d, J=2.1 Hz, 1H); 7.80 (d, J=2.6 Hz, 1H).

Step 2: 5-Bromo-3-iodo-1-tosyl-1H-pyrrolo[2,3-b]pyridine

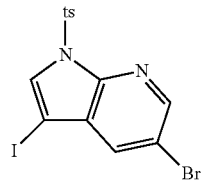

To a solution of 4 g (12.4 mmol) of 5-bromo-3-iodo-1H-pyrrolo[2,3-b]pyridine (described in the previous step) in 80 ml of anhydrous THF at 0° C., is added 0.74 g (18.5 mmol) of sodium hydride (60% in paraffin oil) under argon. The mixture is stirred at this temperature for 15 minutes, then 2.59 g (13.6 mmol) of tosyl chloride are added and the reaction is allowed to reach ambient temperature overnight. The mixture is concentrated under reduced pressure, dissolved in ethyl acetate, washed 3 times with water, dried over anhydrous sodium sulfate and then filtered. The filtrate is concentrated under reduced pressure to give a crude solid which is purified by crystallization in ethyl acetate. 4.08 g of the title compound are obtained.
Yield: 69%.
MH+: 476.5; 478.4.
$^1$H NMR (DMSO-d6, 300 MHz): δ 8.51 (d, J=1.8 Hz, 1H); 8.22 (s, 1H); 8.02-7.98 (m, 3H); 7.43 (d, J=8.1 Hz, 2H); 2.34 (s, 3H).

Step 3: 1-(3-Chlorobenzyl)-2-oxo-1,2-dihydropyridine-4-boronic Acid

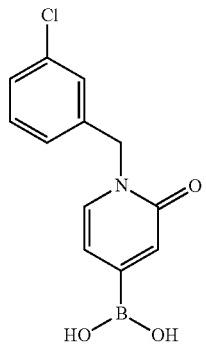

To a solution of 200 mg (0.91 mmol) of 4-(4,4,5,5-tetramethyl-[1,3,2]dioxaborolan-2-yl)-1H-pyridin-2-one, 442 mg (1.36 mmol) of cesium carbonate in 1 ml of anhydrous DMF, is added 0.13 ml (1.00 mmol) of 3-chlorobenzyl bromide at ambient temperature. The reaction is stirred overnight under argon. Reaction mixture is then diluted with ethyl acetate, and the precipitate is filtered and rinsed with a small amount of ethyl acetate. The filtrate is concentrated under vacuum and directly purified by flash chromatography with a 30 g C18 column and a water/acetonitrile mixture as eluent. 109 mg of the title compound are obtained.

Yield: 45%.
MH+: 264.0; 266.0.

Step 4: 4-(5-Bromo-1-tosyl-1H-pyrrolo[2,3-b]pyridin-3-yl)-1-(3-chlorobenzyl)-1H-pyridin-2-one

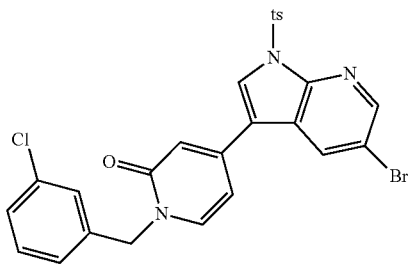

326 mg (0.68 mmol) of 5-bromo-3-iodo-1-tosyl-1H-pyrrolo[2,3-b]pyridine (described in the step 2) and 198 mg (0.75 mmol) of 1-(3-chlorobenzyl)-2-oxo-1,2-dihydropyridine-4-boronic acid (described in the previous step) are dissolved in a mixture of 40 ml of acetonitrile and 20 ml of an aqueous 2M solution of $Na_2CO_3$. Argon is bubbled through the solution for 10 minutes, then 32 mg of $PdCl_2(PPh_3)_2$ is added under argon. Argon is bubbled for another 10 minutes and the reaction is stirred at 70° C. for 1 h30. The reaction medium is diluted with water, extracted 3 times with ethyl acetate, dried over sodium sulfate, filtered and evaporated under reduced pressure. Crude product is purified by flash chromatography on a 10 g silica gel column with an ethyl acetate/hexane mixture as eluent. 129 mg of the title compound are obtained as a white solid.

Yield: 33%.
MH+: 567.6; 569.6.
$^1$H NMR (DMSO-d6, 300 MHz): δ 8.57-8.52 (m, 3H); 8.04 (d, J=8.4 Hz, 2H); 7.93 (d, J=7.1 Hz, 1H); 7.46-7.29 (m, 6H); 6.86 (d, J=1.9 Hz, 1H); 6.80 (dd, J=7.1 and 1.9 Hz, 1H); 5.14 (s, 2H); 2.35 (s, 3H).

Step 5: 1-(3-Chlorobenzyl)-4-[5-(4-fluorophenyl)-1H-pyrrolo[2,3-b]pyridin-3-yl]-1H-pyridin-2-one

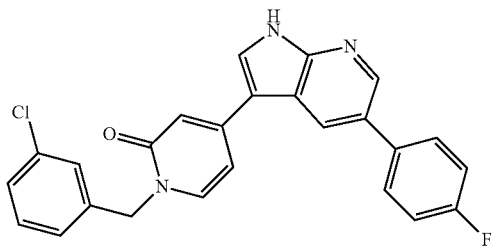 [SMILES: O=c1cc(-c2c[nH]c3ncc(-c4ccc(F)cc4)cc23)ccn1Cc1cccc(Cl)c1]

15 mg (0.026 mmol) of 4-(5-bromo-1-tosyl-1H-pyrrolo[2,3-b]pyridin-3-yl)-1-(3-chlorobenzyl)-1H-pyridin-2-one (described in the previous step) and 4 mg (0.028 mmol) of 4-fluorophenylboronic acid are dissolved in a mixture of 2 ml of acetonitrile and 1 ml of an aqueous 2M solution of $Na_2CO_3$. Argon is bubbled through the solution for 10 minutes, then 2 mg of $PdCl_2(PPh_3)_2$ is added under argon. Argon is bubbled for another 10 minutes and the reaction is heated at 150° C. under microwaves irradiation for 1 hour. The reaction medium is diluted with water, extracted 3 times with ethyl acetate, dried over sodium sulfate, filtered and evaporated under reduced pressure. Crude product is purified by flash chromatography with a 30 g C18 column and a water/acetonitrile mixture as eluent. 5.9 mg of the title compound are obtained.

Yield: 52%.
MH+: 429.8; 431.8.
$^1$H NMR (DMSO-d6, 300 MHz): δ 12.37 (br s, 1H); 8.57 (d, J=1.5 Hz, 1H); 8.44 (d, J=1.6 Hz, 1H); 8.23 (s, 1H); 7.86-7.80 (m, 3H); 7.42-7.28 (m, 6H); 6.86-6.79 (m, 2H); 5.12 (s, 2H).

Example 2: 1-(3-Chlorobenzyl)-4-[5-(4-hydroxymethylphenyl)-1H-pyrrolo[2,3-b]pyridin-3-yl]-1H-pyridin-2-one

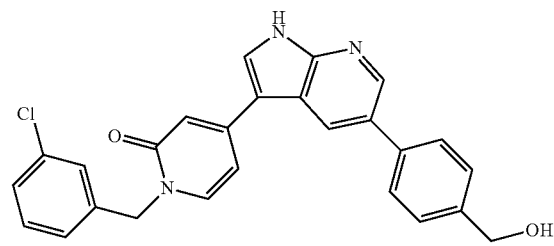 [SMILES: O=c1cc(-c2c[nH]c3ncc(-c4ccc(CO)cc4)cc23)ccn1Cc1cccc(Cl)c1]

The compound is obtained by the procedure described in example 1 step 5, using 4.4 mg (0.029 mmol) of 4-hydroxymethylboronic acid instead of 4-fluorophenylboronic acid. 5.5 mg of the title compound are obtained.

Yield: 47%.
MH+: 441.8; 443.8.
$^1$H NMR (DMSO-d6, 300 MHz): δ 12.36 (br s, 1H); 8.56 (d, J=1.6 Hz, 1H); 8.43 (d, J=1.6 Hz, 1H); 8.23 (s, 1H); 7.83 (d, J=7.0 Hz, 1H); 7.75 (d, J=8.4 Hz, 2H); 7.44-7.28 (m, 6H); 6.86-6.78 (m, 2H); 5.23 (br t, 1H); 5.12 (s, 2H); 4.55 (d, J=5.5 Hz, 2H).

Example 3: 4-{3-[1-(3-Chlorobenzyl)-2-oxo-1,2-dihydropyridin-4-yl]-1H-pyrrolo[2,3-b]pyridin-5-yl}-N-methylbenzamide

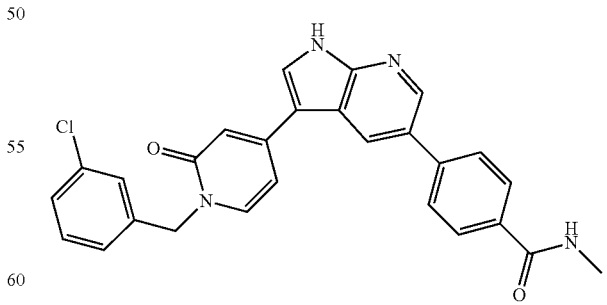

The compound is obtained by the procedure described in example 1 step 5, using 5.2 mg (0.029 mmol) of 4-(N-methylaminocarbonyl)phenylboronic acid instead of 4-fluorophenylboronic acid. 8.5 mg of the title compound are obtained.

Yield: 68%.

MH+: 468.8; 470.8.

¹H NMR (DMSO-d6, 300 MHz): δ 12.41 (br s, 1H); 8.65 (d, J=1.5 Hz, 1H); 8.54-8.48 (m, 2H); 8.25 (s, 1H); 7.98-7.87 (m, 5H); 7.44-7.28 (m, 4H); 6.88-6.79 (m, 2H); 5.13 (s, 2H); 2.81 (d, J=4.4 Hz, 3H).

Example 4: 1-(3-Chlorobenzyl)-4-[5-(6-fluoropyridin-3-yl)-1H-pyrrolo[2,3-b]pyridin-3-yl]-1H-pyridin-2-one

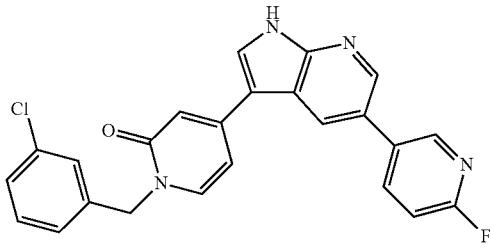 [SMILES: O=c1cc(-c2c[nH]c3ncc(-c4ccc(F)nc4)cc23)ccn1Cc1cccc(Cl)c1]

The compound is obtained by the procedure described in example 1 step 5, using 4.1 mg (0.029 mmol) of 2-fluoropyridine-5-boronic acid instead of 4-fluorophenylboronic acid. 3.3 mg of the title compound are obtained.

Yield: 29%.

MH+: 430.8; 432.8.

¹H NMR (DMSO-d6, 300 MHz): δ 12.42 (br s, 1H); 8.69-8.68 (m, 1H); 8.63-8.60 (m, 1H); 8.57-8.54 (m, 1H); 8.26 (s, 1H); 7.83 (d, J=6.9 Hz, 1H); 7.43-7.28 (m, 6H); 6.92-6.78 (m, 2H); 5.12 (s, 2H).

Example 5: 1-(3-Chlorobenzyl)-4-(5-thiophen-3-yl-1H-pyrrolo[2,3-b]pyridin-3-yl)-1H-pyridin-2-one

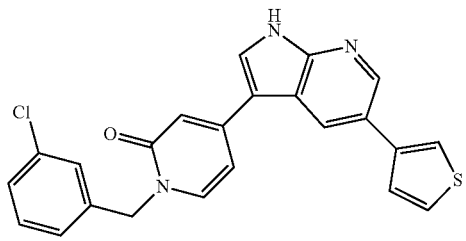 [SMILES: O=c1cc(-c2c[nH]c3ncc(-c4ccsc4)cc23)ccn1Cc1cccc(Cl)c1]

The compound is obtained by the procedure described in example 1 step 5, using 4.0 mg (0.031 mmol) of thiophene-3-boronic acid instead of 4-fluorophenylboronic acid. 7.9 mg of the title compound are obtained.

Yield: 72%.

MH+: 417.8; 419.8.

¹H NMR (DMSO-d6, 300 MHz): δ 12.35 (br s, 1H); 8.68 (d, J=1.9 Hz, 1H); 8.51 (d, J=1.9 Hz, 1H); 8.21 (s, 1H); 8.03-7.99 (m, 1H); 7.83 (d, J=7.1 Hz, 1H); 7.74-7.65 (m, 2H); 7.44-7.29 (m, 4H); 6.86 (d, J=1.6 Hz, 1H); 6.81 (dd, J=1.9 and 7.1 Hz, 1H); 5.13 (s, 2H).

Example 6: 1-(3-Chlorobenzyl)-4-[5-(5-chlorothiophen-2-yl)-1H-pyrrolo[2,3-b]pyridin-3-yl]-1H-pyridin-2-one

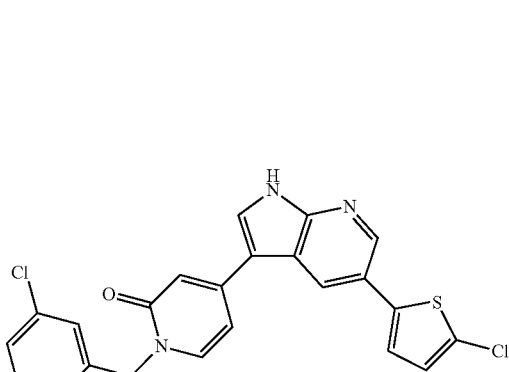

The compound is obtained by the procedure described in example 1 step 5, using 4.7 mg (0.029 mmol) of 5-chlorothiophene-2-boronic acid instead of 4-fluorophenylboronic acid. 6.5 mg of the title compound are obtained.

Yield: 55%.

MH+: 451.8; 453.7; 455.8.

¹H NMR (DMSO-d6, 300 MHz): δ 12.45 (br s, 1H); 8.56 (d, J=1.9 Hz, 1H); 8.41 (d, J=2.0 Hz, 1H); 8.25 (s, 1H); 7.84 (d, J=6.6 Hz, 1H); 7.53 (d, J=3.9 Hz, 1H); 7.44-7.28 (m, 4H); 7.19 (d, J=3.9 Hz, 1H); 6.83-6.75 (m, 2H); 5.13 (s, 2H).

Example 7: 1-(3-Chlorobenzyl)-4-[5-(1H-pyrazol-4-yl)-1H-pyrrolo[2,3-b]pyridin-3-yl]-1H-pyridin-2-one

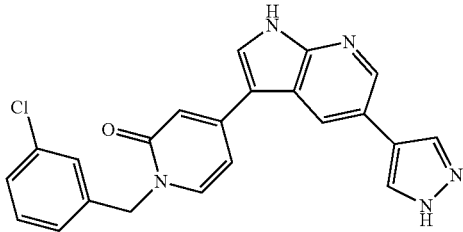 [SMILES: O=c1cc(-c2c[nH]c3ncc(-c4cn[nH]c4)cc23)ccn1Cc1cccc(Cl)c1]

The compound is obtained by the procedure described in example 1 step 5, using 5.6 mg (0.029 mmol) of 4-pyrazoleboronic acid pinacol ester instead of 4-fluorophenylboronic acid. 2.3 mg of the title compound are obtained.

Yield: 22%.

MH+: 401.8; 403.9.

¹H NMR (DMSO-d6, 300 MHz): δ 12.97 (br s, 1H); 12.23 (br s, 1H); 8.59 (d, J=1.8 Hz, 1H); 8.42 (d, J=2.0 Hz, 1H); 8.37-8.32 (m, 1H); 8.17 (s, 1H); 8.08-8.02 (m, 1H); 7.82 (d, J=7.2 Hz, 1H); 7.44-7.29 (m, 4H); 6.85 (d, J=1.7 Hz, 1H); 6.80 (dd, J=1.8 and 7.3 Hz, 1H); 5.13 (s, 2H).

Example 8: 1-(3-Chlorobenzyl)-4-[5-(5-methyl-1H-pyrazol-4-yl)-1H-pyrrolo[2,3-b]pyridin-3-yl]-1H-pyridin-2-one

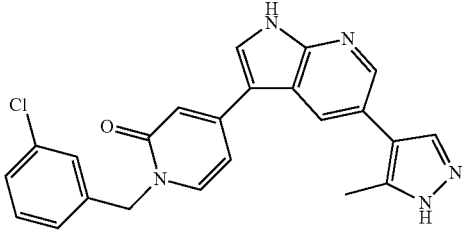 [SMILES: Cc1[nH]ncc1-c1cnc2[nH]cc(-c3ccn(Cc4cccc(Cl)c4)c(=O)c3)c2c1]

The compound is obtained by the procedure described in example 1 step 5, using 20 mg (0.035 mmol) of 4-(5-bromo-1-tosyl-1H-pyrrolo[2,3-b]pyridin-3-yl)-1-(3-chlorobenzyl)-1H-pyridin-2-one (described in example 1 step 4), 8.0 mg (0.038 mmol) of 5-methyl-1H-pyrazole-4-boronic acid pinacol ester instead of 4-fluorophenylboronic acid, and 2 mg of PdCl$_2$(PPh$_3$)$_2$. 2.1 mg of the title compound are obtained.

Yield: 14%.

MH+: 415.9; 417.9.

$^1$H NMR (DMSO-d6, 300 MHz): δ 12.67 (br s, 1H); 12.27 (br s, 1H); 8.39 (d, J=1.8 Hz, 1H); 8.23 (d, J=1.9 Hz, 1H); 8.19 (s, 1H); 7.92-7.84 (m, 1H); 7.64 (d, J=7.6 Hz, 1H); 7.44-7.28 (m, 4H); 6.80-6.74 (m, 2H); 5.11 (s, 2H); 2.39 (s, 3H).

Example 9: 1-(3-Chlorobenzyl)-4-(5-piperidin-1-yl-1H-pyrrolo[2,3-b]pyridin-3-yl)-1H-pyridin-2-one

Step 1: 5-Piperidin-1-yl-1H-pyrrolo[2,3-b]pyridine

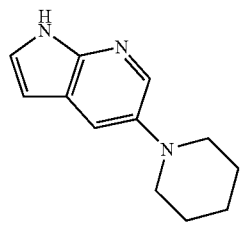 [SMILES: c1cc2cc(N3CCCCC3)cnc2[nH]1]

In 6 ml of anhydrous THF are dissolved 0.5 g (2.53 mmol) of 5-bromo-1H-pyrrolo[2,3-b]pyridine, 300 µl (3.05 mmol) of piperidine, 12 mg (0.025 mmol) of RuPhos and 20 mg (0.025 mmol) of RuPhos Pd G2 under argon. To the solution is added 6 ml (6 mmol) of LiHMDS (1M in THF) at ambient temperature. Then the reaction is heated at 60° C. until LC/MS shows that the reaction is complete (2 hours). After cooling to ambient temperature, the solvent is removed under reduced pressure. 150 ml of a solution of saturated NH$_4$Cl is added and the mixture is extracted 3 times with ethyl acetate. The combined organic layers are dried over sodium sulfate, filtered, and evaporated under reduced pressure to give 0.6 g of a red solid. The compound is used in the next step without further purification.

Yield: Quantitative.

MH+: 202.1.

Step 2: 3-Iodo-5-piperidin-1-yl-1H-pyrrolo[2,3-b]pyridine

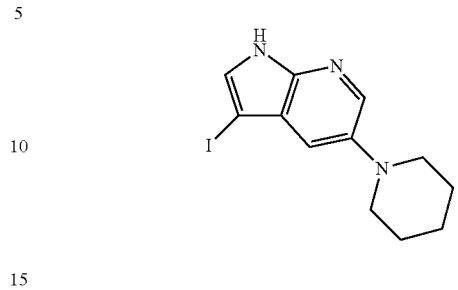

855 mg (3.80 mmol) of N-iodosuccinimide are added portionwise to a solution of 510 mg (2.54 mmol) of 5-piperidin-1-yl-1H-pyrrolo[2,3-b]pyridine (described in the previous step) in 10 ml of acetone. The mixture is stirred for 1 hour at ambient temperature. TLC shows that the reaction is complete. Solvent is then removed under reduced pressure. The reaction mixture is diluted with ethyl acetate and washed 2 times with water and another time with brine. The organic layer is dried over sodium sulfate, filtered, and evaporated under reduced pressure. Crude product is purified by flash chromatography with a 30 g silica gel column with an ethyl acetate/hexane mixture as eluent. 501 mg of the title compound are obtained.

Yield: 61%.

MH+: 327.9.

Step 3: 3-Iodo-5-piperidin-1-yl-1-tosyl-1H-pyrrolo[2,3-b]pyridine

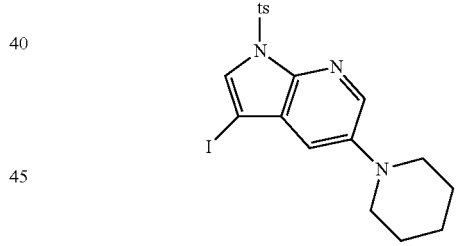

500 mg (1.53 mmol) of 3-iodo-5-piperidin-1-yl-1H-pyrrolo[2,3-b]pyridine (described in the previous step) are diluted in 10 ml of anhydrous DMF under argon. 92 mg (2.30 mmol) of sodium hydride (60% in paraffin oil) are slowly added to the mixture at 0° C. and the solution is stirred at this temperature for 15 minutes. Then 320 mg (1.70 mmol) of tosyl chloride are added under argon at 0° C. and the mixture is allowed to reach ambient temperature overnight. The reaction mixture is diluted with ethyl acetate and washed 3 times with water and then with brine. The organic layer is dried over sodium sulfate, filtered, and evaporated under reduced pressure. Crude product is purified by flash chromatography with a 30 g silica gel column with an ethyl acetate/hexane mixture as eluent. 502 mg of the title compound are obtained.

Yield: 68%.

MH+: 481.8.

Step 4: 1-(3-Chlorobenzyl)-4-(5-piperidin-1-yl-1H-pyrrolo[2,3-b]pyridin-3-yl)-1H-pyridin-2-one

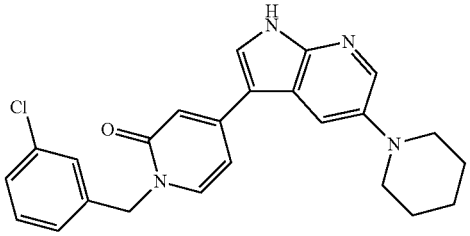 [SMILES: O=c1cc(-c2c[nH]c3ncc(N4CCCCC4)cc23)ccn1Cc1cccc(Cl)c1]

20 mg (0.042 mmol) of 3-iodo-5-piperidin-1-yl-1-tosyl-1H-pyrrolo[2,3-b]pyridine (described in previous step) and 12 mg (0.046 mmol) of 1-(3-chlorobenzyl)-2-oxo-1,2-dihydropyridine-4-boronic acid (described in example 1 step 3) are dissolved in a mixture of 3 ml of acetonitrile and 1.5 ml of an aqueous 2M solution of $Na_2CO_3$. Argon is bubbled through the solution for 10 minutes, then 2 mg of $PdCl_2(PPh_3)_2$ are added under argon. Argon is bubbled for another 10 minutes and the reaction is stirred at 70° C. for 1 hour. The reaction mixture is transferred in a microwave sealed tube and the reaction is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 10 g silica gel column with an ethyl acetate/hexane mixture as eluent. The obtained product is purified another time by flash chromatography on a 30 g C18 column with a water/acetonitrile mixture as eluent. 3.6 mg of the title compound are obtained.

Yield: 21%.

MH+: 419.0; 421.0.

$^1$H NMR (DMSO-d6, 300 MHz): δ 12.02 (br s, 1H); 8.13 (d, J=2.2 Hz, 1H); 8.07 (s, 1H); 7.80 (d, J=6.9 Hz, 1H); 7.69 (d, J=2.2 Hz, 1H); 7.42-7.27 (m, 4H); 6.75-6.67 (m, 2H); 5.10 (s, 2H); 3.14-3.00 (m, 4H); 1.76-1.62 (m, 4H); 1.57-1.45 (m, 2H).

Example 10: 1-(3-Chlorobenzyl)-4-(5-(4-cyanopiperidin-1-yl)-1H-pyrrolo[2,3-b]pyridin-3-yl)-1H-pyridin-2-one Step 1: 5-Bromo-1-(2-trimethylsilylethoxymethyl)-1H-pyrrolo[2,3-b]pyridine

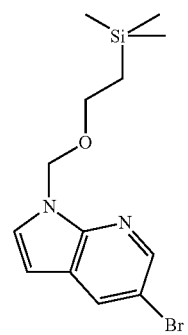 [SMILES: C[Si](C)(C)CCOCn1ccc2cc(Br)cnc21]

2 g (10 mmol) of 5-bromo-1H-pyrrolo[2,3-b]pyridine are diluted in 20 ml of anhydrous DMF under argon. 0.61 g (15 mmol) of sodium hydride (60% in paraffin oil) is slowly added to the mixture at 0° C. The solution is stirred at 0° C. for 5 minutes and at ambient temperature for another 25 minutes. The mixture is cooled again to 0° C. and 2.7 ml (15 mmol) of (2-(chloromethoxy)ethyl)trimethylsilane are added dropwise. The reaction is allowed to reach ambient temperature overnight. The reaction mixture is diluted with brine, extracted 3 times with ethyl acetate. The combined organic layers are dried over sodium sulfate, filtered, and evaporated under reduced pressure. Crude product is purified by flash chromatography with a 100 g silica gel column and an ethyl acetate/hexane mixture as eluent. 3.44 g of the title compound are obtained.

Yield: Quantitative.

MH+: 327.0; 329.0.

$^1$H NMR (DMSO-d6, 300 MHz): δ 8.34 (d, J=2.2 Hz, 1H); 8.24 (d, J=2.2 Hz, 1H); 7.71 (d, J=3.6 Hz, 1H); 6.53 (d, J=3.6 Hz, 1H); 5.60 (s, 2H); 3.49 (t, J=7.8 Hz, 2H); 0.80 (t, J=8.0 Hz, 2H); 0.12 (s, 9H).

Step 2: 5-(4-cyanopiperidin-1-yl)-1-(2-trimethylsilylethoxymethyl)-1H-pyrrolo[2,3-b]pyridine

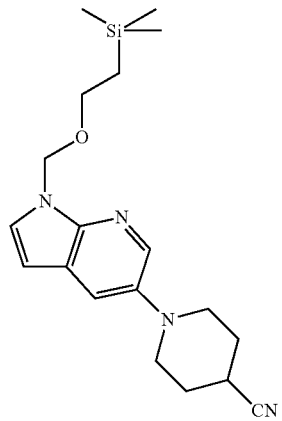 [SMILES: C[Si](C)(C)CCOCn1ccc2cc(N3CCC(C#N)CC3)cnc21]

In 5 ml of anhydrous toluene are dissolved 0.5 g (1.53 mmol) of 5-bromo-1-(2-trimethylsilylethoxymethyl)-1H-pyrrolo[2,3-b]pyridine (described in the previous step) and 0.2 ml (1.82 mmol) of 4-cyanopiperidine. Argon is bubbled through the solution for 10 minutes, then 27 mg (0.3 mmol) of $Pd(dba)_3$, 52 mg (0.09 mmol) of xantphos and 216 mg (2.30 mmol) of sodium tert-butoxide are added. Argon is bubbled for another 10 minutes and the solution is stirred at 110° C. overnight. After cooling to ambient temperature, the reaction mixture is diluted with ethyl acetate, washed 3 times with water, dried over sodium sulfate, filtered, and evaporated under reduced pressure. Crude product is purified by flash chromatography with a 30 g silica gel column and an ethyl acetate/hexane mixture as eluent. 296 mg of the title compound are obtained.

Yield: 55%.

MH+: 357.1.

Step 3: 5-(4-cyanopiperidin-1-yl)-1H-pyrrolo[2,3-b]pyridine

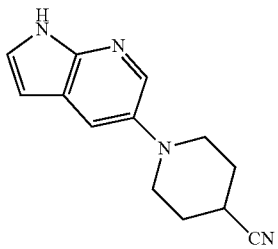 [SMILES: N#CC1CCN(c2cnc3[nH]ccc3c2)CC1]

296 mg (0.83 mmol) of 5-(4-cyanopiperidin-1-yl)-1-(2-trimethylsilylethoxymethyl)-1H-pyrrolo[2,3-b]pyridine (described in the previous step) are dissolved in 7 ml of anhydrous THF under argon. 83 µl (1.25 mmol) of ethylenediamine are added to the solution, followed by 2.49 ml (2.49 mmol) of TBAF (1M in THF). The reaction is stirred at 66° C. for 4 h and another 1.66 ml (1.66 mmol) of TBAF (1M in THF) is added. The reaction is stirred at 66° C. overnight. After cooling to ambient temperature, the reaction mixture is poured into a saturated solution of NaHCO$_3$, extracted 3 times with ethyl acetate, dried over sodium sulfate, filtered, and evaporated under reduced pressure. Crude product is purified by flash chromatography with a 30 g silica gel column and an ethyl acetate/hexane mixture as eluent. 141 mg of the title compound are obtained.

Yield: 75%.

MH+: 227.1.

Step 4: 3-Iodo-5-(4-cyanopiperidin-1-yl)-1H-pyrrolo[2,3-b]pyridine

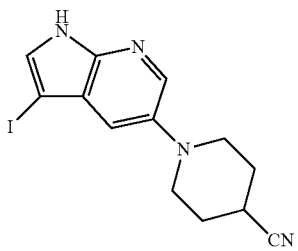 [SMILES: N#CC1CCN(c2cnc3[nH]cc(I)c3c2)CC1]

The compound is obtained by the procedure described in example 9 step 2, using 141 mg (0.62 mmol) of 5-(4-cyanopiperidin-1-yl)-1H-pyrrolo[2,3-b]pyridine (described in the previous step) instead of 5-piperidin-1-yl-1H-pyrrolo[2,3-b]pyridine and 210 mg (0.94 mmol) of N-iodosuccinimide in 5 ml of acetone. 139 mg of the title compound are obtained.

Yield: 63%.

MH+: 352.8.

Step 5: 3-Iodo-5-(4-cyanopiperidin-1-yl)-1-tosyl-1H-pyrrolo[2,3-b]pyridine

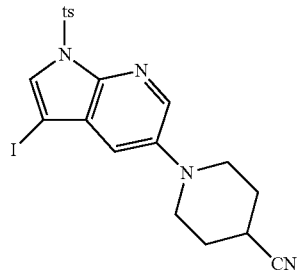

The compound is obtained by the procedure described in example 9 step 3, using 139 mg (0.40 mmol) of 3-iodo-5-(4-cyanopiperidin-1-yl)-1H-pyrrolo[2,3-b]pyridine (described in the previous step) instead of 3-iodo-5-piperidin-1-yl-1H-pyrrolo[2,3-b]pyridine, 24 mg (0.59 mmol) of sodium hydride (60% in paraffin oil) and 83 mg (0.44 mmol) of tosyl chloride in 10 ml of anhydrous DMF. 137 mg of the title compound are obtained.

Yield: 67%.

MH+: 506.8.

Step 6: 1-(3-Chlorobenzyl)-4-(5-(4-cyanopiperidin-1-yl)-1H-pyrrolo[2,3-b]pyridin-3-yl)-1H-pyridin-2-one

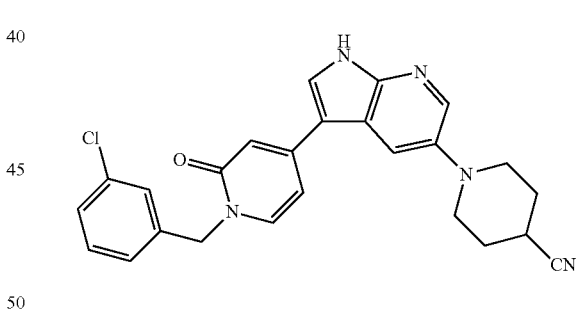

The compound is obtained by the procedure described in example 9 step 4, using 137 mg (0.27 mmol) of 3-iodo-5-(4-cyanopiperidin-1-yl)-1-tosyl-1H-pyrrolo[2,3-b]pyridine (described in the previous step) instead of 3-iodo-5-piperidin-1-yl-1-tosyl-1H-pyrrolo[2,3-b]pyridine, 71 mg (0.30 mmol) of 1-(3-chlorobenzyl)-2-oxo-1,2-dihydropyridine-4-boronic acid and 14 mg of PdCl$_2$(PPh$_3$)$_2$. 52 mg of the title compound are obtained.

Yield: 43%.

MH+: 444.0; 446.0.

$^1$H NMR (DMSO-d6, 300 MHz): δ 12.06 (br s, 1H); 8.15 (d, J=2.0 Hz, 1H); 8.09 (d, J=2.5 Hz, 1H); 7.79 (d, J=7.3 Hz, 1H); 7.77-7.71 (m, 1H); 7.44-7.34 (m, 4H); 6.76-6.69 (m, 2H); 5.10 (s, 2H); 3.11-2.95 (m, 4H); 2.13-1.99 (m, 4H); 1.97-1.82 (m, 1H).

Example 11: 1-(3-Chlorobenzyl)-4-[5-(4-hydroxymethylpiperidin-1-yl)-1H-pyrrolo[2,3-b]pyridin-3-yl]-1H-pyridin-2-one

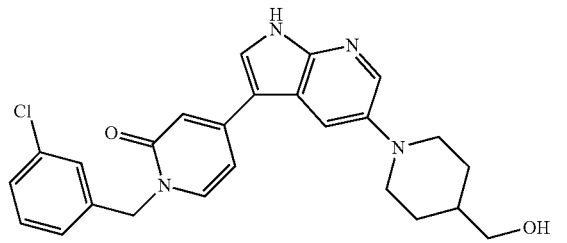 [SMILES: O=c1cc(-c2c[nH]c3ncc(N4CCC(CO)CC4)cc23)ccn1Cc1cccc(Cl)c1]

5 mg (0.011 mmol) of 1-(3-chlorobenzyl)-4-(5-(4-cyanopiperidin-1-yl)-1H-pyrrolo[2,3-b]pyridin-3-yl)-1H-pyridin-2-one (described in example 10 step 6) are dissolved in 1 ml of a mixture pyridine/acetic acid/water (2/1/1). Several drops of Raney nickel in water are added, and the mixture is placed under an atmosphere of H$_2$ and heated at 50° C. overnight. The reaction mixture is filtered on celite. The celite is washed 3 times with ethyl acetate. The filtrate is evaporated under reduced pressure and directly purified by flash chromatography with a 10 g silica gel column and a dichloromethane/methanol mixture as eluent. 0.5 mg of the title compound is obtained.

Yield: 10%.
MH+: 449.1; 451.0.
$^1$H NMR (DMSO-d6, 300 MHz): δ 12.03 (br s, 1H); 8.14 (d, J=2.2 Hz, 1H); 8.07 (s, 1H); 7.79 (d, J=7.0 Hz, 1H); 7.70 (d, J=2.3 Hz, 1H); 7.43-7.27 (m, 4H); 6.75-6.67 (m, 2H); 5.10 (s, 2H); 4.49 (br t, 1H); 3.60 (d, J=11.9 Hz, 2H); 2.78-2.60 (m, 4H); 1.86-1.73 (m, 2H); 1.67-1.41 (m, 1H); 1.40-1.19 (m, 2H).

Example 12: 1-(3-Chlorobenzyl)-4-[5-(1,4-dioxa-8-azaspiro[4.5]dec-8-yl)-1H-pyrrolo[2,3-]pyridin-3-yl]-1H-pyridin-2-one

Step 1: 8-[1-(2-Trimethylsilylethoxymethyl)-1H-pyrrolo[2,3-b]pyridin-5-yl]-1,4-dioxa-8-azaspiro[4.5]decane

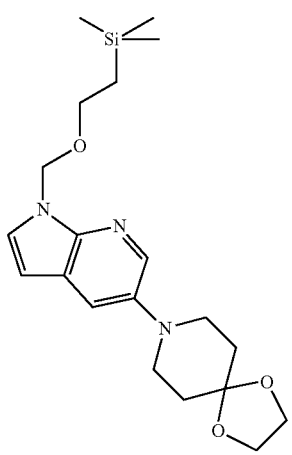 [SMILES: C[Si](C)(C)CCOCn1ccc2cc(N3CCC4(CC3)OCCO4)cnc21]

The compound is obtained by the procedure described in example 10 step 2, using 476 mg (1.45 mmol) of 5-bromo-1-(2-trimethylsilylethoxymethyl)-1H-pyrrolo[2,3-b]pyridine, 224 µl (1.75 mmol) of 1,4-dioxa-8-azaspiro[4.5]decane instead of 4-cyanopiperidine, 27 mg (0.03 mmol) of Pd(dba)$_3$, 50 mg (0.09 mmol) of xantphos and 209 mg (2.30 mmol) of tBuONa. 443 mg of the title compound are obtained. LC/MS shows a purity of 47%. The compound is used in the next step without further purification.

Yield: 78% (HPLC purity: 47%).
MH+: 390.0.

Step 2: 8-(1H-Pyrrolo[2,3-b]pyridin-5-yl)-1,4-dioxa-8-azaspiro[4.5]decane

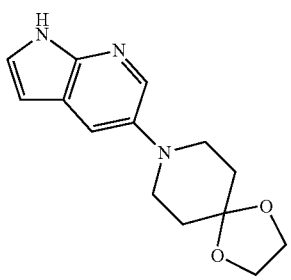 [SMILES: c1cc2cc(N3CCC4(CC3)OCCO4)cnc2[nH]1]

The compound is obtained by the procedure described in example 10 step 3, using 443 mg (1.13 mmol) of 8-[1-(2-trimethylsilylethoxymethyl)-1H-pyrrolo[2,3-b]pyridin-5-yl]-1,4-dioxa-8-azaspiro[4.5]decane (described in the previous step) instead of 5-(4-cyanopiperidin-1-yl)-1-(2-trimethylsilylethoxymethyl)-1H-pyrrolo[2,3-b]pyridine, 114 µl (1.7 mmol) of ethylenediamine, 3.4 ml+2.3 ml (3.4 mmol+2.27 mmol) of TBAF (1M in THF) in 8 ml of anhydrous THF. 128 mg of the title compound are obtained.

Yield: 43%.
MH+: 260.1.

Step 3: 8-(3-Iodo-1H-pyrrolo[2,3-b]pyridin-5-yl)-1,4-dioxa-8-azaspiro[4.5]decane

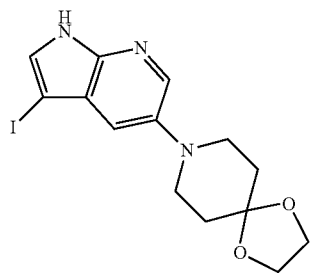 [SMILES: Ic1c[nH]c2ncc(N3CCC4(CC3)OCCO4)cc12]

The compound is obtained by the procedure described in example 9 step 2, using 128 mg (0.49 mmol) of 8-(1H-pyrrolo[2,3-b]pyridin-5-yl)-1,4-dioxa-8-azaspiro[4.5]decane (described in the previous step) instead of 5-piperidin-1-yl-1H-pyrrolo[2,3-b]pyridine and 122 mg (0.54 mmol) of N-iodosuccinimide in 2 ml of acetone. 134 mg of the title compound are obtained.

Yield: 71%.
MH+: 385.9.

Step 4: 8-(3-Iodo-1-tosyl-1H-pyrrolo[2,3-b]pyridin-5-yl)-1,4-dioxa-8-azaspiro[4.5]decane

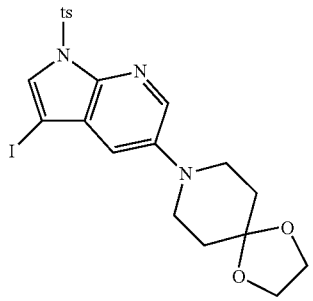

The compound is obtained by the procedure described in example 9 step 3, using 134 mg (0.35 mmol) of 8-(3-iodo-1H-pyrrolo[2,3-b]pyridin-5-yl)-1,4-dioxa-8-azaspiro[4.5]decane (described in the previous step) instead of 3-iodo-5-piperidin-1-yl-1H-pyrrolo[2,3-b]pyridine, 21 mg (0.52 mmol) of sodium hydride (60% in paraffin oil) and 73 mg (0.39 mmol) of tosyl chloride in 5 ml of anhydrous DMF. 136 mg of the title compound are obtained.

Yield: 72%.
MH+: 539.8.

Step 5: 1-(3-Chlorobenzyl)-4-[5-(1,4-dioxa-8-azaspiro[4.5]dec-8-yl)-1-tosyl-1H-pyrrolo[2,3-]pyridin-3-yl]-1H-pyridin-2-one

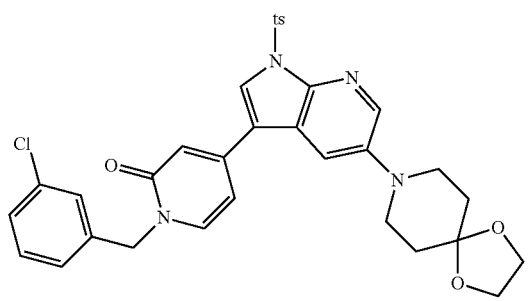

134 mg (0.25 mmol) of 8-(3-iodo-1-tosyl-1H-pyrrolo[2,3-b]pyridin-5-yl)-1,4-dioxa-8-azaspiro[4.5]decane (described in previous step) and 85 mg (0.32 mmol) of 1-(3-chlorobenzyl)-2-oxo-1,2-dihydropyridine-4-boronic acid (described in example 1 step 3) are dissolved in a mixture of 3 ml of acetonitrile and 1.5 ml of an aqueous 2M solution of Na₂CO₃. Argon is bubbled through the solution for 10 minutes, then 13 mg of PdCl₂(PPh₃)₂ are added under argon. Argon is bubbled for another 10 minutes and the reaction is stirred at 70° C. for 1 hour. After cooling, the solution is diluted with water, extracted 3 times with ethyl acetate, dried over sodium sulfate, filtered and evaporated under reduced pressure. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 55 mg of the title compound are obtained.

Yield: 35%.
MH+: 631.0; 632.9.

Step 6: 1-(3-Chlorobenzyl)-4-[5-(1,4-dioxa-8-azaspiro[4.5]dec-8-yl)-1H-pyrrolo[2,3-]pyridin-3-yl]-1H-pyridin-2-one

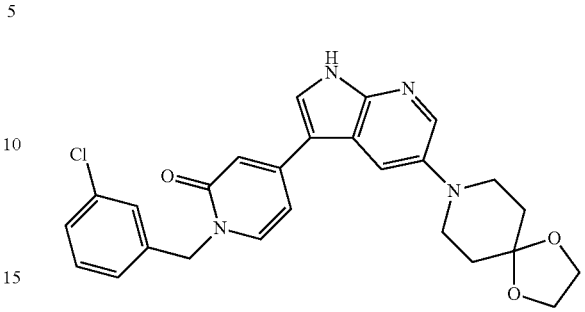

5 mg (0.008 mmol) of 1-(3-chlorobenzyl)-4-[5-(1,4-dioxa-8-azaspiro[4.5]dec-8-yl)-1-tosyl-1H-pyrrolo[2,3-]pyridin-3-yl]-1H-pyridin-2-one (described in previous step) are dissolved in a mixture of 3 ml of acetonitrile and 1.5 ml of an aqueous 2M solution of Na₂CO₃. The reaction mixture is transferred in a microwave sealed tube and the reaction is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 30 g C18 column with a water/acetonitrile mixture as eluent. 2.2 mg of the title compound are obtained.

Yield: 58%.
MH+: 476.9; 478.9.

Example 13: 1-(3-Chlorobenzyl)-4-[5-(4-oxopiperidin-1-yl)-1H-pyrrolo[2,3-b]pyridin-3-yl]-1H-pyridin-2-one Step 1: 1-(3-Chlorobenzyl)-4-[5-(4-oxopiperidin-1-yl)-1-tosyl-1H-pyrrolo[2,3-b]pyridin-3-yl]-1H-pyridin-2-one

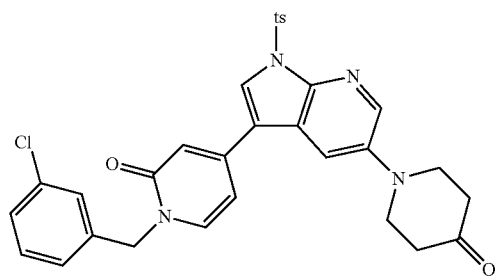

52 mg (0.082 mmol) of 1-(3-chlorobenzyl)-4-[5-(1,4-dioxa-8-azaspiro[4.5]dec-8-yl)-1-tosyl-1H-pyrrolo[2,3-]pyridin-3-yl]-1H-pyridin-2-one (described in example 12 step 5) are dissolved in a mixture of 5 ml of THF and 5 ml of HCl 1N and the reaction is stirred for 48 hours. The mixture is poured into an aqueous solution of saturated NaHCO₃, extracted 3 times with ethyl acetate, dried over sodium sulfate, filtered and evaporated under reduced pressure to give 44 mg of a yellow solid. Crude product is used in the next step without further purification.

Yield: 92%.
MH+: 586.9; 588.9.

Step 2: 1-(3-Chlorobenzyl)-4-[5-(4-oxopiperidin-1-yl)-1H-pyrrolo[2,3-b]pyridin-3-yl]-1H-pyridin-2-one

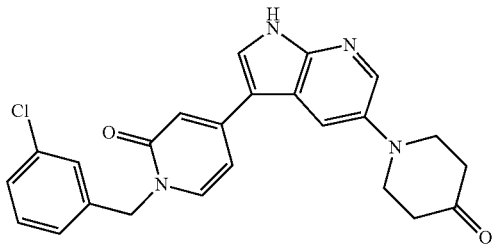 [SMILES: O=C1CCN(c2cnc3[nH]cc(-c4ccn(Cc5cccc(Cl)c5)c(=O)c4)c3c2)CC1]

4 mg (0.007 mmol) of 1-(3-chlorobenzyl)-4-[5-(4-oxopiperidin-1-yl)-1-tosyl-1H-pyrrolo[2,3-b]pyridin-3-yl]-1H-pyridin-2-one (described in previous step) are dissolved in a mixture of 2 ml of acetonitrile and 1 ml of an aqueous 2M solution of $Na_2CO_3$. The reaction mixture is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 30 g C18 column with a water/acetonitrile mixture as eluent. 0.8 mg of the title compound is obtained.
Yield: 27%.
MH+: 432.9; 434.9.

Example 14: 1-(3-Chlorobenzyl)-4-[5-(4-hydroxypiperidin-1-yl)-1H-pyrrolo[2,3-b]pyridin-3-yl]-1H-pyridin-2-one

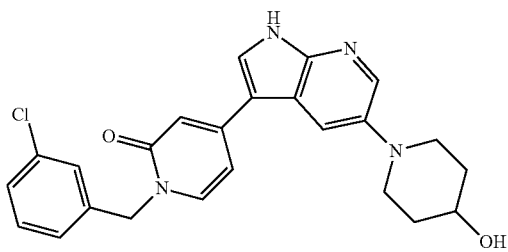 [SMILES: O=c1cc(-c2c[nH]c3ncc(N4CCC(O)CC4)cc23)ccn1Cc1cccc(Cl)c1]

12 mg (0.020 mmol) of 1-(3-chlorobenzyl)-4-[5-(4-oxopiperidin-1-yl)-1-tosyl-1H-pyrrolo[2,3-b]pyridin-3-yl]-1H-pyridin-2-one (described in example 13 step 1) are dissolved in 1 ml of ethanol. 1.3 mg (0.020 mmol) of $NaBH_3CN$ is added and the reaction is stirred at ambient temperature overnight. The mixture is poured into an aqueous solution of saturated $NaHCO_3$, extracted 3 times with ethyl acetate, dried over sodium sulfate, filtered and evaporated under reduced pressure. The residue is dissolved in a mixture of 2 ml of acetonitrile and 1 ml of an aqueous 2M solution of $Na_2CO_3$. The reaction mixture is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 30 g C18 column with a water/acetonitrile mixture as eluent. 3.2 mg of the title compound are obtained.

Yield: 36%.
MH+: 434.9; 436.9.

Example 15: 1-(3-Chlorobenzyl)-4-[5-(4-methoxyaminopiperidin-1-yl)-1H-pyrrolo[2,3-b]pyridin-3-yl]-1H-pyridin-2-one

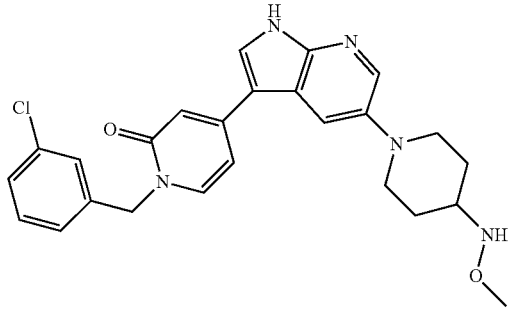 [SMILES: CONC1CCN(c2cnc3[nH]cc(-c4ccn(Cc5cccc(Cl)c5)c(=O)c4)c3c2)CC1]

12 mg (0.020 mmol) of 1-(3-chlorobenzyl)-4-[5-(4-oxopiperidin-1-yl)-1-tosyl-1H-pyrrolo[2,3-b]pyridin-3-yl]-1H-pyridin-2-one (described in example 13 step 1) and 1.9 mg (0.022 mmol) of O-methylhydroxylamine hydrochloride are dissolved in 1 ml of a mixture of methanol/acetic acid (9/1). 1.4 mg (0.022 mmol) of $NaBH_3CN$ is added and the reaction is stirred at ambient temperature overnight. The mixture is poured into an aqueous solution of saturated $NaHCO_3$, extracted 3 times with ethyl acetate, dried over sodium sulfate, filtered and evaporated under reduced pressure. The residue is dissolved in a mixture of 2 ml of acetonitrile and 1 ml of an aqueous 2M solution of $Na_2CO_3$. The reaction mixture is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 30 g C18 column with a water/acetonitrile mixture as eluent. Product is purified a second time by flash chromatography on a 10 g silica gel column with a dichloromethane/methanol mixture as eluent. 1.4 mg of the title compound is obtained.
Yield: 16%.
MH+: 464.0; 465.9.

Example 16: 1-(3-Chlorobenzyl)-4-(5-pyrrolidin-1-yl-1H-pyrrolo[2,3-b]pyridin-3-yl)-1H-pyridin-2-one Step 1: 5-Pyrrolidin-1-yl-1H-pyrrolo[2,3-b]pyridine

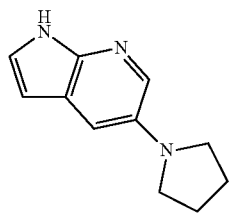 [SMILES: c1cc2cc(N3CCCC3)cnc2[nH]1]

The compound is obtained by the procedure described in example 9 step 1, using 253 µl (3 mmol) of pyrrolidine instead of piperidine. 530 mg of the title compound are obtained.

Yield: Quantitative.
MH+: 188.2.

Step 2: 3-Iodo-5-pyrrolidin-1-yl-1H-pyrrolo[2,3-b]pyridine

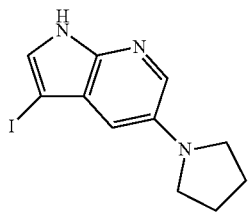 [SMILES: Ic1c[nH]c2ncc(N3CCCC3)cc12]

The compound is obtained by the procedure described in example 9 step 2, using 480 mg (2.5 mmol) of 5-pyrrolidin-1-yl-1H-pyrrolo[2,3-b]pyridine (described in the previous step) instead of 5-piperidin-1-yl-1H-pyrrolo[2,3-b]pyridine and 865 mg (3.8 mmol) of N-iodosuccinimide in 10 ml of acetone. 234 mg of the title compound are obtained.
Yield: 30%.
MH+: 313.9.

Step 3: 3-Iodo-5-pyrrolidin-1-yl-1-tosyl-1H-pyrrolo[2,3-b]pyridine

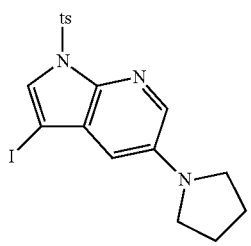

The compound is obtained by the procedure described in example 9 step 3, using 234 mg (0.75 mmol) of 3-iodo-5-pyrrolidin-1-yl-1H-pyrrolo[2,3-b]pyridine (described in the previous step) instead of 3-iodo-5-piperidin-1-yl-1H-pyrrolo[2,3-b]pyridine, 45 mg (1.1 mmol) of sodium hydride (60% in paraffin oil) and 156 mg (0.82 mmol) of tosyl chloride in 10 ml of anhydrous DMF. 201 mg of the title compound are obtained.
Yield: 58%.
MH+: 467.8.

Step 4: 1-(3-Chlorobenzyl)-4-(5-pyrrolidin-1-yl-1H-pyrrolo[2,3-b]pyridin-3-yl)-1H-pyridin-2-one

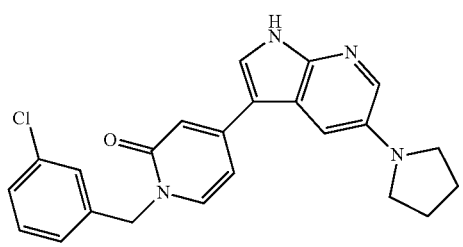 [SMILES: O=c1cc(-c2c[nH]c3ncc(N4CCCC4)cc23)ccn1Cc1cccc(Cl)c1]

The compound is obtained by the procedure described in example 9 step 4, using 20 mg (0.043 mmol) of 3-iodo-5-pyrrolidin-1-yl-1-tosyl-1H-pyrrolo[2,3-b]pyridine (described in the previous step) instead of 3-iodo-5-piperidin-1-yl-1-tosyl-1H-pyrrolo[2,3-b]pyridine, 12.4 mg (0.047 mmol) of 1-(3-chlorobenzyl)-2-oxo-1,2-dihydropyridine-4-boronic acid and 2 mg of PdCl$_2$(PPh$_3$)$_2$. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 1.7 mg of the title compound is obtained.
Yield: 10%.
MH+: 405.0; 407.0.
$^1$H NMR (DMSO-d6, 300 MHz): δ 11.87 (br s, 1H); 8.02 (s, 1H); 7.83 (d, J=2.3 Hz, 1H); 7.77 (d, J=6.9 Hz, 1H); 7.42-7.20 (m, 5H); 6.75-6.65 (m, 2H); 5.10 (s, 2H); 3.30-3.20 (m, 4H); 2.02-1.93 (m, 4H).

Example 17: 1-(3-Chlorobenzyl)-4-(5-morpholin-4-yl-1H-pyrrolo[2,3-b]pyridin-3-yl)-1H-pyridin-2-one Step 1: 5-Morpholin-4-yl-1H-pyrrolo[2,3-b]pyridine

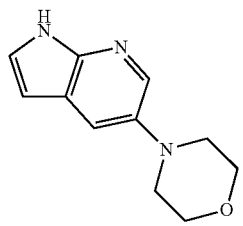 [SMILES: c1cc2cc(N3CCOCC3)cnc2[nH]1]

The compound is obtained by the procedure described in example 9 step 1, using 800 mg (4.06 mmol) of 5-bromo-1H-pyrrolo[2,3-b]pyridine, 421 µl (4.87 mmol) of morpholine instead of piperidine, 19 mg (0.04 mmol) of RuPhos, 34 mg (0.04 mmol) of RuPhos Pd G2 and 10 ml (10 mmol) of LiHMDS (1M in THF). 795 mg of the title compound are obtained.
Yield: 96%.
MH+: 204.1.

Step 2: 3-Iodo-5-morpholin-4-yl-1H-pyrrolo[2,3-b]pyridine

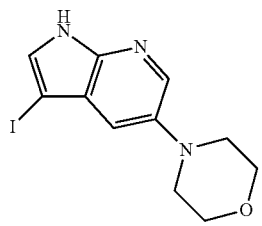 [SMILES: Ic1c[nH]c2ncc(N3CCOCC3)cc12]

The compound is obtained by the procedure described in example 9 step 2, using 795 mg (3.92 mmol) of 5-morpholin-4-yl-1H-pyrrolo[2,3-b]pyridine (described in the previous step) instead of 5-piperidin-1-yl-1H-pyrrolo[2,3-b]pyridine and 1.32 g (5.87 mmol) of N-iodosuccinimide in 15 ml of acetone. 234 mg of the title compound are obtained.
Yield: 59%.
MH+: 329.9.

Step 3: 3-Iodo-5-morpholin-1-yl-1-tosyl-1H-pyrrolo[2,3-b]pyridine

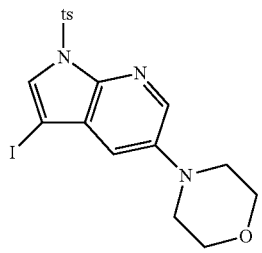

The compound is obtained by the procedure described in example 9 step 3, using 760 mg (2.31 mmol) of 3-iodo-5-morpholin-1-yl-1H-pyrrolo[2,3-b]pyridine (described in the previous step) instead of 3-iodo-5-piperidin-1-yl-1H-pyrrolo[2,3-b]pyridine, 139 mg (3.46 mmol) of sodium hydride (60% in paraffin oil) and 485 mg (2.54 mmol) of tosyl chloride in 8 ml of anhydrous DMF. 655 mg of the title compound are obtained.

Yield: 60%.
MH+: 483.8.

Step 4: 1-(3-Chlorobenzyl)-4-(5-morpholin-4-yl-1H-pyrrolo[2,3-b]pyridin-3-yl)-1H-pyridin-2-one

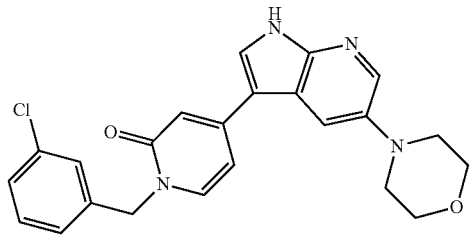 [SMILES: O=c1cc(-c2c[nH]c3ncc(N4CCOCC4)cc23)ccn1Cc1cccc(Cl)c1]

The compound is obtained by the procedure described in example 9 step 4, using 20 mg (0.043 mmol) of 3-iodo-5-morpholin-1-yl-1-tosyl-1H-pyrrolo[2,3-b]pyridine (described in the previous step) instead of 3-iodo-5-piperidin-1-yl-1-tosyl-1H-pyrrolo[2,3-b]pyridine, 14.2 mg (0.054 mmol) of 1-(3-chlorobenzyl)-2-oxo-1,2-dihydropyridine-4-boronic acid and 2 mg of PdCl$_2$(PPh$_3$)$_2$. Crude product is purified by flash chromatography on a 10 g silica gel column with an ethyl acetate/hexane mixture as eluent. The obtained product is purified another time by flash chromatography on a 30 g C18 column with a water/acetonitrile mixture as eluent. 3.7 mg of the title compound are obtained.

Yield: 21%.
MH+: 420.9; 422.9.
$^1$H NMR (DMSO-d6, 300 MHz): δ 12.03 (br s, 1H); 8.16 (d, J=2.4 Hz, 1H); 8.09 (s, 1H); 7.79 (d, J=7.4 Hz, 1H); 7.71 (d, J=2.5 Hz, 1H); 7.45-7.27 (m, 4H); 6.76-6.69 (m, 2H); 5.10 (s, 2H); 3.83-3.73 (m, 4H); 3.19-3.09 (m, 4H).

Example 18: 1-(3-Chlorobenzyl)-4-[5-(3-methylmorpholin-4-yl)-1H-pyrrolo[2,3-b]pyridin-3-yl]-1H-pyridin-2-one

Step 1: 5-(3-Methylmorpholin-4-yl)-1H-pyrrolo[2,3-b]pyridine

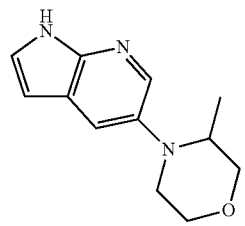 [SMILES: CC1COCCN1c1cnc2[nH]ccc2c1]

The compound is obtained by the procedure described in example 9 step 1, using 650 mg (3.30 mmol) of 5-bromo-1H-pyrrolo[2,3-b]pyridine, 400 mg (4.29 mmol) of 3-methylmorpholine instead of piperidine, 15 mg (0.043 mmol) of RuPhos, 28 mg (0.043 mmol) of RuPhos Pd G2 and 7.9 ml (7.9 mmol) of LiHMDS (1M in THF). 240 mg of the title compound are obtained.

Yield: 33%.
MH+: 218.1.
$^1$H NMR (DMSO-d6, 300 MHz): δ 11.43 (br s, 1H); 8.02 (d, J=2.4 Hz, 1H); 7.60 (d, J=2.4 Hz, 1H); 7.39 (t, J=2.9 Hz, 1H); 6.34 (dd, J=1.9 and 3.2 Hz, 1H); 3.86-3.64 (m, 3H); 3.50-3.38 (m, 2H); 3.02-2.94 (m, 2H); 0.81 (d, J=5.9 Hz, 3H).

Step 2: 3-Iodo-5-(3-methylmorpholin-4-yl)-1H-pyrrolo[2,3-b]pyridine

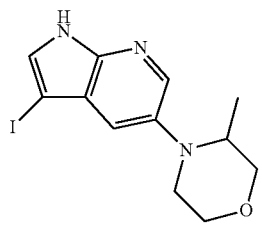 [SMILES: CC1COCCN1c1cnc2[nH]cc(I)c2c1]

The compound is obtained by the procedure described in example 9 step 2, using 240 mg (1.11 mmol) of 5-(3-methylmorpholin-4-yl)-1H-pyrrolo[2,3-b]pyridine (described in the previous step) instead of 5-piperidin-1-yl-1H-pyrrolo[2,3-b]pyridine and 373 mg (1.65 mmol) of N-iodosuccinimide in 5 ml of acetone. 231 mg of the title compound are obtained.

Yield: 61%.
MH+: 343.9.

Step 3: 3-Iodo-5-(3-methylmorpholin-4-yl)-1-tosyl-1H-pyrrolo[2,3-b]pyridine

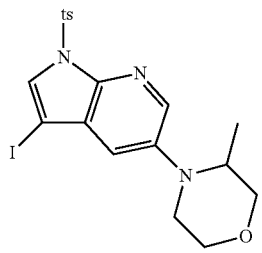

The compound is obtained by the procedure described in example 9 step 3, using 231 mg (0.67 mmol) of 3-iodo-5-(3-methylmorpholin-4-yl)-1H-pyrrolo[2,3-b]pyridine (described in the previous step) instead of 3-iodo-5-piperidin-1-yl-1H-pyrrolo[2,3-b]pyridine, 40 mg (1.01 mmol) of sodium hydride (60% in paraffin oil) and 142 mg (0.74 mmol) of tosyl chloride in 5 ml of anhydrous DMF. 195 mg of the title compound are obtained.

Yield: 61%.
MH+: 497.7.

Step 4: 1-(3-Chlorobenzyl)-4-[5-(3-methylmorpholin-4-yl)-1H-pyrrolo[2,3-b]pyridin-3-yl]-1H-pyridin-2-one

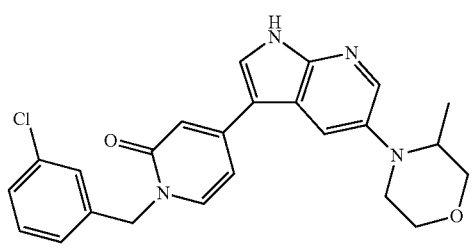 [SMILES: CC1COCCN1c1cnc2[nH]cc(-c3ccn(Cc4cccc(Cl)c4)c(=O)c3)c2c1]

The compound is obtained by the procedure described in example 9 step 4, using 20 mg (0.043 mmol) of 3-iodo-5-(3-methylmorpholin-4-yl)-1-tosyl-1H-pyrrolo[2,3-b]pyridine (described in the previous step) instead of 3-iodo-5-piperidin-1-yl-1-tosyl-1H-pyrrolo[2,3-b]pyridine, 11.7 mg (0.044 mmol) of 1-(3-chlorobenzyl)-2-oxo-1,2-dihydropyridine-4-boronic acid and 2 mg of PdCl$_2$(PPh$_3$)$_2$. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 4.0 mg of the title compound are obtained.

Yield: 22%.
MH+: 434.9; 436.9.

Example 19: 1-(3-Chlorobenzyl)-4-[5-(2-methylmorpholin-4-yl)-1H-pyrrolo[2,3-b]pyridin-3-yl]-1H-pyridin-2-one

Step 1: 5-(2-Methylmorpholin-4-yl)-1H-pyrrolo[2,3-b]pyridine

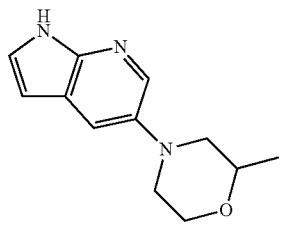 [SMILES: CC1CN(c2cnc3[nH]ccc3c2)CCO1]

The compound is obtained by the procedure described in example 9 step 1, using 650 mg (3.30 mmol) of 5-bromo-1H-pyrrolo[2,3-b]pyridine, 400 mg (4.29 mmol) of 2-methylmorpholine instead of piperidine, 15 mg (0.043 mmol) of RuPhos, 28 mg (0.043 mmol) of RuPhos Pd G2 and 7.9 ml (7.9 mmol) of LiHMDS (1M in THF). 640 mg of the title compound are obtained.

Yield: 89%.
MH+: 218.1.
$^1$H NMR (DMSO-d6, 300 MHz): δ 11.35 (br s, 1H); 8.06 (d, J=2.6 Hz, 1H); 7.47 (d, J=2.6 Hz, 1H); 7.36 (t, J=2.9 Hz, 1H); 6.31 (dd, J=1.9 and 3.3 Hz, 1H); 3.95-3.85 (m, 1H); 3.75-3.63 (m, 2H); 3.49-3.33 (m, 2H); 2.69 (dt, J=3.4 and 11.6 Hz, 1H); 2.36 (dt, J=1.3 and 11.4 Hz, 1H); 1.15 (d, J=6.4 Hz, 3H).

Step 2: 3-Iodo-5-(2-methylmorpholin-4-yl)-1H-pyrrolo[2,3-b]pyridine

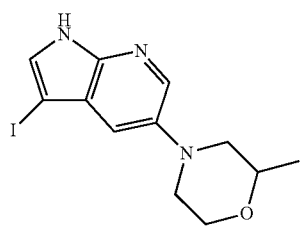 [SMILES: CC1CN(c2cnc3[nH]cc(I)c3c2)CCO1]

The compound is obtained by the procedure described in example 9 step 2, using 300 mg (1.11 mmol) of 5-(2-methylmorpholin-4-yl)-1H-pyrrolo[2,3-b]pyridine (described in the previous step) instead of 5-piperidin-1-yl-1H-pyrrolo[2,3-b]pyridine and 466 mg (2.07 mmol) of N-iodosuccinimide in 5 ml of acetone. 219 mg of the title compound are obtained.

Yield: 46%.
MH+: 343.9.

Step 3: 3-Iodo-5-(2-methylmorpholin-4-yl)-1-tosyl-1H-pyrrolo[2,3-b]pyridine

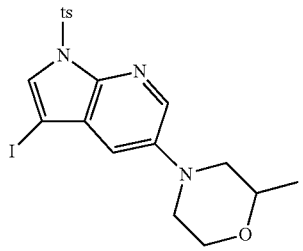

The compound is obtained by the procedure described in example 9 step 3, using 219 mg (0.64 mmol) of 3-iodo-5-(2-methylmorpholin-4-yl)-1H-pyrrolo[2,3-b]pyridine (described in the previous step) instead of 3-iodo-5-piperidin-1-yl-1H-pyrrolo[2,3-b]pyridine, 38 mg (0.96 mmol) of sodium hydride (60% in paraffin oil) and 134 mg (0.70 mmol) of tosyl chloride in 5 ml of anhydrous DMF. 105 mg of the title compound are obtained.

Yield: 33%.

MH+: 497.8.

Step 4: 1-(2-Chlorobenzyl)-4-[5-(2-methylmorpholin-4-yl)-1H-pyrrolo[2,3-b]pyridin-3-yl]-1H-pyridin-2-one

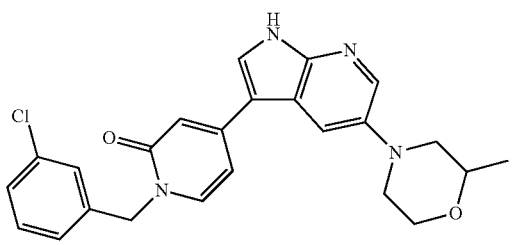 [SMILES: CC1CN(c2cnc3[nH]cc(-c4ccn(Cc5cccc(Cl)c5)c(=O)c4)c3c2)CCO1]

The compound is obtained by the procedure described in example 9 step 4, using 20 mg (0.043 mmol) of 3-iodo-5-(2-methylmorpholin-4-yl)-1-tosyl-1H-pyrrolo[2,3-b]pyridine (described in the previous step) instead of 3-iodo-5-piperidin-1-yl-1-tosyl-1H-pyrrolo[2,3-b]pyridine, 12 mg (0.044 mmol) of 1-(3-chlorobenzyl)-2-oxo-1,2-dihydropyridine-4-boronic acid and 2 mg of PdCl$_2$(PPh$_3$)$_2$. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 3.0 mg of the title compound are obtained.

Yield: 17%.

MH+: 434.9; 436.9.

$^1$H NMR (DMSO-d6, 300 MHz): δ 12.06 (br s, 1H); 8.16 (d, J=2.5 Hz, 1H); 8.09 (s, 1H); 7.80 (d, J=7.0 Hz, 1H); 7.70 (d, J=2.6 Hz, 1H); 7.44-7.28 (m, 4H); 6.76-6.69 (m, 2H); 5.11 (s, 2H); 3.97-3.87 (m, 1H); 3.77-3.65 (m, 2H); 3.60-3.42 (m, 2H); 2.78-2.76 (m, 1H); 2.40-2.36 (m, 1H); 1.17 (d, J=6.2 Hz, 3H).

Example 20: 4-(3-(1-(3-Chlorobenzyl)-2-oxo-1,2-dihydropyridin-4-yl)-1H-pyrrolo[2,3-b]pyridin-5-yl)-N-methylmorpholine-2-carboxamide

Step 1: N-Methyl-4-(1-((2-(trimethylsilyl)ethoxy)methyl)-1H-pyrrolo[2,3-b]pyridin-5-yl)morpholine-2-carboxamide

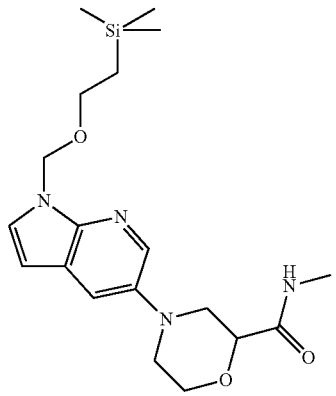 [SMILES: CNC(=O)C1CN(c2cnc3c(ccn3COCC[Si](C)(C)C)c2)CCO1]

The compound is obtained by the procedure described in example 10 step 2, using 452 mg (1.38 mmol) of 5-bromo-1-(2-trimethylsilylethoxymethyl)-1H-pyrrolo[2,3-b]pyridine, 240 mg (1.65 mmol) of N-methylmorpholine-2-carboxamide instead of 4-cyanopiperidine, 24 mg (0.03 mmol) of Pd(dba)$_3$, 48 mg (0.09 mmol) of xantphos and 200 mg (2.47 mmol) of tBuONa. 357 mg of the title compound are obtained. LC/MS shows a purity of 47%. The compound is used in the next step without further purification.

Yield: 66% (HPLC purity: 52%).

MH+: 391.0.

Step 2: N-Methyl-4-(1H-pyrrolo[2,3-b]pyridin-5-yl)morpholine-2-carboxamide

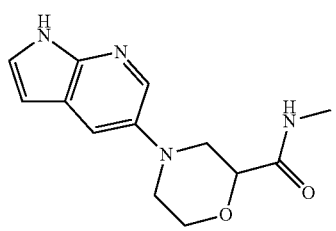 [SMILES: CNC(=O)C1CN(c2cnc3[nH]ccc3c2)CCO1]

The compound is obtained by the procedure described in example 10 step 3, using 357 mg (0.91 mmol) of N-methyl-4-(1-((2-(trimethylsilyl)ethoxy)methyl)-1H-pyrrolo[2,3-b]pyridin-5-yl)morpholine-2-carboxamide (described in the previous step) instead of 5-(4-cyanopiperidin-1-yl)-1-(2-trimethylsilylethoxymethyl)-1H-pyrrolo[2,3-b]pyridine, 92 µl (1.37 mmol) of ethylenediamine, 2.7 ml+1.8 ml (2.7 mmol+1.8 mmol) of TBAF (1M in THF) in 7 ml oh anhydrous THF. 386 mg of the title compound are obtained.

Yield: Quantitative.

MH+: 261.1.

Step 3: 4-(3-Iodo-1H-pyrrolo[2,3-b]pyridin-5-yl)-N-methylmorpholine-2-carboxamide

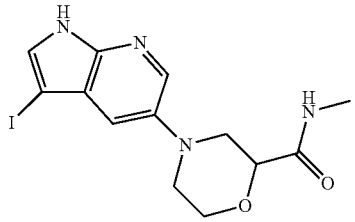 [SMILES: CNC(=O)C1CN(c2cnc3[nH]cc(I)c3c2)CCO1]

The compound is obtained by the procedure described in example 9 step 2, using 386 mg (1.48 mmol) of N-methyl-4-(1H-pyrrolo[2,3-b]pyridin-5-yl)morpholine-2-carboxamide (described in the previous step) instead of 5-piperidin-1-yl-1H-pyrrolo[2,3-b]pyridine and 367 mg (1.63 mmol) of N-iodosuccinimide in 3 ml of acetone. 70 mg of the title compound are obtained.
Yield: 12%.
MH+: 386.9.

Step 4: 4-(3-Iodo-1-tosyl-1H-pyrrolo[2,3-b]pyridin-5-yl)-N-methylmorpholine-2-carboxamide

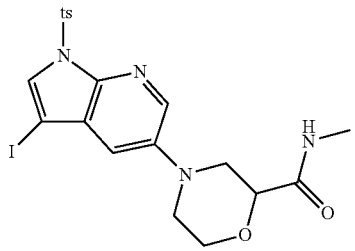

The compound is obtained by the procedure described in example 9 step 3, using 70 mg (0.18 mmol) of 4-(3-iodo-1H-pyrrolo[2,3-b]pyridin-5-yl)-N-methylmorpholine-2-carboxamide (described in the previous step) instead of 3-iodo-5-piperidin-1-yl-1H-pyrrolo[2,3-b]pyridine, 11 mg (0.27 mmol) of sodium hydride (60% in paraffin oil) and 38 mg (0.20 mmol) of tosyl chloride in 5 ml of anhydrous DMF. 34 mg of the title compound are obtained.
Yield: 35%.
MH+: 540.8.

Step 5: 4-(3-(1-(3-Chlorobenzyl)-2-oxo-1,2-dihydropyridin-4-yl)-1H-pyrrolo[2,3-b]pyridin-5-yl)-N-methylmorpholine-2-carboxamide

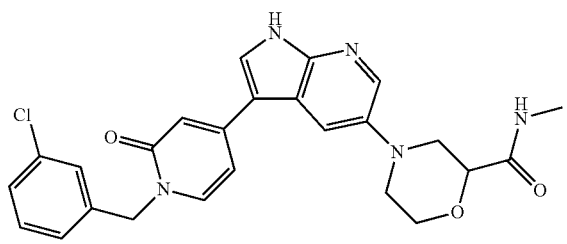 [SMILES: CNC(=O)C1CN(c2cnc3[nH]cc(-c4ccn(Cc5cccc(Cl)c5)c(=O)c4)c3c2)CCO1]

The compound is obtained by the procedure described in example 9 step 4, using mg (0.031 mmol) of 4-(3-iodo-1-tosyl-1H-pyrrolo[2,3-b]pyridin-5-yl)-N-methylmorpholine-2-carboxamide (described in the previous step) instead of 3-iodo-5-piperidin-1-yl-1-tosyl-1H-pyrrolo[2,3-b]pyridine, 11 mg (0.042 mmol) of 1-(3-chlorobenzyl)-2-oxo-1,2-dihydropyridine-4-boronic acid and 2 mg of PdCl$_2$(PPh$_3$)$_2$. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 4.8 mg of the title compound are obtained.
Yield: 32%.
MH+: 478.0; 479.9.
$^1$H NMR (DMSO-d6, 300 MHz): δ 12.08 (br s, 1H); 8.17 (d, J=1.9 Hz, 1H); 8.10 (s, 1H); 7.89-7.81 (m, 1H); 7.80 (d, J=7.6 Hz, 1H); 7.74 (d, J=2.1 Hz, 1H); 7.43-7.27 (m, 4H); 6.77-6.69 (m, 2H); 5.11 (s, 2H); 4.18-3.99 (m, 2H); 3.86-3.74 (m, 1H); 3.71-3.61 (m, 1H); 2.78-2.76 (m, 1H); 2.90-2.68 (m, 3H); 2.64 (d, J=4.6 Hz, 3H).

Example 21: Tert-butyl 4-(3-(1-(3-chlorobenzyl)-2-oxo-1,2-dihydropyridin-4-yl)-1H-pyrrolo[2,3-b]pyridin-5-yl)piperazine-1-carboxylate Step 1: Tert-butyl 4-(1H-pyrrolo[2,3-b]pyridin-5-yl)piperazine-1-carboxylate

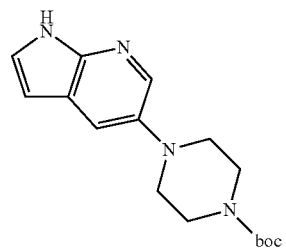

The compound is obtained by the procedure described in example 9 step 1, using 500 mg (2.53 mmol) of 5-bromo-1H-pyrrolo[2,3-b]pyridine, 566 mg (3.05 mmol) of tert-butyl piperazine-1-carboxylate instead of piperidine, 12 mg (0.025 mmol) of RuPhos, 20 mg (0.025 mmol) of RuPhos Pd G2 and 6 ml (6 mmol) of LiHMDS (1M in THF). 651 mg of the title compound are obtained.
Yield: 85%.
MH+: 303.0.
$^1$H NMR (DMSO-d6, 300 MHz): δ 11.39 (br s, 1H); 8.06 (d, J=2.6 Hz, 1H); 7.51 (d, J=2.5 Hz, 1H); 7.37 (t, J=2.9 Hz, 1H); 6.32 (dd, J=1.9 and 3.3 Hz, 1H); 3.54-3.44 (m, 4H); 3.05-2.96 (m, 4H); 1.43 (s, 9H).

Step 2: Tert-butyl 4-(3-iodo-1H-pyrrolo[2,3-b]pyridin-5-yl)piperazine-1-carboxylate

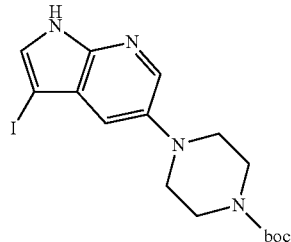

The compound is obtained by the procedure described in example 9 step 2, using 650 mg (2.15 mmol) of tert-butyl 4-(1H-pyrrolo[2,3-b]pyridin-5-yl)piperazine-1-carboxylate (described in the previous step) instead of 5-piperidin-1-yl-1H-pyrrolo[2,3-b]pyridine and 725 mg (3.22 mmol) of N-iodosuccinimide in 12 ml of acetone. 750 mg of the title compound are obtained.

Yield: 82%.

MH+: 428.7.

$^1$H NMR (DMSO-d6, 300 MHz): δ 11.88 (br s, 1H); 8.12 (d, J=2.5 Hz, 1H); 7.61 (d, J=2.6 Hz, 1H); 7.13 (d, J=2.4 Hz, 1H); 3.56-3.44 (m, 4H); 3.11-3.02 (m, 4H); 1.43 (s, 9H).

Step 3: Tert-butyl 4-(3-iodo-1-tosyl-1H-pyrrolo[2,3-b]pyridin-5-yl)piperazine-1-carboxylate

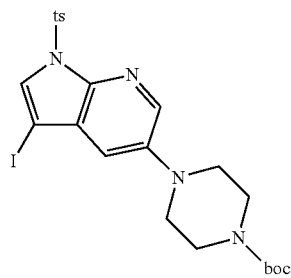

The compound is obtained by the procedure described in example 9 step 3, using 750 mg (1.75 mmol) of tert-butyl 4-(3-iodo-1H-pyrrolo[2,3-b]pyridin-5-yl)piperazine-1-carboxylate (described in the previous step) instead of 3-iodo-5-piperidin-1-yl-1H-pyrrolo[2,3-b]pyridine, 105 mg (2.63 mmol) of sodium hydride (60% in paraffin oil) and 366 mg (1.93 mmol) of tosyl chloride in 15 ml of anhydrous THF instead of DMF. 275 mg of the title compound are obtained.

Yield: 27%.

MH+: 582.7.

$^1$H NMR (DMSO-d6, 300 MHz): δ 8.22 (d, J=2.6 Hz, 1H); 8.03 (s, 1H); 7.95 (d, J=8.4 Hz, 1H); 7.41 (d, J=8.1 Hz, 1H); 7.61 (d, J=2.6 Hz, 1H); 7.14 (d, J=2.6 Hz, 1H); 3.52-3.42 (m, 4H); 3.20-3.10 (m, 4H); 2.34 (s, 3H); 1.41 (s, 9H).

Step 4: Tert-butyl 4-(3-(1-(3-chlorobenzyl)-2-oxo-1,2-dihydropyridin-4-yl)-1-tosyl-1H-pyrrolo[2,3-b]pyridin-5-yl)piperazine-1-carboxylate

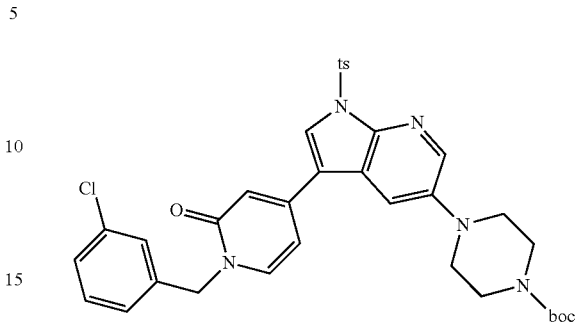

160 mg (0.28 mmol) of tert-butyl 4-(3-iodo-1-tosyl-1H-pyrrolo[2,3-b]pyridin-5-yl)piperazine-1-carboxylate (described in previous step) and 94 mg (0.36 mmol) of 1-(3-chlorobenzyl)-2-oxo-1,2-dihydropyridine-4-boronic acid (described in example 1 step 3) are dissolved in a mixture of 3 ml of acetonitrile and 1.5 ml of an aqueous 2M solution of Na$_2$CO$_3$. Argon is bubbled through the solution for 10 minutes, then 16 mg of PdCl$_2$(PPh$_3$)$_2$ are added under argon. Argon is bubbled for another 10 minutes and the reaction is stirred at 70° C. for 1 hour. After cooling, the solution is diluted with water, extracted 3 times with ethyl acetate, dried over sodium sulfate, filtered and evaporated under reduced pressure. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 70 mg of the title compound are obtained.

Yield: 37%.

MH+: 673.9; 676.0.

Step 5: Tert-butyl 4-(3-(1-(3-chlorobenzyl)-2-oxo-1,2-dihydropyridin-4-yl)-1H-pyrrolo[2,3-b]pyridin-5-yl)piperazine-1-carboxylate

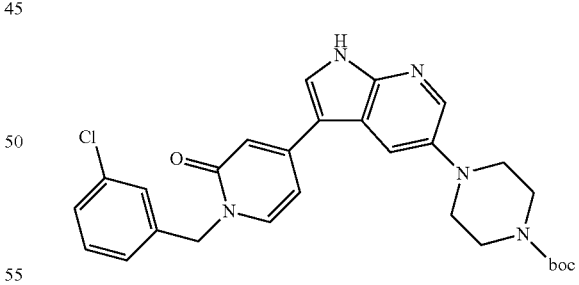

5 mg (0.007 mmol) of tert-butyl 4-(3-(1-(3-chlorobenzyl)-2-oxo-1,2-dihydropyridin-4-yl)-1-tosyl-1H-pyrrolo[2,3-b]pyridin-5-yl)piperazine-1-carboxylate (described in previous step) are dissolved in a mixture of 3 ml of acetonitrile and 1.5 ml of an aqueous 2M solution of Na$_2$CO$_3$. The reaction mixture is transferred in a microwave sealed tube and the reaction is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 30 g C18 column with a water/acetonitrile mixture as eluent. 2.7 mg of the title compound are obtained.
Yield: 63%.
MH+: 519.9; 522.0.

Example 22: 1-(3-Chlorobenzyl)-4-(5-(piperazin-1-yl)-1H-pyrrolo[2,3-b]pyridin-3-yl)pyridin-2(1H)-one Step 1: 1-(3-Chlorobenzyl)-4-(5-(piperazin-1-yl)-1-tosyl-1H-pyrrolo[2,3-b]pyridin-3-yl)pyridin-2(1H)-one

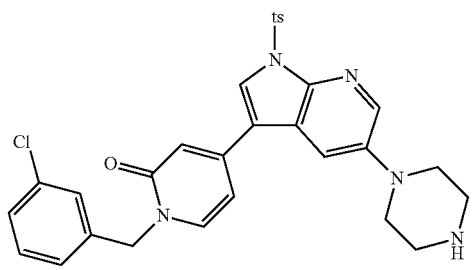

68 mg (0.10 mmol) of tert-butyl 4-(3-(1-(3-chlorobenzyl)-2-oxo-1,2-dihydropyridin-4-yl)-1-tosyl-1H-pyrrolo[2,3-b]pyridin-5-yl)piperazine-1-carboxylate (described in example 21 step 4) are dissolved in a mixture of 1 ml of trifluoroacetic acid and 9 ml of dichloromethane and the reaction is stirred at ambient temperature for 1 hour. The mixture is poured into an aqueous solution of saturated NaHCO$_3$, extracted 3 times with ethyl acetate, dried over sodium sulfate, filtered and evaporated under reduced pressure. 55 mg of a yellow solid are obtained. Crude product is used without further purification in the next step.
Yield: 95%.
MH+: 573.9; 575.9.

Step 2: 1-(3-Chlorobenzyl)-4-(5-(piperazin-1-yl)-1H-pyrrolo[2,3-b]pyridin-3-yl)pyridin-2(1H)-one

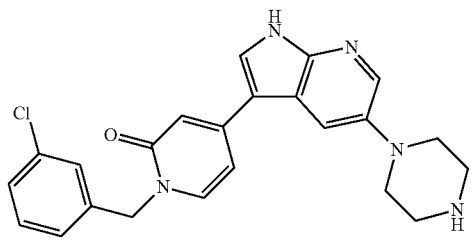 [SMILES: O=c1cc(-c2c[nH]c3ncc(N4CCNCC4)cc23)ccn1Cc1cccc(Cl)c1]

33 mg (0.057 mmol) of 1-(3-chlorobenzyl)-4-(5-(piperazin-1-yl)-1-tosyl-1H-pyrrolo[2,3-b]pyridin-3-yl)pyridin-2(1H)-one (described in previous step) are dissolved in a mixture of 3 ml of acetonitrile and 1.5 ml of an aqueous 2M solution of Na$_2$CO$_3$. The reaction mixture is transferred in a microwave sealed tube and the reaction is heated at 150° C. under microwave irradiation for 15 minutes. After cooling, the solution is diluted with water, extracted 3 times with ethyl acetate, dried over sodium sulfate, filtered and evaporated under reduced pressure. 34 mg of crude product are obtained.
Yield: Quantitative.
MH+: 420.0; 421.9.

Example 23: 4-(3-(1-(3-Chlorobenzyl)-2-oxo-1,2-dihydropyridin-4-yl)-1H-pyrrolo[2,3-b]pyridin-5-yl)-N-ethylpiperazine-1-carboxamide

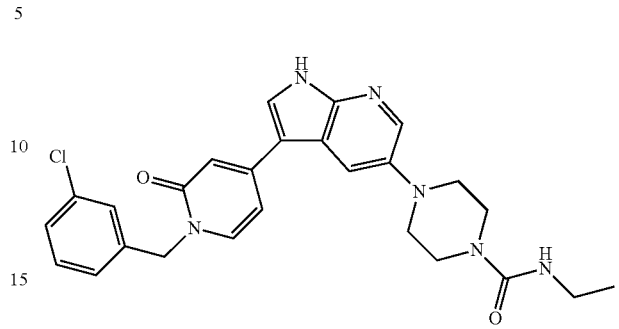

8 mg (0.019 mmol) of 1-(3-chlorobenzyl)-4-(5-(piperazin-1-yl)-1H-pyrrolo[2,3-b]pyridin-3-yl)pyridin-2(1H)-one (described in example 22 step 2) are dissolved in 1 ml of anhydrous THF. Then 1.7 µl (0.021 mmol) of ethyl isocyanate are added under argon, followed by 4 µl (0.023 mmol) of DIEA and the reaction is stirred at ambient temperature for 1 hour. The mixture is poured into an aqueous solution of saturated NaHCO$_3$, extracted 3 times with ethyl acetate, dried over sodium sulfate, filtered and evaporated under reduced pressure. Crude product is purified by flash chromatography on a 30 g C18 column with a water/acetonitrile mixture as eluent. 2.4 mg of the title compound are obtained.
Yield: 26%.
MH+: 491.0; 493.0.
$^1$H NMR (DMSO-d6, 300 MHz): δ 12.06 (br s, 1H); 8.17 (d, J=2.3 Hz, 1H); 8.09 (s, 1H); 7.80 (d, J=7.8 Hz, 1H); 7.75 (d, J=2.3 Hz, 1H); 7.44-7.27 (m, 4H); 7.77-7.70 (m, 2H); 6.57 (br t, 1H); 5.11 (s, 2H); 3.54-3.41 (m, 4H); 3.13-2.99 (m, 6H); 1.02 (t, J=7.1 Hz, 3H).

Example 24: 4-(3-(1-(3-Chlorobenzyl)-2-oxo-1,2-dihydropyridin-4-yl)-1H-pyrrolo[2,3-b]pyridin-5-yl)-N-(2-hydroxyethyl)piperazine-1-carboxamide

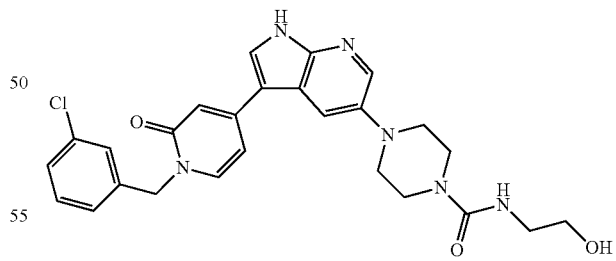

To a solution of 13 mg (0.031 mmol) of 1-(3-chlorobenzyl)-4-(5-(piperazin-1-yl)-1H-pyrrolo[2,3-b]pyridin-3-yl)pyridin-2(1H)-one (described in example 22 step 2), 5.5 mg (0.034 mmol) of 1,1'-carbonyldiimidazole, in 1 ml of anhydrous dichloromethane, are added 6.5 µl (0.037 mmol) of DIEA. The solution is stirred at ambient temperature for 30 minutes. Then 2 µl (0.034 mmol) of ethanolamine are added and the reaction is stirred overnight. The mixture is poured into an aqueous solution of saturated NaHCO$_3$, extracted 3

Example 25: 1-Benzyl-4-(5-morpholino-1H-pyrrolo[2,3-b]pyridin-3-yl)pyridin-2(1H)-one Step 1:
1-Benzyl-2-oxo-1,2-dihydropyridin-4-ylboronic Acid

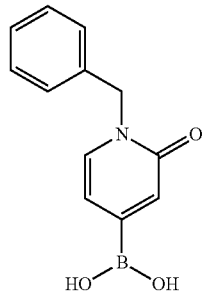 [SMILES: O=c1cc(B(O)O)ccn1Cc1ccccc1]

To a solution of 30 mg (0.14 mmol) of 4-(4,4,5,5-tetramethyl-[1,3,2]dioxaborolan-2-yl)-1H-pyridin-2-one and 66 mg (0.20 mmol) of cesium carbonate in 1 ml of anhydrous DMF, are added 18 µl (0.15 mmol) of benzyl bromide at ambient temperature. The reaction is stirred overnight under argon. Reaction mixture is then diluted with ethyl acetate, and the precipitate is filtered and rinsed with a small amount of ethyl acetate. The filtrate is concentrated under vacuum and directly purified by flash chromatography with a 30 g C18 column and a water/acetonitrile mixture as eluent. 20 mg of the title compound are obtained.
Yield: 65%.
MH+: 230.1.

Step 2: 1-Benzyl-4-(5-morpholino-1H-pyrrolo[2,3-b]pyridin-3-yl)pyridin-2(1H)-one

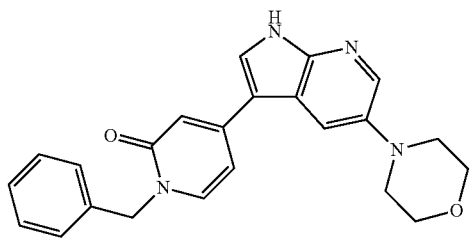 [SMILES: O=c1cc(-c2c[nH]c3ncc(N4CCOCC4)cc23)ccn1Cc1ccccc1]

20 mg (0.041 mmol) of 3-iodo-5-morpholin-1-yl-1-tosyl-1H-pyrrolo[2,3-b]pyridine (described in example 17 step 3) and 12 mg (0.052 mmol) of 1-benzyl-2-oxo-1,2-dihydropyridin-4-ylboronic acid (described in the previous step) are dissolved in a mixture of 3 ml of acetonitrile and 1.5 ml of an aqueous 2M solution of $Na_2CO_3$. Argon is bubbled through the solution for 10 minutes, then 2 mg of $PdCl_2(PPh_3)_2$ are added under argon. Argon is bubbled for another 10 minutes and the reaction is stirred at 70° C. for 1 hour. The reaction mixture is transferred in a microwave sealed tube and the reaction is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 10 g silica gel column with an ethyl acetate/methanol mixture as eluent. The obtained product is purified another time by flash chromatography on a 30 g C18 column with a water/acetonitrile mixture as eluent. 1.5 mg of the title compound is obtained.
Yield: 10%.
MH+: 387.1.
$^1$H NMR (DMSO-d6, 300 MHz): δ 12.04 (br s, 1H); 8.17 (d, J=2.5 Hz, 1H); 8.07 (s, 1H); 7.75 (d, J=7.8 Hz, 1H); 7.70 (d, J=2.5 Hz, 1H); 7.39-7.24 (m, 5H); 6.74-6.66 (m, 2H); 5.11 (s, 2H); 3.83-3.74 (m, 4H); 3.20-3.09 (m, 4H).

Example 26: 1-(4-Bromobenzyl)-4-(5-morpholino-1H-pyrrolo[2,3-b]pyridin-3-yl)pyridin-2(1H)-one Step 1: 1-(4-Bromobenzyl)-2-oxo-1,2-dihydropyridin-4-ylboronic Acid

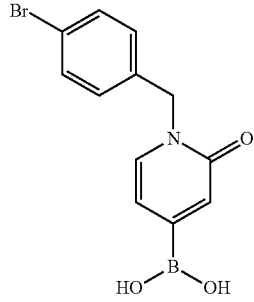

The compound is obtained by the procedure described in example 25 step 1, using 37 mg (0.15 mmol) of 4-bromobenzyl bromide instead of benzyl bromide. 8 mg of the title compound are obtained.
Yield: 20%.
MH+: 307.9; 309.9.

Step 2: 1-(4-Bromobenzyl)-4-(5-morpholino-1H-pyrrolo[2,3-b]pyridin-3-yl)pyridin-2(1H)-one

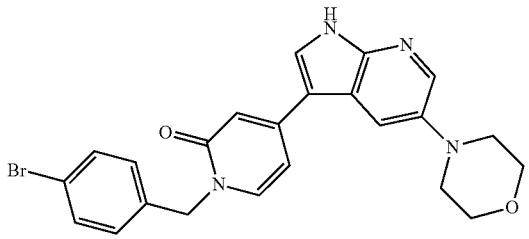 [SMILES: O=c1cc(-c2c[nH]c3ncc(N4CCOCC4)cc23)ccn1Cc1ccc(Br)cc1]

The compound is obtained by the procedure described in example 25 step 2, using 12 mg (0.025 mmol) of 3-iodo-5-morpholin-1-yl-1-tosyl-1H-pyrrolo[2,3-b]pyridine (described in example 17 step 3) and 8 mg (0.026 mmol) of 1-(4-bromobenzyl)-2-oxo-1,2-dihydropyridin-4-ylboronic acid (described in the previous step) instead of 1-benzyl-2-oxo-1,2-dihydropyridin-4-ylboronic acid. 1.9 mg of the title compound is obtained.

Yield: 17%.

MH+: 464.9; 466.9.

¹H NMR (DMSO-d6, 300 MHz): δ 12.05 (br s, 1H); 8.17 (d, J=2.5 Hz, 1H); 8.08 (s, 1H); 7.76 (d, J=7.1 Hz, 1H); 7.70 (d, J=2.5 Hz, 1H); 7.56 (d, J=8.4 Hz, 2H); 7.29 (d, J=8.4 Hz, 2H); 6.74-6.68 (m, 2H); 5.08 (s, 2H); 3.82-3.73 (m, 4H); 3.18-3.10 (m, 4H).

Example 27: 1-(3-Iodobenzyl)-4-(5-morpholino-1H-pyrrolo[2,3-b]pyridin-3-yl)pyridin-2(1H)-one Step 1: 1-(3-Iodobenzyl)-2-oxo-1,2-dihydropyridin-4-ylboronic Acid

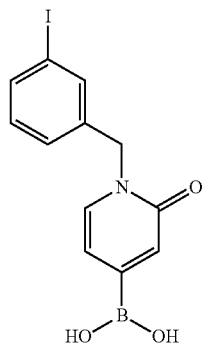

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 74 mg (0.25 mmol) of 3-iodobenzyl bromide instead of benzyl bromide. 28 mg of the title compound are obtained.

Yield: 35%.

MH+: 355.8.

Step 2: 1-(3-Iodobenzyl)-4-(5-morpholino-1H-pyrrolo[2,3-b]pyridin-3-yl)pyridin-2(1H)-one

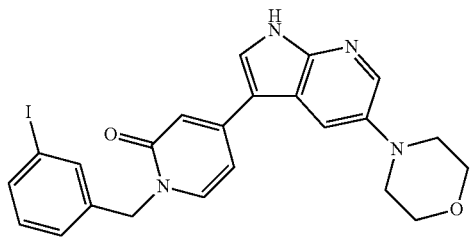 [SMILES: O=c1cc(-c2c[nH]c3ncc(N4CCOCC4)cc23)ccn1Cc1cccc(I)c1]

The compound is obtained by the procedure described in example 25 step 2, using 18 mg (0.047 mmol) of 1-(3-iodobenzyl)-2-oxo-1,2-dihydropyridin-4-ylboronic acid (described in the previous step) instead of 1-benzyl-2-oxo-1,2-dihydropyridin-4-ylboronic acid. 4.0 mg of the title compound are obtained.

Yield: 19%.

MH+: 512.9.

¹H NMR (DMSO-d6, 300 MHz): δ 12.05 (br s, 1H); 8.17 (d, J=2.5 Hz, 1H); 8.09 (s, 1H); 7.81-7.63 (m, 4H); 7.36 (d, J=7.5 Hz, 1H); 7.16 (d, J=7.8 Hz, 1H); 6.75-6.68 (m, 2H); 5.06 (s, 2H); 3.84-3.72 (m, 4H); 3.19-3.06 (m, 4H).

Example 28: 4-(5-Morpholino-1H-pyrrolo[2,3-b]pyridin-3-yl)-1-(3-(trifluoromethyl)benzyl)pyridin-2(1H)-one Step 1: 2-Oxo-1-(3-(trifluoromethyl)benzyl)-1,2-dihydropyridin-4-ylboronic Acid

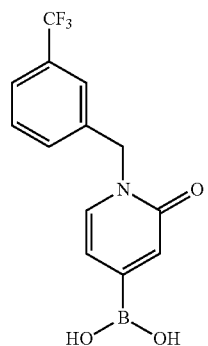

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 38 µl (0.25 mmol) of 3-(trifluoromethyl)benzyl bromide instead of benzyl bromide. 27 mg of the title compound are obtained.

Yield: 40%.

MH+: 298.0.

Step 2: 4-(5-Morpholino-1H-pyrrolo[2,3-b]pyridin-3-yl)-1-(3-(trifluoromethyl)benzyl)pyridin-2(1H)-one

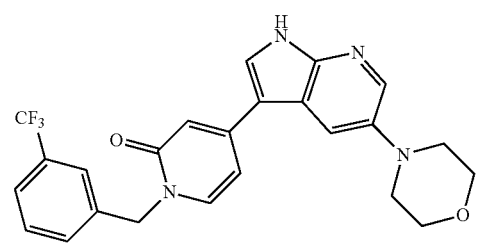 [SMILES: O=c1cc(-c2c[nH]c3ncc(N4CCOCC4)cc23)ccn1Cc1cccc(C(F)(F)F)c1]

The compound is obtained by the procedure described in example 25 step 2, using 14 mg (0.047 mmol) of 2-oxo-1-(3-(trifluoromethyl)benzyl)-1,2-dihydropyridin-4-ylboronic acid (described in the previous step) instead of 1-benzyl-2-oxo-1,2-dihydropyridin-4-ylboronic acid. 4.0 mg of the title compound are obtained.

Yield: 21%.

MH+: 454.9.

¹H NMR (DMSO-d6, 300 MHz): δ 12.07 (br s, 1H); 8.16 (d, J=2.6 Hz, 1H); 8.10 (s, 1H); 7.85 (d, J=7.1 Hz, 1H); 7.75-7.51 (m, 5H); 6.77-6.70 (m, 2H); 5.20 (s, 2H); 3.83-3.72 (m, 4H); 3.18-3.09 (m, 4H).

Example 29: 1-(3-Methoxybenzyl)-4-(5-morpholino-1H-pyrrolo[2,3-b]pyridin-3-yl)pyridin-2(1H)-one

Step 1: 1-(3-Methoxybenzyl)-2-oxo-1,2-dihydropyridin-4-ylboronic Acid

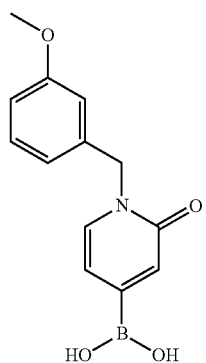 [SMILES: COc1cccc(Cn2ccc(B(O)O)cc2=O)c1]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 34 µl (0.25 mmol) of 3-methoxybenzyl bromide instead of benzyl bromide. 78 mg of the title compound are obtained.

Yield: Quantitative.
MH+: 260.1.

Step 2: 1-(3-Methoxybenzyl)-4-(5-morpholino-1H-pyrrolo[2,3-b]pyridin-3-yl)pyridin-2(1H)-one

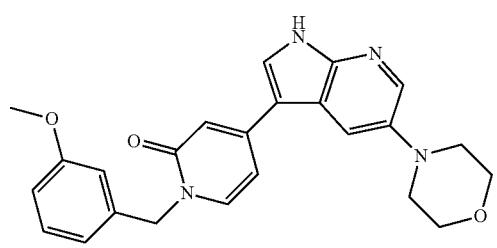 [SMILES: COc1cccc(Cn2ccc(-c3c[nH]c4ncc(N5CCOCC5)cc34)cc2=O)c1]

The compound is obtained by the procedure described in example 25 step 2, using 15 mg (0.046 mmol) of 1-(3-methoxybenzyl)-2-oxo-1,2-dihydropyridin-4-ylboronic acid (described in the previous step) instead of 1-benzyl-2-oxo-1,2-dihydropyridin-4-ylboronic acid. 7.7 mg of the title compound are obtained.

Yield: 45%.
MH+: 417.0.
$^1$H NMR (DMSO-d6, 300 MHz): δ 12.05 (br s, 1H); 8.17 (d, J=2.3 Hz, 1H); 8.08 (s, 1H); 7.77-7.67 (m, 2H); 7.27 (t, J=8.0 Hz, 1H); 6.94-6.82 (m, 3H); 6.75-6.67 (m, 2H); 5.07 (s, 2H); 3.83-3.73 (m, 4H); 3.73 (s, 3H); 3.20-3.08 (m, 4H).

Example 30: 1-(4-Chloro-3-fluorobenzyl)-4-(5-morpholino-1H-pyrrolo[2,3-b]pyridin-3-yl)pyridin-2(1H)-one

Step 1: 1-(4-Chloro-3-fluorobenzyl)-2-oxo-1,2-dihydropyridin-4-ylboronic Acid

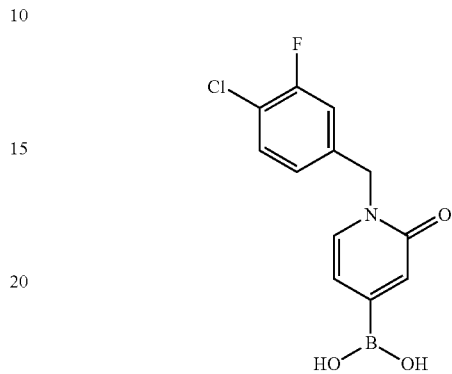

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 33 µl (0.25 mmol) of 4-chloro-3-fluorobenzyl bromide instead of benzyl bromide. 48 mg of the title compound are obtained.

Yield: 76%.
MH+: 282.0; 284.0.

Step 2: 1-(4-Chloro-3-fluorobenzyl)-4-(5-morpholino-1H-pyrrolo[2,3-b]pyridin-3-yl)pyridin-2(1H)-one

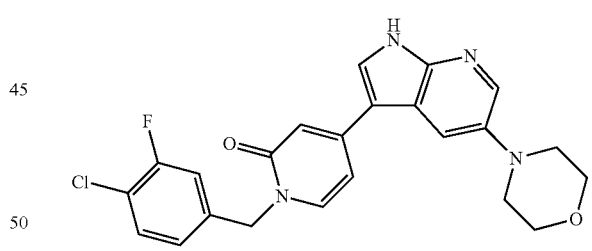

The compound is obtained by the procedure described in example 25 step 2, using 13 mg (0.046 mmol) of 1-(4-chloro-3-fluorobenzyl)-2-oxo-1,2-dihydropyridin-4-ylboronic acid (described in the previous step) instead of 1-benzyl-2-oxo-1,2-dihydropyridin-4-ylboronic acid. 4.1 mg of the title compound are obtained.

Yield: 22%.
MH+: 438.9; 440.9.
$^1$H NMR (DMSO-d6, 300 MHz): δ 12.06 (br s, 1H); 8.17 (d, J=2.4 Hz, 1H); 8.09 (s, 1H); 7.79 (d, J=7.2 Hz, 1H); 7.70 (d, J=2.3 Hz, 1H); 7.58 (t, J=8.0 Hz, 1H); 7.40 (dd, J=1.4 and 10.2 Hz, 1H); 7.21 (dd, J=1.1 and 8.0 Hz, 1H); 6.76-6.67 (m, 2H); 5.10 (s, 2H); 3.84-3.74 (m, 4H); 3.20-3.09 (m, 4H).

Example 31: 1-(3-Chloro-4-fluorobenzyl)-4-(5-morpholino-1H-pyrrolo[2,3-b]pyridin-3-yl)pyridin-2(1H)-one Step 1: 1-(3-Chloro-4-fluorobenzyl)-2-oxo-1,2-dihydropyridin-4-ylboronic Acid

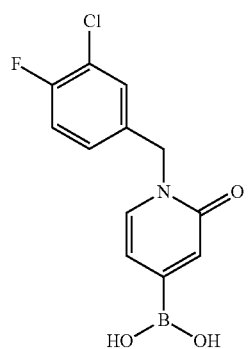

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 34 µl (0.25 mmol) of 3-chloro-4-fluorobenzyl bromide instead of benzyl bromide. 44 mg of the title compound are obtained.

Yield: 69%.
MH+: 282.0; 284.0.

Step 2: 1-(3-Chloro-4-fluorobenzyl)-4-(5-morpholino-1H-pyrrolo[2,3-b]pyridin-3-yl)pyridin-2(1H)-one

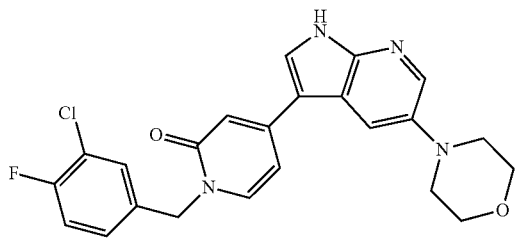 [SMILES: O=c1cc(-c2c[nH]c3ncc(N4CCOCC4)cc23)ccn1Cc1ccc(F)c(Cl)c1]

The compound is obtained by the procedure described in example 25 step 2, using 13 mg (0.046 mmol) of 1-(3-chloro-4-fluorobenzyl)-2-oxo-1,2-dihydropyridin-4-ylboronic acid (described in the previous step) instead of 1-benzyl-2-oxo-1,2-dihydropyridin-4-ylboronic acid. 4.0 mg of the title compound are obtained.

Yield: 22%.
MH+: 438.9; 440.9.
$^1$H NMR (DMSO-d6, 300 MHz): δ 12.05 (br s, 1H); 8.17 (d, J=2.1 Hz, 1H); 8.09 (s, 1H); 7.81 (d, J=6.1 Hz, 1H); 7.70 (d, J=2.2 Hz, 1H); 7.61 (dd, J=1.9 and 7.9 Hz, 1H); 7.44-7.36 (m, 2H); 6.76-6.69 (m, 2H); 5.08 (s, 2H); 3.84-3.74 (m, 4H); 3.19-3.10 (m, 4H).

Example 32: 1-(3-Chloro-2-fluorobenzyl)-4-(5-morpholino-1H-pyrrolo[2,3-b]pyridin-3-yl)pyridin-2(1H)-one Step 1: 1-(3-Chloro-2-fluorobenzyl)-2-oxo-1,2-dihydropyridin-4-ylboronic Acid

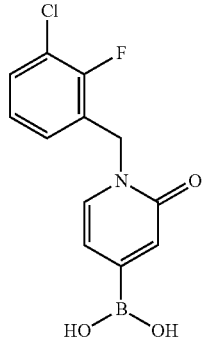

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 34 µl (0.25 mmol) of 3-chloro-2-fluorobenzyl bromide instead of benzyl bromide. 39 mg of the title compound are obtained.

Yield: 61%.
MH+: 282.0; 284.0.

Step 2: 1-(3-Chloro-2-fluorobenzyl)-4-(5-morpholino-1H-pyrrolo[2,3-b]pyridin-3-yl)pyridin-2(1H)-one

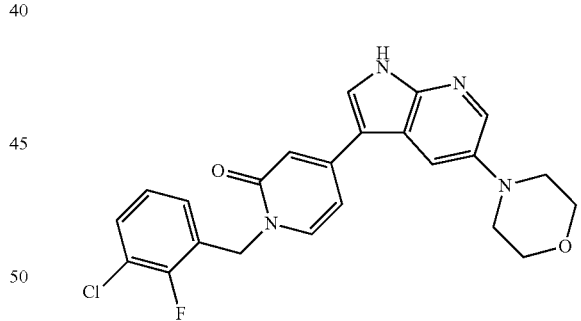

The compound is obtained by the procedure described in example 25 step 2, using 19 mg (0.068 mmol) of 1-(3-chloro-2-fluorobenzyl)-2-oxo-1,2-dihydropyridin-4-ylboronic acid (described in the previous step) instead of 1-benzyl-2-oxo-1,2-dihydropyridin-4-ylboronic acid. 12.7 mg of the title compound are obtained.

Yield: 71%.
MH+: 439.0; 441.0.
$^1$H NMR (DMSO-d6, 300 MHz): δ 12.07 (br s, 1H); 8.17 (d, J=2.4 Hz, 1H); 8.10 (s, 1H); 7.74 (d, J=7.2 Hz, 1H); 7.71 (d, J=2.4 Hz, 1H); 7.54 (t, J=5.9 Hz, 1H); 7.26-7.10 (m, 2H); 6.76 (dd, J=1.8 and 9.0 Hz, 1H); 6.71 (s, 1H); 5.18 (s, 2H); 3.83-3.72 (m, 4H); 3.20-3.09 (m, 4H).

Example 33: 1-(3,4-Dichlorobenzyl)-4-(5-morpholino-1H-pyrrolo[2,3-b]pyridin-3-yl)pyridin-2(1H)-one

Step 1: 1-(3,4-Dichlorobenzyl)-2-oxo-1,2-dihydropyridin-4-ylboronic Acid

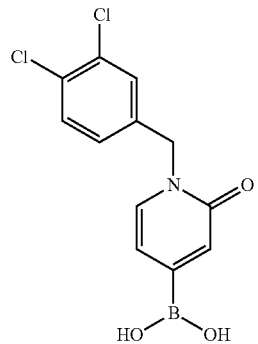 [SMILES: O=c1cc(B(O)O)ccn1Cc1ccc(Cl)c(Cl)c1]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 36 µl (0.25 mmol) of 3,4-dichlorobenzyl bromide instead of benzyl bromide. 22 mg of the title compound are obtained.

Yield: 33%.

MH+: 297.9; 299.9; 301.9.

Step 2: 1-(3,4-Dichlorobenzyl)-4-(5-morpholino-1H-pyrrolo[2,3-b]pyridin-3-yl)pyridin-2(1H)-one

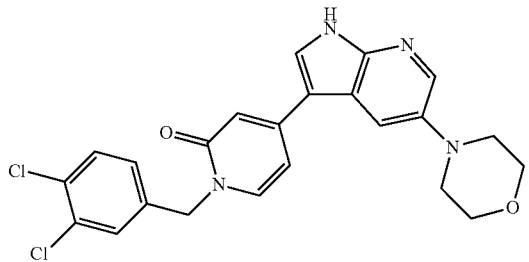

The compound is obtained by the procedure described in example 25 step 2, using 15 mg (0.050 mmol) of 1-(3,4-dichlorobenzyl)-2-oxo-1,2-dihydropyridin-4-ylboronic acid (described in the previous step) instead of 1-benzyl-2-oxo-1,2-dihydropyridin-4-ylboronic acid. 5.2 mg of the title compound are obtained.

Yield: 27%.

MH+: 454.9; 456.9; 458.9.

$^1$H NMR (DMSO-d6, 300 MHz): δ 12.06 (br s, 1H); 8.17 (d, J=2.4 Hz, 1H); 8.10 (s, 1H); 7.81 (d, J=7.0 Hz, 1H); 7.71 (d, J=2.3 Hz, 1H); 7.66-7.60 (m, 2H); 7.33 (dd, J=1.8 and 8.4 Hz, 1H); 6.77-6.69 (m, 2H); 5.10 (s, 2H); 3.83-3.72 (m, 4H); 3.21-3.10 (m, 4H).

Example 34: 1-(2,4-Dichlorobenzyl)-4-(5-morpholino-1H-pyrrolo[2,3-b]pyridin-3-yl)pyridin-2(1H)-one

Step 1: 1-(2,4-Dichlorobenzyl)-2-oxo-1,2-dihydropyridin-4-ylboronic Acid

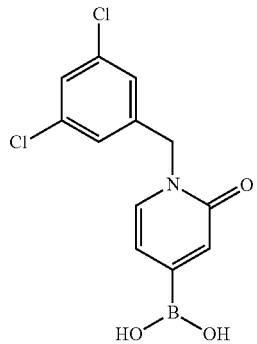 [SMILES: O=c1cc(B(O)O)ccn1Cc1cc(Cl)cc(Cl)c1]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 48 mg (0.25 mmol) of 2,4-dichlorobenzyl chloride instead of benzyl bromide. 12 mg of the title compound are obtained.

Yield: 17%.

MH+: 297.9; 299.9; 301.9.

Step 2: 1-(2,4-Dichlorobenzyl)-4-(5-morpholino-1H-pyrrolo[2,3-b]pyridin-3-yl)pyridin-2(1H)-one

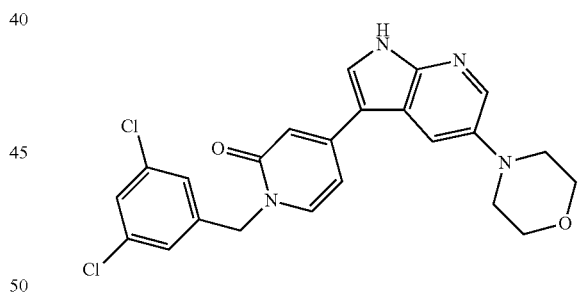

The compound is obtained by the procedure described in example 25 step 2, using 15 mg (0.031 mmol) of 3-iodo-5-morpholin-1-yl-1-tosyl-1H-pyrrolo[2,3-b]pyridine (described in example 17 step 3) and 11 mg (0.037 mmol) of 1-(2,4-dichlorobenzyl)-2-oxo-1,2-dihydropyridin-4-ylboronic acid (described in the previous step) instead of 1-benzyl-2-oxo-1,2-dihydropyridin-4-ylboronic acid. 3.4 mg of the title compound are obtained.

Yield: 24%.

MH+: 454.9; 456.9; 458.9.

$^1$H NMR (DMSO-d6, 300 MHz): δ 12.07 (br s, 1H); 8.17 (d, J=2.3 Hz, 1H); 8.11 (s, 1H); 7.82 (d, J=7.3 Hz, 1H); 7.72 (d, J=2.3 Hz, 1H); 7.64-7.52 (m, 2H); 7.41 (d, J=1.4 Hz, 2H); 6.79-6.69 (m, 2H); 5.10 (s, 2H); 3.86-3.73 (m, 4H); 3.20-3.09 (m, 4H).

Example 35: 1-(5-Chloro-2-hydroxybenzyl)-4-(5-morpholino-1H-pyrrolo[2,3-b]pyridin-3-yl)pyridin-2(1H)-one Step 1: 4-Chloro-2-(hydroxymethyl)phenol

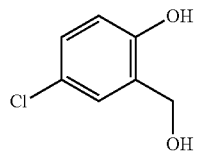

200 mg (1.07 mmol) of methyl 5-chloro-2-hydroxybenzoate are added slowly to 4.3 ml (4.3 mmol) of a solution of BH$_3$ (1M in THF) at 0° C. The solution is stirred at 0° C. for 30 minutes under argon. LC/MS shows complete conversion of the substrate. Then pieces of ice are slowly added until the end of gas evolution. NaHCO3 in powder is added until pH 8-9. The solution is then diluted with water, extracted 3 times with ethyl acetate, dried over sodium sulfate, filtered and evaporated under reduced pressure. 158 mg of a white solid are obtained. Crude product is used in the next step without purification.
Yield: 93%.

Step 2: 2-(Bromomethyl)-4-chlorophenol

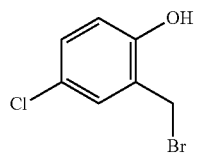

158 mg (0.84 mmol) of 4-chloro-2-(hydroxymethyl)phenol (described in the previous step) and 119 µl (1.27 mmol) of phosphorus tribromide are dissolved in 10 ml of anhydrous THF under argon, and the mixture is stirred at ambient temperature for 2 h 30. Then the solution is diluted with ethyl acetate. The organic layer is washed 3 times with water, dried over sodium sulfate, filtered and evaporated under reduced pressure to give 546 mg of a brown solid. Crude product is used in the next step without purification.
Yield: Quantitative.

Step 3: 1-(5-Chloro-2-hydroxybenzyl)-2-oxo-1,2-dihydropyridin-4-ylboronic Acid

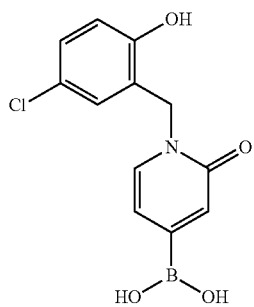 [SMILES: O=c1cc(B(O)O)ccn1Cc1cc(Cl)ccc1O]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 100 mg (0.45 mmol) of 2-(bromomethyl)-4-chlorophenol (described in the previous step) instead of benzyl bromide. 14 mg of the title compound are obtained.
Yield: 22%.
MH+: 280.0; 282.1.

Step 4: 1-(5-Chloro-2-hydroxybenzyl)-4-(5-morpholino-1H-pyrrolo[2,3-b]pyridin-3-yl)pyridin-2(1H)-one

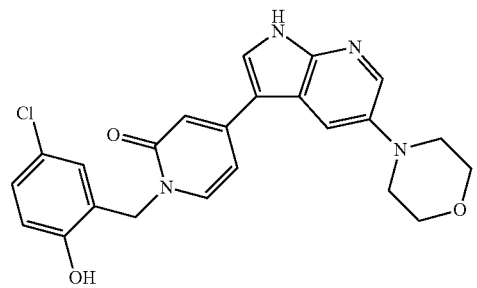 [SMILES: O=c1cc(-c2c[nH]c3ncc(N4CCOCC4)cc23)ccn1Cc1cc(Cl)ccc1O]

The compound is obtained by the procedure described in example 25 step 2, using 22 mg (0.045 mmol) of 3-iodo-5-morpholin-1-yl-1-tosyl-1H-pyrrolo[2,3-b]pyridine (described in example 17 step 3) and 14 mg (0.050 mmol) of 1-(5-chloro-2-hydroxybenzyl)-2-oxo-1,2-dihydropyridin-4-ylboronic acid (described in the previous step) instead of 1-benzyl-2-oxo-1,2-dihydropyridin-4-ylboronic acid. 3.2 mg of the title compound are obtained.
Yield: 16%.
MH+: 437.0; 439.0.
$^1$H NMR (DMSO-d6, 300 MHz): δ 12.08 (br s, 1H); 10.47 (br s, 1H); 8.17 (d, J=2.4 Hz, 1H); 8.11 (s, 1H); 7.82 (d, J=7.1 Hz, 1H); 7.72 (d, J=2.3 Hz, 1H); 7.23-7.15 (m, 2H); 6.90-6.73 (m, 3H); 5.01 (s, 2H); 3.84-3.73 (m, 4H); 3.20-3.09 (m, 4H).

Example 36: 1-(5-Chloro-3-hydroxybenzyl)-4-(5-morpholino-1H-pyrrolo[2,3-b]pyridin-3-yl)pyridin-2(1H)-one Step 1: 3-Chloro-5-hydroxybenzaldehyde

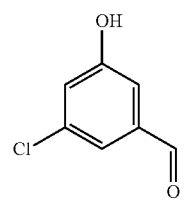

500 mg (3.27 mmol) of 3-chloro-5-hydroxybenzonitrile are dissolved in a mixture of 4 ml of pyridine/acetic acid/water (2/1/1). 630 mg (6.54 mmol) of sodium hypophosphite monohydrate are added, followed by several drops of Raney nickel in water, and the mixture is stirred at 50° C. for 1 hour under argon. After cooling to ambient temperature, the mixture is filtered carefully on celite and the celite is washed several times with ethyl acetate. The combined filtrates are evaporated under reduced pressure to give the crude product which is directly purified by flash chromatography on a 60 g silica gel column with an ethyl acetate/hexane mixture as eluent. 426 mg of a white solid are obtained.

Yield: 84%.

Step 2: 3-Chloro-5-(hydroxymethyl)phenol

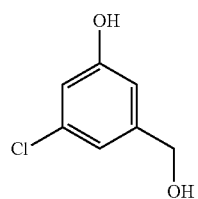

426 mg (2.73 mmol) of 3-chloro-5-hydroxybenzaldehyde (described in the previous step) are added slowly to 4.1 ml (4.1 mmol) of a solution of $BH_3$ (1M in THF) at 0° C. The solution is stirred at 0° C. for 30 minutes under argon. LC/MS shows complete conversion of the substrate. Then pieces of ice are slowly added until the end of gas evolution. $NaHCO_3$ in powder is added until pH 8-9. The solution is then diluted with water, extracted 3 times with ethyl acetate, dried over sodium sulfate, filtered and evaporated under reduced pressure. 483 mg of a solid are obtained. Crude product is used in the next step without purification.

Yield: Quantitative.

Step 3: 3-(Bromomethyl)-5-chlorophenol

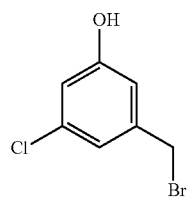

483 mg (3.06 mmol) of 5-chloro-3-(hydroxymethyl)phenol (described in the previous step) and 0.41 ml (4.38 mmol) of phosphorus tribromide are dissolved in 40 ml of anhydrous THF under argon, and the mixture is stirred at ambient temperature overnight. Then the solution is diluted with diethyl ether. The organic layer is washed 3 times with water, dried over sodium sulfate, filtered and evaporated under reduced pressure to give 654 mg of a brown solid. Crude product is used in the next step without purification.

Yield: Quantitative.

Step 4: 1-(3-Chloro-5-hydroxybenzyl)-2-oxo-1,2-dihydropyridin-4-ylboronic Acid

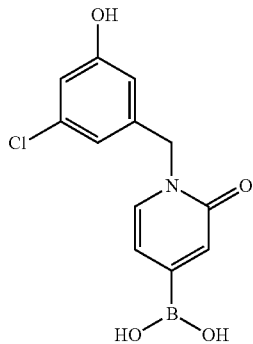 [SMILES: O=c1cc(B(O)O)ccn1Cc1cc(O)cc(Cl)c1]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 55 mg (0.25 mmol) of 3-(bromomethyl)-5-chlorophenol (described in the previous step) instead of benzyl bromide. 26 mg of the title compound are obtained.

Yield: 41%.

MH+: 280.1; 282.1.

Step 5: 1-(3-Chloro-5-hydroxybenzyl)-4-(5-morpholino-1H-pyrrolo[2,3-b]pyridin-3-yl)pyridin-2 (1H)-one

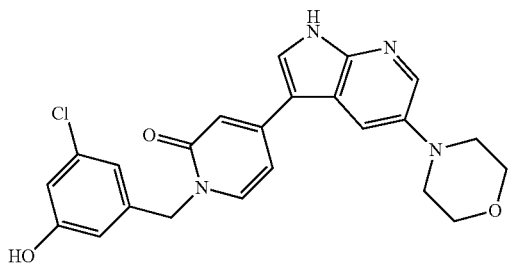 [SMILES: O=c1cc(-c2c[nH]c3ncc(N4CCOCC4)cc23)ccn1Cc1cc(O)cc(Cl)c1]

The compound is obtained by the procedure described in example 25 step 2, using 41 mg (0.085 mmol) of 3-iodo-5-morpholin-1-yl-1-tosyl-1H-pyrrolo[2,3-b]pyridine (described in example 17 step 3) and 26 mg (0.093 mmol) of 1-(3-chloro-5-hydroxybenzyl)-2-oxo-1,2-dihydropyridin-4-ylboronic acid (described in the previous step) instead of 1-benzyl-2-oxo-1,2-dihydropyridin-4-ylboronic acid. 6 mg of the title compound are obtained.

Yield: 16%.

MH+: 437.0; 439.0.

$^1$H NMR (DMSO-d6, 300 MHz): δ 12.05 (br s, 1H); 10.05 (br s, 1H); 8.17 (d, J=2.3 Hz, 1H); 8.09 (s, 1H); 7.77-7.68 (m, 2H); 6.84-6.63 (m, 5H); 5.01 (s, 2H); 3.87-3.75 (m, 4H); 3.22-3.11 (m, 4H).

Example 37: 1-(5-Chloro-2-(2-methoxyethoxy)benzyl)-4-(5-morpholino-1H-pyrrolo[2,3-b]pyridin-3-yl)pyridin-2(1H)-one

Step 1: Methyl 5-chloro-2-(2-methoxyethoxy)benzoate

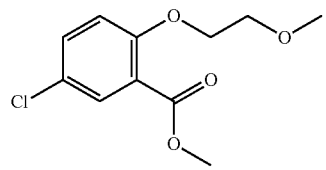 [SMILES: COCCOc1ccc(Cl)cc1C(=O)OC]

In 5 ml of anhydrous DMF, are added under argon 500 mg (2.7 mmol) of methyl 5-chloro-2-hydroxybenzoate, 277 μl (2.9 mmol) of 2-bromoethyl methyl ether and 1.3 g (4 mmol) of cesium carbonate. The mixture is stirred at ambient temperature overnight. The mixture is then diluted with diethyl ether, filtered on celite and the celite is washed several times with diethyl ether. The combined filtrates are evaporated under reduced pressure to give 580 mg of a yellow oil which crystallizes at ambient temperature. Crude product is used in the next step without further purification.

Yield: 88%.

$^1$H NMR (DMSO-d6, 300 MHz): δ 7.67 (d, J=2. Hz, 1H); 7.56 (dd, J=2.7 and 8.9 Hz, 1H); 7.67 (d, J=8.9 Hz, 1H); 4.17 (t, J=4.5 Hz, 2H); 3.79 (s, 3H); 3.65 (t, J=4.6 Hz, 2H); 3.31 (s, 3H).

Step 2: (5-Chloro-2-(2-methoxyethoxy)phenyl)methanol

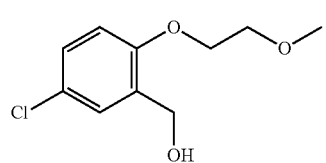

580 mg (2.37 mmol) of methyl 5-chloro-2-(2-methoxyethoxy)benzoate (described in the previous step) are added slowly to a solution of 90 mg (2.37 mmol) of lithium aluminum hydride in 7 ml of anhydrous THF at 0° C. The solution is stirred at 0° C. for 30 minutes under argon and the temperature is allowed to reach ambient temperature overnight. The solution is cooled to 0° C. and water is slowly added. The layer is then extracted 3 times with ethyl acetate, dried over sodium sulfate, filtered and evaporated under reduced pressure. 510 mg of a colorless oil are obtained. Crude product is used in the next step without purification.

Yield: 99%.

MH+: 199.1; 201.1 (—H$_2$O).

$^1$H NMR (DMSO-d6, 300 MHz): δ 7.35 (d, J=2.6 Hz, 1H); 7.22 (dd, J=2.7 and 8.7 Hz, 1H); 6.97 (d, J=8.7 Hz, 1H); 5.17 (t, J=5.7 Hz, 1H); 4.47 (d, J=5.7 Hz, 2H); 4.09 (t, J=4.5 Hz, 2H); 3.64 (t, J=4.6 Hz, 2H); 3.31 (s, 3H).

Step 3: 2-(Bromomethyl)-4-chloro-1-(2-methoxyethoxy)benzene

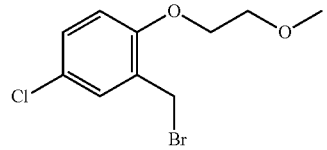

510 mg (2.35 mmol) of (5-chloro-2-(2-methoxyethoxy)phenyl)methanol (described in the previous step) and 351 μl (3.5 mmol) of phosphorus tribromide are dissolved in 10 ml of anhydrous THF under argon, and the mixture is stirred at ambient temperature overnight. Then the solution is diluted with ethyl acetate. The organic layer is washed 3 times with water, dried over sodium sulfate, filtered and evaporated under reduced pressure. Crude product is purified by flash chromatography on a 30 g silica gel column with an ethyl acetate/hexane mixture as eluent. 528 mg of a colorless oil which crystallizes at ambient temperature, are obtained.

Yield: 80%.

MH+: 280.1; 282.1.

$^1$H NMR (DMSO-d6, 300 MHz): δ 7.50 (d, J=2.6 Hz, 1H); 7.36 (dd, J=2.6 and 8.8 Hz, 1H); 7.08 (d, J=8.9 Hz, 1H); 4.61 (s, 2H); 4.19 (t, J=4.4 Hz, 2H); 3.70 (t, J=4.5 Hz, 2H); 3.34 (s, 3H).

Step 4: 1-(5-Chloro-2-(2-methoxyethoxy)benzyl)-2-oxo-1,2-dihydropyridin-4-ylboronic Acid

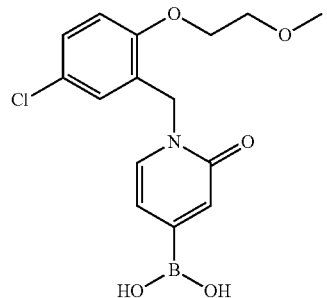 [SMILES: COCCOc1ccc(Cl)cc1Cn1ccc(B(O)O)cc1=O]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 70 mg (0.25 mmol) of 2-(bromomethyl)-4-chloro-1-(2-methoxyethoxy)benzene (described in the previous step) instead of benzyl bromide. 55 mg of the title compound are obtained.

Yield: 72%.

MH+: 338.0; 340.0.

Step 5: 1-(5-Chloro-2-(2-methoxyethoxy)benzyl)-4-(5-morpholino-1H-pyrrolo[2,3-b]pyridin-3-yl)pyridin-2(1H)-one

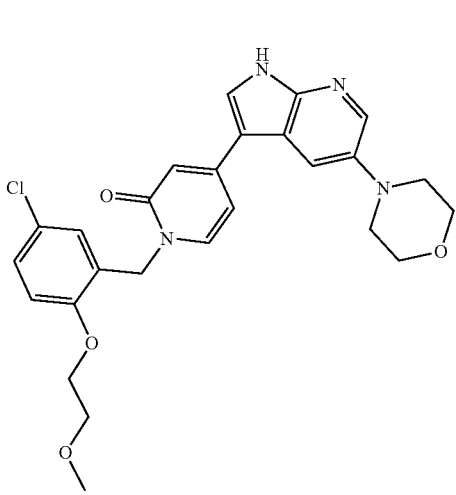 [SMILES: COCCOc1ccc(Cl)cc1Cn1ccc(-c2c[nH]c3ncc(N4CCOCC4)cc23)cc1=O]

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 16 mg (0.046 mmol) of 1-(5-chloro-2-(2-methoxyethoxy)benzyl)-2-oxo-1,2-dihydropyridin-4-ylboronic acid (described in the previous step) instead of 1-benzyl-2-oxo-1,2-dihydropyridin-4-ylboronic acid. 14 mg of the title compound are obtained.

Yield: 68%.

MH+: 495.0; 497.0.

$^1$H NMR (DMSO-d6, 300 MHz): δ 12.06 (br s, 1H); 8.17 (d, J=2.0 Hz, 1H); 8.10 (s, 1H); 7.78-7.67 (m, 2H); 7.32 (dd, J=2.5 and 8.5 Hz, 1H); 7.15-7.05 (m, 2H); 6.77-6.66 (m, 2H); 5.01 (s, 2H); 4.17 (t, J=3.9 Hz, 2H); 3.86-3.75 (m, 4H); 3.74 (t, J=4.1 Hz, 2H); 3.34 (s, 3H); 3.21-3.09 (m, 4H).

Example 38: 1-(3-Chloro-5-(2-methoxyethoxy)benzyl)-4-(5-morpholino-1H-pyrrolo[2,3-b]pyridin-3-yl)pyridin-2(1H)-one Step 1: 3-Chloro-5-(2-methoxyethoxy)benzonitrile

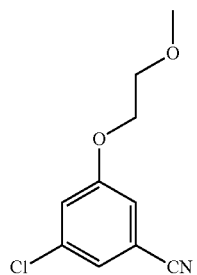

The compound is obtained by the procedure described in example 37 step 1, using 500 mg (3.25 mmol) of 3-chloro-5-hydroxybenzonitrile instead of methyl 5-chloro-2-hydroxybenzoate, 337 µl (3.60 mmol) of 2-bromoethyl methyl ether and 1.6 g (4.9 mmol) of cesium carbonate. 663 mg of a yellow oil are obtained.

Yield: 96%.

$^1$H NMR (DMSO-d6, 300 MHz): δ 7.59-7.55 (m, 1H); 7.49-7.45 (m, 1H); 7.45-7.41 (m, 1H); 4.20 (t, J=4.3 Hz, 2H); 3.65 (t, J=4.5 Hz, 2H); 3.29 (s, 3H).

Step 2: 3-Chloro-5-(2-methoxyethoxy)benzaldehyde

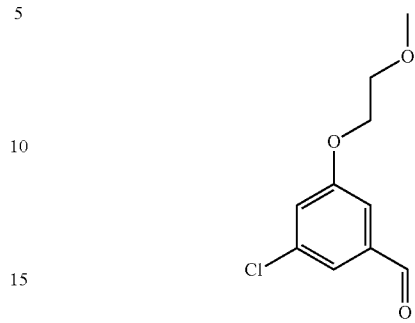

The compound is obtained by the procedure described in example 36 step 1, using 663 mg (3.13 mmol) of 3-chloro-5-(2-methoxyethoxy)benzonitrile (described in the previous step) instead of 3-chloro-5-hydroxybenzonitrile, 664 mg (6.30 mmol) of sodium hypophosphite monohydrate and several drops of Raney nickel in water. 479 mg of a colorless oil are obtained.

Yield: 99%.

$^1$H NMR (DMSO-d6, 300 MHz): δ 9.94 (s, 1H); 7.55-7.49 (m, 1H); 7.46-7.41 (m, 1H); 7.41-7.36 (m, 1H); 4.22 (t, J=4.4 Hz, 2H); 3.68 (t, J=4.5 Hz, 2H); 3.31 (s, 3H).

Step 3: (3-Chloro-5-(2-methoxyethoxy)phenyl)methanol

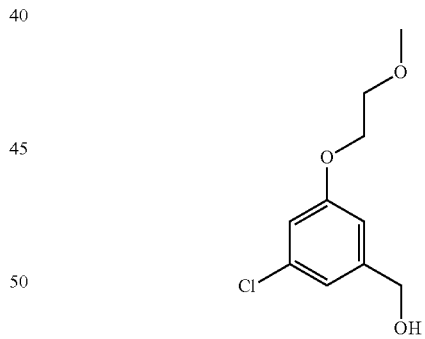

The compound is obtained by the procedure described in example 36 step 2, using 479 mg (2.22 mmol) of 3-chloro-5-(2-methoxyethoxy)benzaldehyde (described in the previous step) instead of 3-chloro-5-hydroxybenzaldehyde and 3.3 ml (3.3 mmol) of a solution of BH$_3$ (1M in THF). 467 mg of a colorless oil are obtained.

Yield: 96%.

MH+: 217.2; 219.2.

$^1$H NMR (DMSO-d6, 300 MHz): δ 6.96-6.90 (m, 1H); 6.90-6.81 (m, 2H); 5.31 (t, J=5.8 Hz, 1H); 4.45 (d, J=5. Hz, 2H); 4.10 (t, J=4.4 Hz, 2H); 3.64 (t, J=4.6 Hz, 2H); 3.30 (s, 3H).

Step 4: 1-(Bromomethyl)-3-chloro-5-(2-methoxy-ethoxy)benzene

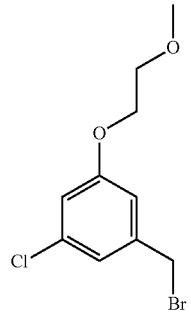

The compound is obtained by the procedure described in example 37 step 3, using 467 mg (2.16 mmol) of (3-chloro-5-(2-methoxyethoxy)phenyl)methanol (described in the previous step) instead of (5-chloro-2-(2-methoxyethoxy)phenyl)methanol and 303 μl (3.23 mmol) of phosphorus tribromide. 616 mg of a colorless oil are obtained.

Yield: Quantitative.

Step 5: 1-(3-Chloro-5-(2-methoxyethoxy)benzyl)-2-oxo-1,2-dihydropyridin-4-ylboronic Acid

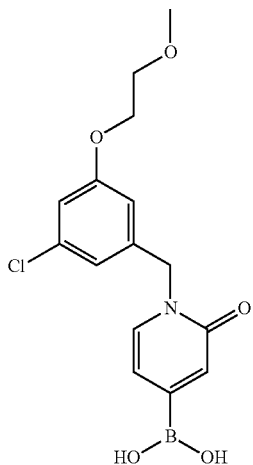 [SMILES: COCCOc1cc(Cl)cc(Cn2ccc(B(O)O)cc2=O)c1]

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 70 mg (0.25 mmol) of 1-(bromomethyl)-3-chloro-5-(2-methoxyethoxy)benzene (described in the previous step) instead of benzyl bromide. 45 mg of the title compound are obtained.

Yield: 59%.
MH+: 338.0; 340.0.

Step 6: 1-(3-Chloro-5-(2-methoxyethoxy)benzyl)-4-(5-morpholino-1H-pyrrolo[2,3-b]pyridin-3-yl)pyridin-2(1H)-one

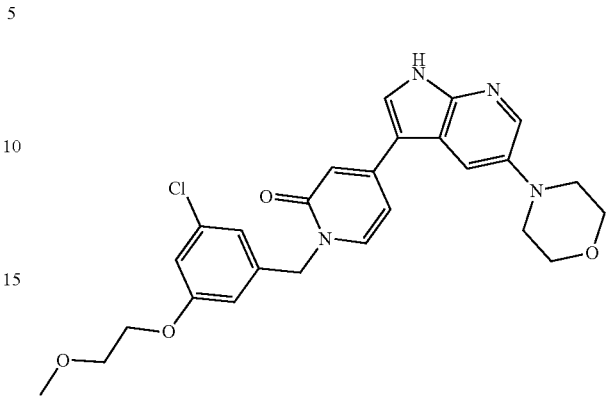

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 16 mg (0.046 mmol) of 1-(3-chloro-5-(2-methoxyethoxy)benzyl)-2-oxo-1,2-dihydropyridin-4-ylboronic acid (described in the previous step) instead of 1-benzyl-2-oxo-1,2-dihydropyridin-4-ylboronic acid. 7 mg of the title compound are obtained.

Yield: 34%.
MH+: 495.0; 497.0.
$^1$H NMR (DMSO-d6, 300 MHz): δ 12.05 (br s, 1H); 8.17 (d, J=2.3 Hz, 1H); 8.09 (s, 1H); 7.77 (d, J=7.8 Hz, 1H); 7.71 (d, J=2.4 Hz, 1H); 6.99-6.94 (m, 2H); 6.88 (s, 1H); 6.76-6.69 (m, 2H); 5.05 (s, 2H); 4.10 (t, J=4.3 Hz, 2H); 3.83-3.73 (m, 4H); 3.61 (t, J=4.5 Hz, 2H); 3.28 (s, 3H); 3.20-3.09 (m, 4H).

Example 39: 4-(5-Morpholino-1H-pyrrolo[2,3-b]pyridin-3-yl)-1-(pyridin-3-ylmethyl)pyridin-2(1H)-one

Step 1: 2-Oxo-1-(pyridin-3-ylmethyl)-1,2-dihydropyridin-4-ylboronic Acid

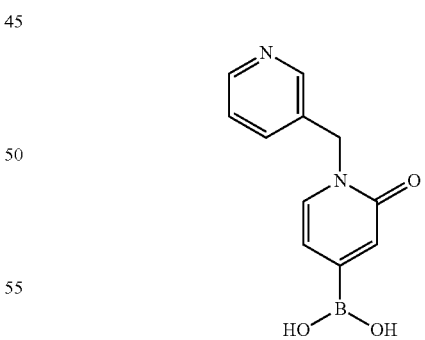

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 184 mg (0.57 mmol) of cesium carbonate and 65 mg (0.25 mmol) of 3-(bromomethyl)pyridine hydrobromide instead of benzyl bromide. 11 mg of the title compound are obtained.

Yield: 21%.
MH+: 231.1.

Step 2: 4-(5-Morpholino-1H-pyrrolo[2,3-b]pyridin-3-yl)-1-(pyridin-3-ylmethyl)pyridin-2(1H)-one

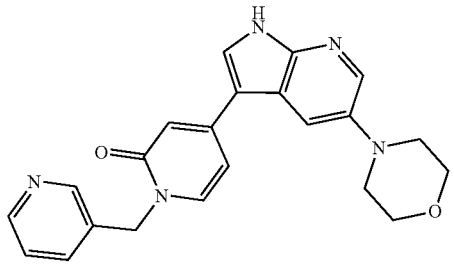 [SMILES: O=c1cc(-c2c[nH]c3ncc(N4CCOCC4)cc23)ccn1Cc1cccnc1]

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 11 mg (0.048 mmol) of 2-oxo-1-(pyridin-3-ylmethyl)-1,2-dihydropyridin-4-ylboronic acid (described in the previous step) instead of 1-benzyl-2-oxo-1,2-dihydropyridin-4-ylboronic acid. 5.3 mg of the title compound are obtained.

Yield: 33%.

MH+: 388.0.

$^1$H NMR (DMSO-d6, 300 MHz): δ 12.05 (br s, 1H); 8.61 (d, J=1.4 Hz, 1H); 8.50 (dd, J=1.4 and 4.8 Hz, 1H); 8.16 (d, J=2.3 Hz, 1H); 8.08 (s, 1H); 7.84 (d, J=7.0 Hz, 1H); 7.78-7.66 (m, 2H); 7.39 (dd, J=4.9 and 7.3 Hz, 1H); 6.76-6.68 (m, 2H); 5.13 (s, 2H); 3.84-3.72 (m, 4H); 3.20-3.06 (m, 4H).

Example 40: 1-((6-Chloropyridin-3-yl)methyl)-4-(5-morpholino-1H-pyrrolo[2,3-b]pyridin-3-yl)pyridin-2(1H)-one Step 1: 1-((6-Chloropyridin-3-yl)methyl)-2-oxo-1,2-dihydropyridin-4-ylboronic Acid

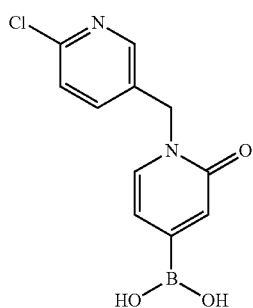

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 40 mg (0.25 mmol) of 2-chloro-5-chloromethylpyridine instead of benzyl bromide. 16 mg of the title compound are obtained.

Yield: 27%.

MH+: 265.1; 267.1.

Step 2: 1-((6-Chloropyridin-3-yl)methyl)-4-(5-morpholino-1H-pyrrolo[2,3-b]pyridin-3-yl)pyridin-2(1H)-one

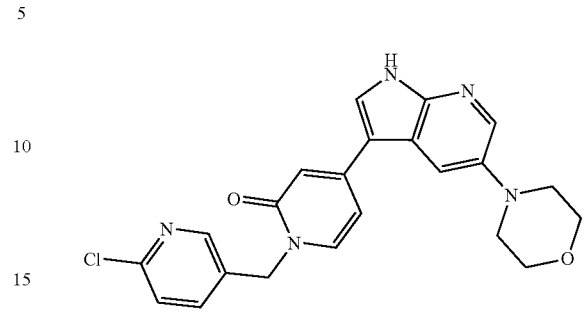

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 12 mg (0.045 mmol) of 1-((6-chloropyridin-3-yl)methyl)-2-oxo-1,2-dihydropyridin-4-ylboronic acid (described in the previous step) instead of 1-benzyl-2-oxo-1,2-dihydropyridin-4-ylboronic acid. 3.4 mg of the title compound are obtained.

Yield: 20%.

MH+: 421.9; 424.0.

$^1$H NMR (DMSO-d6, 300 MHz): δ 12.07 (br s, 1H); 8.46 (d, J=1.9 Hz, 1H); 8.16 (d, J=2.3 Hz, 1H); 8.09 (s, 1H); 7.88-7.78 (m, 2H); 7.70 (d, J=2.6 Hz, 1H); 7.52 (d, J=8.1 Hz, 1H); 6.78-6.68 (m, 2H); 5.12 (s, 2H); 3.83-3.73 (m, 4H); 3.18-3.08 (m, 4H).

Example 41: 1-((6-Chloropyridin-2-yl)methyl)-4-(5-morpholino-1H-pyrrolo[2,3-b]pyridin-3-yl)pyridin-2(1H)-one Step 1: 1-((6-Chloropyridin-2-yl)methyl)-2-oxo-1,2-dihydropyridin-4-ylboronic Acid

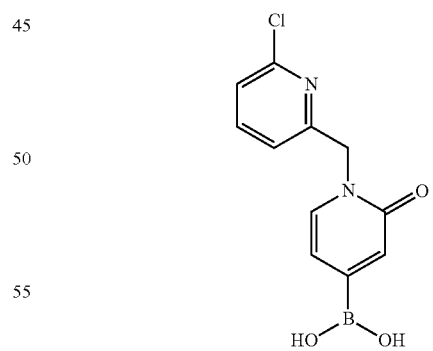

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 30 μl (0.25 mmol) of 2-chloro-6-(chloromethyl)pyridine instead of benzyl bromide. 15 mg of the title compound are obtained.

Yield: 25%.

MH+: 265.1; 267.1.

Step 2: 1-((6-Chloropyridin-2-yl)methyl)-4-(5-morpholino-1H-pyrrolo[2,3-b]pyridin-3-yl)pyridin-2(1H)-one

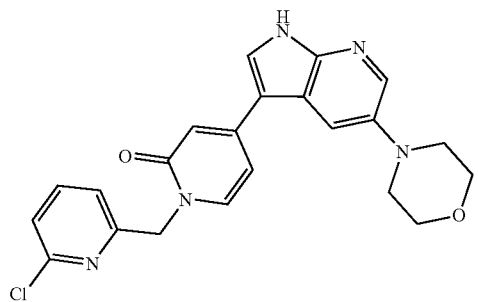 [SMILES: O=c1cc(-c2c[nH]c3ncc(N4CCOCC4)cc23)ccn1Cc1cccc(Cl)n1]

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 12 mg (0.045 mmol) of 1-((6-chloropyridin-2-yl)methyl)-2-oxo-1,2-dihydropyridin-4-ylboronic acid (described in the previous step) instead of 1-benzyl-2-oxo-1,2-dihydropyridin-4-ylboronic acid. 6.3 mg of the title compound are obtained.
Yield: 36%.
MH+: 421.9; 423.9.
$^1$H NMR (DMSO-d6, 300 MHz): δ 12.07 (br s, 1H); 8.17 (d, J=2.2 Hz, 1H); 8.12 (s, 1H); 7.87 (t, J=7. Hz, 1H); 7.77 (d, J=7.0 Hz, 1H); 7.72 (d, J=2.4 Hz, 1H); 7.43 (d, J=7.9 Hz, 1H); 7.22 (d, J=7. Hz, 1H); 6.77 (dd, J=1.4 and 6.0 Hz, 1H); 6.71 (d, J=1.5 Hz, 1H); 5.17 (s, 2H); 3.83-3.73 (m, 4H); 3.20-3.10 (m, 4H).

Example 42: 1-(1-(3-Chlorophenyl)-2-hydroxyethyl)-4-(5-morpholino-1H-pyrrolo[2,3-b]pyridin-3-yl)pyridin-2(1H)-one Step 1: Ethyl 2-(4-bromo-2-oxopyridin-1(2H)-yl)-2-(3-chlorophenyl)acetate

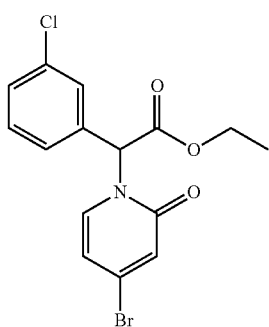 [SMILES: CCOC(=O)C(c1cccc(Cl)c1)n1ccc(Br)cc1=O]

To a solution of 200 mg (1.15 mmol) of 4-bromopyridin-2(1H)-one and 561 mg (1.73 mmol) of cesium carbonate in 2 ml of anhydrous DMF, are added 253 µl (1.26 mmol) of ethyl 2-bromo-2-(3-chlorophenyl)acetate at ambient temperature. The reaction is stirred overnight under argon. Reaction mixture is then diluted with ethyl acetate, and the precipitate is filtered and rinsed with a small amount of ethyl acetate. The combined filtrates are concentrated under vacuum and directly purified by flash chromatography with a 30 g C18 column and a water/acetonitrile mixture as eluent. 238 mg of the title compound are obtained.
Yield: 56%.
MH+: 369.8; 371.8; 373.8.

Step 2: 4-Bromo-1-(1-(3-chlorophenyl)-2-hydroxyethyl)pyridin-2(1H)-one

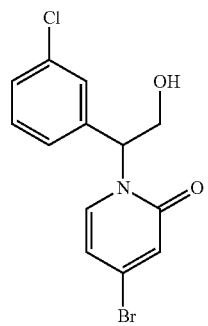 [SMILES: O=c1cc(Br)ccn1C(CO)c1cccc(Cl)c1]

To a solution of 160 mg (0.43 mmol) of ethyl 2-(4-bromo-2-oxopyridin-1(2H)-yl)-2-(3-chlorophenyl)acetate (described in the previous step) in 5 ml of ethanol at 0° C., are added 16 mg (0.43 mmol) of sodium borohydride. The reaction is stirred for 1 hour at 0° C. Reaction mixture is then diluted with dichloromethane, washed 3 times with water, dried over sodium sulfate, filtered and evaporated under reduced pressure. Crude product is purified by flash chromatography on a 10 g silica gel column with a dichloromethane/methanol mixture as eluent. 37 mg of the title compound are obtained.
Yield: 26%.
MH+: 327.9; 329.8; 331.8.

Step 3: 1-(1-(3-Chlorophenyl)-2-hydroxyethyl)-4-(4,4,5,5-tetramethyl-1,3,2-dioxaborolan-2-yl)pyridin-2(1H)-one

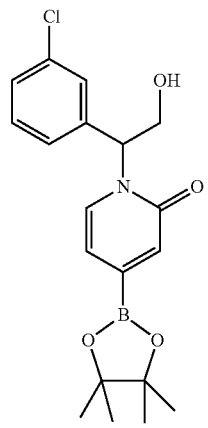 [SMILES: CC1(C)OB(c2ccn(C(CO)c3cccc(Cl)c3)c(=O)c2)OC1(C)C]

37 mg (0.11 mmol) of 4-bromo-1-(1-(3-chlorophenyl)-2-hydroxyethyl)pyridin-2(1H)-one (described in the previous step), 28 mg (0.11 mmol) of bis(pinacolato)diboron and 22 mg (0.22 mmol) of sodium acetate are dissolved in 2 ml of dioxane. Argon is bubbled through the solution for 10 minutes, then 2 mg of PdCl$_2$(PPh$_3$)$_2$ are added under argon.

Argon is bubbled for another 10 minutes and the reaction is stirred at 85° C. overnight. After cooling to ambient temperature, the reaction mixture is concentrated under reduced pressure and crude product is directly purified by flash chromatography on a 10 g silica gel column with an ethyl acetate/methanol mixture as eluent. 20 mg of the title compound are obtained.

Yield: 47%.

MH+: 294.0; 296.0 (Boronic acid derivative).

Step 4: 1-(1-(3-Chlorophenyl)-2-hydroxyethyl)-4-(5-morpholino-1H-pyrrolo[2,3-b]pyridin-3-yl)pyridin-2(1H)-one

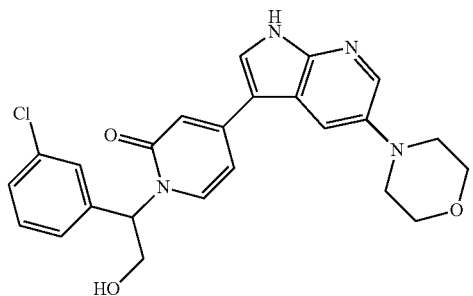 [SMILES: O=c1cc(-c2c[nH]c3ncc(N4CCOCC4)cc23)ccn1C(CO)c1cccc(Cl)c1]

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 13 mg (0.044 mmol) of 1-(1-(3-chlorophenyl)-2-hydroxyethyl)-4-(4,4,5,5-tetramethyl-1,3,2-dioxaborolan-2-yl)pyridin-2(1H)-one (described in the previous step) instead of 1-benzyl-2-oxo-1,2-dihydropyridin-4-ylboronic acid. 3.2 mg of the title compound are obtained.

Yield: 16%.

MH+: 451.0; 453.1.

$^1$H NMR (DMSO-d6, 300 MHz): δ 12.08 (br s, 1H); 8.17 (d, J=2.1 Hz, 1H); 8.08 (s, 1H); 7.7-7.67 (m, 2H); 7.47-7.26 (m, 4H); 6.75-6.67 (m, 2H); 6.00 (br t, 1H); 5.39-5.19 (m, 1H); 4.23-3.97 (m, 2H); 3.86-3.73 (m, 4H); 3.21-3.08 (m, 4H).

Step 5: (+)-1-(1-(3-Chlorophenyl)-2-hydroxyethyl)-4-(5-morpholino-1H-pyrrolo[2,3-b]pyridin-3-yl)pyridin-2(1H)-one and (−)-1-(1-(3-Chlorophenyl)-2-hydroxyethyl)-4-(5-morpholino-1H-pyrrolo[2,3-b]pyridin-3-yl)pyridin-2(1H)-one Enantiomers are obtained by semi-preparative chiral chromatography starting from 20 mg (0.044 mmol) of racemate compound described in the previous step using a Chiralpak IA column and a mixture of heptane/Isopropanol (50/50) as the mobile phase. First fraction to be eluted is the (−)-enantiomer (9 mg with an ee=98.9%), followed by the (+)-enantiomer (8 mg with an ee=98.5%).

Example 43: 2-(3-Chlorophenyl)-2-(4-(5-morpholino-1H-pyrrolo[2,3-b]pyridin-3-yl)-2-oxopyridin-1(2H)-yl)acetic acid

Step 1: 1-(1-(3-Chlorophenyl)-2-ethoxy-2-oxoethyl)-2-oxo-1,2-dihydropyridin-4-ylboronic Acid

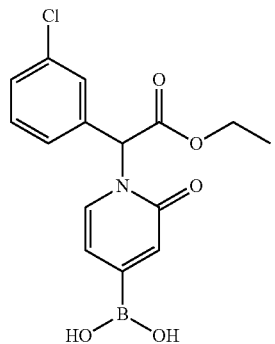 [SMILES: CCOC(=O)C(c1cccc(Cl)c1)n1ccc(B(O)O)cc1=O]

The compound is obtained by the procedure described in example 25 step 1, using 80 mg (0.36 mmol) of 4-(4,4,5,5-tetramethyl-[1,3,2]dioxaborolan-2-yl)-1H-pyridin-2-one, 176 mg (0.54 mmol) of cesium carbonate and 80 µl (0.40 mmol) of ethyl 2-bromo-2-(3-chlorophenyl)acetate instead of benzyl bromide. 36 mg of the title compound are obtained.

Yield: 30%.

MH+: 336.0; 337.9.

Step 2: 2-(3-Chlorophenyl)-2-(4-(5-morpholino-1H-pyrrolo[2,3-b]pyridin-3-yl)-2-oxopyridin-1(2H)-yl) acetic Acid

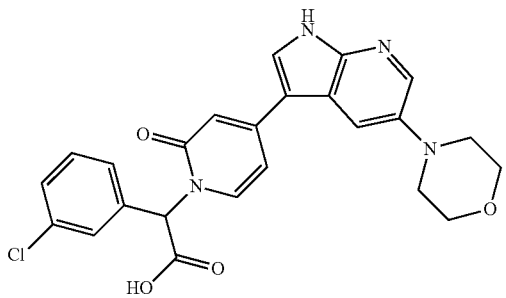 [SMILES: O=C(O)C(c1cccc(Cl)c1)n1ccc(-c2c[nH]c3ncc(N4CCOCC4)cc23)cc1=O]

20 mg (0.041 mmol) of 3-iodo-5-morpholin-1-yl-1-tosyl-1H-pyrrolo[2,3-b]pyridine (described in example 17 step 3) and 16 mg (0.048 mmol) of 1-(1-(3-chlorophenyl)-2-ethoxy-2-oxoethyl)-2-oxo-1,2-dihydropyridin-4-ylboronic acid (described in the previous step) are dissolved in a mixture of 3 ml of acetonitrile and 1.5 ml of an aqueous 2M solution of Na$_2$CO$_3$. Argon is bubbled through the solution for 10 minutes, then 2 mg of PdCl$_2$(PPh$_3$)$_2$ are added under argon. Argon is bubbled for another 10 minutes and the reaction is stirred at 70° C. for 1 hour. The reaction mixture is transferred in a microwave sealed tube and the reaction is heated at 150° C. under microwave irradiation for 15 minutes. After cooling, the solution is concentrated under reduced pressure, diluted with water and acidified to pH 2-3 with HCl 2N. Aqueous layer is extracted 3 times with ethyl acetate, dried over sodium sulfate, filtered and evaporated under reduced pressure. 11 mg of the title compound are obtained.
Yield: 55%.
MH+: 464.9; 466.9.

Example 44: 1-(2-(3-Chlorophenyl)-2-hydroxy-ethyl)-4-(5-morpholino-1H-pyrrolo[2,3-b]pyridin-3-yl)pyridin-2(1H)-one Step 1: 1-(2-(3-Chlorophenyl)-2-hydroxyethyl)-2-oxo-1,2-dihydropyridin-4-ylboronic Acid

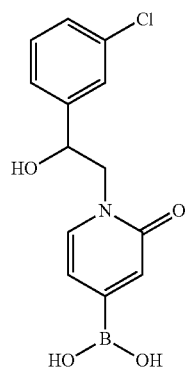

The compound is obtained by the procedure described in example 25 step 1, using 50 mg (0.23 mmol) of 4-(4,4,5,5-tetramethyl-[1,3,2]dioxaborolan-2-yl)-1H-pyridin-2-one, 110 mg (0.34 mmol) of cesium carbonate and 38 mg (0.25 mmol) of 2-(3-chlorophenyl)-oxirane instead of benzyl bromide. 30 mg of the title compound are obtained.
Yield: 45%.
MH+: 294.1; 296.0.

Step 2: 1-(2-(3-Chlorophenyl)-2-hydroxyethyl)-4-(5-morpholino-1H-pyrrolo[2,3-b]pyridin-3-yl)pyridin-2(1H)-one

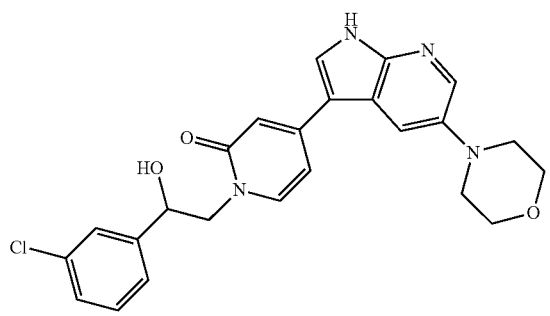 [SMILES: O=c1cc(-c2c[nH]c3ncc(N4CCOCC4)cc23)ccn1CC(O)c1cccc(Cl)c1]

The compound is obtained by the procedure described in example 25 step 2, using 20 mg (0.041 mmol) of 3-iodo-5-morpholin-1-yl-1-tosyl-1H-pyrrolo[2,3-b]pyridine (described in example 17 step 3) and 13 mg (0.044 mmol) of 1-(2-(3-chlorophenyl)-2-hydroxyethyl)-2-oxo-1,2-dihydropyridin-4-ylboronic acid (described in the previous step) instead of 1-benzyl-2-oxo-1,2-dihydropyridin-4-ylboronic acid. 3.9 mg of the title compound are obtained.
Yield: 22%.
MH+: 450.9; 452.9.

$^1$H NMR (DMSO-d6, 300 MHz): δ 12.04 (br s, 1H); 8.17 (d, J=2.2 Hz, 1H); 8.07 (s, 1H); 7.71 (d, J=2.3 Hz, 1H); 7.51 (d, J=7.2 Hz, 1H); 7.45 (s, 1H); 7.42-7.30 (m, 3H); 6.70 (s, 1H); 6.64 (dd, J=1.6 and 5.5 Hz, 1H); 5.85 (brs, 1H); 4.97-4.86 (m, 1H); 4.19 (dd, J=3.6 and 13.0 Hz, 1H); 3.89-3.73 (m, 5H); 3.20-3.08 (m, 4H).

Example 110: 4-(5-(3-Oxa-8-azabicyclo[3.2.1]octan-8-yl)-1H-pyrrolo[2,3-b]pyridin-3-yl)-1-(3,4-dichlorobenzyl)pyridin-2(1H)-one Step 1: 8-(1-((2-(Trimethylsilyl)ethoxy)methyl)-1H-pyrrolo[2,3-b]pyridin-5-yl)-3-oxa-8-azabicyclo[3.2.1]octane

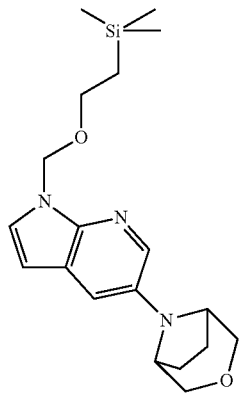 [SMILES: C[Si](C)(C)CCOCn1ccc2cc(N3C4CCC3COC4)cnc21]

The compound is obtained by the procedure described in example 10 step 2, using 912 mg (2.79 mmol) of 5-bromo-1-(2-trimethylsilylethoxymethyl)-1H-pyrrolo[2,3-b]pyridine, 500 mg (3.34 mmol) of 3-oxa-8-azabicyclo[3.2.1]octane hydrochloride instead of 4-cyanopiperidine, 26 mg (0.03 mmol) of Pd(dba)$_3$, 48 mg (0.09 mmol) of xantphos and 670 mg (6.97 mmol) of tBuONa. Crude product is purified by flash chromatography on a 30 g silica gel column with a dichloromethane/methanol mixture as eluent. 582 mg of the title compound are obtained. LC/MS shows a purity of 75%.
Yield: 58% (HPLC purity: 75%).
MH+: 360.5; 361.5.

Step 2: 8-(1H-Pyrrolo[2,3-b]pyridin-5-yl)-3-oxa-8-azabicyclo[3.2.1]octane

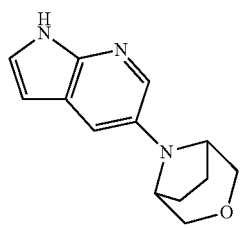 [SMILES: c1cc2cc(N3C4CCC3COC4)cnc2[nH]1]

The compound is obtained by the procedure described in example 10 step 3, using 582 mg (1.62 mmol) of 8-(1-((2-(trimethylsilyl)ethoxy)methyl)-1H-pyrrolo[2,3-b]pyridin-5-yl)-3-oxa-8-azabicyclo[3.2.1]octane (described in the previous step) instead of 5-(4-cyanopiperidin-1-yl)-1-(2- trimethylsilylethoxymethyl)-1H-pyrrolo[2,3-b]pyridine, 162 μl (2.43 mmol) of ethylenediamine, 4.8 ml+3.2 ml (4.8 mmol+3.2 mmol) of TBAF (1M in THF) in 14 ml oh anhydrous THF. 207 mg of the title compound are obtained.

Yield: 54%.

MH+: 230.3; 231.3.

Step 3: 8-(3-Iodo-1H-pyrrolo[2,3-b]pyridin-5-yl)-3-oxa-8-azabicyclo[3.2.1]octane

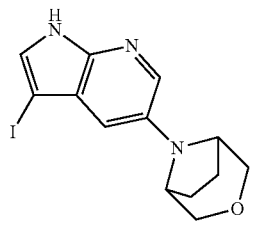 [SMILES: Ic1c[nH]c2ncc(N3C4CCC3COC4)cc12]

The compound is obtained by the procedure described in example 9 step 2, using 201 mg (0.88 mmol) of 8-(1H-pyrrolo[2,3-b]pyridin-5-yl)-3-oxa-8-azabicyclo[3.2.1]octane (described in the previous step) instead of 5-piperidin-1-yl-1H-pyrrolo[2,3-b]pyridine and 296 mg (1.3 mmol) of N-iodosuccinimide in 10 ml of acetone. 111 mg of the title compound are obtained.

Yield: 36%.

MH+: 356.2; 357.3.

Step 4: 8-(3-Iodo-1-tosyl-1H-pyrrolo[2,3-b]pyridin-5-yl)-3-oxa-8-azabicyclo[3.2.1]octane

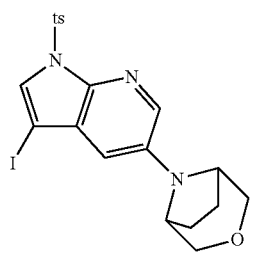

The compound is obtained by the procedure described in example 9 step 3, using 111 mg (0.31 mmol) of 8-(3-iodo-1H-pyrrolo[2,3-b]pyridin-5-yl)-3-oxa-8-azabicyclo[3.2.1]octane (described in the previous step) instead of 3-iodo-5-piperidin-1-yl-1H-pyrrolo[2,3-b]pyridine, 19 mg (0.47 mmol) of sodium hydride (60% in paraffin oil) and 66 mg (0.34 mmol) of tosyl chloride in 5 ml of anhydrous DMF. 110 mg of the title compound are obtained.

Yield: 69%.

MH+: 510.2; 511.2.

Step 5: 4-(5-(3-Oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one

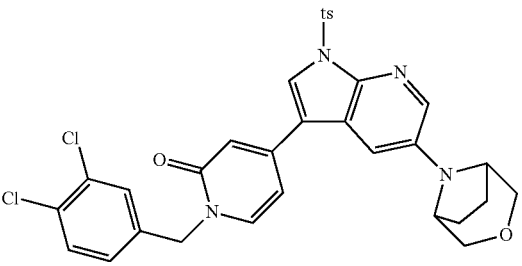

50 mg (0.098 mmol) of 8-(3-iodo-1-tosyl-1H-pyrrolo[2,3-b]pyridin-5-yl)-3-oxa-8-azabicyclo[3.2.1]octane (described in previous step) and 45 mg (0.118 mmol) of 1-(3,4-dichlorobenzyl)-2-oxo-1,2-dihydropyridin-4-ylboronic acid (described in example 33 step 1) are dissolved in a mixture of 3 ml of acetonitrile and 1.5 ml of an aqueous 2M solution of $Na_2CO_3$. Argon is bubbled through the solution for 10 minutes, then 5 mg of $PdCl_2(PPh_3)_2$ are added under argon. Argon is bubbled for another 10 minutes and the reaction is stirred at 70° C. for 1 hour. Crude product is purified by flash chromatography on a 10 g silica gel column with a dichloromethane/methanol mixture as eluent. 68 mg of the title compound are obtained.

Yield: Quantitative.

MH+: 635.4; 637.4; 639.3.

Step 6: 4-(5-(3-Oxa-8-azabicyclo[3.2.1]octan-8-yl)-1H-pyrrolo[2,3-b]pyridin-3-yl)-1-(3,4-dichlorobenzyl)pyridin-2(1H)-one 68 mg (0.107 mmol) of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one (described in previous step) are dissolved in a mixture of 3 ml of acetonitrile and 1.5 ml of an aqueous 2M solution of $Na_2CO_3$. The reaction mixture is heated at 150° C. under microwave irradiation for 15 minutes. After cooling, the solution is diluted with water, extracted 3 times with ethyl acetate, dried over sodium sulfate, filtered and evaporated under reduced pressure. Crude product is purified by flash chromatography on a 10 g silica gel column with a dichloromethane/methanol mixture as eluent. The obtained product is purified another time by flash chromatography on a 30 g C18 column with a water/acetonitrile mixture as eluent. 5.3 mg of the title compound are obtained.

Yield: 11%.

MH+: 481.3; 483.3; 485.3.

¹H NMR (DMSO-d6, 300 MHz): δ 11.98 (br s, 1H); 8.11-8.03 (m, 2H); 7.79 (d, J=7.1 Hz, 1H); 7.67-7.59 (m, 3H); 7.34 (dd, J=8.4 and 2.0 Hz, 1H); 6.76-6.67 (m, 2H); 5.09 (s, 2H); 4.29-4.20 (m, 2H); 3.78 (d, J=10.5 Hz, 2H); 3.49 (d, J=10.5 Hz, 2H); 2.00-1.82 (m, 4H).

Example 111: 1-(3-Chloro-2-fluorobenzyl)-4-(5-(cis-2,6-dimethylmorpholino)-1H-pyrrolo[2,3-b]pyridin-3-yl)pyridin-2(1H)-one Step 1: Cis-2,6-dimethyl-4-(1H-pyrrolo[2,3-b]pyridin-5-yl)morpholine

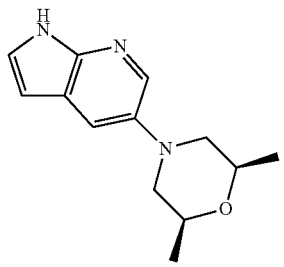 [SMILES: C[C@@H]1CN(c2cnc3[nH]ccc3c2)C[C@H](C)O1]

The compound is obtained by the procedure described in example 9 step 1, using 500 mg (2.54 mmol) of 5-bromo-1H-pyrrolo[2,3-b]pyridine, 472 µl (3.80 mmol) of cis-2,6-dimethylmorpholine instead of piperidine, 12 mg (0.025 mmol) of RuPhos, 20 mg (0.025 mmol) of RuPhos Pd G2 and 6.1 ml (6.1 mmol) of LiHMDS (1M in THF). 577 mg of the title compound are obtained.

Yield: 89%.

MH+: 232.4.

Step 2: 4-(3-Iodo-1H-pyrrolo[2,3-b]pyridin-5-yl)-cis-2,6-dimethylmorpholine

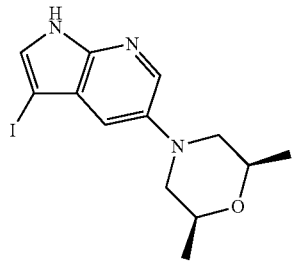 [SMILES: C[C@@H]1CN(c2cnc3[nH]cc(I)c3c2)C[C@H](C)O1]

The compound is obtained by the procedure described in example 9 step 2, using 577 mg (2.50 mmol) of cis-2,6-dimethyl-4-(1H-pyrrolo[2,3-b]pyridin-5-yl)morpholine (described in the previous step) instead of 5-piperidin-1-yl-1H-pyrrolo[2,3-b]pyridine and 617 mg (2.74 mmol) of N-iodosuccinimide in 20 ml of acetone. 787 mg of the title compound are obtained.

Yield: 88%.

MH+: 358.3.

Step 3: 4-(3-Iodo-1-tosyl-1H-pyrrolo[2,3-b]pyridin-5-yl)-cis-2,6-dimethylmorpholine

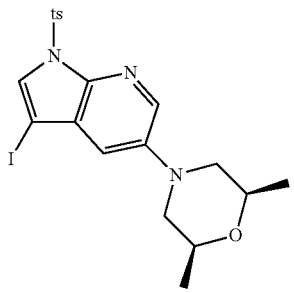

The compound is obtained by the procedure described in example 9 step 3, using 787 mg (2.20 mmol) of 4-(3-iodo-1H-pyrrolo[2,3-b]pyridin-5-yl)-cis-2,6-dimethylmorpholine (described in the previous step) instead of 3-iodo-5-piperidin-1-yl-1H-pyrrolo[2,3-b]pyridine, 132 mg (3.30 mmol) of sodium hydride (60% in paraffin oil) and 504 mg (2.60 mmol) of tosyl chloride in 10 ml of anhydrous DMF. 1.06 g of the title compound are obtained.

Yield: 94%.

MH+: 512.4.

Step 4: 1-(3-Chloro-2-fluorobenzyl)-4-(5-(cis-2,6-dimethylmorpholino)-1-tosyl-1H-pyrrolo[2,3-b]pyridin-3-yl)pyridin-2(1H)-one

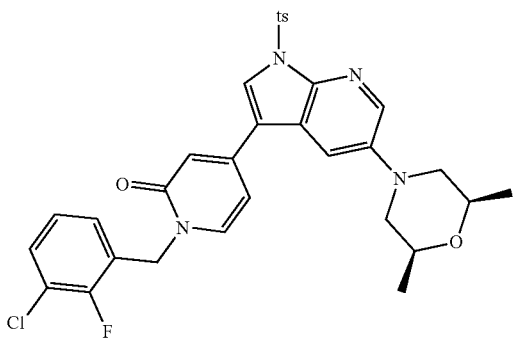

The compound is obtained by the procedure described in example 9 step 4, using mg (0.098 mmol) of 4-(3-iodo-1-tosyl-1H-pyrrolo[2,3-b]pyridin-5-yl)-cis-2,6-dimethylmorpholine (described in the previous step) instead of 3-iodo-5-piperidin-1-yl-1-tosyl-1H-pyrrolo[2,3-b]pyridine, 39 mg (0.137 mmol) of 1-(3-chloro-2-fluorobenzyl)-2-oxo-1,2-dihydropyridin-4-ylboronic acid (described in example 32 step 1) and 10 mg of PdCl₂(PPh₃)₂. 33 mg of the title compound are obtained.

Yield: 54%.

MH+: 621.6; 623.6.

Step 5: 1-(3-Chloro-2-fluorobenzyl)-4-(5-(cis-2,6-dimethylmorpholino)-1H-pyrrolo[2,3-b]pyridin-3-yl)pyridin-2(1H)-one

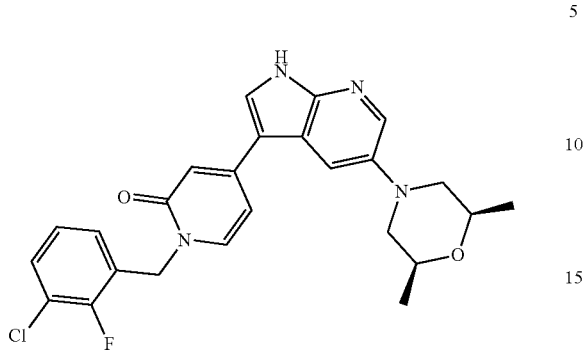

The compound is obtained by the procedure described in example 110 step 6, using 33 mg (0.053 mmol) of 1-(3-chloro-2-fluorobenzyl)-4-(5-(cis-2,6-dimethylmorpholino)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 8.1 mg of the title compound are obtained.

Yield: 33%.

MH+: 467.5; 469.5.

¹H NMR (DMSO-d6, 300 MHz): δ 12.06 (br s, 1H); 8.16 (d, J=2.5 Hz, 1H); 8.09 (s, 1H); 7.75 (d, J=7.1 Hz, 1H); 7.69 (d, J=2.5 Hz, 1H); 7.58-7.49 (m, 1H); 7.26-7.11 (m, 2H); 6.75 (dd, J=7.2 and 1.9 Hz, 1H); 6.71 (d, J=1.9 Hz, 1H); 5.18 (s, 2H); 3.86-3.69 (m, 2H); 3.58-3.48 (m, 2H); 2.40-2.28 (m, 2H); 1.17 (s, 3H); 1.15 (s, 3H).

Example 112: 1-(3-Chloro-2-fluorobenzyl)-4-(5-(trans-2,6-dimethylmorpholino)-1H-pyrrolo[2,3-b]pyridin-3-yl)pyridin-2(1H)-one

Step 1: Trans-2,6-dimethyl-4-(1H-pyrrolo[2,3-b]pyridin-5-yl)morpholine

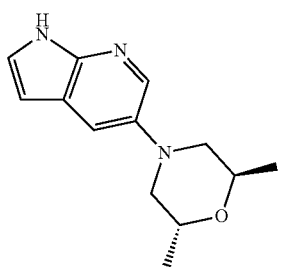 [SMILES: C[C@@H]1CN(c2cnc3[nH]ccc3c2)C[C@@H](C)O1]

The compound is obtained by the procedure described in example 9 step 1, using 500 mg (2.54 mmol) of 5-bromo-1H-pyrrolo[2,3-b]pyridine, 439 mg (3.80 mmol) of trans-2,6-dimethylmorpholine instead of piperidine, 12 mg (0.025 mmol) of RuPhos, 20 mg (0.025 mmol) of RuPhos Pd G2 and 6.1 ml (6.1 mmol) of LiHMDS (1M in THF). 585 mg of the title compound are obtained.

Yield: 91%.

MH+: 232.4.

Step 2: 4-(3-Iodo-1H-pyrrolo[2,3-b]pyridin-5-yl)-trans-2,6-dimethylmorpholine

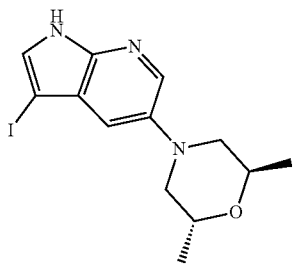 [SMILES: C[C@@H]1CN(c2cnc3[nH]cc(I)c3c2)C[C@@H](C)O1]

The compound is obtained by the procedure described in example 9 step 2, using 585 mg (2.50 mmol) of trans-2,6-dimethyl-4-(1H-pyrrolo[2,3-b]pyridin-5-yl)morpholine (described in the previous step) instead of 5-piperidin-1-yl-1H-pyrrolo[2,3-b]pyridine and 626 mg (2.78 mmol) of N-iodosuccinimide in 20 ml of acetone. 825 mg of the title compound are obtained.

Yield: 91%.

MH+: 358.3.

Step 3: 4-(3-Iodo-1-tosyl-1H-pyrrolo[2,3-b]pyridin-5-yl)-trans-2,6-dimethylmorpholine

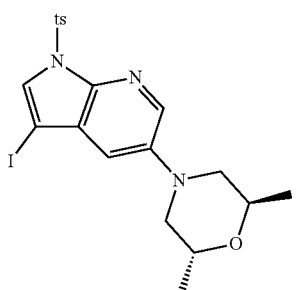

The compound is obtained by the procedure described in example 9 step 3, using 825 mg (2.30 mmol) of 4-(3-iodo-1H-pyrrolo[2,3-b]pyridin-5-yl)-trans-2,6-dimethylmorpholine (described in the previous step) instead of 3-iodo-5-piperidin-1-yl-1H-pyrrolo[2,3-b]pyridine, 139 mg (3.50 mmol) of sodium hydride (60% in paraffin oil) and 529 mg (2.80 mmol) of tosyl chloride in 10 ml of anhydrous DMF. 1.08 g of the title compound are obtained.

Yield: 92%.

MH+: 512.4.

Step 4: 1-(3-Chloro-2-fluorobenzyl)-4-(5-(trans-2,6-dimethylmorpholino)-1-tosyl-1H-pyrrolo[2,3-b]pyridin-3-yl)pyridin-2(1H)-one

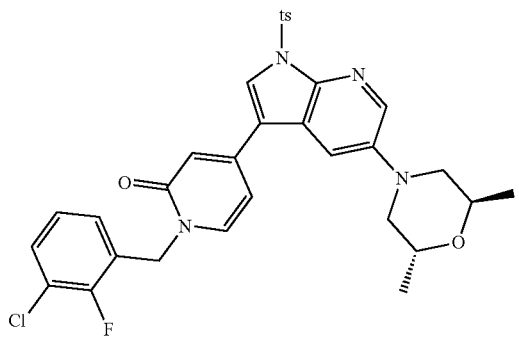

The compound is obtained by the procedure described in example 9 step 4, using 50 mg (0.098 mmol) of 4-(3-iodo-1-tosyl-1H-pyrrolo[2,3-b]pyridin-5-yl)-trans-2,6-dimethylmorpholine (described in the previous step) instead of 3-iodo-5-piperidin-1-yl-1-tosyl-1H-pyrrolo[2,3-b]pyridine, 39 mg (0.137 mmol) of 1-(3-chloro-2-fluorobenzyl)-2-oxo-1,2-dihydropyridin-4-ylboronic acid (described in example 32 step 1) and 10 mg of PdCl$_2$(PPh$_3$)$_2$. 15 mg of the title compound are obtained.
Yield: 25%.
MH+: 621.6; 623.6.

Step 5: 1-(3-Chloro-2-fluorobenzyl)-4-(5-(trans-2,6-dimethylmorpholino)-1H-pyrrolo[2,3-b]pyridin-3-yl)pyridin-2(1H)-one

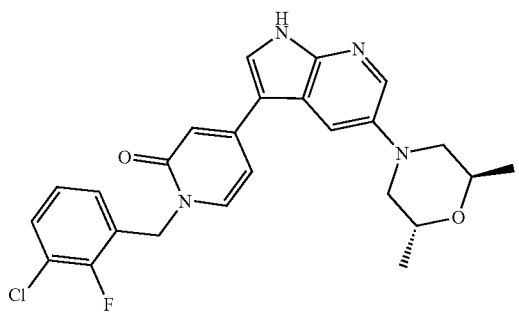 [SMILES: C[C@@H]1CN(c2cnc3[nH]cc(-c4ccn(Cc5cccc(Cl)c5F)c(=O)c4)c3c2)C[C@@H](C)O1]

The compound is obtained by the procedure described in example 110 step 6, using 33 mg (0.053 mmol) of 1-(3-chloro-2-fluorobenzyl)-4-(5-(trans-2,6-dimethylmorpholino)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 5.0 mg of the title compound are obtained.
Yield: 44%.
MH+: 467.5; 469.5.
$^1$H NMR (DMSO-d6, 300 MHz): δ 12.06 (br s, 1H); 8.14 (d, J=2.5 Hz, 1H); 8.09 (s, 1H); 7.75 (d, J=7.0 Hz, 1H); 7.66 (d, J=2.6 Hz, 1H); 7.57-7.49 (m, 1H); 7.25-7.10 (m, 2H); 6.75 (dd, J=7.2 and 1.9 Hz, 1H); 6.71 (d, J=1.8 Hz, 1H); 5.18 (s, 2H); 4.17-4.03 (m, 2H); 3.23-3.11 (m, 2H); 2.91-2.79 (m, 2H); 1.26 (s, 3H); 1.24 (s, 3H).

Example 113: 1-(3-Chloro-2-fluorobenzyl)-4-(5-(2,2,6,6-tetrafluoromorpholino)-1H-pyrrolo[2,3-b]pyridin-3-yl)pyridin-2(1H)-one Step 1: 2,2,6,6-Tetrafluoro-4-(1-((2-(trimethylsilyl)ethoxy)methyl)-1H-pyrrolo[2,3-b]pyridin-5-yl)morpholine

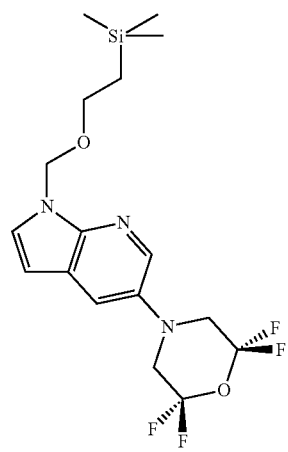

In 5 ml of anhydrous toluene are dissolved 313 mg (1.20 mmol) of 5-bromo-1-(2-trimethylsilylethoxymethyl)-1H-pyrrolo[2,3-b]pyridine (described in example 10 step 1) and 200 mg (1.26 mmol) of 2,2,6,6-tetrafluoromorpholine. Argon is bubbled through the solution for 10 minutes, then 123 mg (0.24 mmol) of Pd(PtBu$_3$)$_2$ and 288 mg (3.00 mmol) of sodium tert-butoxide are added. Argon is bubbled for another 10 minutes and the solution is stirred at 110° C. for 16 h. After cooling to ambient temperature, the reaction mixture is diluted with ethyl acetate, washed 3 times with water, dried over sodium sulfate, filtered, and evaporated under reduced pressure. Crude product is purified by flash chromatography with a 30 g silica gel column and an ethyl acetate/hexane mixture as eluent. 396 mg of the title compound are obtained.
Yield: 83%.
MH+: 406.6.

Step 2: 2,2,6,6-Tetrafluoro-4-(1H-pyrrolo[2,3-b]pyridin-5-yl)morpholine

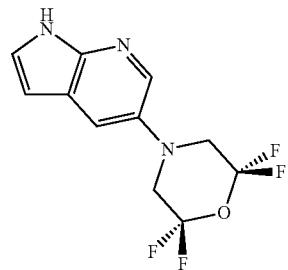

The compound is obtained by the procedure described in example 10 step 3, using 396 mg (0.98 mmol) of 2,2,6,6-tetrafluoro-4-(1-((2-(trimethylsilyl)ethoxy)methyl)-1H-pyrrolo[2,3-b]pyridin-5-yl)morpholine (described in the previous step) instead of 5-(4-cyanopiperidin-1-yl)-1-(2-trimethylsilylethoxymethyl)-1H-pyrrolo[2,3-b]pyridine, 98 µl (1.47 mmol) of ethylenediamine, 4.9 ml+4.9 ml (4.9 mmol+4.9 mmol) of TBAF (1M in THF) in 4 ml of anhydrous THF. 179 mg of the title compound are obtained.

Yield: 67%.

MH+: 276.4.

Step 3: 2,2,6,6-Tetrafluoro-4-(3-iodo-1H-pyrrolo[2,3-b]pyridin-5-yl)morpholine

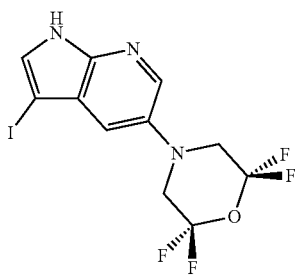

The compound is obtained by the procedure described in example 9 step 2, using 179 mg (0.65 mmol) of 2,2,6,6-tetrafluoro-4-(1H-pyrrolo[2,3-b]pyridin-5-yl)morpholine (described in the previous step) instead of 5-piperidin-1-yl-1H-pyrrolo[2,3-b]pyridine and 161 mg (0.72 mmol) of N-iodosuccinimide in 4 ml of acetone. 215 mg of the title compound are obtained.

Yield: 82%.

MH+: 402.4.

Step 4: 2,2,6,6-Tetrafluoro-4-(3-iodo-1-tosyl-1H-pyrrolo[2,3-b]pyridin-5-yl)morpholine

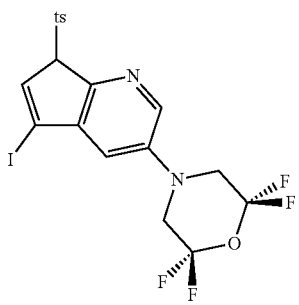

The compound is obtained by the procedure described in example 9 step 3, using 215 mg (0.54 mmol) of 2,2,6,6-tetrafluoro-4-(3-iodo-1H-pyrrolo[2,3-b]pyridin-5-yl)morpholine (described in the previous step) instead of 3-iodo-5-piperidin-1-yl-1H-pyrrolo[2,3-b]pyridine, 32 mg (0.80 mmol) of sodium hydride (60% in paraffin oil) and 113 mg (0.59 mmol) of tosyl chloride in 3 ml of anhydrous DMF. 259 mg of the title compound are obtained.

Yield: 87%.

MH+: 556.4.

Step 5: 1-(3-Chloro-2-fluorobenzyl)-4-(5-(2,2,6,6-tetrafluoromorpholino)-1-tosyl-1H-pyrrolo[2,3-b]pyridin-3-yl)pyridin-2(1H)-one

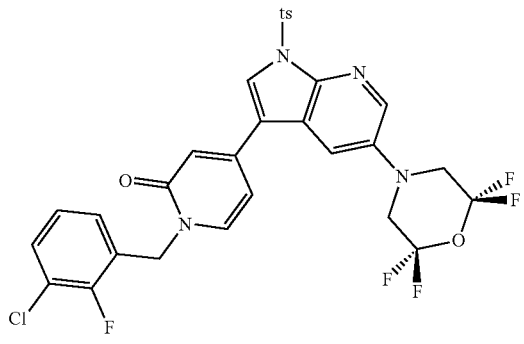

The compound is obtained by the procedure described in example 110 step 5, using 90 mg (0.162 mmol) of 2,2,6,6-tetrafluoro-4-(3-iodo-1-tosyl-1H-pyrrolo[2,3-b]pyridin-5-yl)morpholine (described in previous step) instead of 8-(3-iodo-1-tosyl-1H-pyrrolo[2,3-b]pyridin-5-yl)-3-oxa-8-azabicyclo[3.2.1]octane, 50 mg (0.178 mmol) of 1-(3-chloro-2-fluorobenzyl)-2-oxo-1,2-dihydropyridin-4-ylboronic acid (described in example 32 step 1) and 11 mg of PdCl$_2$(PPh$_3$)$_2$. 44 mg of the title compound are obtained.

Yield: 41%.

MH+: 665.5; 667.5.

Step 6: 1-(3-Chloro-2-fluorobenzyl)-4-(5-(2,2,6,6-tetrafluoromorpholino)-1H-pyrrolo[2,3-b]pyridin-3-yl)pyridin-2(1H)-one

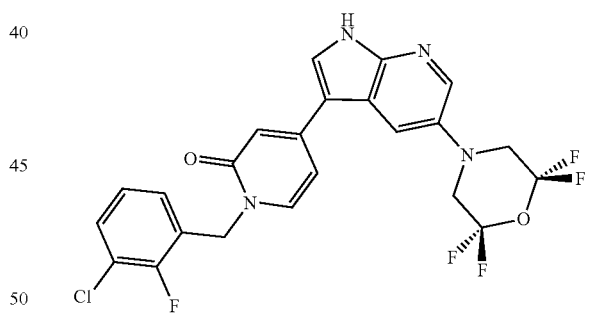

The compound is obtained by the procedure described in example 110 step 6, using 44 mg (0.066 mmol) of 1-(3-chloro-2-fluorobenzyl)-4-(5-(2,2,6,6-tetrafluoromorpholino)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 17.5 mg of the title compound are obtained.

Yield: 51%.

MH+: 511.5; 513.5.

$^1$H NMR (DMSO-d6, 300 MHz): δ 12.18 (br s, 1H); 8.23 (d, J=2.5 Hz, 1H); 8.18 (s, 1H); 7.96 (d, J=2.5 Hz, 1H); 7.76 (d, J=7.1 Hz, 1H); 7.58-7.49 (m, 1H); 7.26-7.11 (m, 2H); 6.84 (d, J=1.8 Hz, 1H); 6.79 (dd, J=7.2 and 2.0 Hz, 1H); 5.19 (s, 2H); 4.10-3.95 (m, 4H).

Example 114: 4-(5-(6-Oxa-3-azabicyclo[3.1.1]heptan-3-yl)-1H-pyrrolo[2,3-b]pyridin-3-yl)-1-(3-chloro-2-fluorobenzyl)pyridin-2(1H)-one

Step 1: 3-(1-((2-(Trimethylsilyl)ethoxy)methyl)-1H-pyrrolo[2,3-b]pyridin-5-yl)-6-oxa-3-azabicyclo[3.1.1]heptane

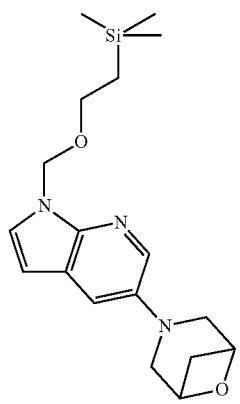 [SMILES: C[Si](C)(C)CCOCn1ccc2cc(N3CC4CC(C3)O4)cnc21]

The compound is obtained by the procedure described in example 10 step 2, using 251 mg (0.77 mmol) of 5-bromo-1-(2-trimethylsilylethoxymethyl)-1H-pyrrolo[2,3-b]pyridine, 250 mg (0.92 mmol) of 6-oxa-3-azabicyclo[3.1.1]heptane tosylate instead of 4-cyanopiperidine, 21 mg (0.023 mmol) of Pd(dba)$_3$, 40 mg (0.069 mmol) of xantphos and 199 mg (2.07 mmol) of tBuONa. Crude product is purified by flash chromatography on a 30 g silica gel column with an ethyl acetate/hexane mixture as eluent. 148 mg of the title compound are obtained.

Yield: 56%.
MH+: 346.5.

Step 2: 3-(1H-Pyrrolo[2,3-b]pyridin-5-yl)-6-oxa-3-azabicyclo[3.1.1]heptane

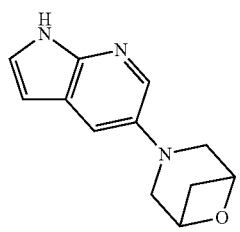 [SMILES: c1cc2cc(N3CC4CC(C3)O4)cnc2[nH]1]

The compound is obtained by the procedure described in example 10 step 3, using 148 mg (0.43 mmol) of 3-(1-((2-(trimethylsilyl)ethoxy)methyl)-1H-pyrrolo[2,3-b]pyridin-5-yl)-6-oxa-3-azabicyclo[3.1.1]heptane (described in the previous step) instead of 5-(4-cyanopiperidin-1-yl)-1-(2-trimethylsilylethoxymethyl)-1H-pyrrolo[2,3-b]pyridine, 43 µl (0.64 mmol) of ethylenediamine, 1.3 ml+0.9 ml (1.3 mmol+0.9 mmol) of TBAF (1M in THF) in 2 ml of anhydrous THF. 81 mg of the title compound are obtained.

Yield: 88%.
MH+: 216.3.

Step 3: 3-(3-Iodo-1H-pyrrolo[2,3-b]pyridin-5-yl)-6-oxa-3-azabicyclo[3.1.1]heptane

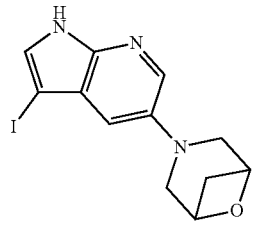 [SMILES: Ic1c[nH]c2ncc(N3CC4CC(C3)O4)cc12]

The compound is obtained by the procedure described in example 9 step 2, using 81 mg (0.37 mmol) of 3-(1H-pyrrolo[2,3-b]pyridin-5-yl)-6-oxa-3-azabicyclo[3.1.1]heptane (described in the previous step) instead of 5-piperidin-1-yl-1H-pyrrolo[2,3-b]pyridine and 93 mg (0.41 mmol) of N-iodosuccinimide in 10 ml of acetone. 73 mg of the title compound are obtained.

Yield: 57%.
MH+: 342.4.

Step 4: 3-(3-Iodo-1-tosyl-1H-pyrrolo[2,3-b]pyridin-5-yl)-6-oxa-3-azabicyclo[3.1.1]heptane

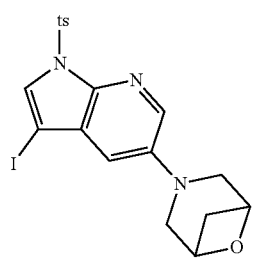

The compound is obtained by the procedure described in example 9 step 3, using mg (0.21 mmol) of 3-(3-iodo-1H-pyrrolo[2,3-b]pyridin-5-yl)-6-oxa-3-azabicyclo[3.1.1]heptane (described in the previous step) instead of 3-iodo-5-piperidin-1-yl-1H-pyrrolo[2,3-b]pyridine, 13 mg (0.32 mmol) of sodium hydride (60% in paraffin oil) and 49 mg (0.26 mmol) of tosyl chloride in 10 ml of anhydrous DMF. 103 mg of the title compound are obtained.

Yield: 97%.
MH+: 496.4.

Step 5: 4-(5-(6-Oxa-3-azabicyclo[3.1.1]heptan-3-yl)-1-tosyl-1H-pyrrolo[2,3-b]pyridin-3-yl)-1-(3-chloro-2-fluorobenzyl)pyridin-2(1H)-one

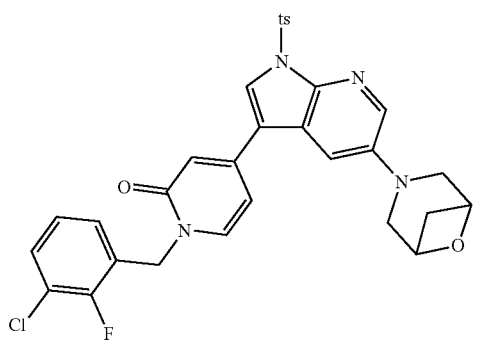

The compound is obtained by the procedure described in example 110 step 5, using 103 mg (0.208 mmol) of 3-(3-iodo-1-tosyl-1H-pyrrolo[2,3-b]pyridin-5-yl)-6-oxa-3-azabicyclo[3.1.1]heptane (described in previous step) instead of 8-(3-iodo-1-tosyl-1H-pyrrolo[2,3-b]pyridin-5-yl)-3-oxa-8-azabicyclo[3.2.1]octane, 82 mg (0.291 mmol) of 1-(3-chloro-2-fluorobenzyl)-2-oxo-1,2-dihydropyridin-4-ylboronic acid (described in example 32 step 1) and 20 mg of PdCl$_2$(PPh$_3$)$_2$. 45 mg of the title compound are obtained.
Yield: 36%.
MH+: 605.6; 607.6.

Step 6: 4-(5-(6-Oxa-3-azabicyclo[3.1.1]heptan-3-yl)-1H-pyrrolo[2,3-b]pyridin-3-yl)-1-(3-chloro-2-fluorobenzyl)pyridin-2(1H)-one

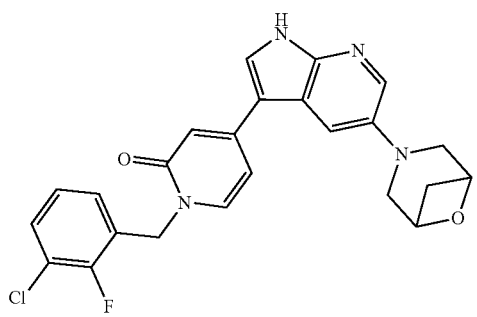 [SMILES: O=c1cc(-c2c[nH]c3ncc(N4CC5CC(C4)O5)cc23)ccn1Cc1cccc(Cl)c1F]

The compound is obtained by the procedure described in example 110 step 6, using 45 mg (0.074 mmol) of 4-(5-(6-oxa-3-azabicyclo[3.1.1]heptan-3-yl)-1-tosyl-1H-pyrrolo[2,3-b]pyridin-3-yl)-1-(3-chloro-2-fluorobenzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one.
14 mg of the title compound are obtained.
Yield: 42%.
MH+: 451.4; 453.5.
$^1$H NMR (DMSO-d6, 300 MHz): δ 11.94 (br s, 1H); 8.06 (s, 1H); 8.01 (d, J=2.4 Hz, 1H); 7.73 (d, J=7.2 Hz, 1H); 7.57-7.49 (m, 1H); 7.45 (d, J=2.6 Hz, 1H); 7.25-7.11 (m, 2H); 6.77 (dd, J=7.2 and 1.8 Hz, 1H); 6.71 (d, J=1. Hz, 1H); 5.17 (s, 2H); 4.74 (d, J=6.1 Hz, 2H) 3.69 (d, J=11.2 Hz, 2H); 3.45 (d, J=11.3 Hz, 2H); 2.00 (d, J=8.4 Hz, 2H).

Example 115: 4-(5-(2-Oxa-5-azabicyclo[2.2.1]heptan-5-yl)-1H-pyrrolo[2,3-b]pyridin-3-yl)-1-(3-chloro-2-fluorobenzyl)pyridin-2(1H)-one Step 1: 5-(1-((2-(Trimethylsilyl)ethoxy)methyl)-1H-pyrrolo[2,3-b]pyridin-5-yl)-2-oxa-5-azabicyclo[2.2.1]heptane

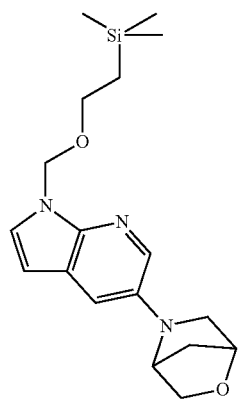 [SMILES: C[Si](C)(C)CCOCn1ccc2cc(N3CC4CC3CO4)cnc21]

The compound is obtained by the procedure described in example 10 step 2, using 503 mg (1.54 mmol) of 5-bromo-1-(2-trimethylsilylethoxymethyl)-1H-pyrrolo[2,3-b]pyridine, 250 mg (1.8 mmol) of 2-oxa-5-azabicyclo[2.2.1]heptane hydrochloride instead of 4-cyanopiperidine, 42 mg (0.046 mmol) of Pd(dba)$_3$, 80 mg (0.138 mmol) of xantphos and 399 mg (4.14 mmol) of tBuONa. Crude product is purified by flash chromatography on a 30 g silica gel column with an ethyl acetate/hexane mixture as eluent. 82 mg of the title compound are obtained.
Yield: 15%.
MH+: 346.5.

Step 2: 5-(1H-Pyrrolo[2,3-b]pyridin-5-yl)-2-oxa-5-azabicyclo[2.2.1]heptane

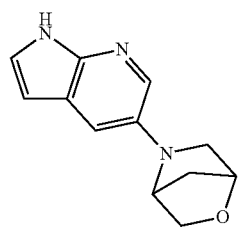 [SMILES: c1cc2cc(N3CC4CC3CO4)cnc2[nH]1]

The compound is obtained by the procedure described in example 10 step 3, using 82 mg (0.24 mmol) of 5-(1-((2-(trimethylsilyl)ethoxy)methyl)-1H-pyrrolo[2,3-b]pyridin-5-yl)-2-oxa-5-azabicyclo[2.2.1]heptane (described in the previous step) instead of 5-(4-cyanopiperidin-1-yl)-1-(2-trimethylsilylethoxymethyl)-1H-pyrrolo[2,3-b]pyridine, 24 µl (0.35 mmol) of ethylenediamine, 0.72 ml+0.47 ml (0.72 mmol+0.47 mmol) of TBAF (1M in THF) in 2 ml of anhydrous THF. 22 mg of the title compound are obtained.
Yield: 43%.
MH+: 216.3.

Step 3: 5-(3-Iodo-1H-pyrrolo[2,3-b]pyridin-5-yl)-2-oxa-5-azabicyclo[2.2.1]heptane

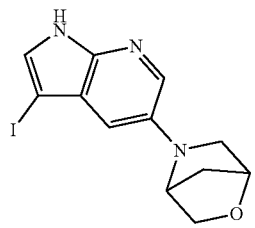 [SMILES: Ic1c[nH]c2ncc(N3CC4CC3CO4)cc12]

The compound is obtained by the procedure described in example 9 step 2, using mg (0.102 mmol) of 5-(1H-pyrrolo[2,3-b]pyridin-5-yl)-2-oxa-5-azabicyclo[2.2.1]heptane (described in the previous step) instead of 5-piperidin-1-yl-1H-pyrrolo[2,3-b]pyridine and 35 mg (0.153 mmol) of N-iodosuccinimide in 5 ml of acetone. 9 mg of the title compound are obtained.

Yield: 26%.
MH+: 342.4.

Step 4: 5-(3-Iodo-1-tosyl-1H-pyrrolo[2,3-b]pyridin-5-yl)-2-oxa-5-azabicyclo[2.2.1]heptane

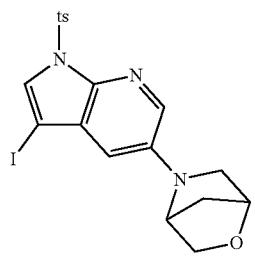

The compound is obtained by the procedure described in example 9 step 3, using mg (0.026 mmol) of 5-(3-iodo-1H-pyrrolo[2,3-b]pyridin-5-yl)-2-oxa-5-azabicyclo[2.2.1]heptane (described in the previous step) instead of 3-iodo-5-piperidin-1-yl-1H-pyrrolo[2,3-b]pyridine, 1.6 mg (0.04 mmol) of sodium hydride (60% in paraffin oil) and 5.5 mg (0.029 mmol) of tosyl chloride in 1 ml of anhydrous DMF. 6 mg of the title compound are obtained.

Yield: 77%.
MH+: 496.3.

Step 5: 4-(5-(2-Oxa-5-azabicyclo[2.2.1]heptan-5-yl)-1-tosyl-1H-pyrrolo[2,3-b]pyridin-3-yl)-1-(3-chloro-2-fluorobenzyl)pyridin-2(1H)-one

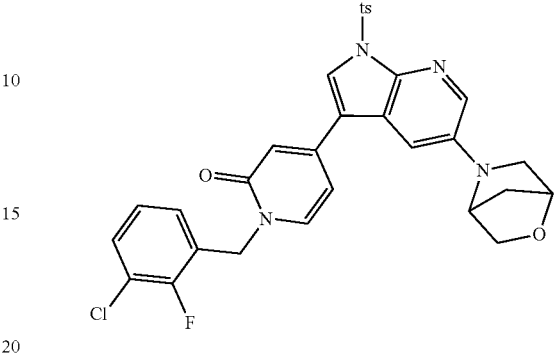

The compound is obtained by the procedure described in example 110 step 5, using 10 mg (0.02 mmol) of 5-(3-iodo-1-tosyl-1H-pyrrolo[2,3-b]pyridin-5-yl)-2-oxa-5-azabicyclo[2.2.1]heptane (described in previous step) instead of 8-(3-iodo-1-tosyl-1H-pyrrolo[2,3-b]pyridin-5-yl)-3-oxa-8-azabicyclo[3.2.1]octane, 6.3 mg (0.022 mmol) of 1-(3-chloro-2-fluorobenzyl)-2-oxo-1,2-dihydropyridin-4-ylboronic acid (described in example 32 step 1) and 1 mg of $PdCl_2(PPh_3)_2$. 1.7 mg of the title compound are obtained.

Yield: 14%.
MH+: 605.6; 607.6.

Step 6: 4-(5-(2-Oxa-5-azabicyclo[2.2.1]heptan-5-yl)-1H-pyrrolo[2,3-b]pyridin-3-yl)-1-(3-chloro-2-fluorobenzyl)pyridin-2(1H)-one

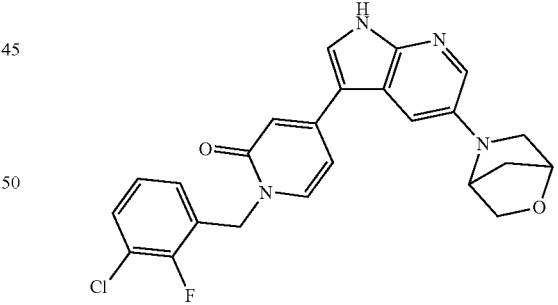

The compound is obtained by the procedure described in example 110 step 6, using 1.7 mg (0.003 mmol) of 4-(5-(2-oxa-5-azabicyclo[2.2.1]heptan-5-yl)-1-tosyl-1H-pyrrolo[2,3-b]pyridin-3-yl)-1-(3-chloro-2-fluorobenzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 1.1 mg of the title compound are obtained.

Yield: 85%.
MH+: 451.4; 453.4.

Example 116: 1-(3,4-Dichlorobenzyl)-4-(5-(3-hydroxypyrrolidin-1-yl)-1H-pyrrolo[2,3-b]pyridin-3-yl)pyridin-2(1H)-one

Step 1: Tert-butyl 3-hydroxypyrrolidine-1-carboxylate

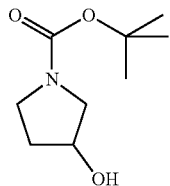

200 mg (2.30 mmol) of 3-hydroxypyrrolidine and 552 mg (2.53 mmol) of di-tert-butyl dicarbonate are dissolved in 10 ml of water and stirred at 35° C. for 3 h. After cooling to ambient temperature, the solution is diluted with water, extracted 3 times with ethyl acetate, dried over sodium sulfate, filtered and evaporated under reduced pressure. Crude product is used in the next step without further purification. 240 mg of the title compound are obtained.

Yield: Quantitative.
MH+: 188.2.

Step 2: Tert-butyl 3-(benzyloxy)pyrrolidine-1-carboxylate

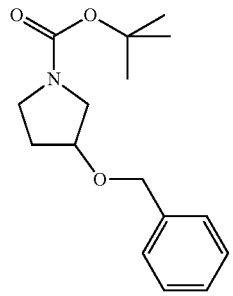 [SMILES: CC(C)(C)OC(=O)N1CCC(OCc2ccccc2)C1]

55 mg (1.39 mmol) of sodium hydride (60% in paraffin oil) are slowly added to a solution of 235 mg (1.26 mmol) of tert-butyl 3-hydroxypyrrolidine-1-carboxylate (described in the previous step) and 165 µl (1.39 mmol) of benzyl bromide in 4 ml of anhydrous DMF at 0° C. The reaction is stirred at room temperature for the night. The solution is diluted in 60 ml of water, extracted 3 times with 30 ml of DCM, dried over sodium sulfate, filtered and evaporated under reduced pressure. Crude product is used in the next step without further purification. 400 mg of the title compound are obtained.

Yield: Quantitative.
MH+: 278.4.

Step 3: 3-(Benzyloxy)pyrrolidine

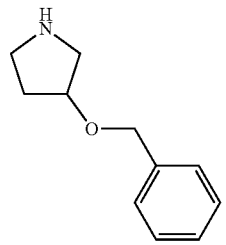 [SMILES: c1ccc(COC2CCNC2)cc1]

349 mg (1.26 mmol) of tert-butyl 3-(benzyloxy)pyrrolidine-1-carboxylate (described in the previous step) are dissolved in 12 ml of DCM and 4 ml of trifluoroacetic acid at 0° C. Ice water bath is removed after 15 min and the reaction is stirred at room temperature for 1 h. The solution is concentrated under reduced pressure and crude product is directly purified by flash chromatography on a 30 g C18 column with a water/acetonitrile mixture as eluent. 275 mg of the title compound are obtained.

Yield: Quantitative.
MH+: 178.1.

Step 4: 5-(3-(Benzyloxy)pyrrolidin-1-yl)-1-((2-(trimethylsilyl)ethoxy)methyl)-1H-pyrrolo[2,3-b]pyridine

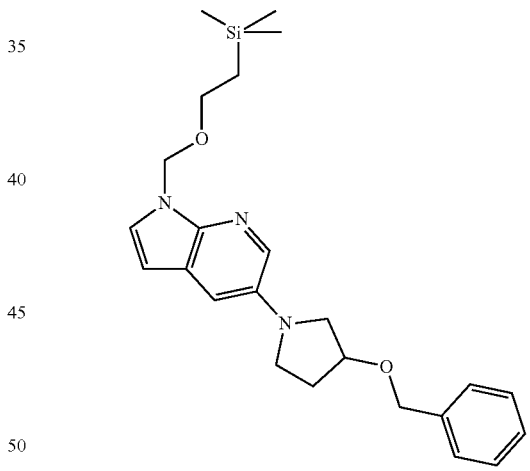

In 10 ml of anhydrous toluene are dissolved 612 mg (1.87 mmol) of 5-bromo-1-(2-trimethylsilylethoxymethyl)-1H-pyrrolo[2,3-b]pyridine (described in example 10 step 1) and 366 mg (2.06 mmol) of 3-(benzyloxy)pyrrolidine (described in the previous step). Argon is bubbled through the solution for 10 minutes, then 96 mg (0.187 mmol) of Pd(PtBu₃)₂ and 647 mg (6.73 mmol) of sodium tert-butoxide are added. Argon is bubbled for another 10 minutes and the solution is stirred at 110° C. for 45 min. After cooling to ambient temperature, the reaction mixture is diluted with ethyl acetate, washed 3 times with water, dried over sodium sulfate, filtered, and evaporated under reduced pressure. Crude product is purified by flash chromatography with a 30 g silica gel column and an ethyl acetate/hexane mixture as eluent. 286 mg of the title compound are obtained.

Yield: 36%.

MH+: 424.5.

Step 5: 5-((3-(Benzyloxy)pyrrolidin-1-yl)-1H-pyrrolo[2,3-b]pyridine

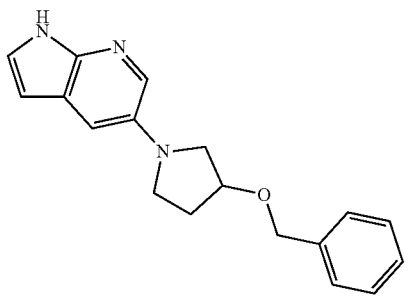 [SMILES: c1ccc(COC2CCN(c3cnc4[nH]ccc4c3)C2)cc1]

The compound is obtained by the procedure described in example 10 step 3, using 286 mg (0.75 mmol) of 5-(3-(benzyloxy)pyrrolidin-1-yl)-1-((2-(trimethylsilyl)ethoxy)methyl)-1H-pyrrolo[2,3-b]pyridine (described in the previous step) instead of 5-(4-cyanopiperidin-1-yl)-1-(2-trimethylsilylethoxymethyl)-1H-pyrrolo[2,3-b]pyridine, 68 μl (0.90 mmol) of ethylenediamine, 6.75 ml+3.37 ml (6.75 mmol+3.37 mmol) of TBAF (1M in THF) in 4 ml oh anhydrous THF. 137 mg of the title compound are obtained.

Yield: 69%.

MH+: 294.4.

Step 6: 5-(3-(Benzyloxy)pyrrolidin-1-yl)-3-iodo-1H-pyrrolo[2,3-b]pyridine

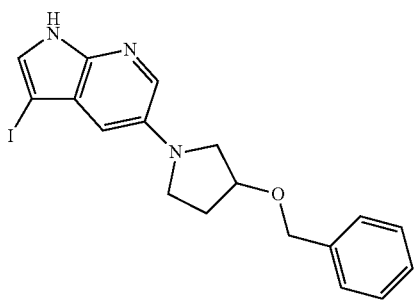 [SMILES: Ic1c[nH]c2ncc(N3CCC(OCc4ccccc4)C3)cc12]

The compound is obtained by the procedure described in example 9 step 2, using 135 mg (0.46 mmol) of 5-(3-(benzyloxy)pyrrolidin-1-yl)-1H-pyrrolo[2,3-b]pyridine (described in the previous step) instead of 5-piperidin-1-yl-1H-pyrrolo[2,3-b]pyridine and 155 mg (0.69 mmol) of N-iodosuccinimide in 6 ml of acetone. 40 mg of the title compound are obtained.

Yield: 21%.

MH+: 420.4.

Step 7: 5-(3-(Benzyloxy)pyrrolidin-1-yl)-3-iodo-1-tosyl-1H-pyrrolo[2,3-b]pyridine

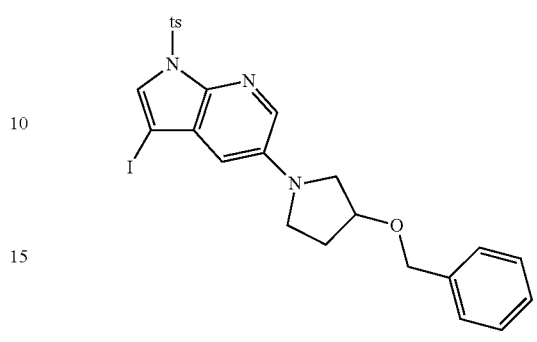

The compound is obtained by the procedure described in example 9 step 3, using 40 mg (0.095 mmol) of 5-(3-(benzyloxy)pyrrolidin-1-yl)-3-iodo-1H-pyrrolo[2,3-b]pyridine (described in the previous step) instead of 3-iodo-5-piperidin-1-yl-1H-pyrrolo[2,3-b]pyridine, 6 mg (0.143 mmol) of sodium hydride (60% in paraffin oil) and 20 mg (0.105 mmol) of tosyl chloride in 5 ml of anhydrous DMF. 28 mg of the title compound are obtained.

Yield: 51%.

MH+: 574.3.

Step 8: 4-(5-(3-(Benzyloxy)pyrrolidin-1-yl)-1-tosyl-1H-pyrrolo[2,3-b]pyridin-3-yl)-1-(3,4-dichlorobenzyl)pyridin-2(1H)-one

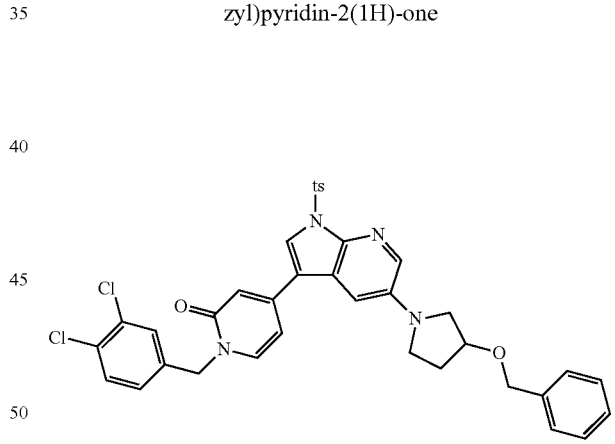

The compound is obtained by the procedure described in example 110 step 5, using 28 mg (0.049 mmol) of 5-(3-(benzyloxy)pyrrolidin-1-yl)-3-iodo-1-tosyl-1H-pyrrolo[2,3-b]pyridine (described in previous step) instead of 8-(3-iodo-1-tosyl-1H-pyrrolo[2,3-b]pyridin-5-yl)-3-oxa-8-azabicyclo[3.2.1]octane, 23 mg (0.059 mmol) of 1-(3,4-dichlorobenzyl)-2-oxo-1,2-dihydropyridin-4-ylboronic acid (described in example 33 step 1) and 6 mg of PdCl$_2$(PPh$_3$)$_2$. 8.5 mg of the title compound are obtained.

Yield: 25%.

MH+: 699.5; 701.5; 703.6.

Step 9: 1-(3,4-Dichlorobenzyl)-4-(5-(3-hydroxypyr-rolidin-1-yl)-1-tosyl-1H-pyrrolo[2,3-b]pyridin-3-yl)pyridin-2(1H)-one

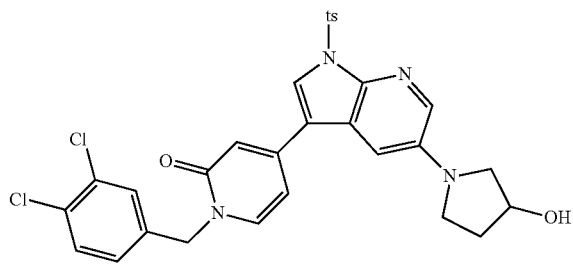

8.5 mg (0.012 mmol) of 1-(3,4-dichlorobenzyl)-4-(5-(3-hydroxypyrrolidin-1-yl)-1-tosyl-1H-pyrrolo[2,3-b]pyridin-3-yl)pyridin-2(1H)-one (described in previous step) are dissolved in a mixture of 1 ml of DCM, 4 ml of MeOH and several drops of HCl 37% under argon. 17 mg of Pd/C are added and the solution is bubbled with hydrogen for 2 h. The mixture is then filtrated on celite and evaporated under reduced pressure. Crude product is directly purified by flash chromatography with a 10 g silica gel column and an DCM/MeOH mixture as eluent. 7 mg of the title compound are obtained.

Yield: Quantitative.

MH+: 609.4; 611.3; 613.4.

Step 10: 1-(3,4-Dichlorobenzyl)-4-(5-(3-hydroxy-pyrrolidin-1-yl)-1H-pyrrolo[2,3-b]pyridin-3-yl)pyridin-2(1H)-one

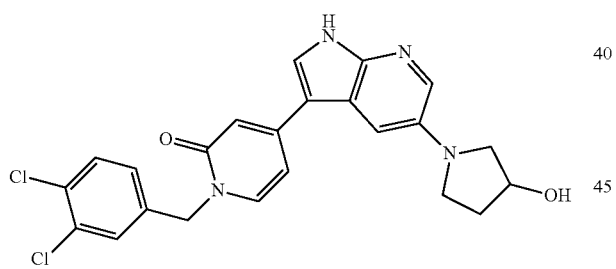

The compound is obtained by the procedure described in example 110 step 6, using 7 mg (0.011 mmol) of 1-(3,4-dichlorobenzyl)-4-(5-(3-hydroxypyrrolidin-1-yl)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 1.7 mg of the title compound are obtained.

Yield: 32%.

MH+: 455.4; 457.4; 459.4.

$^1$H NMR (DMSO-d6, 300 MHz): δ 11.88 (br s, 1H); 8.03 (d, J=1.5 Hz, 1H); 7.83-7.77 (m, 2H); 7.65-7.60 (m, 2H); 7.33 (dd, J=8.4 and 1.8 Hz, 1H); 7.21 (d, J=2.1 Hz, 1H); 6.73 (dd, J=7.9 and 1.2 Hz, 1H); 6.68 (d, J=2.0 Hz, 1H); 5.08 (s, 2H); 4.97 (d, J=3.9 Hz, 1H); 4.48-4.40 (m, 1H); 3.57-3.47 (m, 2H); 3.20-3.11 (m, 2H); 2.15-2.01 (m, 1H); 1.98-1.87 (m, 1H).

Example 117: 1-(3-Chloro-2-fluorobenzyl)-4-(5-(2-(hydroxymethyl)morpholino)-1H-pyrrolo[2,3-b]pyridin-3-yl)pyridin-2(1H)-one Step 1: Tert-butyl 2-(hydroxymethyl)morpholine-4-carboxylate

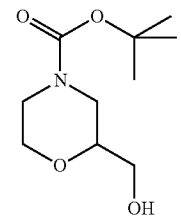

800 mg (6.83 mmol) of morpholin-2-ylmethanol and 1.64 g (7.51 mmol) of di-tert-butyl dicarbonate are dissolved in 24 ml of anhydrous THF at 0° C. The solution is stirred at room temperature for 16 h. The solution is then diluted with 60 ml of DCM, washed 2 times with 20 ml of water and 1 time with 20 ml of brine, dried over sodium sulfate, filtered and evaporated under reduced pressure. Crude product is used in the next step without further purification. 1.56 g of the title compound are obtained.

Yield: Quantitative.

MNa+: 240.4

Step 2: Tert-butyl 2-(benzyloxymethyl)morpholine-4-carboxylate

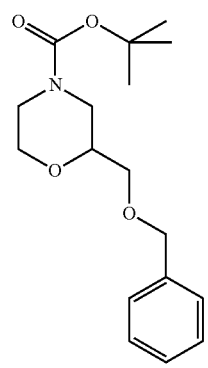 [SMILES: CC(C)(C)OC(=O)N1CCOC(COCc2ccccc2)C1]

The compound is obtained by the procedure described in example 116 step 2, using 190 mg (0.25 mmol) of sodium hydride (60% in paraffin oil), 1.56 g (7.18 mmol) of tert-butyl 2-(hydroxymethyl)morpholine-4-carboxylate (described in the previous step) instead of tert-butyl 3-hydroxy-pyrrolidine-1-carboxylate, and 165 μl (1.39 mmol) of benzyl bromide in 16 ml of anhydrous DMF. 826 mg of the title compound are obtained.

Yield: 37%.

MNa+: 330.5.

101

Step 3: 2-(Benzyloxymethyl)morpholine

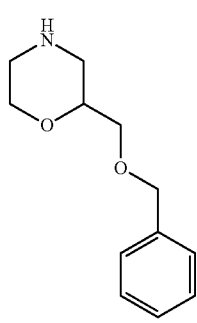 [SMILES: c1ccc(COCC2CNCCO2)cc1]

The compound is obtained by the procedure described in example 116 step 3, using 826 mg (2.69 mmol) of tert-butyl 2-(benzyloxymethyl)morpholine-4-carboxylate (described in the previous step) instead of tert-butyl 3-(benzyloxy)pyrrolidine-1-carboxylate. 474 mg of the title compound are obtained.

Yield: 85%.

MH+: 208.3.

Step 4: 2-(Benzyloxymethyl)-4-(1-((2-(trimethylsilyl)ethoxy)methyl)-1H-pyrrolo[2,3-b]pyridin-5-yl)morpholine

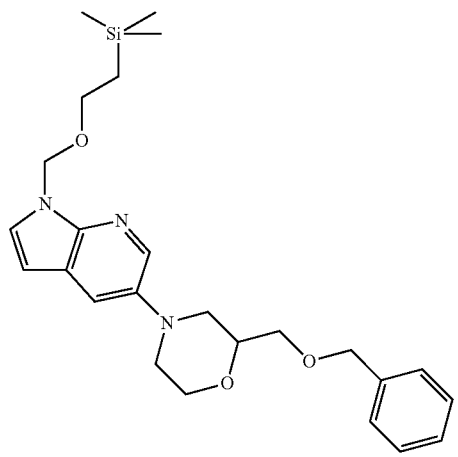 [SMILES: C[Si](C)(C)CCOCn1ccc2cc(N3CCOC(COCc4ccccc4)C3)cnc21]

The compound is obtained by the procedure described in example 116 step 4, using 553 mg (1.69 mmol) of 5-bromo-1-(2-trimethylsilylethoxymethyl)-1H-pyrrolo[2,3-b]pyridine, 420 mg (2.03 mmol) of 2-(benzyloxymethyl)morpholine instead of 3-(benzyloxy)pyrrolidine, 86 mg (0.169 mmol) of Pd(PtBu₃)₂ and 407 mg (4.23 mmol) of sodium tert-butoxide. Crude product is purified by flash chromatography on a 30 g silica gel column with an ethyl acetate/hexane mixture as eluent. 533 mg of the title compound are obtained.

Yield: 69%.

MH+: 454.8.

102

Step 5: 2-(Benzyloxymethyl)-4-(1H-pyrrolo[2,3-b]pyridin-5-yl)morpholine

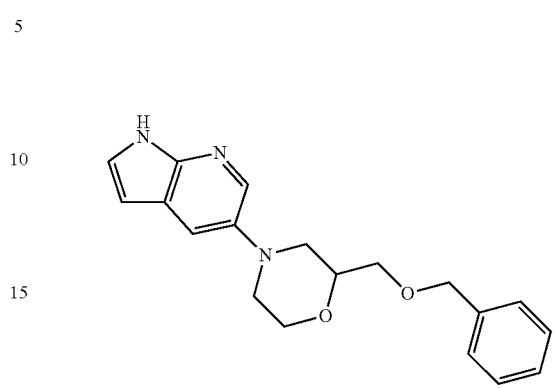

The compound is obtained by the procedure described in example 10 step 3, using 530 mg (1.17 mmol) of 2-(benzyloxymethyl)-4-(1-((2-(trimethylsilyl)ethoxy)methyl)-1H-pyrrolo[2,3-b]pyridin-5-yl)morpholine (described in the previous step) instead of 5-(4-cyanopiperidin-1-yl)-1-(2-trimethylsilylethoxymethyl)-1H-pyrrolo[2,3-b]pyridine, 118 µl (1.76 mmol) of ethylenediamine, 5.85 ml+5.85 ml (5.85 mmol+5.85 mmol) of TBAF (1M in THF) in 5 ml of anhydrous THF. 322 mg of the title compound are obtained.

Yield: 85%.

MH+: 324.4.

Step 6: 2-(Benzyloxymethyl)-4-(3-iodo-1H-pyrrolo[2,3-b]pyridin-5-yl)morpholine

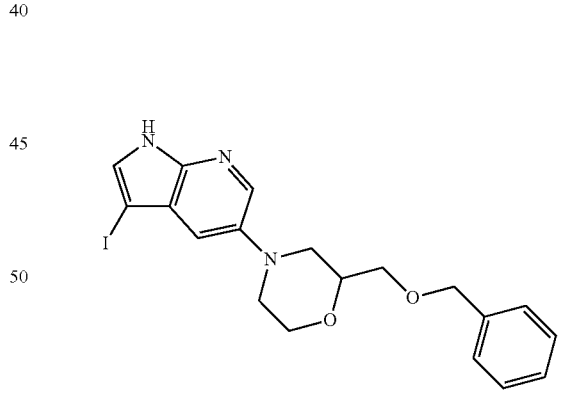

The compound is obtained by the procedure described in example 9 step 2, using 322 mg (0.99 mmol) of 2-(benzyloxymethyl)-4-(1H-pyrrolo[2,3-b]pyridin-5-yl)morpholine (described in the previous step) instead of 5-piperidin-1-yl-1H-pyrrolo[2,3-b]pyridine and 335 mg (1.49 mmol) of N-iodosuccinimide in 10 ml of acetone. 216 mg of the title compound are obtained.

Yield: 48%.

MH+: 450.3.

Step 7: 2-(Benzyloxymethyl)-4-(3-iodo-1-tosyl-1H-pyrrolo[2,3-b]pyridin-5-yl)morpholine

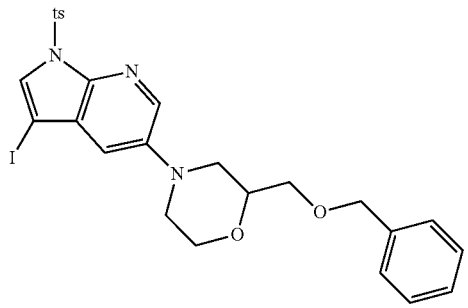

The compound is obtained by the procedure described in example 9 step 3, using 216 mg (0.48 mmol) of 2-(benzyloxymethyl)-4-(3-iodo-1H-pyrrolo[2,3-b]pyridin-5-yl)morpholine (described in the previous step) instead of 3-iodo-5-piperidin-1-yl-1H-pyrrolo[2,3-b]pyridine, 28 mg (0.72 mmol) of sodium hydride (60% in paraffin oil) and 101 mg (0.53 mmol) of tosyl chloride in 6 ml of anhydrous DMF. 235 mg of the title compound are obtained.

Yield: 81%.

MH+: 604.4.

Step 8: 4-(5-(2-(Benzyloxymethyl)morpholino)-1-tosyl-1H-pyrrolo[2,3-b]pyridin-3-yl)-1-(3-chloro-2-fluorobenzyl)pyridin-2(1H)-one

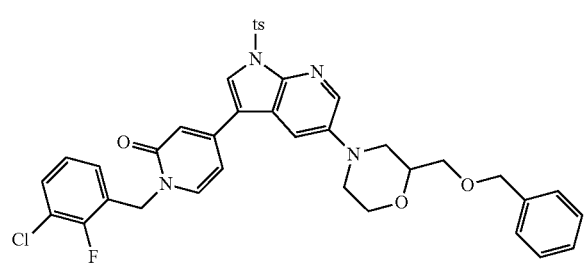

The compound is obtained by the procedure described in example 110 step 5, using 142 mg (0.235 mmol) of 2-(benzyloxymethyl)-4-(3-iodo-1-tosyl-1H-pyrrolo[2,3-b]pyridin-5-yl)morpholine (described in previous step) instead of 8-(3-iodo-1-tosyl-1H-pyrrolo[2,3-b]pyridin-5-yl)-3-oxa-8-azabicyclo[3.2.1]octane, 73 mg (0.259 mmol) of 1-(3-chloro-2-fluorobenzyl)-2-oxo-1,2-dihydropyridin-4-ylboronic acid (described in example 32 step 1) and 8 mg of PdCl$_2$(PPh$_3$)$_2$. 57 mg of the title compound are obtained.

Yield: 34%.

MH+: 713.6; 715.6; 717.6.

Step 9: 1-(3-Chloro-2-fluorobenzyl)-4-(5-(2-(hydroxymethyl)morpholino)-1-tosyl-1H-pyrrolo[2,3-b]pyridin-3-yl)pyridin-2(1H)-one

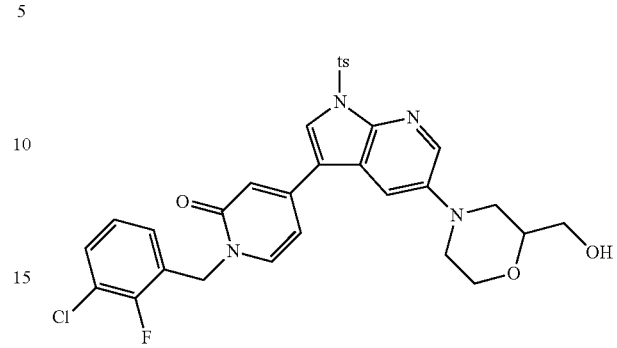

The compound is obtained by the procedure described in example 116 step 9, using 85 mg (0.119 mmol) of 4-(5-(2-(benzyloxymethyl)morpholino)-1-tosyl-1H-pyrrolo[2,3-b]pyridin-3-yl)-1-(3-chloro-2-fluorobenzyl)pyridin-2(1H)-one (described in previous step) instead of 1-(3,4-dichlorobenzyl)-4-(5-(3-hydroxypyrrolidin-1-yl)-1-tosyl-1H-pyrrolo[2,3-b]pyridin-3-yl)pyridin-2(1H)-one and 150 mg of Pd/C. 9.5 mg of the title compound are obtained.

Yield: 13%.

MH+: 623.3; 625.3; 627.3.

Step 10: 1-(3-Chloro-2-fluorobenzyl)-4-(5-(2-(hydroxymethyl)morpholino)-1H-pyrrolo[2,3-b]pyridin-3-yl)pyridin-2(1H)-one

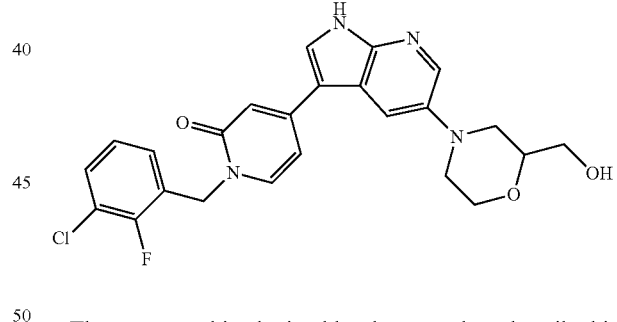

The compound is obtained by the procedure described in example 110 step 6, using 9 mg (0.014 mmol) of 1-(3-chloro-2-fluorobenzyl)-4-(5-(2-(hydroxymethyl)morpholino)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 3.8 mg of the title compound are obtained.

Yield: 55%.

MH+: 469.5; 471.4; 473.4.

$^1$H NMR (DMSO-d6, 300 MHz): δ 12.07 (br s, 1H); 8.17 (d, J=2.4 Hz, 1H); 8.10 (s, 1H); 7.75 (d, J=7.2 Hz, 1H); 7.70 (d, J=2.5 Hz, 1H); 7.57-7.49 (m, 1H); 7.26-7.11 (m, 2H); 6.75 (dd, J=7.2 and 2.0 Hz, 1H); 6.71 (d, J=1.8 Hz, 1H); 5.18 (s, 2H); 4.78 (t, J=5.6 Hz, 1H); 4.00-3.90 (m, 1H); 3.78-3.38 (m, 8H).

Example 118: 4-(5-(8-Oxa-3-azabicyclo[3.2.1]octan-3-yl)-1H-pyrrolo[2,3-b]pyridin-3-yl)-1-(3,4-dichlorobenzyl)pyridin-2(1H)-one Step 1: 3-(1-((2-(Trimethylsilyl)ethoxy)methyl)-1H-pyrrolo[2,3-b]pyridin-5-yl)-8-oxa-3-azabicyclo[3.2.1]octane

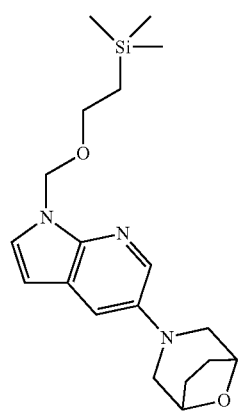 [SMILES: C[Si](C)(C)CCOCn1ccc2cc(N3CC4CCC(C3)O4)cnc21]

The compound is obtained by the procedure described in example 10 step 2, using 677 mg (2.07 mmol) of 5-bromo-1-(2-trimethylsilylethoxymethyl)-1H-pyrrolo[2,3-b]pyridine, 371 mg (2.48 mmol) of 8-oxa-3-azabicyclo[3.2.1]octane hydrochloride instead of 4-cyanopiperidine, 19 mg (0.021 mmol) of Pd(dba)₃, 36 mg (0.062 mmol) of xantphos and 497 mg (5.20 mmol) of tBuONa. Crude product is purified by flash chromatography on a 30 g silica gel column with an ethyl acetate/hexane mixture as eluent. 186 mg of the title compound are obtained.

Yield: 25%.
MH+: 360.5.

Step 2: 3-(1H-Pyrrolo[2,3-b]pyridin-5-yl)-8-oxa-3-azabicyclo[3.2.1]octane

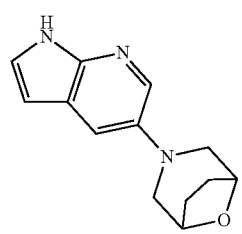 [SMILES: c1cc2cc(N3CC4CCC(C3)O4)cnc2[nH]1]

The compound is obtained by the procedure described in example 10 step 3, using 126 mg (0.52 mmol) of 3-(1-((2-(trimethylsilyl)ethoxy)methyl)-1H-pyrrolo[2,3-b]pyridin-5-yl)-8-oxa-3-azabicyclo[3.2.1]octane (described in the previous step) instead of 5-(4-cyanopiperidin-1-yl)-1-(2-trimethylsilylethoxymethyl)-1H-pyrrolo[2,3-b]pyridine, 52 µl (0.78 mmol) of ethylenediamine, 1.55 ml+1.03 ml (1.55 mmol+1.03 mmol) of TBAF (1M in THF) in 4 ml of anhydrous THF. 58 mg of the title compound are obtained.

Yield: 48%.
MH+: 230.3.

Step 3: 3-(3-Iodo-1H-pyrrolo[2,3-b]pyridin-5-yl)-8-oxa-3-azabicyclo[3.2.1]octane

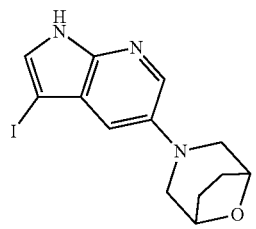 [SMILES: Ic1c[nH]c2ncc(N3CC4CCC(C3)O4)cc12]

The compound is obtained by the procedure described in example 9 step 2, using 58 mg (0.25 mmol) of 3-(1H-pyrrolo[2,3-b]pyridin-5-yl)-8-oxa-3-azabicyclo[3.2.1]octane (described in the previous step) instead of 5-piperidin-1-yl-1H-pyrrolo[2,3-b]pyridine and 85 mg (0.38 mmol) of N-iodosuccinimide in 10 ml of acetone. 50 mg of the title compound are obtained.

Yield: 56%.
MH+: 356.2.

Step 4: 3-(3-Iodo-1-tosyl-1H-pyrrolo[2,3-b]pyridin-5-yl)-8-oxa-3-azabicyclo[3.2.1]octane

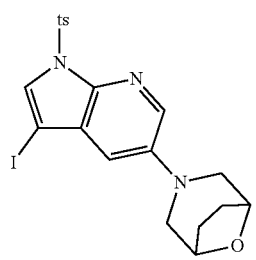

The compound is obtained by the procedure described in example 9 step 3, using mg (0.13 mmol) of 3-(3-iodo-1H-pyrrolo[2,3-b]pyridin-5-yl)-8-oxa-3-azabicyclo[3.2.1]octane (described in the previous step) instead of 3-iodo-5-piperidin-1-yl-1H-pyrrolo[2,3-b]pyridine, 8 mg (0.20 mmol) of sodium hydride (60% in paraffin oil) and 27 mg (0.14 mmol) of tosyl chloride in 2 ml of anhydrous DMF. 38 mg of the title compound are obtained.

Yield: 58%.
MH+: 510.2.

Step 5: 4-(5-(8-Oxa-3-azabicyclo[3.2.1]octan-3-yl)-1-tosyl-1H-pyrrolo[2,3-b]pyridin-3-yl)-1-(3,4-dichlorobenzyl)pyridin-2(1H)-one

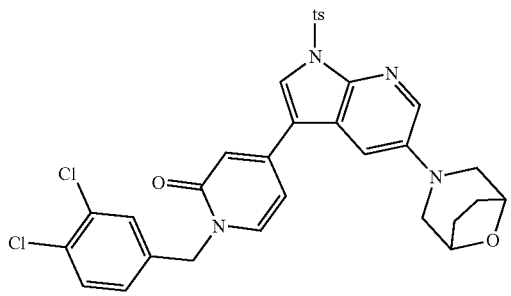

The compound is obtained by the procedure described in example 110 step 5, using 38 mg (0.075 mmol) of 3-(3-iodo-1-tosyl-1H-pyrrolo[2,3-b]pyridin-5-yl)-8-oxa-3-azabicyclo[3.2.1]octane (described in previous step) instead of 8-(3-iodo-1-tosyl-1H-pyrrolo[2,3-b]pyridin-5-yl)-3-oxa-8-azabicyclo[3.2.1]octane, 34 mg (0.090 mmol) of 1-(3,4-dichlorobenzyl)-2-oxo-1,2-dihydropyridin-4-ylboronic acid (described in example 33 step 1) and 3 mg of $PdCl_2(PPh_3)_2$. 46 mg of the title compound are obtained.

Yield: 98%.

MH+: 635.3; 637.3; 639.3.

Step 6: 4-(5-(8-Oxa-3-azabicyclo[3.2.1]octan-3-yl)-1H-pyrrolo[2,3-b]pyridin-3-yl)-1-(3,4-dichlorobenzyl)pyridin-2(1H)-one

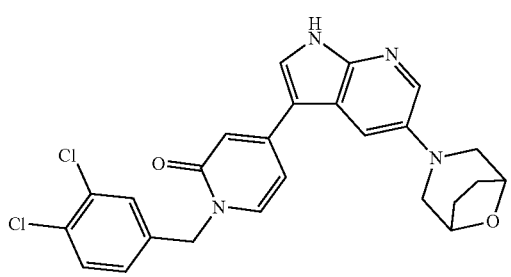 [SMILES: O=c1cc(-c2c[nH]c3ncc(N4CC5CCC(C4)O5)cc23)ccn1Cc1ccc(Cl)c(Cl)c1]

The compound is obtained by the procedure described in example 110 step 6, using 46 mg (0.072 mmol) of 4-(5-(8-oxa-3-azabicyclo[3.2.1]octan-3-yl)-1-tosyl-1H-pyrrolo[2,3-b]pyridin-3-yl)-1-(3,4-dichlorobenzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 21 mg of the title compound are obtained.

Yield: 60%.

MH+: 481.3; 483.3; 485.3.

$^1$H NMR (DMSO-d6, 300 MHz): δ 12.00 (br s, 1H); 8.10 (d, J=2.5 Hz, 1H); 8.07 (s, 1H); 7.80 (d, J=7.1 Hz, 1H); 7.67-7.60 (m, 2H); 7.58 (d, J=2.5 Hz, 1H); 7.33 (dd, J=8.4 and 2.0 Hz, 1H); 6.77-6.67 (m, 2H); 5.09 (s, 2H); 4.50-4.38 (m, 2H); 3.52-3.40 (m, 2H); 2.94-2.81 (m, 2H); 2.00-1.78 (m, 4H).

Example 119: 4-(5-(1,4-Oxazepan-4-yl)-1H-pyrrolo[2,3-b]pyridin-3-yl)-1-(3,4-dichlorobenzyl)pyridin-2(1H)-one Step 1: 4-(1H-Pyrrolo[2,3-b]pyridin-5-yl)-1,4-oxazepane

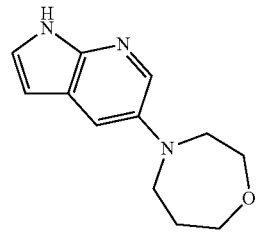 [SMILES: c1cc2cc(N3CCCOCC3)cnc2[nH]1]

The compound is obtained by the procedure described in example 9 step 1, using 500 mg (2.54 mmol) of 5-bromo-1H-pyrrolo[2,3-b]pyridine, 280 μl (3.05 mmol) of [1,4]oxazepane instead of piperidine, 12 mg (0.025 mmol) of RuPhos, 20 mg (0.025 mmol) of RuPhos Pd G2 and 6.1 ml (6.1 mmol) of LiHMDS (1M in THF). 418 mg of the title compound are obtained.

Yield: 76%.

MH+: 218.3.

Step 2: 4-(3-Iodo-1H-pyrrolo[2,3-b]pyridin-5-yl)-1,4-oxazepane

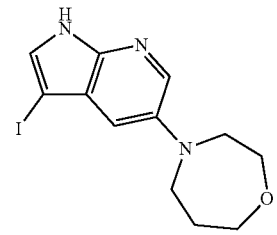 [SMILES: Ic1c[nH]c2ncc(N3CCCOCC3)cc12]

The compound is obtained by the procedure described in example 9 step 2, using 418 mg (1.92 mmol) of 4-(1H-pyrrolo[2,3-b]pyridin-5-yl)-1,4-oxazepane (described in the previous step) instead of 5-piperidin-1-yl-1H-pyrrolo[2,3-b]pyridine and 648 mg (2.88 mmol) of N-iodosuccinimide in 20 ml of acetone. 355 mg of the title compound are obtained.

Yield: 54%.

MH+: 344.3.

Step 3: 4-(3-Iodo-1-tosyl-1H-pyrrolo[2,3-b]pyridin-5-yl)-1,4-oxazepane

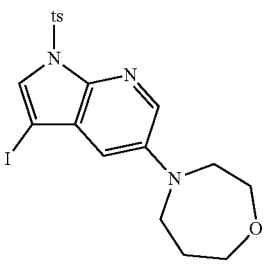

The compound is obtained by the procedure described in example 9 step 3, using 344 mg (1.00 mmol) of 4-(3-iodo-1H-pyrrolo[2,3-b]pyridin-5-yl)-1,4-oxazepane (described in the previous step) instead of 3-iodo-5-piperidin-1-yl-1H-pyrrolo[2,3-b]pyridine, 60 mg (1.50 mmol) of sodium hydride (60% in paraffin oil) and 210 mg (1.10 mmol) of tosyl chloride in 4 ml of anhydrous DMF. 352 mg of the title compound are obtained.

Yield: 71%.
MH+: 498.3.

Step 4: 4-(5-(1,4-Oxazepan-4-yl)-1-tosyl-1H-pyrrolo[2,3-b]pyridin-3-yl)-1-(3,4-dichlorobenzyl)pyridin-2(1H)-one

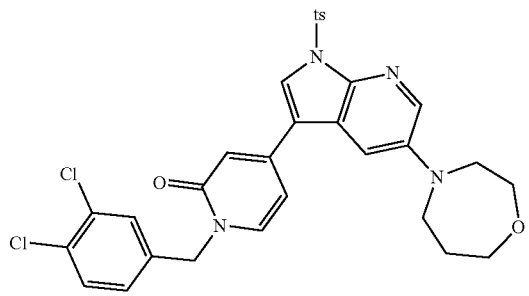

The compound is obtained by the procedure described in example 9 step 4, using 50 mg (0.101 mmol) of 4-(3-iodo-1-tosyl-1H-pyrrolo[2,3-b]pyridin-5-yl)-1,4-oxazepane (described in the previous step) instead of 3-iodo-5-piperidin-1-yl-1-tosyl-1H-pyrrolo[2,3-b]pyridine, 46 mg (0.121 mmol) of 1-(3,4-dichlorobenzyl)-2-oxo-1,2-dihydropyridin-4-ylboronic acid (described in example 33 step 1) and 4 mg of PdCl$_2$(PPh$_3$)$_2$. 60 mg of the title compound are obtained.

Yield: 95%.
MH+: 623.3; 625.3; 627.3.

Step 5: 4-(5-(1,4-Oxazepan-4-yl)-1H-pyrrolo[2,3-b]pyridin-3-yl)-1-(3,4-dichlorobenzyl)pyridin-2(1H)-one

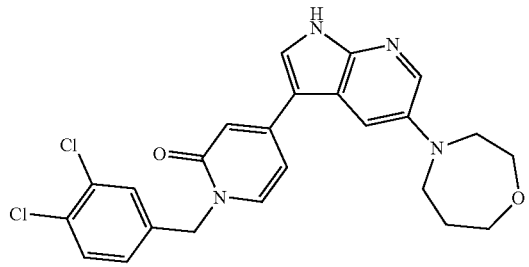 [SMILES: O=c1cc(-c2c[nH]c3ncc(N4CCCOCC4)cc23)ccn1Cc1ccc(Cl)c(Cl)c1]

The compound is obtained by the procedure described in example 110 step 6, using 60 mg (0.096 mmol) of 4-(5-(1,4-oxazepan-4-yl)-1-tosyl-1H-pyrrolo[2,3-b]pyridin-3-yl)-1-(3,4-dichlorobenzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 18 mg of the title compound are obtained.

Yield: 40%.

MH+: 469.3; 471.4; 473.3.

$^1$H NMR (DMSO-d6, 300 MHz): δ 11.93 (br s, 1H); 8.03 (s, 1H); 8.02 (d, J=2.6 Hz, 1H); 7.80 (d, J=7.2 Hz, 1H); 7.65-7.60 (m, 2H); 7.45 (d, J=2.6 Hz, 1H); 7.33 (dd, J=8.3 and 2.0 Hz, 1H); 6.72 (dd, J=7.2 and 2.0 Hz, 1H); 6.67 (d, J=1.9 Hz, 1H); 5.08 (s, 2H); 3.81-3.74 (m, 2H); 3.68-3.56 (m, 6H); 2.02-1.90 (m, 2H).

Example 120: 1-(3-Chloro-2-fluorobenzyl)-4-(5-(6-hydroxy-1,4-oxazepan-4-yl)-1H-pyrrolo[2,3-b]pyridin-3-yl)pyridin-2(1H)-one Step 1: Tert-butyl 6-(benzyloxy)-1,4-oxazepane-4-carboxylate

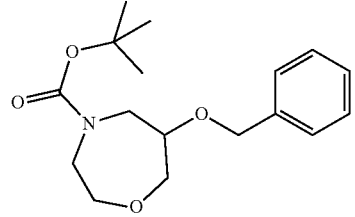 [SMILES: CC(C)(C)OC(=O)N1CCOCC(OCc2ccccc2)C1]

The compound is obtained by the procedure described in example 116 step 2, using 203 mg (5.06 mmol) of sodium hydride (60% in paraffin oil), 1 g (4.60 mmol) of tert-butyl 6-hydroxy-1,4-oxazepane-4-carboxylate instead of tert-butyl 3-hydroxypyrrolidine-1-carboxylate, and 602 µl (5.06 mmol) of benzyl bromide in 10 ml of anhydrous DMF. 780 mg of the title compound are obtained.

Yield: 55%.
MNa+: 330.6.

Step 2: 6-(Benzyloxy)-1,4-oxazepane

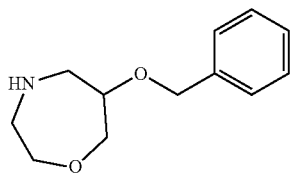 [SMILES: c1ccc(COC2CNCCOC2)cc1]

The compound is obtained by the procedure described in example 116 step 3, using 780 mg (2.54 mmol) of tert-butyl 6-(benzyloxy)-1,4-oxazepane-4-carboxylate (described in the previous step) instead of tert-butyl 3-(benzyloxy)pyrrolidine-1-carboxylate. 487 mg of the title compound are obtained.

Yield: 93%.
MH+: 208.4.

Step 3: 6-(Benzyloxy)-4-(1-((2-(trimethylsilyl)ethoxy)methyl)-1H-pyrrolo[2,3-b]pyridin-5-yl)-1,4-oxazepane

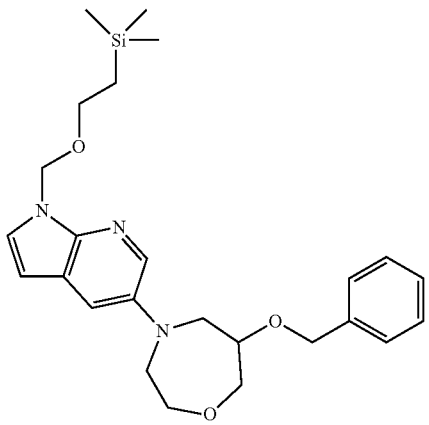 [SMILES: C[Si](C)(C)CCOCn1ccc2cc(N3CCOCC(OCc4ccccc4)C3)cnc21]

The compound is obtained by the procedure described in example 116 step 4, using 736 mg (2.25 mmol) of 5-bromo-1-(2-trimethylsilylethoxymethyl)-1H-pyrrolo[2,3-b]pyridine, 490 mg (2.36 mmol) of 6-(benzyloxy)-1,4-oxazepane instead of 3-(benzyloxy)pyrrolidine, 115 mg (0.225 mmol) of Pd(PtBu₃)₂ and 541 mg (5.63 mmol) of sodium tert-butoxide. Crude product is purified by flash chromatography on a 30 g silica gel column with an ethyl acetate/hexane mixture as eluent. 700 mg of the title compound are obtained.

Yield: 69%.

MH+: 454.7.

Step 4: 6-(Benzyloxy)-4-(1H-pyrrolo[2,3-b]pyridin-5-yl)-1,4-oxazepane

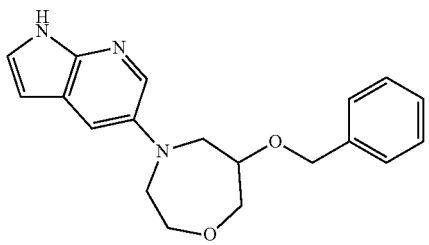 [SMILES: c1ccc(COC2COCCN(c3cnc4[nH]ccc4c3)C2)cc1]

The compound is obtained by the procedure described in example 10 step 3, using 700 mg (1.54 mmol) of 6-(benzyloxy)-4-(1-((2-(trimethylsilyl)ethoxy)methyl)-1H-pyrrolo[2,3-b]pyridin-5-yl)-1,4-oxazepane (described in the previous step) instead of 5-(4-cyanopiperidin-1-yl)-1-(2-trimethylsilylethoxymethyl)-1H-pyrrolo[2,3-b]pyridine, 155 µl (2.31 mmol) of ethylenediamine, 12.3 ml+4.15 ml (12.3 mmol+4.15 mmol) of TBAF (1M in THF) in 5 ml of anhydrous THF. 500 mg of the title compound are obtained.

Yield: Quantitative.

MH+: 324.5.

Step 5: 6-(Benzyloxy)-4-(3-iodo-1H-pyrrolo[2,3-b]pyridin-5-yl)-1,4-oxazepane

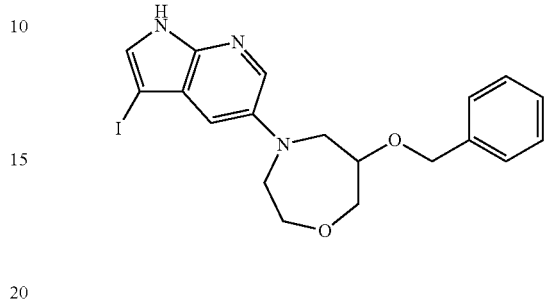

The compound is obtained by the procedure described in example 9 step 2, using 500 mg (1.55 mmol) of 6-(benzyloxy)-4-(1H-pyrrolo[2,3-b]pyridin-5-yl)-1,4-oxazepane (described in the previous step) instead of 5-piperidin-1-yl-1H-pyrrolo[2,3-b]pyridine and 385 mg (1.71 mmol) of N-iodosuccinimide in 5 ml of acetone. 222 mg of the title compound are obtained.

Yield: 32%.

MH+: 450.5.

Step 6: 6-(Benzyloxy)-4-(3-iodo-1-tosyl-1H-pyrrolo[2,3-b]pyridin-5-yl)-1,4-oxazepane

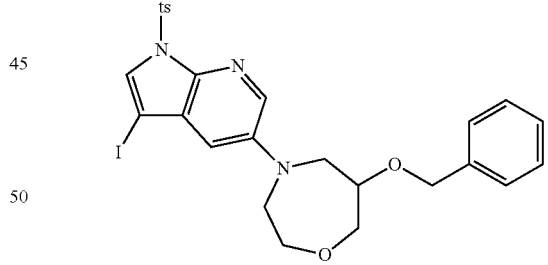

The compound is obtained by the procedure described in example 9 step 3, using 222 mg (0.49 mmol) of 6-(benzyloxy)-4-(3-iodo-1H-pyrrolo[2,3-b]pyridin-5-yl)-1,4-oxazepane (described in the previous step) instead of 3-iodo-5-piperidin-1-yl-1H-pyrrolo[2,3-b]pyridine, 30 mg (0.74 mmol) of sodium hydride (60% in paraffin oil) and 104 mg (0.54 mmol) of tosyl chloride in 4 ml of anhydrous DMF. 206 mg of the title compound are obtained.

Yield: 69%.

MH+: 604.4.

Step 7: 4-(5-(6-(Benzyloxy)-1,4-oxazepan-4-yl)-1-tosyl-1H-pyrrolo[2,3-b]pyridin-3-yl)-1-(3-chloro-2-fluorobenzyl)pyridin-2(1H)-one

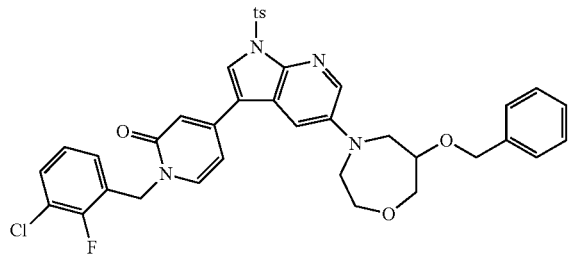

The compound is obtained by the procedure described in example 110 step 5, using 100 mg (0.166 mmol) of 6-(benzyloxy)-4-(3-iodo-1-tosyl-1H-pyrrolo[2,3-b]pyridin-5-yl)-1,4-oxazepane (described in previous step) instead of 8-(3-iodo-1-tosyl-1H-pyrrolo[2,3-b]pyridin-5-yl)-3-oxa-8-azabicyclo[3.2.1]octane, 52 mg (0.183 mmol) of 1-(3-chloro-2-fluorobenzyl)-2-oxo-1,2-dihydropyridin-4-ylboronic acid (described in example 32 step 1) and 12 mg of PdCl$_2$(PPh$_3$)$_2$. 27 mg of the title compound are obtained.

Yield: 23%.

MH+: 713.5; 715.5; 717.6.

Step 8: 1-(3-Chloro-2-fluorobenzyl)-4-(5-(6-hydroxy-1,4-oxazepan-4-yl)-1-tosyl-1H-pyrrolo[2,3-b]pyridin-3-yl)pyridin-2(1H)-one

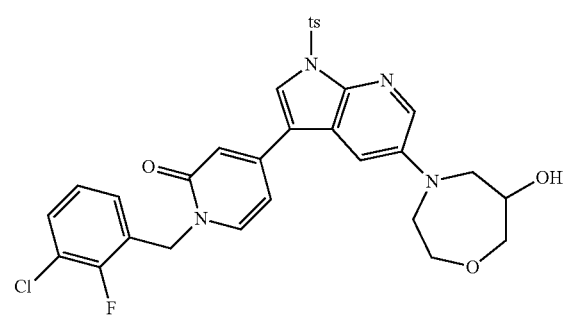

The compound is obtained by the procedure described in example 116 step 9, using 27 mg (0.038 mmol) of 4-(5-(6-(benzyloxy)-1,4-oxazepan-4-yl)-1-tosyl-1H-pyrrolo[2,3-b]pyridin-3-yl)-1-(3-chloro-2-fluorobenzyl)pyridin-2(1H)-one (described in previous step) instead of 1-(3,4-dichlorobenzyl)-4-(5-(3-hydroxypyrrolidin-1-yl)-1-tosyl-1H-pyrrolo[2,3-b]pyridin-3-yl)pyridin-2(1H)-one and 80 mg of Pd/C. 10 mg of the title compound are obtained.

Yield: 42%.

MH+: 623.5; 625.5; 627.5.

Step 9: 1-(3-Chloro-2-fluorobenzyl)-4-(5-(6-hydroxy-1,4-oxazepan-4-yl)-1H-pyrrolo[2,3-b]pyridin-3-yl)pyridin-2(1H)-one

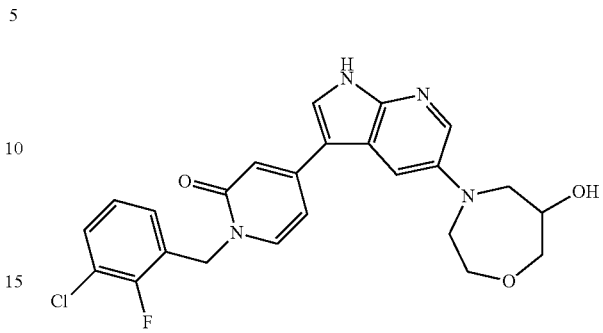

The compound is obtained by the procedure described in example 110 step 6, using 10 mg (0.016 mmol) of 1-(3-chloro-2-fluorobenzyl)-4-(5-(6-hydroxy-1,4-oxazepan-4-yl)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 3.8 mg of the title compound are obtained.

Yield: 51%.

MH+: 469.5; 471.5; 473.5.

$^1$H NMR (DMSO-d6, 300 MHz): δ 11.93 (br s, 1H); 8.07 (d, J=2.6 Hz, 1H); 8.04 (s, 1H); 7.73 (d, J=7.1 Hz, 1H); 7.60 (d, J=2.6 Hz, 1H); 7.56-7.49 (m, 1H); 7.26-7.12 (m, 2H); 6.74 (dd, J=7.2 and 2.0 Hz, 1H); 6.68 (d, J=1.8 Hz, 1H); 5.17 (s, 2H); 5.08 (m, 1H); 4.09-3.96 (m, 1H); 3.92-3.41 (m, 8H).

Example 122: 4-(5-(1,2,5-Oxadiazepan-5-yl)-1H-pyrrolo[2,3-b]pyridin-3-yl)-1-(3-chloro-2-fluorobenzyl)pyridin-2(1H)-one

Step 1: Tert-butyl 5-(1-((2-(trimethylsilyl)ethoxy)methyl)-1H-pyrrolo[2,3-b]pyridin-5-yl)-1,2,5-oxadiazepane-2-carboxylate

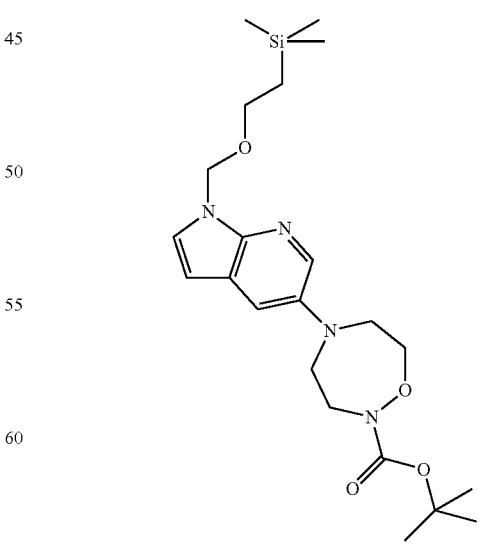

The compound is obtained by the procedure described in example 116 step 4, using 700 mg (2.14 mmol) of 5-bromo- 1-(2-trimethylsilylethoxymethyl)-1H-pyrrolo[2,3-b]pyridine, 561 mg (2.35 mmol) of [1,2,5]-oxadiazepane-2-carboxylic acid tert-butyl ester hydrochloride instead of 3-(benzyloxy)pyrrolidine, 55 mg (0.107 mmol) of Pd(PtBu$_3$)$_2$ and 494 mg (5.14 mmol) of sodium tert-butoxide. Crude product is purified by flash chromatography on a 30 g silica gel column with an ethyl acetate/hexane mixture as eluent. 540 mg of the title compound are obtained.
Yield: 56%.
MH+: 449.7.

Step 2: Tert-butyl 5-(1H-pyrrolo[2,3-b]pyridin-5-yl)-1,2,5-oxadiazepane-2-carboxylate

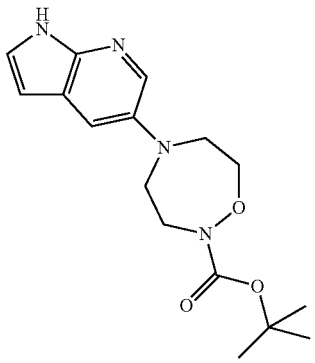 [SMILES: CC(C)(C)OC(=O)N1CCN(c2cnc3[nH]ccc3c2)CCO1]

The compound is obtained by the procedure described in example 10 step 3, using 540 mg (1.20 mmol) of tert-butyl 5-(1-((2-(trimethylsilyl)ethoxy)methyl)-1H-pyrrolo[2,3-b]pyridin-5-yl)-1,2,5-oxadiazepane-2-carboxylate (described in the previous step) instead of 5-(4-cyanopiperidin-1-yl)-1-(2-trimethylsilylethoxymethyl)-1H-pyrrolo[2,3-b]pyridine, 120 µl (1.80 mmol) of ethylenediamine, 6 ml+9.6 ml (6 mmol+9.6 mmol) of TBAF (1M in THF) in 5 ml of anhydrous THF. 278 mg of the title compound are obtained.
Yield: 73%.
MH+: 319.5.

Step 3: Tert-butyl 5-(3-iodo-1H-pyrrolo[2,3-b]pyridin-5-yl)-1,2,5-oxadiazepane-2-carboxylate

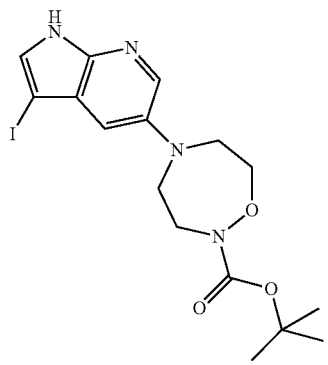 [SMILES: CC(C)(C)OC(=O)N1CCN(c2cnc3[nH]cc(I)c3c2)CCO1]

The compound is obtained by the procedure described in example 9 step 2, using 278 mg (0.873 mmol) of tert-butyl 5-(1H-pyrrolo[2,3-b]pyridin-5-yl)-1,2,5-oxadiazepane-2-carboxylate (described in the previous step) instead of 5-piperidin-1-yl-1H-pyrrolo[2,3-b]pyridine and 216 mg (0.96 mmol) of N-iodosuccinimide in 12 ml of acetone. 306 mg of the title compound are obtained.
Yield: 79%.
MH+: 445.5.

Step 4: Tert-butyl 5-(3-iodo-1-tosyl-1H-pyrrolo[2,3-b]pyridin-5-yl)-1,2,5-oxadiazepane-2-carboxylate

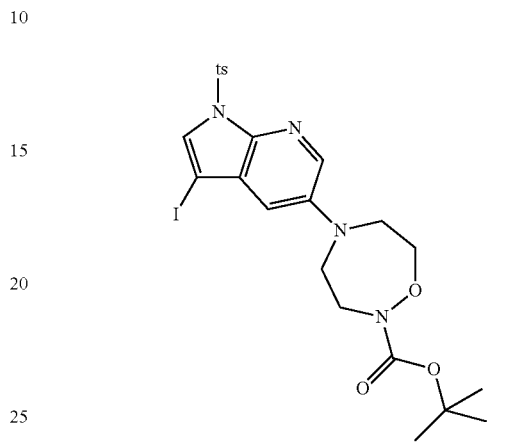

The compound is obtained by the procedure described in example 9 step 3, using 306 mg (0.689 mmol) of tert-butyl 5-(3-iodo-1H-pyrrolo[2,3-b]pyridin-5-yl)-1,2,5-oxadiazepane-2-carboxylate (described in the previous step) instead of 3-iodo-5-piperidin-1-yl-1H-pyrrolo[2,3-b]pyridine, 42 mg (1.03 mmol) of sodium hydride (60% in paraffin oil) and 158 mg (0.827 mmol) of tosyl chloride in 4 ml of anhydrous DMF. 296 mg of the title compound are obtained.
Yield: 72%.
MH+: 599.6.

Step 5: Tert-butyl 5-(3-(1-(3-chloro-2-fluorobenzyl)-2-oxo-1,2-dihydropyridin-4-yl)-1-tosyl-1H-pyrrolo[2,3-b]pyridin-5-yl)-1,2,5-oxadiazepane-2-carboxylate

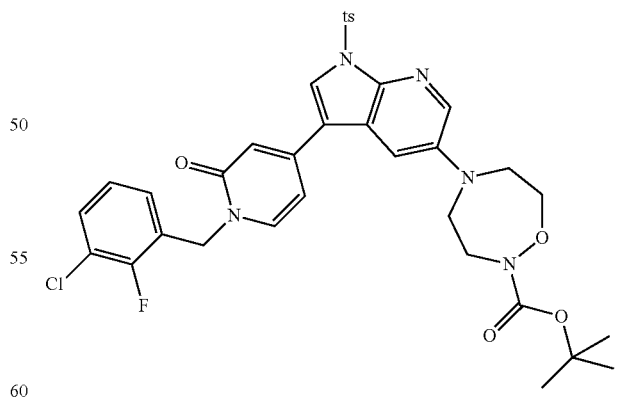

The compound is obtained by the procedure described in example 110 step 5, using 334 mg (0.558 mmol) of tert-butyl 5-(3-iodo-1-tosyl-1H-pyrrolo[2,3-b]pyridin-5-yl)-1,2,5-oxadiazepane-2-carboxylate (described in previous step) instead of 8-(3-iodo-1-tosyl-1H-pyrrolo[2,3-b]pyridin-5-yl)-3-oxa-8-azabicyclo[3.2.1]octane, 165 mg (0.586 mmol)

of 1-(3-chloro-2-fluorobenzyl)-2-oxo-1,2-dihydropyridin-4-ylboronic acid (described in example 32 step 1) and 39 mg of PdCl$_2$(PPh$_3$)$_2$. 130 mg of the title compound are obtained.
Yield: 33%.
MH+: 708.6; 710.6.

Step 6: 4-(5-(1,2,5-Oxadiazepan-5-yl)-1H-pyrrolo[2,3-b]pyridin-3-yl)-1-(3-chloro-2-fluorobenzyl)pyridin-2(1H)-one

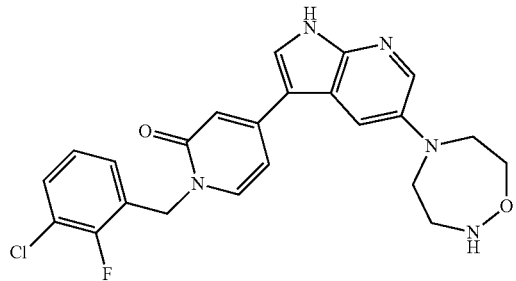 [SMILES: O=c1cc(-c2c[nH]c3ncc(N4CCNOCC4)cc23)ccn1Cc1cccc(Cl)c1F]

The compound is obtained by the procedure described in example 110 step 6, using 130 mg (0.184 mmol) of tert-butyl 5-(3-(1-(3-chloro-2-fluorobenzyl)-2-oxo-1,2-dihydropyridin-4-yl)-1-tosyl-1H-pyrrolo[2,3-b]pyridin-5-yl)-1,2,5-oxadiazepane-2-carboxylate (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 19 mg of the title compound are obtained.
Yield: 23%.
MH+: 454.5; 456.5.
$^1$H NMR (DMSO-d6, 300 MHz): δ 11.90 (br s, 1H); 8.09-7.95 (m, 2H); 7.73 (d, J=7.2 Hz, 1H); 7.58-7.39 (m, 2H); 7.26-7.10 (m, 2H); 6.88 (s, 1H); 6.73 (dd, J=7.2 and 1.9 Hz, 1H); 6.65 (d, J=1. Hz, 1H); 5.17 (s, 2H); 3.90-3.73 (m, 4H); 3.71-3.61 (m, 2H); 3.15-3.04 (m, 2H).

Example 123: 4-(5-(2-Oxa-6-azaspiro[3.3]heptan-6-yl)-1H-pyrrolo[2,3-b]pyridin-3-yl)-1-(3,4-dichlorobenzyl)pyridin-2(1H)-one Step 1: 6-(1-((2-(Trimethylsilyl)ethoxy)methyl)-1H-pyrrolo[2,3-b]pyridin-5-yl)-2-oxa-6-azaspiro[3.3]heptane

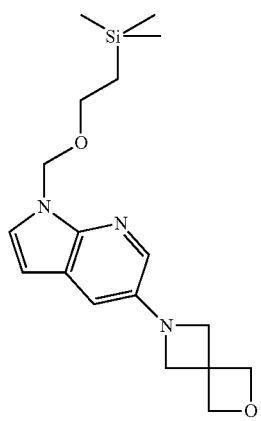 [SMILES: C[Si](C)(C)CCOCn1ccc2cc(N3CC4(COC4)C3)cnc21]

The compound is obtained by the procedure described in example 10 step 2, using 1.00 g (3.10 mmol) of 5-bromo-1-(2-trimethylsilylethoxymethyl)-1H-pyrrolo[2,3-b]pyridine, 369 mg (3.72 mmol) of 2-oxo-6-azaspiro[3.3]-heptane instead of 4-cyanopiperidine, 28 mg (0.031 mmol) of Pd(dba)$_3$, 54 mg (0.093 mmol) of xantphos and 452 mg (4.70 mmol) of tBuONa. Crude product is purified by flash chromatography on a 30 g silica gel column with an ethyl acetate/hexane mixture as eluent. 676 mg of the title compound are obtained.
Yield: 63%.
MH+: 346.5.

Step 2: 6-(1H-Pyrrolo[2,3-b]pyridin-5-yl)-2-oxa-6-azaspiro[3.3]heptane

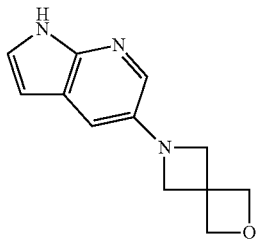 [SMILES: c1cc2cc(N3CC4(COC4)C3)cnc2[nH]1]

The compound is obtained by the procedure described in example 10 step 3, using 676 mg (1.96 mmol) of 6-(1-((2-(trimethylsilyl)ethoxy)methyl)-1H-pyrrolo[2,3-b]pyridin-5-yl)-2-oxa-6-azaspiro[3.3]heptane (described in the previous step) instead of 5-(4-cyanopiperidin-1-yl)-1-(2-trimethylsilylethoxymethyl)-1H-pyrrolo[2,3-b]pyridine, 197 μl (2.94 mmol) of ethylenediamine, 5.88 ml+3.92 ml (5.88 mmol+3.92 mmol) of TBAF (1M in THF) in 17 ml of anhydrous THF. 130 mg of the title compound are obtained.
Yield: 31%.
MH+: 216.2.

Step 3: 6-(3-Iodo-1H-pyrrolo[2,3-b]pyridin-5-yl)-2-oxa-6-azaspiro[3.3]heptane

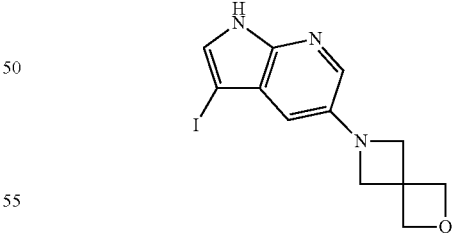

The compound is obtained by the procedure described in example 9 step 2, using 130 mg (0.60 mmol) of 6-(1H-pyrrolo[2,3-b]pyridin-5-yl)-2-oxa-6-azaspiro[3.3]heptane (described in the previous step) instead of 5-piperidin-1-yl-1H-pyrrolo[2,3-b]pyridine and 204 mg (0.91 mmol) of N-iodosuccinimide in 10 ml of acetone. 80 mg of the title compound are obtained.
Yield: 39%.
MH+: 342.2.

Step 4: 6-(3-Iodo-1-tosyl-1H-pyrrolo[2,3-b]pyridin-5-yl)-2-oxa-6-azaspiro[3.3]heptane

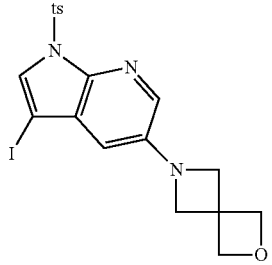

The compound is obtained by the procedure described in example 9 step 3, using 125 mg (0.37 mmol) of 6-(3-iodo-1H-pyrrolo[2,3-b]pyridin-5-yl)-2-oxa-6-azaspiro[3.3]heptane (described in the previous step) instead of 3-iodo-5-piperidin-1-yl-1H-pyrrolo[2,3-b]pyridine, 22 mg (0.55 mmol) of sodium hydride (60% in paraffin oil) and 77 mg (0.40 mmol) of tosyl chloride in 5 ml of anhydrous DMF. 45 mg of the title compound are obtained.

Yield: 25%.

MH+: 496.3.

Step 5: 4-(5-(2-Oxa-6-azaspiro[3.3]heptan-6-yl)-1-tosyl-1H-pyrrolo[2,3-b]pyridin-3-yl)-1-(3,4-dichlorobenzyl)pyridin-2(1H)-one

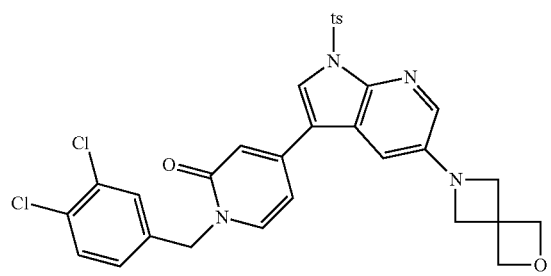

The compound is obtained by the procedure described in example 110 step 5, using 45 mg (0.091 mmol) of 6-(3-iodo-1-tosyl-1H-pyrrolo[2,3-b]pyridin-5-yl)-2-oxa-6-azaspiro[3.3]heptane (described in previous step) instead of 8-(3-iodo-1-tosyl-1H-pyrrolo[2,3-b]pyridin-5-yl)-3-oxa-8-azabicyclo[3.2.1]octane, 41 mg (0.110 mmol) of 1-(3,4-dichlorobenzyl)-2-oxo-1,2-dihydropyridin-4-ylboronic acid (described in example 33 step 1) and 3 mg of PdCl$_2$(PPh$_3$)$_2$. 32 mg of the title compound are obtained.

Yield: 57%.

MH+: 621.4; 623.4; 625.4.

Step 6: 4-(5-(2-Oxa-6-azaspiro[3.3]heptan-6-yl)-1H-pyrrolo[2,3-b]pyridin-3-yl)-1-(3,4-dichlorobenzyl)pyridin-2(1H)-one

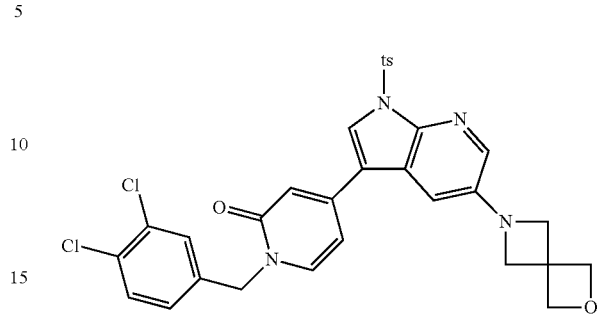

The compound is obtained by the procedure described in example 110 step 6, using 32 mg (0.052 mmol) of 4-(5-(2-oxa-6-azaspiro[3.3]heptan-6-yl)-1-tosyl-1H-pyrrolo[2,3-b]pyridin-3-yl)-1-(3,4-dichlorobenzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 6.5 mg of the title compound are obtained.

Yield: 36%.

MH+: 467.4; 469.4; 471.4.

$^1$H NMR (DMSO-d6, 300 MHz): δ 12.00 (br s, 1H); 8.07 (s, 1H); 7.80 (d, J=7.1 Hz, 1H); 7.70-7.59 (m, 3H); 7.33 (dd, J=8.3 and 2.0 Hz, 1H); 7.21 (d, J=2.5 Hz, 1H); 6.75-6.65 (m, 2H); 5.09 (s, 2H); 4.73 (s, 4H); 4.06 (s, 4H).

Example 124: 1-(3,4-Dichlorobenzyl)-4-(5-(cis-hexahydro-1H-furo[3,4-c]pyrrol-5-yl)-1H-pyrrolo[2,3-b]pyridin-3-yl)pyridin-2(1H)-one

Step 1: 5-(1-((2-(Trimethylsilyl)ethoxy)methyl)-1H-pyrrolo[2,3-b]pyridin-5-yl)-cis-hexahydro-1H-furo[3,4-c]pyrrole

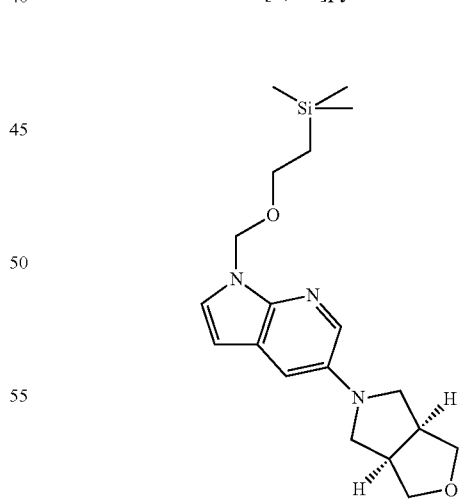

The compound is obtained by the procedure described in example 10 step 2, using 390 mg (1.19 mmol) of 5-bromo-1-(2-trimethylsilylethoxymethyl)-1H-pyrrolo[2,3-b]pyridine, 214 mg (1.43 mmol) of cis-hexahydro-1H-furo[3,4-c]pyrrole hydrochloride instead of 4-cyanopiperidine, 33 mg (0.036 mmol) of Pd(dba)$_3$, 62 mg (0.107 mmol) of xantphos and 286 mg (3.00 mmol) of tBuONa. Crude product is

121 purified by flash chromatography on a 30 g silica gel column with an ethyl acetate/hexane mixture as eluent. 191 mg of the title compound are obtained.

Yield: 45%.
MH+: 360.5.

Step 2: 5-(1H-Pyrrolo[2,3-b]pyridin-5-yl)-cis-hexahydro-1H-furo[3,4-c]pyrrole

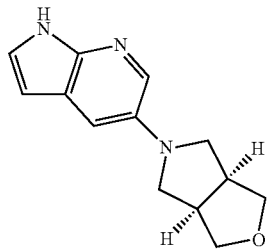 [SMILES: c1cc2cc(N3C[C@H]4COC[C@H]4C3)cnc2[nH]1]

The compound is obtained by the procedure described in example 10 step 3, using 191 mg (0.531 mmol) of 5-(1-((2-(trimethylsilyl)ethoxy)methyl)-1H-pyrrolo[2,3-b]pyridin-5-yl)-cis-hexahydro-1H-furo[3,4-c]pyrrole (described in the previous step) instead of 5-(4-cyanopiperidin-1-yl)-1-(2-trimethylsilylethoxymethyl)-1H-pyrrolo[2,3-b]pyridine, 53 µl (0.797 mmol) of ethylenediamine, 1.59 ml+1.06 ml (1.59 mmol+1.06 mmol) of TBAF (1M in THF) in 3 ml of anhydrous THF. 85 mg of the title compound are obtained.

Yield: 70%.
MH+: 230.3.

Step 3: 5-(3-Iodo-1H-pyrrolo[2,3-b]pyridin-5-yl)-cis-hexahydro-1H-furo[3,4-c]pyrrole

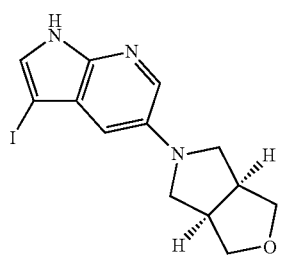 [SMILES: Ic1c[nH]c2ncc(N3C[C@H]4COC[C@H]4C3)cc12]

The compound is obtained by the procedure described in example 9 step 2, using 85 mg (0.371 mmol) of 5-(1H-pyrrolo[2,3-b]pyridin-5-yl)-cis-hexahydro-1H-furo[3,4-c]pyrrole (described in the previous step) instead of 5-piperidin-1-yl-1H-pyrrolo[2,3-b]pyridine and 125 mg (0.556 mmol) of N-iodosuccinimide in 5 ml of acetone. 28 mg of the title compound are obtained.

Yield: 21%.
MH+: 356.2.

Step 4: 5-(3-Iodo-1-tosyl-1H-pyrrolo[2,3-b]pyridin-5-yl)-cis-hexahydro-1H-furo[3,4-c]pyrrole

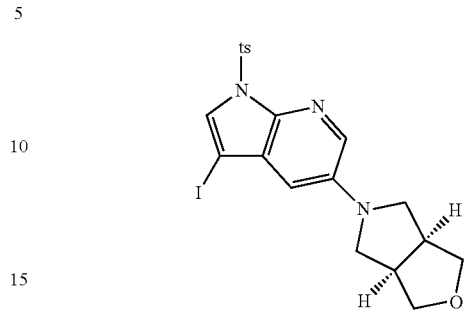

The compound is obtained by the procedure described in example 9 step 3, using 28 mg (0.079 mmol) of 5-(3-iodo-1H-pyrrolo[2,3-b]pyridin-5-yl)-cis-hexahydro-1H-furo[3,4-c]pyrrole (described in the previous step) instead of 3-iodo-5-piperidin-1-yl-1H-pyrrolo[2,3-b]pyridine, 5 mg (0.118 mmol) of sodium hydride (60% in paraffin oil) and 17 mg (0.087 mmol) of tosyl chloride in 3 ml of anhydrous DMF. 26 mg of the title compound are obtained.

Yield: 65%.
MH+: 510.2.

Step 5: 1-(3,4-Dichlorobenzyl)-4-(5-(cis-dihydro-1H-furo[3,4-c]pyrrol-5-yl)-1-tosyl-1H-pyrrolo[2,3-b]pyridin-3-yl)pyridin-2(1H)-one

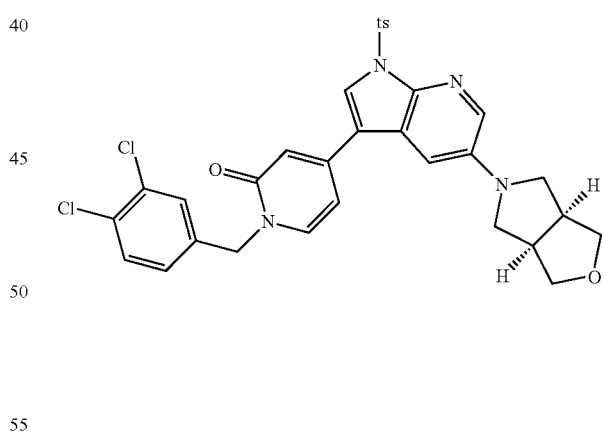

The compound is obtained by the procedure described in example 110 step 5, using 26 mg (0.051 mmol) of 5-(3-iodo-1-tosyl-1H-pyrrolo[2,3-b]pyridin-5-yl)-cis-hexahydro-1H-furo[3,4-c]pyrrole (described in previous step) instead of 8-(3-iodo-1-tosyl-1H-pyrrolo[2,3-b]pyridin-5-yl)-3-oxa-8-azabicyclo[3.2.1]octane, 24 mg (0.061 mmol) of 1-(3,4-dichlorobenzyl)-2-oxo-1,2-dihydropyridin-4-ylboronic acid (described in example 33 step 1) and 3 mg of PdCl$_2$(PPh$_3$)$_2$. 19 mg of the title compound are obtained.

Yield: 59%.
MH+: 635.2; 637.2; 639.1.

Step 6: 1-(3,4-Dichlorobenzyl)-4-(5-(cis-hexahydro-1H-furo[3,4-c]pyrrol-5-yl)-1H-pyrrolo[2,3-b]pyridin-3-yl)pyridin-2(1H)-one

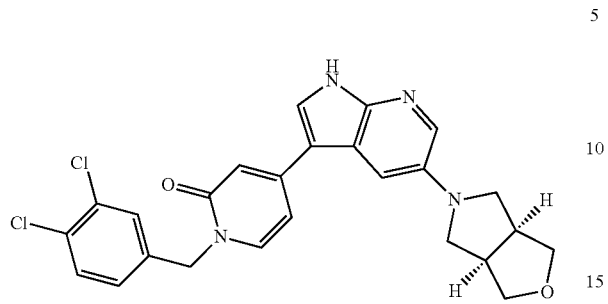

The compound is obtained by the procedure described in example 110 step 6, using 19 mg (0.030 mmol) of 1-(3,4-dichlorobenzyl)-4-(5-(cis-dihydro-1H-furo[3,4-c]pyrrol-5-yl)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 8.8 mg of the title compound are obtained.

Yield: 61%.

MH+: 481.3; 483.4; 485.3.

$^1$H NMR (DMSO-d6, 300 MHz): δ 11.95 (br s, 1H); 8.06 (s, 1H); 7.93 (d, J=2.5 Hz, 1H); 7.79 (d, J=7.2 Hz, 1H); 7.67-7.60 (m, 2H); 7.39 (d, J=2.5 Hz, 1H); 7.33 (dd, J=8.3 and 2.0 Hz, 1H); 6.73 (dd, J=7.2 and 2.0 Hz, 1H); 6.69 (d, J=1.8 Hz, 1H); 5.09 (s, 2H); 3.91-3.79 (m, 2H); 3.63-3.53 (m, 2H); 3.43-3.35 (m, 2H); 3.29-3.21 (m, 2H); 3.07-2.93 (m, 2H).

Example 127: 1-(3,4-Dichlorobenzyl)-4-(5-(3-hydroxyazetidin-1-yl)-1H-pyrrolo[2,3-b]pyridin-3-yl)pyridin-2(1H)-one Step 1: Tert-butyl 3-hydroxyazetidine-1-carboxylate

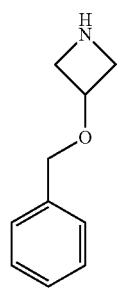

1 g (9.13 mmol) of 3-hydroxyazetidine hydrochloride, 1.27 ml (9.13 mmol) of triethylamine and 2.18 g (10 mmol) of di-tert-butyl dicarbonate are dissolved in a mixture of 25 ml of anhydrous THF and 4 ml of water at 0° C. The solution is stirred at room temperature for 16 h. The solution is then diluted with 60 ml of DCM, washed 2 times with 20 ml of water and 1 time with 20 ml of brine, dried over sodium sulfate, filtered and evaporated under reduced pressure. Crude product is used in the next step without further purification. 1.07 g of the title compound are obtained.

Yield: 68%.

MNa+: 196.2.

Step 2: Tert-butyl 3-(benzyloxy)azetidine-1-carboxylate

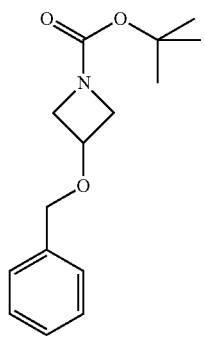 [SMILES: CC(C)(C)OC(=O)N1CC(OCc2ccccc2)C1]

The compound is obtained by the procedure described in example 116 step 2, using 248 mg (6.19 mmol) of sodium hydride (60% in paraffin oil), 1.07 g (6.19 mmol) of tert-butyl 3-hydroxyazetidine-1-carboxylate (described in the previous step) instead of tert-butyl 3-hydroxypyrrolidine-1-carboxylate, and 810 µl (6.81 mmol) of benzyl bromide in 12 ml of anhydrous DMF. 1.3 g of the title compound are obtained.

Yield: 80%.

MH+: 264.4.

Step 3: 3-(Benzyloxy)azetidine

The compound is obtained by the procedure described in example 116 step 3, using 1.3 g (4.94 mmol) of tert-butyl 3-(benzyloxy)azetidine-1-carboxylate (described in the previous step) instead of tert-butyl 3-(benzyloxy)pyrrolidine-1-carboxylate. 522 mg of the title compound are obtained.

Yield: 65%.

MH+: 164.2.

Step 4: 5-(3-(Benzyloxy)azetidin-1-yl)-1-((2-(trimethylsilyl)ethoxy)methyl)-1H-pyrrolo[2,3-b]pyridine

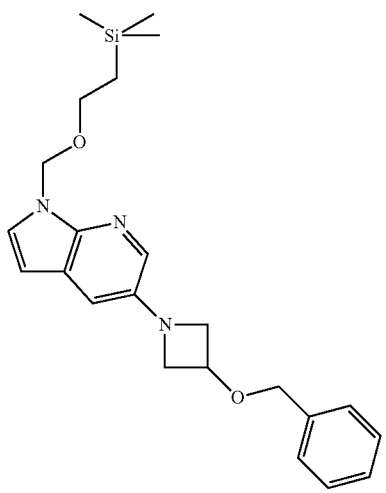 [SMILES: C[Si](C)(C)CCOCn1ccc2cc(N3CC(OCc4ccccc4)C3)cnc21]

The compound is obtained by the procedure described in example 116 step 4, using 1.05 g (3.22 mmol) of 5-bromo-1-(2-trimethylsilylethoxymethyl)-1H-pyrrolo[2,3-b]pyridine, 630 mg (3.86 mmol) of 3-(benzyloxy)azetidine instead of 3-(benzyloxy)pyrrolidine, 165 mg (0.322 mmol) of Pd(PtBu$_3$)$_2$ and 774 mg (8.05 mmol) of sodium tert-butoxide. Crude product is purified by flash chromatography on a 30 g silica gel column with an ethyl acetate/hexane mixture as eluent. 809 mg of the title compound are obtained.

Yield: 61%.
MH+: 410.5.

Step 5: 5-(3-(Benzyloxy)azetidin-1-yl)-1H-pyrrolo[2,3-b]pyridine

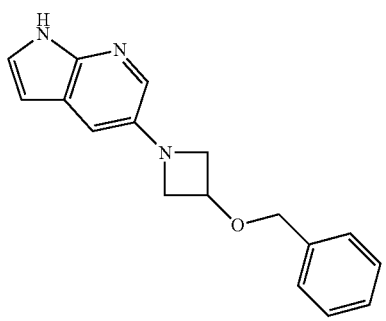 [SMILES: c1ccc(COC2CN(c3cnc4[nH]ccc4c3)C2)cc1]

The compound is obtained by the procedure described in example 10 step 3, using 805 mg (1.97 mmol) of 5-(3-(benzyloxy)azetidin-1-yl)-1-((2-(trimethylsilyl)ethoxy)methyl)-1H-pyrrolo[2,3-b]pyridine (described in the previous step) instead of 5-(4-cyanopiperidin-1-yl)-1-(2-trimethylsilylethoxymethyl)-1H-pyrrolo[2,3-b]pyridine, 198 µl (2.96 mmol) of ethylenediamine, 9.85 ml+9.85 ml (9.85 mmol+9.85 mmol) of TBAF (1M in THF) in 7 ml of anhydrous THF. 1.01 g of the title compound are obtained.

Yield: 77%.
MH+: 280.3.

Step 6: 5-(3-(Benzyloxy)azetidin-1-yl)-3-iodo-1H-pyrrolo[2,3-b]pyridine

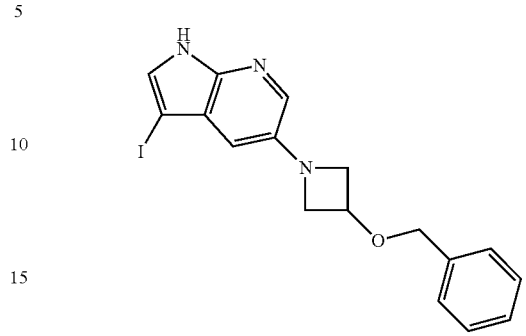

The compound is obtained by the procedure described in example 9 step 2, using 426 mg (1.53 mmol) of 5-(3-(benzyloxy)azetidin-1-yl)-1H-pyrrolo[2,3-b]pyridine (described in the previous step) instead of 5-piperidin-1-yl-1H-pyrrolo[2,3-b]pyridine and 518 mg (2.30 mmol) of N-iodosuccinimide in 15 ml of acetone. 284 mg of the title compound are obtained.

Yield: 46%.
MH+: 406.2.

Step 7: 5-(3-(Benzyloxy)azetidin-1-yl)-3-iodo-1-tosyl-1H-pyrrolo[2,3-b]pyridine

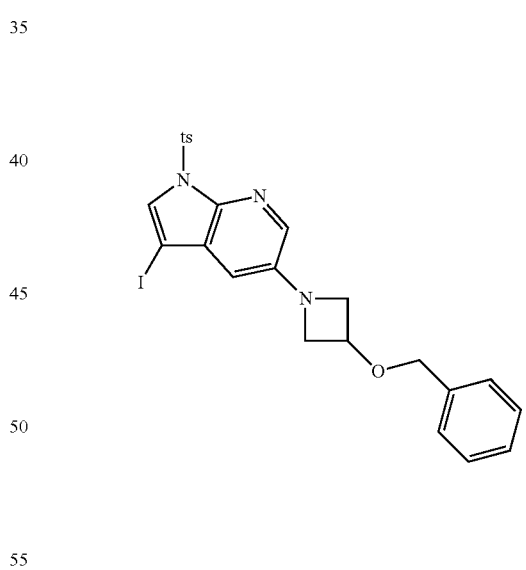

The compound is obtained by the procedure described in example 9 step 3, using 284 mg (0.70 mmol) of 5-(3-(benzyloxy)azetidin-1-yl)-3-iodo-1H-pyrrolo[2,3-b]pyridine (described in the previous step) instead of 3-iodo-5-piperidin-1-yl-1H-pyrrolo[2,3-b]pyridine, 42 mg (1.05 mmol) of sodium hydride (60% in paraffin oil) and 147 mg (0.77 mmol) of tosyl chloride in 7 ml of anhydrous DMF. 245 mg of the title compound are obtained.

Yield: 63%.
MH+: 560.4.

Step 8: 4-(5-(3-(Benzyloxy)azetidin-1-yl)-1-tosyl-1H-pyrrolo[2,3-b]pyridin-3-yl)-1-(3,4-dichlorobenzyl)pyridin-2(1H)-one

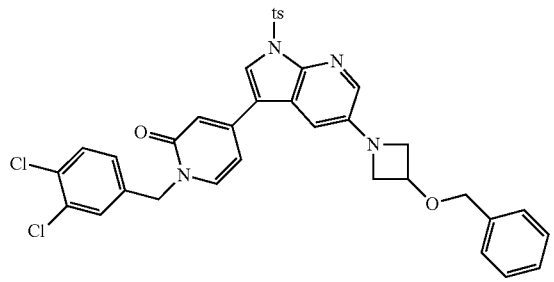

The compound is obtained by the procedure described in example 110 step 5, using 55 mg (0.098 mmol) of 5-(3-(benzyloxy)azetidin-1-yl)-3-iodo-1-tosyl-1H-pyrrolo[2,3-b]pyridine (described in previous step) instead of 8-(3-iodo-1-tosyl-1H-pyrrolo[2,3-b]pyridin-5-yl)-3-oxa-8-azabicyclo[3.2.1]octane, 45 mg (0.118 mmol) of 1-(3,4-dichlorobenzyl)-2-oxo-1,2-dihydropyridin-4-ylboronic acid (described in example 33 step 1) and 11 mg of PdCl$_2$(PPh$_3$)$_2$. 34 mg of the title compound are obtained.

Yield: 50%.

MH+: 685.5; 687.5; 689.5.

Step 9: 1-(3,4-Dichlorobenzyl)-4-(5-(3-hydroxyazetidin-1-yl)-1-tosyl-1H-pyrrolo[2,3-b]pyridin-3-yl)pyridin-2(1H)-one

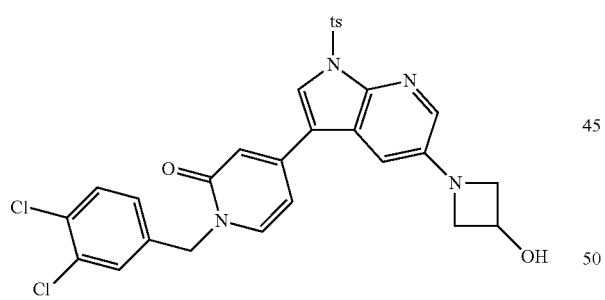

The compound is obtained by the procedure described in example 116 step 9, using 34 mg (0.050 mmol) of 4-(5-(3-(benzyloxy)azetidin-1-yl)-1-tosyl-1H-pyrrolo[2,3-b]pyridin-3-yl)-1-(3,4-dichlorobenzyl)pyridin-2(1H)-one (described in previous step) instead of 1-(3,4-dichlorobenzyl)-4-(5-(3-hydroxypyrrolidin-1-yl)-1-tosyl-1H-pyrrolo[2,3-b]pyridin-3-yl)pyridin-2(1H)-one and 75 mg of Pd/C. 21 mg of the title compound are obtained.

Yield: 70%.

MH+: 597.5; 599.5; 601.5.

Step 10: 1-(3,4-Dichlorobenzyl)-4-(5-(3-hydroxyazetidin-1-yl)-1H-pyrrolo[2,3-b]pyridin-3-yl)pyridin-2(1H)-one

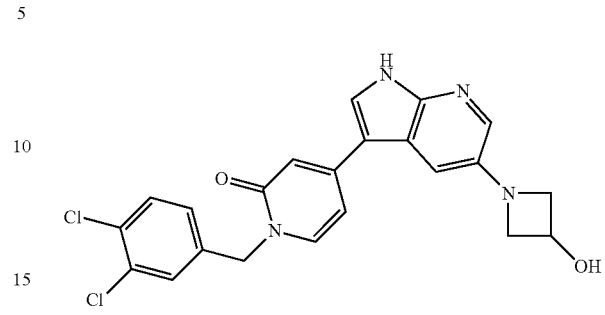

The compound is obtained by the procedure described in example 110 step 6, using 21 mg (0.035 mmol) of 1-(3,4-dichlorobenzyl)-4-(5-(3-hydroxyazetidin-1-yl)-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 4.8 mg of the title compound are obtained.

Yield: 31%.

MH+: 443.4; 445.3; 447.4.

Example 128: 1-(3,4-Dichlorobenzyl)-4-(5-thiomorpholino-1H-pyrrolo[2,3-b]pyridin-3-yl)pyridin-2(1H)-one

Step 1: 4-(1-((2-(Trimethylsilyl)ethoxy)methyl)-1H-pyrrolo[2,3-b]pyridin-5-yl)thiomorpholine

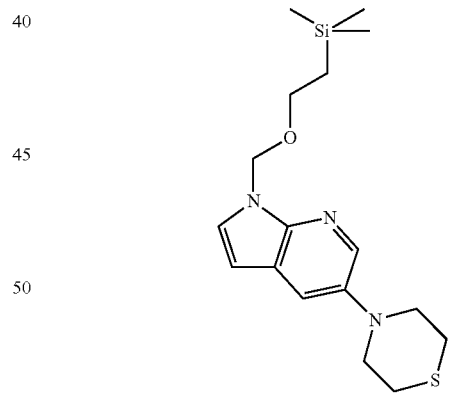

The compound is obtained by the procedure described in example 116 step 4, using 700 mg (2.14 mmol) of 5-bromo-1-(2-trimethylsilylethoxymethyl)-1H-pyrrolo[2,3-b]pyridine, 258 µl (2.57 mmol) of thiomorpholine instead of 4-cyanopiperidine, 328 mg (0.642 mmol) of Pd(PtBu$_3$)$_2$ and 514 mg (5.35 mmol) of sodium tert-butoxide. Crude product is purified by flash chromatography on a 30 g silica gel column with an ethyl acetate/hexane mixture as eluent. 487 mg of the title compound are obtained.

Yield: 65%.

MH+: 350.5.

Step 2: 4-(1H-Pyrrolo[2,3-b]pyridin-5-yl)thiomorpholine

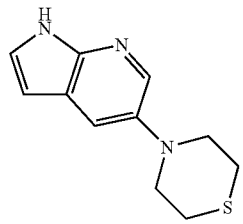

The compound is obtained by the procedure described in example 10 step 3, using 485 mg (1.39 mmol) of 4-(1-((2-(trimethylsilyl)ethoxy)methyl)-1H-pyrrolo[2,3-b]pyridin-5-yl)thiomorpholine (described in the previous step) instead of 5-(4-cyanopiperidin-1-yl)-1-(2-trimethylsilylethoxymethyl)-1H-pyrrolo[2,3-b]pyridine, 139 µl (0.209 mmol) of ethylenediamine, 6.95 ml+4.17 ml (6.95 mmol+4.17 mmol) of TBAF (1M in THF) in 5 ml of anhydrous THF. 346 mg of the title compound are obtained.
Yield: Quantitative.
MH+: 220.3.

Step 3: 4-(3-Iodo-1H-pyrrolo[2,3-b]pyridin-5-yl)thiomorpholine

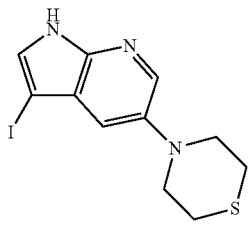 [SMILES: Ic1c[nH]c2ncc(N3CCSCC3)cc12]

The compound is obtained by the procedure described in example 9 step 2, using 346 mg (1.58 mmol) of 4-(1H-pyrrolo[2,3-b]pyridin-5-yl)thiomorpholine (described in the previous step) instead of 5-piperidin-1-yl-1H-pyrrolo[2,3-b]pyridine and 533 mg (2.37 mmol) of N-iodosuccinimide in 15 ml of acetone. 203 mg of the title compound are obtained.
Yield: 37%.
MH+: 346.4.

Step 4: 4-(3-Iodo-1-tosyl-1H-pyrrolo[2,3-b]pyridin-5-yl)thiomorpholine

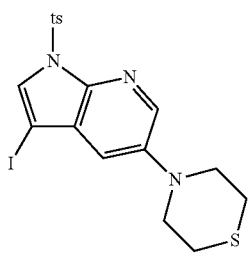

The compound is obtained by the procedure described in example 9 step 3, using 203 mg (0.588 mmol) of 4-(3-iodo-1H-pyrrolo[2,3-b]pyridin-5-yl)thiomorpholine (described in the previous step) instead of 3-iodo-5-piperidin-1-yl-1H-pyrrolo[2,3-b]pyridine, 35 mg (0.882 mmol) of sodium hydride (60% in paraffin oil) and 123 mg (0.647 mmol) of tosyl chloride in 6 ml of anhydrous DMF. 142 mg of the title compound are obtained.
Yield: 48%.
MH+: 500.3.

Step 5: 1-(3,4-Dichlorobenzyl)-4-(5-thiomorpholino-1-tosyl-1H-pyrrolo[2,3-b]pyridin-3-yl)pyridin-2(1H)-one

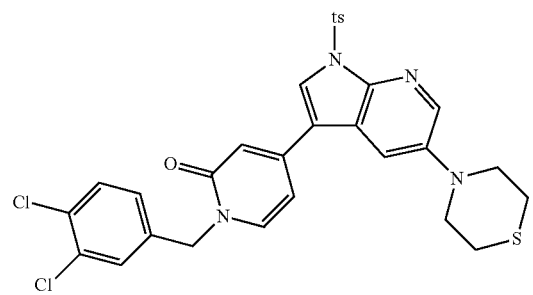

The compound is obtained by the procedure described in example 110 step 5, using 55 mg (0.110 mmol) of 4-(3-iodo-1-tosyl-1H-pyrrolo[2,3-b]pyridin-5-yl)thiomorpholine (described in previous step) instead of 8-(3-iodo-1-tosyl-1H-pyrrolo[2,3-b]pyridin-5-yl)-3-oxa-8-azabicyclo[3.2.1]octane, 50 mg (0.132 mmol) of 1-(3,4-dichlorobenzyl)-2-oxo-1,2-dihydropyridin-4-ylboronic acid (described in example 33 step 1) and 8 mg of PdCl$_2$(PPh$_3$)$_2$. 60 mg of the title compound are obtained.
Yield: 87%.
MH+: 625.3; 627.3; 629.3.

Step 6: 1-(3,4-Dichlorobenzyl)-4-(5-thiomorpholino-1H-pyrrolo[2,3-b]pyridin-3-yl)pyridin-2(1H)-one

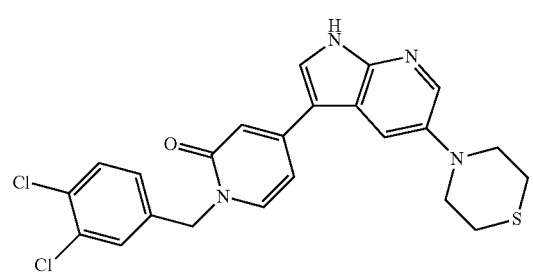 [SMILES: O=c1cc(-c2c[nH]c3ncc(N4CCSCC4)cc23)ccn1Cc1ccc(Cl)c(Cl)c1]

The compound is obtained by the procedure described in example 110 step 6, using 60 mg (0.096 mmol) of 1-(3,4-dichlorobenzyl)-4-(5-thiomorpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 7 mg of the title compound are obtained.

Yield: 27%.

MH+: 471.3; 473.3; 475.3.

¹H NMR (DMSO-d6, 300 MHz): δ 12.07 (br s, 1H); 8.12 (d, J=2.5 Hz, 1H); 8.10 (s, 1H); 7.81 (d, J=7.4 Hz, 1H); 7.75 (d, J=2.5 Hz, 1H); 7.65-7.61 (m, 2H); 7.33 (dd, J=8.4 and 2.0 Hz, 1H); 6.76-6.70 (m, 2H); 5.10 (s, 2H); 3.46-3.39 (m, 4H); 2.83-2.74 (m, 4H).

Example 129: 1-(3-Chloro-2-fluorobenzyl)-4-(5-(1,1-dioxothiomorpholino)-1H-pyrrolo[2,3-b]pyridin-3-yl)pyridin-2(1H)-one Step 1: 1-(3-Chloro-2-fluorobenzyl)-4-(5-thiomorpholino-1-tosyl-1H-pyrrolo[2,3-b]pyridin-3-yl)pyridin-2(1H)-one

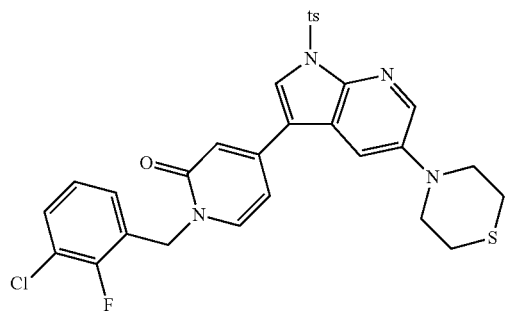

The compound is obtained by the procedure described in example 110 step 5, using 84 mg (0.168 mmol) of 4-(3-iodo-1-tosyl-1H-pyrrolo[2,3-b]pyridin-5-yl)thiomorpholine (described in example 128 step 4) instead of 8-(3-iodo-1-tosyl-1H-pyrrolo[2,3-b]pyridin-5-yl)-3-oxa-8-azabicyclo[3.2.1]octane, 57 mg (0.202 mmol) of 1-(3-chloro-2-fluorobenzyl)-2-oxo-1,2-dihydropyridin-4-ylboronic acid (described in example 32 step 1) and 18 mg of PdCl₂(PPh₃)₂. 18 mg of the title compound are obtained.

Yield: 18%.

MH+: 609.4; 611.4.

Step 2: 1-(3-Chloro-2-fluorobenzyl)-4-(5-thiomorpholino-1H-pyrrolo[2,3-b]pyridin-3-yl)pyridin-2(1H)-one

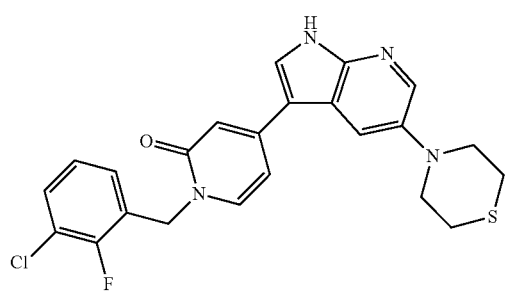 [SMILES: O=c1cc(-c2c[nH]c3ncc(N4CCSCC4)cc23)ccn1Cc1cccc(Cl)c1F]

The compound is obtained by the procedure described in example 110 step 6, using 18 mg (0.030 mmol) of 1-(3-chloro-2-fluorobenzyl)-4-(5-thiomorpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 15 mg of the title compound are obtained.

Yield: Quantitative.

MH+: 455.4; 457.4.

Step 3: 1-(3-Chloro-2-fluorobenzyl)-4-(5-(1,1-dioxothiomorpholino)-1H-pyrrolo[2,3-b]pyridin-3-yl)pyridin-2(1H)-one

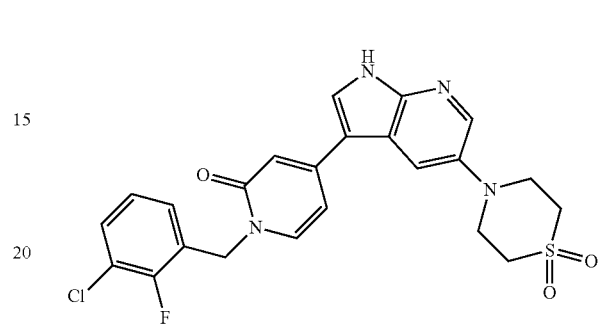

To a solution of 15 mg (0.033 mmol) of 1-(3-chloro-2-fluorobenzyl)-4-(5-thiomorpholino-1H-pyrrolo[2,3-b]pyridin-3-yl)pyridin-2(1H)-one (described in previous step) in 5 ml of anhydrous DCM, are added 16.2 mg (0.073 mmol) of meta-chloroperoxybenzoic acid. The solution is stirred at room temperature for 1 h 30. Reaction mixture is then evaporated under reduced pressure and directly purified by flash chromatography with a 30 g C18 column and a water/acetonitrile mixture as eluent. 1.9 mg of the title compound are obtained.

Yield: 12%.

MH+: 487.3; 489.4.

Example 130: 1-(3,4-Dichlorobenzyl)-4-(5-(tetrahydro-2H-pyran-4-yl)-1H-pyrrolo[2,3-b]pyridin-3-yl)pyridin-2(1H)-one Step 1: 4-(5-Bromo-1-tosyl-1H-pyrrolo[2,3-b]pyridin-3-yl)-1-(3,4-dichlorobenzyl)pyridin-2(1H)-one

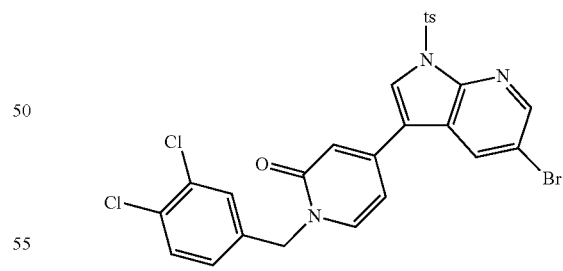

300 mg (0.629 mmol) of 5-bromo-3-iodo-1-tosyl-1H-pyrrolo[2,3-b]pyridine (described in example 1 step 2) and 287 mg (0.755 mmol) of 1-(3,4-dichlorobenzyl)-2-oxo-1,2-dihydropyridin-4-ylboronic acid (described in example 33 step 1) are dissolved in a mixture of 6 ml of acetonitrile and 3 ml of an aqueous 2M solution of Na₂CO₃. Argon is bubbled through the solution for 10 minutes, then 30 mg of PdCl₂(PPh₃)₂ are added under argon. Argon is bubbled for another 10 minutes and the reaction is stirred at 70° C. for 1 h 30. The reaction medium is diluted with water, extracted 3 times with ethyl acetate, dried over sodium sulfate, filtered and evaporated under reduced pressure. Crude product is purified by flash chromatography on a 30 g silica gel column with an ethyl acetate/hexane mixture as eluent. 80 mg of the title compound are obtained as a grey solid.

Yield: 21%.

MH+: 602.2; 604.2; 606.2.

Step 2: 1-(3,4-Dichlorobenzyl)-4-(5-(3,6-dihydro-2H-pyran-4-yl)-1H-pyrrolo[2,3-b]pyridin-3-yl)pyridin-2(1H)-one

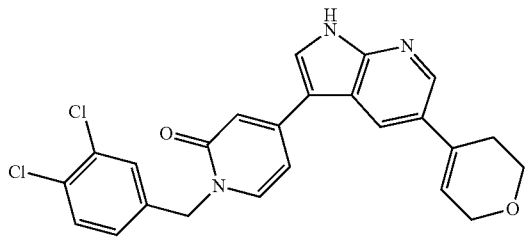 [SMILES: O=c1cc(-c2c[nH]c3ncc(C4=CCOCC4)cc23)ccn1Cc1ccc(Cl)c(Cl)c1]

50 mg (0.083 mmol) of 4-(5-bromo-1-tosyl-1H-pyrrolo[2,3-b]pyridin-3-yl)-1-(3,4-dichlorobenzyl)pyridin-2(1H)-one (described in the previous step) and 21 mg (0.099 mmol) of 2-(3,6-dihydro-2H-pyran-4-yl)-4,4,5,5-tetramethyl-1,3,2-dioxaborolane are dissolved in a mixture of 3 ml of acetonitrile and 1.5 ml of an aqueous 2M solution of $Na_2CO_3$. Argon is bubbled through the solution for 10 minutes, then 5 mg of $PdCl_2(PPh_3)_2$ is added under argon. Argon is bubbled for another 10 minutes and the reaction is heated at 150° C. under microwaves irradiation for 30 min. The reaction medium is diluted with water, extracted 3 times with ethyl acetate, dried over sodium sulfate, filtered and evaporated under reduced pressure. Crude product is purified by flash chromatography with a 30 g C18 column and a water/acetonitrile mixture as eluent. 10.5 mg of the title compound are obtained.

Yield: 28%.

MH+: 451.8; 453.8; 455.8.

$^1$H NMR (DMSO-d6, 300 MHz): δ 12.28 (br s, 1H); 8.45 (d, J=2.0 Hz, 1H); 8.22 (d, J=2.1 Hz, 1H); 8.18 (s, 1H); 7.83 (d, J=7.9 Hz, 1H); 7.67-7.59 (m, 2H); 7.33 (dd, J=8.3 and 2.0 Hz, 1H); 6.81-6.74 (m, 2H); 6.35-6.29 (m, 1H); 5.10 (s, 2H); 4.29-4.22 (m, 2H); 3.87 (t, J=5.5 Hz, 2H); 2.62-2.52 (m, 2H).

Step 3: 1-(3,4-Dichlorobenzyl)-4-(5-(tetrahydro-2H-pyran-4-yl)-1H-pyrrolo[2,3-b]pyridin-3-yl)pyridin-2(1H)-one

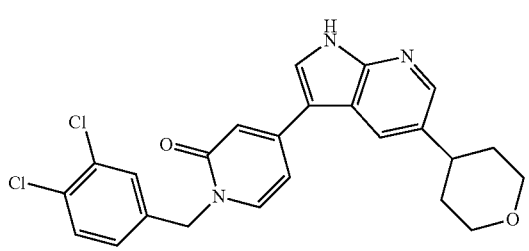 [SMILES: O=c1cc(-c2c[nH]c3ncc(C4CCOCC4)cc23)ccn1Cc1ccc(Cl)c(Cl)c1]

9 mg (0.020 mmol) of 1-(3,4-dichlorobenzyl)-4-(5-(3,6-dihydro-2H-pyran-4-yl)-1H-pyrrolo[2,3-b]pyridin-3-yl)pyridin-2(1H)-one (described in the previous step) and 1 mg of Pd/C 10% are dissolved in a mixture of 2 ml of DCM and 2 ml of methanol. The mixture is placed under hydrogen and stirred for the night at room temperature. The reaction medium is filtrated on celite and evaporated under reduced pressure. Crude product is directly purified by flash chromatography with a 30 g C18 column and a water/acetonitrile mixture as eluent. 3.8 mg of the title compound are obtained.

Yield: 42%.

MH+: 453.9; 455.9; 457.9.

$^1$H NMR (DMSO-d6, 300 MHz): δ 12.19 (br s, 1H); 8.24 (d, J=1.9 Hz, 1H); 8.20-8.12 (m, 2H); 7.82 (d, J=7.0 Hz, 1H); 7.68-7.59 (m, 2H); 7.33 (dd, J=8.4 and 2.0 Hz, 1H); 6.82-6.72 (m, 2H); 5.11 (s, 2H); 4.05-3.92 (m, 2H); 3.55-3.45 (m, 2H); 3.04-2.89 (m, 1H); 1.92-1.67 (m, 4H).

Example 203: 4-(5-Morpholino-1H-pyrrolo[2,3-b]pyridin-3-yl)-1-(naphthalen-1-ylmethyl)pyridin-2(1H)-one Step 1: 4-Bromo-1-(naphthalen-1-ylmethyl)pyridin-2(1H)-one

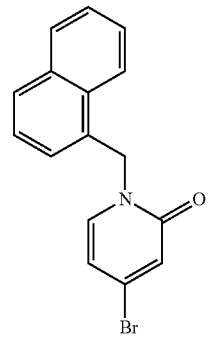 [SMILES: O=c1cc(Br)ccn1Cc1cccc2ccccc12]

To a solution of 100 mg (0.57 mmol) of 4-bromopyridin-2-(1H)-one and 280 mg (0.86 mmol) of cesium carbonate in 2 ml of anhydrous DMF, are added 140 mg (0.63 mmol) of 1-(bromomethyl)naphthalene under argon at ambient temperature. The reaction is stirred overnight under argon. Reaction mixture is then diluted with ethyl acetate, and the precipitate is filtered and rinsed with a small amount of ethyl acetate. The filtrate is concentrated under vacuum and directly purified by flash chromatography with a 30 g C18 column and a water/acetonitrile mixture as eluent. 138 mg of the title compound are obtained.

Yield: 76%.

MH+: 314.2; 316.2.

Step 2: 1-(Naphthalen-1-ylmethyl)-4-(4,4,5,5-tetramethyl-1,3,2-dioxaborolan-2-yl)pyridin-2(1H)-one

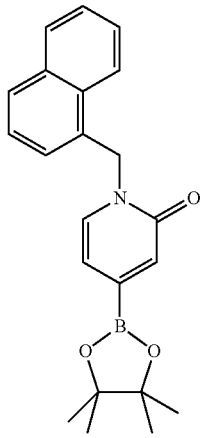 [SMILES: CC1(C)OB(c2ccn(Cc3cccc4ccccc34)c(=O)c2)OC1(C)C]

138 mg (0.43 mmol) of 4-bromo-1-(naphthalen-1-ylmethyl)pyridin-2(1H)-one (described in previous step), 223 mg (0.88 mmol) of bis(pinacolato)diboron and 86 mg (0.88 mmol) of potassium acetate are dissolved in 4 ml of anhydrous dioxane. Argon is bubbled through the solution for 10 minutes, then 14 mg of PdCl$_2$(PPh$_3$)$_2$ are added under argon. Argon is bubbled for another 10 minutes and the reaction is stirred at 85° C. for 30 min. After cooling to ambient temperature, the solution is concentrated under reduced pressure and crude product is directly purified by flash chromatography on a 10 g silica gel column with a dichloromethane/methanol mixture as eluent. 197 mg of the title compound are obtained.
Yield: Quantitative.
MH+: 280.3 (boronic acid).

Step 3: 4-(5-Morpholino-1-tosyl-1H-pyrrolo[2,3-b]pyridin-3-yl)-1-(naphthalen-1-ylmethyl)pyridin-2(1H)-one

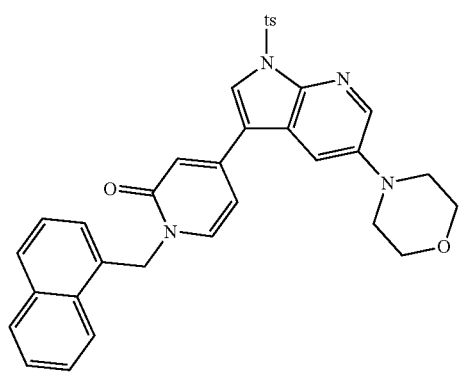

50 mg (0.103 mmol) of 3-iodo-5-morpholin-1-yl-1-tosyl-1H-pyrrolo[2,3-b]pyridine (described in example 17 step 3) and 56 mg (0.155 mmol) of 1-(naphthalen-1-ylmethyl)-4-(4,4,5,5-tetramethyl-1,3,2-dioxaborolan-2-yl)pyridin-2(1H)-one (described in previous step) are dissolved in a mixture of 3 ml of acetonitrile and 1.5 ml of an aqueous 2M solution of Na$_2$CO$_3$. Argon is bubbled through the solution for 10 minutes, then 5 mg of PdCl$_2$(PPh$_3$)$_2$ are added under argon. Argon is bubbled for another 10 minutes and the reaction is stirred at 70° C. for 1 h. After cooling to ambient temperature, reaction mixture is diluted with water, extracted 3 times with ethyl acetate, dried over sodium sulfate and evaporated under reduced pressure. Crude product is purified by flash chromatography on a 10 g silica gel column with a dichloromethane/methanol mixture as eluent. 36 mg of the title compound are obtained.
Yield: 58%.
MH+: 591.4.

Step 4: 4-(5-Morpholino-1H-pyrrolo[2,3-b]pyridin-3-yl)-1-(naphthalen-1-ylmethy)pyridin-2(1H)-one

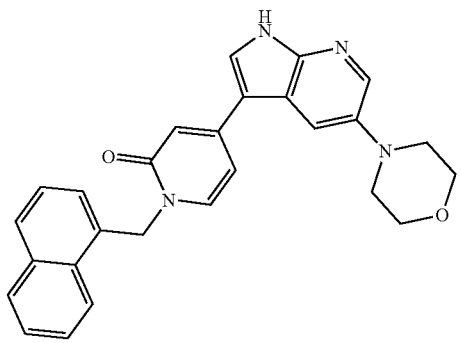 [SMILES: O=c1cc(-c2c[nH]c3ncc(N4CCOCC4)cc23)ccn1Cc1cccc2ccccc12]

The compound is obtained by the procedure described in example 110 step 6, using 36 mg (0.060 mmol) of 4-(5-morpholino-1-tosyl-1H-pyrrolo[2,3-b]pyridin-3-yl)-1-(naphthalen-1-ylmethyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 6.8 mg of the title compound are obtained.
Yield: 25%.
MH+: 437.4.
$^1$H NMR (DMSO-d6, 300 MHz): δ 12.06 (br s, 1H); 8.23-8.15 (m, 2H); 8.09 (s, 1H); 8.02-7.96 (m, 1H); 7.94-7.88 (m, 1H); 7.72 (d, J=2.4 Hz, 1H); 7.67-7.47 (m, 4H); 7.26 (d, J=7.0 Hz, 1H); 6.80 (d, J=2.0 Hz, 1H); 6.73 (dd, J=7.4 and 1.9 Hz, 1H); 5.61 (s, 2H); 3.84-3.74 (m, 4H); 3.18-3.09 (m, 4H).

Example 204: 4-(5-Morpholino-1H-pyrrolo[2,3-b]pyridin-3-yl)-1-(naphthalen-2-ylmethyl)pyridin-2(1H)-one Step 1: 4-Bromo-1-(naphthalen-2-ylmethyl)pyridin-2(1H)-one

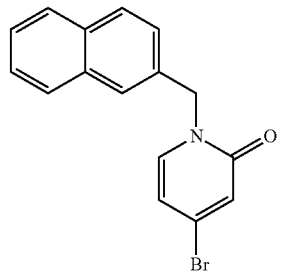 [SMILES: O=c1cc(Br)ccn1Cc1ccc2ccccc2c1]

The compound is obtained by the procedure described in example 203 step 1, using 100 mg (0.57 mmol) of 4-bromopyridin-2-(1H)-one, 140 mg (0.63 mmol) of 2-(bromomethyl)naphthalene instead of 1-(bromomethyl)naphthalene and 280 mg (0.86 mmol) of cesium carbonate. 145 mg of the title compound are obtained.
Yield: 80%.
MH+: 314.2; 316.2.

Step 2: 1-(Naphthalen-2-ylmethyl)-4-(4,4,5,5-tetramethyl-1,3,2-dioxaborolan-2-yl)pyridin-2(1H)-one

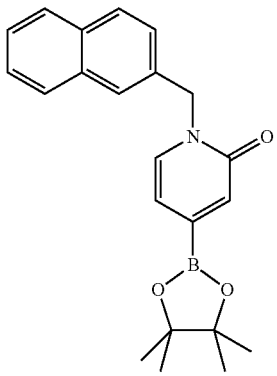 [SMILES: CC1(C)OB(c2ccn(Cc3ccc4ccccc4c3)c(=O)c2)OC1(C)C]

The compound is obtained by the procedure described in example 203 step 2, using 145 mg (0.46 mmol) of 4-bromo-1-(naphthalen-2-ylmethyl)pyridin-2(1H)-one (described in previous step), 234 mg (0.92 mmol) of bis(pinacolato)diboron, 90 mg (0.92 mmol) of potassium acetate and 15 mg of PdCl$_2$(PPh$_3$)$_2$. 192 mg of the title compound are obtained.
Yield: Quantitative.
MH+: 280.3 (boronic acid).

Step 3: 4-(5-Morpholino-1-tosyl-1H-pyrrolo[2,3-b]pyridin-3-yl)-1-(naphthalen-2-ylmethyl)pyridin-2(1H)-one

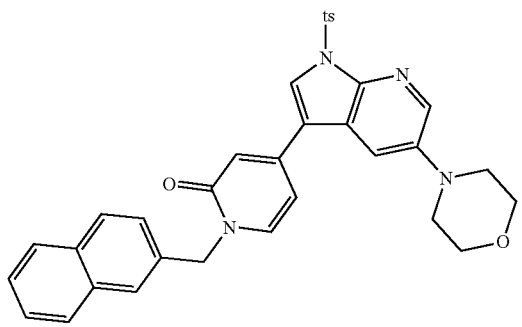

The compound is obtained by the procedure described in example 203 step 3, using 50 mg (0.103 mmol) of 3-iodo-5-morpholin-1-yl-1-tosyl-1H-pyrrolo[2,3-b]pyridine (described in example 17 step 3), 56 mg (0.155 mmol) of 1-(naphthalen-2-ylmethyl)-4-(4,4,5,5-tetramethyl-1,3,2-dioxaborolan-2-yl)pyridin-2(1H)-one (described in previous step) instead of 1-(naphthalen-1-ylmethyl)-4-(4,4,5,5-tetramethyl-1,3,2-dioxaborolan-2-yl)pyridin-2(1H)-one and 5 mg of PdCl$_2$(PPh$_3$)$_2$. 50 mg of the title compound are obtained.
Yield: 81%.
MH+: 591.4.

Step 4: 4-(5-Morpholino-1H-pyrrolo[2,3-b]pyridin-3-yl)-1-(naphthalen-2-ylmethyl)pyridin-2(1H)-one

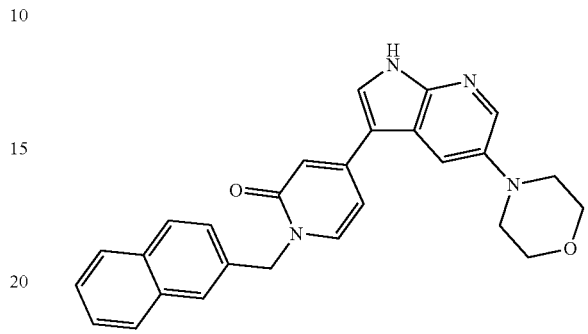

The compound is obtained by the procedure described in example 110 step 6, using 50 mg (0.084 mmol) of 4-(5-morpholino-1-tosyl-1H-pyrrolo[2,3-b]pyridin-3-yl)-1-(naphthalen-2-ylmethyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 14.2 mg of the title compound are obtained.
Yield: 38%.
MH+: 437.5.
$^1$H NMR (DMSO-d6, 300 MHz): δ 12.05 (br s, 1H); 8.17 (d, J=2.6 Hz, 1H); 8.09 (s, 1H); 7.95-7.85 (m, 3H); 7.85-7.79 (m, 2H); 7.71 (d, J=2.6 Hz, 1H); 7.67-7.47 (m, 3H); 6.77-6.70 (m, 2H); 5.28 (s, 2H); 3.84-3.73 (m, 4H); 3.19-3.09 (m, 4H).

Example 208: 1-((2,3-Dihydrobenzo[b][1,4]dioxin-6-yl)methyl)-4-(5-morpholino-1H-pyrrolo[2,3-b]pyridin-3-yl)pyridin-2(1H)-one Step 1: 1-((2,3-Dihydrobenzo[b][1,4]dioxin-6-yl)methyl)-2-oxo-1,2-dihydropyridin-4-ylboronic Acid

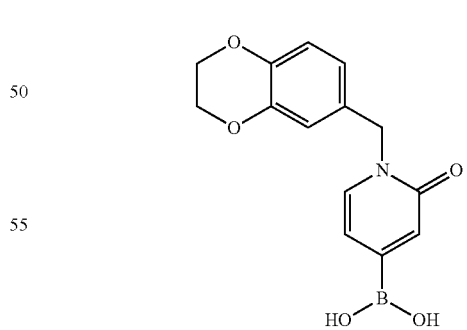

The compound is obtained by the procedure described in example 25 step 1, using 62 mg (0.27 mmol) of 6-(bromomethyl)-2,3-dihydrobenzo[b][1,4]dioxine instead of benzyl bromide, 60 mg (0.27 mmol) of 4-(4,4,5,5-tetramethyl-[1,3,2]dioxaborolan-2-yl)-1H-pyridin-2-one and 97 mg (0.298 mmol) of cesium carbonate. 60 mg of the title compound are obtained.

Yield: 77%.
MH+: 288.5.

Step 2: 1-((2,3-Dihydrobenzo[b][1,4]dioxin-6-yl)methyl)-4-(5-morpholino-1-tosyl-1H-pyrrolo[2,3-b]pyridin-3-yl)pyridin-2(1H)-one

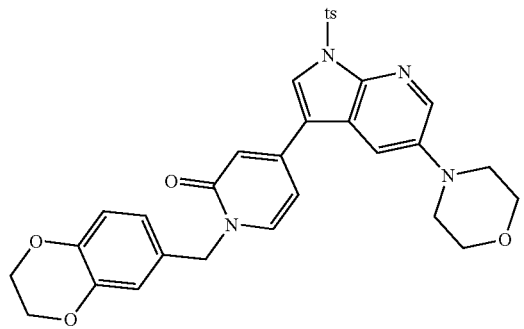

The compound is obtained by the procedure described in example 203 step 3, using 100 mg (0.209 mmol) of 3-iodo-5-morpholin-1-yl-1-tosyl-1H-pyrrolo[2,3-b]pyridine (described in example 17 step 3), 60 mg (0.209 mmol) of 1-((2,3-dihydrobenzo[b][1,4]dioxin-6-yl)methyl)-2-oxo-1,2-dihydropyridin-4-ylboronic acid (described in previous step) instead of 1-(naphthalen-1-ylmethyl)-4-(4,4,5,5-tetramethyl-1,3,2-dioxaborolan-2-yl)pyridin-2(1H)-one and 15 mg of PdCl$_2$(PPh$_3$)$_2$. 14 mg of the title compound are obtained.
Yield: 11%.
MH+: 599.5.

Step 3: 1-((2,3-Dihydrobenzo[b][1,4]dioxin-6-yl)methyl)-4-(5-morpholino-1H-pyrrolo[2,3-b]pyridin-3-yl)pyridin-2(1H)-one

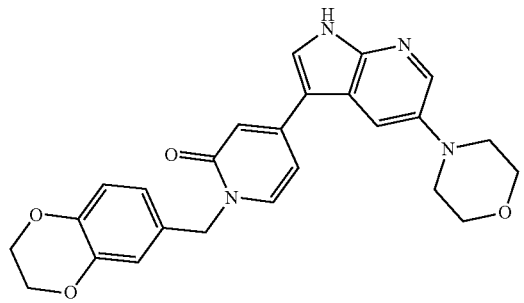 [SMILES: O=c1cc(-c2c[nH]c3ncc(N4CCOCC4)cc23)ccn1Cc1ccc2c(c1)OCCO2]

The compound is obtained by the procedure described in example 110 step 6, using 14 mg (0.023 mmol) of 1-((2,3-dihydrobenzo[b][1,4]dioxin-6-yl)methyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 3.8 mg of the title compound are obtained.
Yield: 38%.
MH+: 445.5.
$^1$H NMR (DMSO-d6, 300 MHz): δ 12.04 (br s, 1H); 8.16 (d, J=2.7 Hz, 1H); 8.05 (s, 1H); 7.75-7.63 (m, 3H); 6.88 (s, 1H); 6.85-6.80 (m, 1H); 6.73-6.64 (m, 2H); 4.97 (s, 2H); 4.20 (s, 4H); 3.83-3.73 (m, 4H); 3.19-3.09 (m, 4H).

Example 210: 1-(4-Chlorobenzyl)-4-(5-morpholino-1H-pyrrolo[2,3-b]pyridin-3-yl)pyridin-2(1H)-one Step 1: 1-(4-Chlorobenzyl)-2-oxo-1,2-dihydropyridin-4-ylboronic Acid

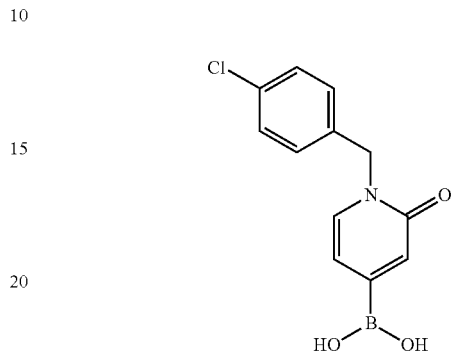

The compound is obtained by the procedure described in example 25 step 1, using 111 mg (0.54 mmol) of 4-chlorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 81 mg of the title compound are obtained.
Yield: 68%.
MH+: 264.3; 266.3.

Step 2: 1-(4-Chlorobenzyl)-4-(5-morpholino-1-tosyl-1H-pyrrolo[2,3-b]pyridin-3-yl)pyridin-2(1H)-one

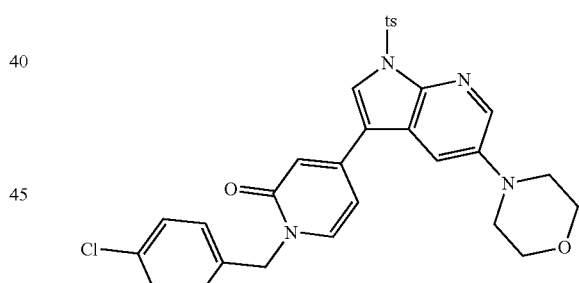

40 mg (0.083 mmol) of 3-iodo-5-morpholin-1-yl-1-tosyl-1H-pyrrolo[2,3-b]pyridine (described in example 17 step 3) and 26 mg (0.100 mmol) of 1-(4-chlorobenzyl)-2-oxo-1,2-dihydropyridin-4-ylboronic acid (described in previous step) are dissolved in a mixture of 3 ml of acetonitrile and 1.5 ml of an aqueous 2M solution of Na$_2$CO$_3$. Argon is bubbled through the solution for 10 minutes, then 6 mg of PdCl$_2$(PPh$_3$)$_2$ are added under argon. Argon is bubbled for another 10 minutes and the reaction is stirred at 70° C. for 1 hour. After cooling to ambient temperature, reaction mixture is diluted with water, extracted 3 times with ethyl acetate, dried over sodium sulfate and evaporated under reduced pressure. Crude product is purified by flash chromatography on a 10 g silica gel column with a dichloromethane/methanol mixture as eluent. 24 mg of the title compound are obtained.
Yield: 51%.
MH+: 575.4; 577.4.

Step 3: 1-(4-Chlorobenzyl)-4-(5-morpholino-1H-pyrrolo[2,3-b]pyridin-3-yl)pyridin-2(1H)-one

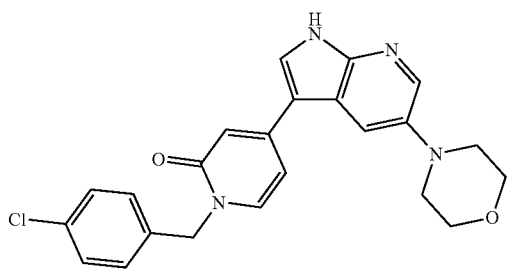 [SMILES: O=c1cc(-c2c[nH]c3ncc(N4CCOCC4)cc23)ccn1Cc1ccc(Cl)cc1]

The compound is obtained by the procedure described in example 110 step 6, using 24 mg (0.042 mmol) of 1-(4-chlorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 4.8 mg of the title compound are obtained.

Yield: 28%.

MH+: 421.6; 423.6.

$^1$H NMR (DMSO-d6, 300 MHz): δ 12.04 (br s, 1H); 8.17 (d, J=2.6 Hz, 1H); 8.08 (d, J=2.9 Hz, 1H); 7.77 (d, J=7.9 Hz, 1H); 7.70 (d, J=2.6 Hz, 1H); 7.45-7.32 (m, 4H); 6.75-6.68 (m, 2H); 5.09 (s, 2H); 3.85-3.74 (m, 4H); 3.19-3.09 (m, 4H).

Example 211: 1-(3-Bromobenzyl)-4-(5-morpholino-1H-pyrrolo[2,3-b]pyridin-3-yl)pyridin-2(1H)-one

Step 1: 1-(3-Bromobenzyl)-2-oxo-1,2-dihydropyridin-4-ylboronic Acid

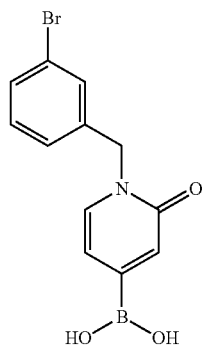 [SMILES: O=c1cc(B(O)O)ccn1Cc1cccc(Br)c1]

The compound is obtained by the procedure described in example 25 step 1, using 85 mg (0.339 mmol) of 3-bromobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 78 mg of the title compound are obtained.

Yield: Quantitative.

MH+: 308.3; 310.3.

Step 2: 1-(3-Bromobenzyl)-4-(5-morpholino-1-tosyl-1H-pyrrolo[2,3-b]pyridin-3-yl)pyridin-2(1H)-one

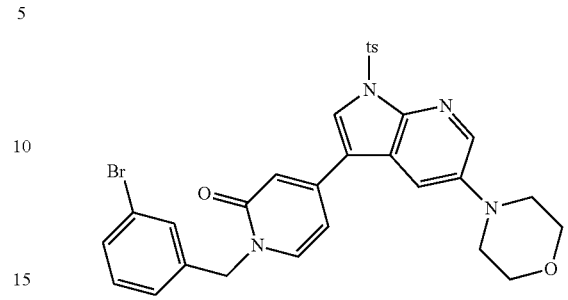

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 78 mg (0.226 mmol) of 1-(3-bromobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$(PPh$_3$)$_2$. 31 mg of the title compound are obtained.

Yield: 60%.

MH+: 619.5; 621.5.

Step 3: 1-(3-Bromobenzyl)-4-(5-morpholino-1H-pyrrolo[2,3-b]pyridin-3-yl)pyridin-2(1H)-one

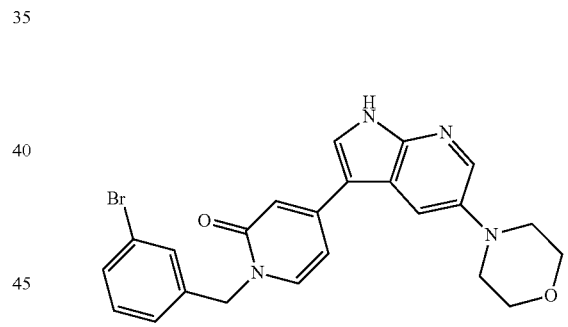

The compound is obtained by the procedure described in example 110 step 6, using 31 mg (0.050 mmol) of 1-(3-bromobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 9.4 mg of the title compound are obtained.

Yield: 49%.

MH+: 465.4; 467.5.

$^1$H NMR (DMSO-d6, 300 MHz): δ 12.05 (br s, 1H); 8.17 (d, J=2.5 Hz, 1H); 8.09 (s, 1H); 7.80 (d, J=7.8 Hz, 1H); 7.71 (d, J=2.6 Hz, 1H); 7.57-7.53 (m, 1H); 7.52-7.46 (m, 1H); 7.36-7.28 (m, 2H); 6.76-6.70 (m, 2H); 5.10 (s, 2H); 3.84-3.73 (m, 4H); 3.19-3.10 (m, 4H).

Example 212: 1-(3-Bromo-4-fluorobenzyl)-4-(5-morpholino-1H-pyrrolo[2,3-b]pyridin-3-yl)pyridin-2(1H)-one Step 1: 1-(3-Bromo-4-fluorobenzyl)-2-oxo-1,2-dihydropyridin-4-ylboronic Acid

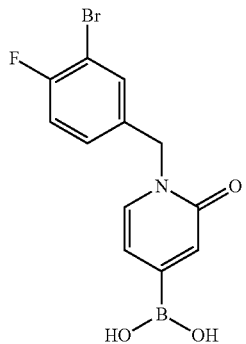

The compound is obtained by the procedure described in example 25 step 1, using 91 mg (0.339 mmol) of 3-bromo-4-fluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 63 mg of the title compound are obtained.

Yield: 86%.

MH+: 326.3; 328.3.

Step 2: 1-(3-Bromo-4-fluorobenzyl)-4-(5-morpholino-1-tosyl-1H-pyrrolo[2,3-b]pyridin-3-yl)pyridin-2(1H)-one

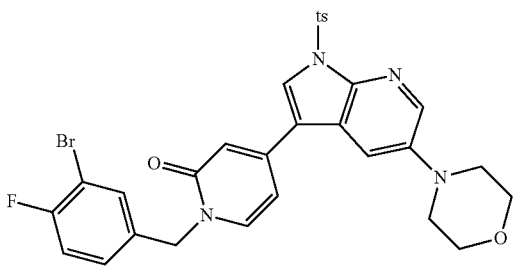

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 63 mg (0.193 mmol) of 1-(3-bromo-4-fluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$(PPh$_3$)$_2$. 26 mg of the title compound are obtained.

Yield: 49%.

MH+: 637.4; 639.4.

Step 3: 1-(3-Bromo-4-fluorobenzyl)-4-(5-morpholino-1H-pyrrolo[2,3-b]pyridin-3-yl)pyridin-2(1H)-one

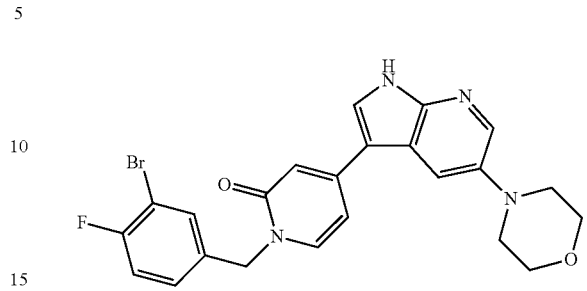

The compound is obtained by the procedure described in example 110 step 6, using 26 mg (0.041 mmol) of 1-(3-bromo-4-fluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]oct-8-yl)-1-tosyl-1H-pyrrolo[2,3-b]pyridin-3-yl)-1-(3,4-dichlorobenzyl)pyridin-2(1H)-one. 8.7 mg of the title compound are obtained.

Yield: 46%.

MH+: 483.4; 485.4.

$^1$H NMR (DMSO-d6, 300 MHz): δ 12.05 (br s, 1H); 8.16 (d, J=2.5 Hz, 1H); 8.09 (s, 1H); 7.81 (d, J=7.4 Hz, 1H); 7.76-7.68 (m, 2H); 7.46-7.33 (m, 2H); 6.76-6.68 (m, 2H); 5.08 (s, 2H); 3.83-3.73 (m, 4H); 3.19-3.09 (m, 4H).

Example 213: 1-(3-Bromo-5-fluorobenzyl)-4-(5-morpholino-1H-pyrrolo[2,3-b]pyridin-3-yl)pyridin-2(1H)-one Step 1: 1-(3-Bromo-5-fluorobenzyl)-2-oxo-1,2-dihydropyridin-4-ylboronic Acid

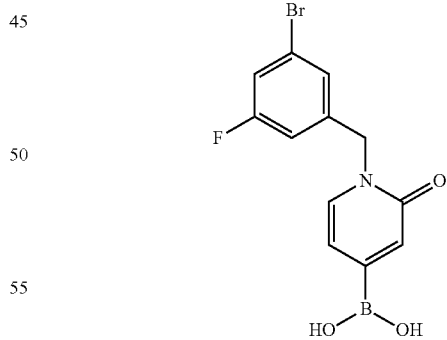

The compound is obtained by the procedure described in example 25 step 1, using 91 mg (0.339 mmol) of 3-bromo-5-fluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 91 mg of the title compound are obtained.

Yield: Quantitative.

MH+: 326.4; 328.3.

Step 2: 1-(3-Bromo-5-fluorobenzyl)-4-(5-morpholino-1-tosyl-1H-pyrrolo[2,3-b]pyridin-3-yl)pyridin-2(1H)-one

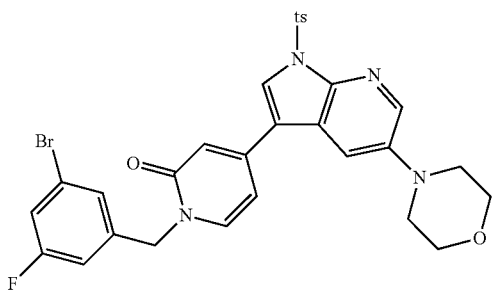

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 91 mg (0.226 mmol) of 1-(3-bromo-5-fluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_3$(PPh$_3$)$_2$. 26 mg of the title compound are obtained.

Yield: 88%.

MH+: 637.4; 639.4.

Step 3: 1-(3-Bromo-5-fluorobenzyl)-4-(5-morpholino-1H-pyrrolo[2,3-b]pyridin-3-yl)pyridin-2(1H)-one

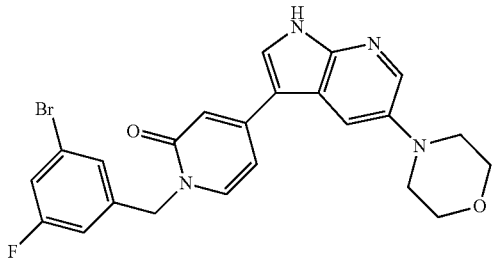 [SMILES: O=c1cc(-c2c[nH]c3ncc(N4CCOCC4)cc23)ccn1Cc1cc(F)cc(Br)c1]

The compound is obtained by the procedure described in example 110 step 6, using 47 mg (0.073 mmol) of 1-(3-bromo-5-fluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 9.7 mg of the title compound are obtained.

Yield: 27%.

MH+: 483.4; 485.4.

$^1$H NMR (DMSO-d6, 300 MHz): δ 12.07 (br s, 1H); 8.17 (d, J=2.5 Hz, 1H); 8.11 (s, 1H); 7.81 (d, J=7.1 Hz, 1H); 7.72 (d, J=2.5 Hz, 1H); 7.54-7.46 (m, 1H); 7.41 (s, 1H); 7.27-7.19 (m, 1H); 6.79-6.70 (m, 2H); 5.10 (s, 2H); 3.83-3.73 (m, 4H); 3.19-3.09 (m, 4H).

Example 214: 1-(3-Bromo-2-fluorobenzyl)-4-(5-morpholino-1H-pyrrolo[2,3-b]pyridin-3-yl)pyridin-2(1H)-one

Step 1: 1-(3-Bromo-2-fluorobenzyl)-2-oxo-1,2-dihydropyridin-4-ylboronic Acid

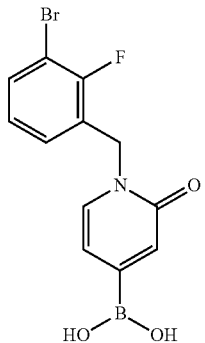

The compound is obtained by the procedure described in example 25 step 1, using 91 mg (0.339 mmol) of 3-bromo-2-fluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 89 mg of the title compound are obtained.

Yield: Quantitative.

MH+: 326.3; 328.3.

Step 2: 1-(3-Bromo-2-fluorobenzyl)-4-(5-morpholino-1-tosyl-1H-pyrrolo[2,3-b]pyridin-3-yl)pyridin-2(1H)-one

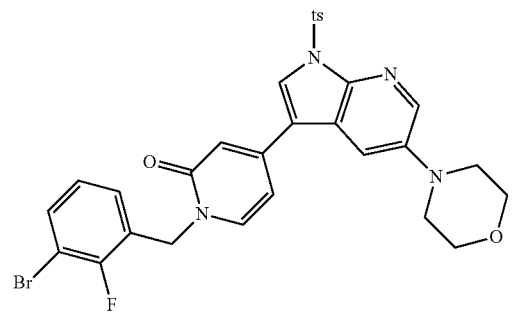

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 89 mg (0.226 mmol) of 1-(3-bromo-2-fluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$(PPh$_3$)$_2$. 26 mg of the title compound are obtained.

Yield: 38%.

MH+: 637.4; 639.5.

Step 3: 1-(3-Bromo-2-fluorobenzyl)-4-(5-morpholino-1H-pyrrolo[2,3-b]pyridin-3-yl)pyridin-2(1H)-one

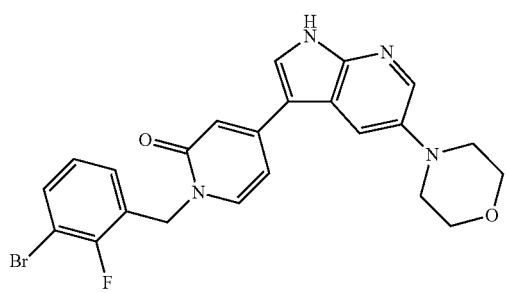

The compound is obtained by the procedure described in example 110 step 6, using 20 mg (0.031 mmol) of 1-(3-bromo-2-fluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 3.1 mg of the title compound are obtained.

Yield: 21%.

MH+: 483.4; 485.4.

$^1$H NMR (DMSO-d6, 300 MHz): δ 12.06 (br s, 1H); 8.17 (d, J=2.5 Hz, 1H); 8.10 (s, 1H); 7.78-7.69 (m, 2H); 7.69-7.61 (m, 1H); 7.22-7.10 (m, 2H); 6.76 (dd, J=7.2 and 2.0 Hz, 1H); 6.77 (d, J=1.8 Hz, 1H); 5.18 (s, 2H); 3.85-3.73 (m, 4H); 3.20-3.10 (m, 4H).

Example 215: 1-(4-Iodobenzyl)-4-(5-morpholino-1H-pyrrolo[2,3-b]pyridin-3-yl)pyridin-2(1H)-one

Step 1: 1-(4-Iodobenzyl)-2-oxo-1,2-dihydropyridin-4-ylboronic Acid

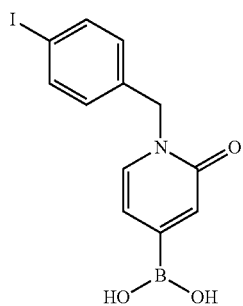 [SMILES: O=c1cc(B(O)O)ccn1Cc1ccc(I)cc1]

The compound is obtained by the procedure described in example 25 step 1, using 101 mg (0.339 mmol) of 4-iodobenzyl bromide instead of benzyl bromide. 118 mg of the title compound are obtained.

Yield: Quantitative.

MH+: 356.4.

Step 2: 1-(4-Iodobenzyl)-4-(5-morpholino-1-tosyl-1H-pyrrolo[2,3-b]pyridin-3-yl)pyridin-2(1H)-one

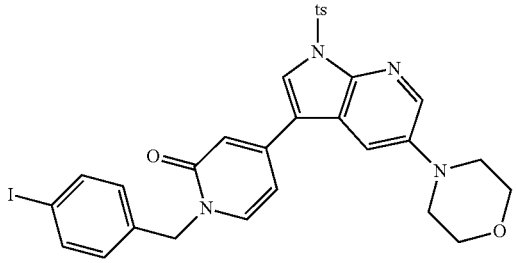

The compound is obtained by the procedure described in example 210 step 2, using 99 mg (0.205 mmol) of 3-iodo-5-morpholin-1-yl-1-tosyl-1H-pyrrolo[2,3-b]pyridine (described in example 17 step 3), 80 mg (0.225 mmol) of 1-(4-iodobenzyl)-2-oxo-1,2-dihydropyridin-4-ylboronic acid (described in previous step) instead of 1-(4-chlorobenzyl)-2-oxo-1,2-dihydropyridin-4-ylboronic acid and 14 mg of PdCl$_2$(PPh$_3$)$_2$. 30 mg of the title compound are obtained.

Yield: 22%.

MH+: 667.6.

Step 3: 1-(4-Iodobenzyl)-4-(5-morpholino-1H-pyrrolo[2,3-b]pyridin-3-yl)pyridin-2(1H)-one

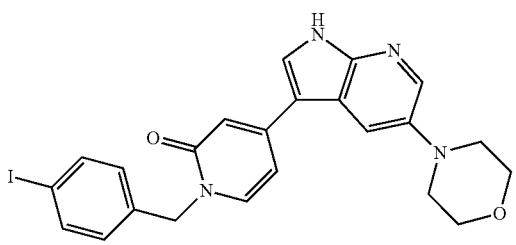 [SMILES: O=c1cc(-c2c[nH]c3ncc(N4CCOCC4)cc23)ccn1Cc1ccc(I)cc1]

The compound is obtained by the procedure described in example 110 step 6, using 30 mg (0.045 mmol) of 1-(4-iodobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 4.5 mg of the title compound are obtained.

Yield: 20%.

MH+: 513.5.

$^1$H NMR (DMSO-d6, 300 MHz): δ 12.05 (br s, 1H); 8.16 (d, J=2.5 Hz, 1H); 8.08 (s, 1H); 7.80-7.67 (m, 4H); 7.14 (d, J=8.3 Hz, 2H); 6.76-6.67 (m, 2H); 5.06 (s, 2H); 3.86-3.73 (m, 4H); 3.20-3.09 (m, 4H).

149

Example 216: 1-(4-Fluoro-3-iodobenzyl)-4-(5-morpholino-1H-pyrrolo[2,3-b]pyridin-3-yl)pyridin-2(1H)-one

Step 1: 1-(4-Fluoro-3-iodobenzyl)-2-oxo-1,2-dihydropyridin-4-ylboronic Acid

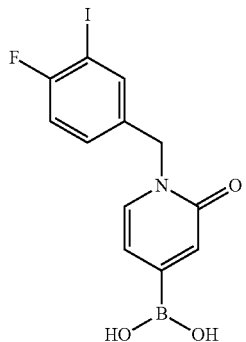

The compound is obtained by the procedure described in example 25 step 1, using 218 mg (0.692 mmol) of 4-fluoro-3-iodobenzyl bromide instead of benzyl bromide, 100 mg (0.452 mmol) of 4-(4,4,5,5-tetramethyl-[1,3,2]dioxaborolan-2-yl)-1H-pyridin-2-one and 220 mg (0.692 mmol) of cesium carbonate. 87 mg of the title compound are obtained.

Yield: 51%.

MH+: 374.2.

Step 2: 1-(4-Fluoro-3-iodobenzyl)-4-(5-morpholino-1-tosyl-1H-pyrrolo[2,3-b]pyridin-3-yl)pyridin-2(1H)-one

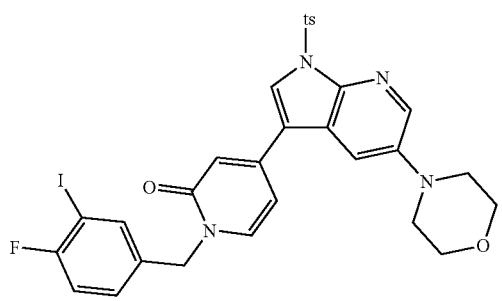

The compound is obtained by the procedure described in example 210 step 2, using 50 mg (0.103 mmol) of 3-iodo-5-morpholin-1-yl-1-tosyl-1H-pyrrolo[2,3-b]pyridine (described in example 17 step 3), 46 mg (0.124 mmol) of 1-(4-fluoro-3-iodobenzyl)-2-oxo-1,2-dihydropyridin-4-ylboronic acid (described in previous step) instead of 1-(4-chlorobenzyl)-2-oxo-1,2-dihydropyridin-4-ylboronic acid and 5 mg of PdCl$_2$ (PPh$_3$)$_2$. 30 mg of the title compound are obtained.

Yield: 42%.

MH+: 685.3.

150

Step 3: 1-(4-Fluoro-3-iodobenzyl)-4-(5-morpholino-1H-pyrrolo[2,3-b]pyridin-3-yl)pyridin-2(1H)-one

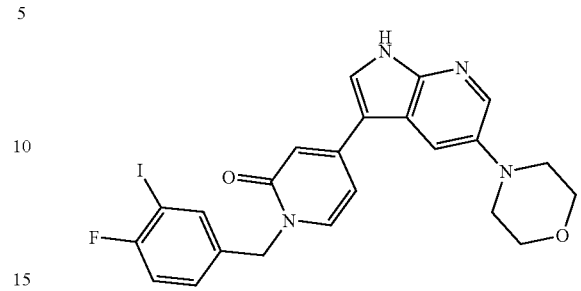

The compound is obtained by the procedure described in example 110 step 6, using 30 mg (0.044 mmol) of 1-(4-fluoro-3-iodobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 8.3 mg of the title compound are obtained.

Yield: 34%.

MH+: 531.3.

$^1$H NMR (DMSO-d6, 300 MHz): δ 12.05 (br s, 1H); 8.17 (d, J=2.5 Hz, 1H); 8.09 (s, 1H); 7.87 (dd, J=6.2 and 2.1 Hz, 1H); 7.80 (d, J=7.1 Hz, 1H); 7.70 (d, J=2.5 Hz, 1H); 7.45-7.38 (m, 1H); 7.26 (t, J=8.3 Hz, 1H); 6.76-6.68 (m, 2H); 5.06 (s, 2H); 3.85-3.73 (m, 4H); 3.20-3.08 (m, 4H).

Example 217: 1-(2-Fluoro-3-iodobenzyl)-4-(5-morpholino-1H-pyrrolo[2,3-b]pyridin-3-yl)pyridin-2(1H)-one

Step 1: 1-(2-Fluoro-3-iodobenzyl)-2-oxo-1,2-dihydropyridin-4-ylboronic Acid

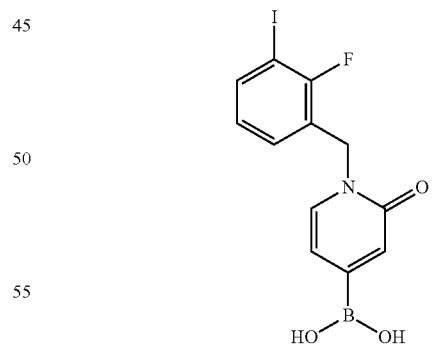

The compound is obtained by the procedure described in example 25 step 1, using 126 mg (0.400 mmol) of 2-fluoro-3-iodobenzyl bromide instead of benzyl bromide, 50 mg (0.226 mmol) of 4-(4,4,5,5-tetramethyl[1,3,2]dioxaborolan-2-yl)-1H-pyridin-2-one and 110 mg (0.339 mmol) of cesium carbonate. 114 mg of the title compound are obtained.

Yield: Quantitative.

MH+: 374.2.

Step 2: 1-(2-fluoro-3-iodobenzyl)-4-(5-morpholino-1-tosyl-1H-pyrrolo[2,3-b]pyridin-3-yl)pyridin-2(1H)-one

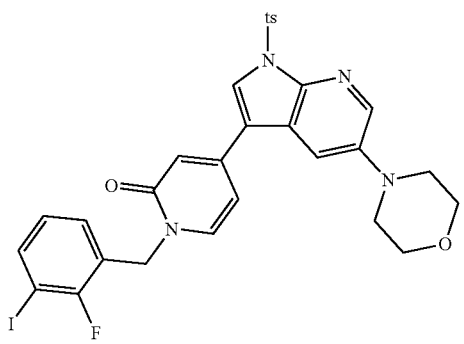

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 126 mg (0.337 mmol) of 1-(2-fluoro-3-iodobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 42 mg of the title compound are obtained.

Yield: 74%.
MH+: 685.3.

Step 3: 1-(2-Fluoro-3-iodobenzyl)-4-(5-morpholino-1H-pyrrolo[2,3-b]pyridin-3-yl)pyridin-2(1H)-one

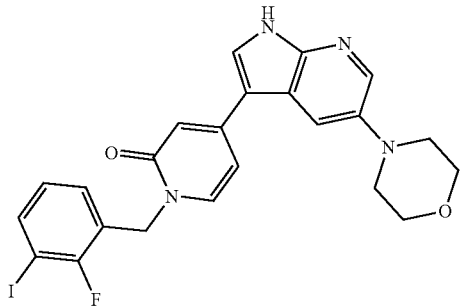 [SMILES: O=c1cc(-c2c[nH]c3ncc(N4CCOCC4)cc23)ccn1Cc1cccc(I)c1F]

The compound is obtained by the procedure described in example 110 step 6, using 30 mg (0.043 mmol) of 1-(2-fluoro-3-iodobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 4.0 mg of the title compound are obtained.

Yield: 17%.
MH+: 531.3.
$^1$H NMR (DMSO-d6, 300 MHz): δ 12.06 (br s, 1H); 8.17 (d, J=2.5 Hz, 1H); 8.10 (s, 1H); 7.83-7.69 (m, 3H); 7.22-7.12 (m, 1H); 7.00 (t, J=7.8 Hz, 1H); 6.76-6.68 (m, 2H); 5.16 (s, 2H); 3.88-3.74 (m, 4H); 3.21-3.09 (m, 4H).

Example 218: 1-(3-Fluoro-5-iodobenzyl)-4-(5-morpholino-1H-pyrrolo[2,3-b]pyridin-3-yl)pyridin-2(1H)-one Step 1: 1-(3-Fluoro-5-iodobenzyl)-2-oxo-1,2-dihydropyridin-4-ylboronic Acid

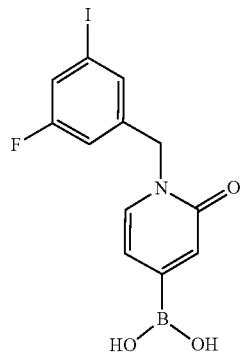 [SMILES: O=c1cc(B(O)O)ccn1Cc1cc(F)cc(I)c1]

The compound is obtained by the procedure described in example 25 step 1, using 106 mg (0.339 mmol) of 3-fluoro-5-iodobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 103 mg of the title compound are obtained.

Yield: Quantitative.
MH+: 374.3.

Step 2: 1-(3-Fluoro-5-iodobenzyl)-4-(5-morpholino-1-tosyl-1H-pyrrolo[2,3-b]pyridin-3-yl)pyridin-2(1H)-one

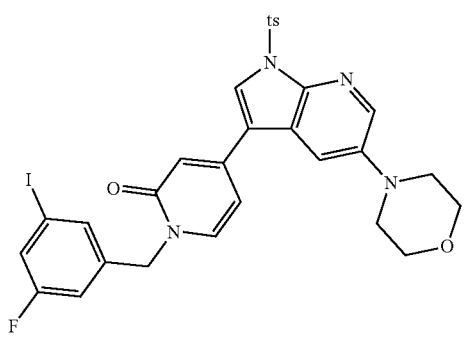

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 103 mg (0.337 mmol) of 1-(3-fluoro-5-iodobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 19 mg of the title compound are obtained.

Yield: 33%.
MH+: 685.5.

Step 3: 1-(3-Fluoro-5-iodobenzyl)-4-(5-morpholino-1H-pyrrolo[2,3-b]pyridin-3-yl)pyridin-2(1H)-one

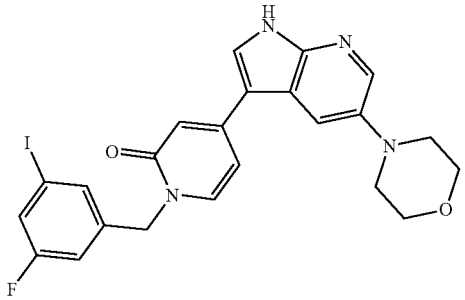 [SMILES: O=c1cc(-c2c[nH]c3ncc(N4CCOCC4)cc23)ccn1Cc1cc(F)cc(I)c1]

The compound is obtained by the procedure described in example 110 step 6, using 19 mg (0.027 mmol) of 1-(3-fluoro-5-iodobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 3.5 mg of the title compound are obtained.

Yield: 25%.

MH+: 531.4.

$^1$H NMR (DMSO-d6, 300 MHz): δ 12.07 (br s, 1H); 8.17 (d, J=2.5 Hz, 1H); 8.10 (s, 1H); 7.80 (d, J=7.0 Hz, 1H); 7.72 (d, J=2.6 Hz, 1H); 7.62-7.52 (m, 2H); 7.25-7.18 (m, 1H); 6.79-6.70 (m, 2H); 5.07 (s, 2H); 3.85-3.73 (m, 4H); 3.20-3.09 (m, 4H).

Example 219: 1-(3-Chloro-5-iodobenzyl)-4-(5-morpholino-1H-pyrrolo[2,3-b]pyridin-3-yl)pyridin-2(1H)-one

Step 1: 1-(3-Chloro-5-iodobenzyl)-2-oxo-1,2-dihydropyridin-4-ylboronic Acid

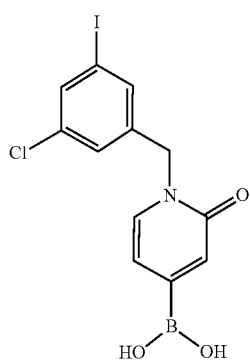 [SMILES: O=c1cc(B(O)O)ccn1Cc1cc(Cl)cc(I)c1]

The compound is obtained by the procedure described in example 25 step 1, using 45 mg (0.136 mmol) of 3-chloro-5-iodobenzyl bromide instead of benzyl bromide, 20 mg (0.090 mmol) of 4-(4,4,5,5-tetramethyl-[1,3,2]dioxaborolan-2-yl)-1H-pyridin-2-one and 44 mg (0.136 mmol) of cesium carbonate. 46 mg of the title compound are obtained.

Yield: Quantitative.

MH+: 390.3; 392.3.

Step 2: 1-(3-Chloro-5-iodobenzyl)-4-(5-morpholino-1-tosyl-1H-pyrrolo[2,3-b]pyridin-3-yl)pyridin-2(1H)-one

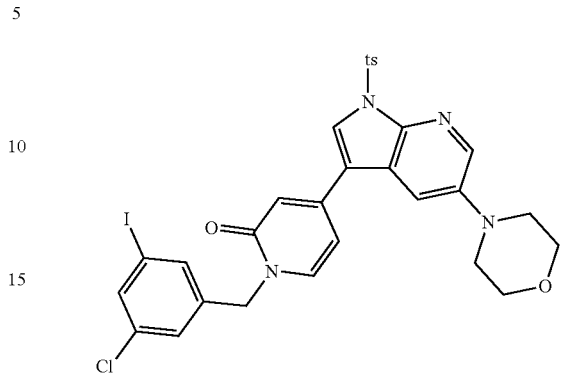

The compound is obtained by the procedure described in example 210 step 2, using 27 mg (0.059 mmol) of 3-iodo-5-morpholin-1-yl-1-tosyl-1H-pyrrolo[2,3-b]pyridine (described in example 17 step 3), 46 mg (0.118 mmol) of 1-(3-chloro-5-iodobenzyl)-2-oxo-1,2-dihydropyridin-4-ylboronic acid (described in previous step) instead of 1-(4-chlorobenzyl)-2-oxo-1,2-dihydropyridin-4-ylboronic acid and 6 mg of PdCl$_2$(PPh$_3$)$_2$. 14 mg of the title compound are obtained.

Yield: 33%.

MH+: 701.5; 703.5.

Step 3: 1-(3-Chloro-5-iodobenzyl)-4-(5-morpholino-1H-pyrrolo[2,3-b]pyridin-3-yl)pyridin-2(1H)-one

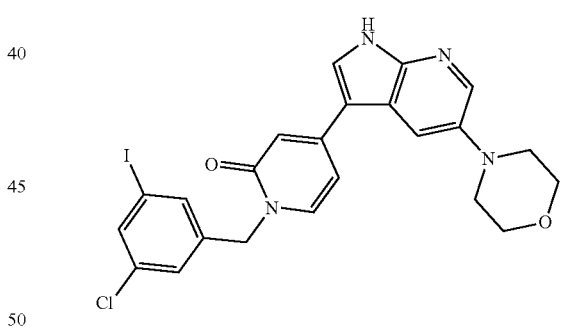

The compound is obtained by the procedure described in example 110 step 6, using 14 mg (0.020 mmol) of 1-(3-chloro-5-iodobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 2.4 mg of the title compound are obtained.

Yield: 22%.

MH+: 547.4; 549.4.

$^1$H NMR (DMSO-d6, 300 MHz): δ 12.07 (br s, 1H); 8.17 (d, J=2.6 Hz, 1H); 8.11 (s, 1H); 7.81 (d, J=7.1 Hz, 1H); 7.79-7.75 (m, 1H); 7.75-7.69 (m, 2H); 7.44 (s, 1H); 6.79-6.69 (m, 2H); 5.06 (s, 2H); 3.84-3.73 (m, 4H); 3.20-3.10 (m, 4H).

Example 220: 1-(4-Chloro-3-iodobenzyl)-4-(5-morpholino-1H-pyrrolo[2,3-b]pyridin-3-yl)pyridin-2(1H)-one

Step 1: 1-(4-Chloro-3-iodobenzyl)-2-oxo-1,2-dihydropyridin-4-ylboronic Acid

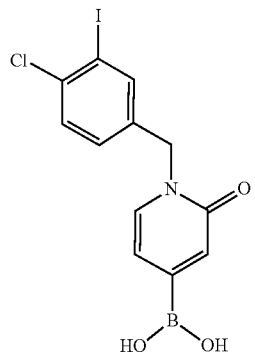 [SMILES: O=c1cc(B(O)O)ccn1Cc1ccc(Cl)c(I)c1]

The compound is obtained by the procedure described in example 25 step 1, using 45 mg (0.136 mmol) of 4-chloro-3-iodobenzyl bromide instead of benzyl bromide, 20 mg (0.090 mmol) of 4-(4,4,5,5-tetramethyl-[1,3,2]dioxaborolan-2-yl)-1H-pyridin-2-one and 44 mg (0.136 mmol) of cesium carbonate. 37 mg of the title compound are obtained.

Yield: Quantitative.

MH+: 390.3; 392.3.

Step 2: 1-(4-Chloro-3-iodobenzyl)-4-(5-morpholino-1-tosyl-1H-pyrrolo[2,3-b]pyridin-3-yl)pyridin-2(1H)-one

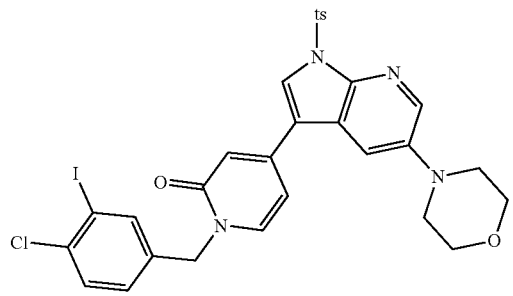

The compound is obtained by the procedure described in example 210 step 2, using 27 mg (0.059 mmol) of 3-iodo-5-morpholin-1-yl-1-tosyl-1H-pyrrolo[2,3-b]pyridine (described in example 17 step 3), 37 mg (0.095 mmol) of 1-(4-chloro-3-iodobenzyl)-2-oxo-1,2-dihydropyridin-4-ylboronic acid (described in previous step) instead of 1-(4-chlorobenzyl)-2-oxo-1,2-dihydropyridin-4-ylboronic acid and 6 mg of PdCl$_2$(PPh$_3$)$_2$. 20 mg of the title compound are obtained.

Yield: 48%.

MH+: 537.5; 539.5.

Step 3: 1-(4-Chloro-3-iodobenzyl)-4-(5-morpholino-1H-pyrrolo[2,3-b]pyridin-3-yl)pyridin-2(1H)-one

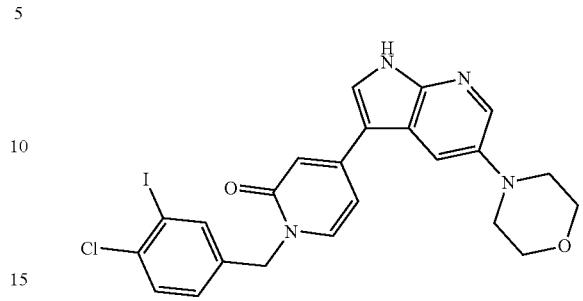

The compound is obtained by the procedure described in example 110 step 6, using 20 mg (0.029 mmol) of 1-(4-chloro-3-iodobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 4.3 mg of the title compound are obtained.

Yield: 28%.

MH+: 547.4; 549.4.

$^1$H NMR (DMSO-d6, 300 MHz): δ 12.06 (br s, 1H); 8.17 (d, J=2.5 Hz, 1H); 8.10 (s, 1H); 7.95 (d, J=1.9 Hz, 1H); 7.81 (d, J=6.8 Hz, 1H); 7.71 (d, J=2.4 Hz, 1H); 7.56 (d, J=8.3 Hz, 1H); 7.37 (d, J=8.4 and 2.0 Hz, 1H); 6.78-6.70 (m, 2H); 5.06 (s, 2H); 3.85-3.74 (m, 4H); 3.20-3.09 (m, 4H).

Example 221: 1-(3-(2-Methoxyethoxy)benzyl)-4-(5-morpholino-1H-pyrrolo[2,3-b]pyridin-3-yl)pyridin-2(1H)-one

Step 1: Methyl 3-(2-methoxyethoxy)benzoate

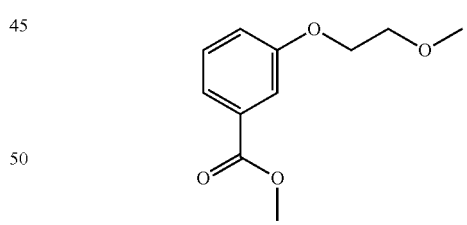

In 4 ml of anhydrous DMF, are added under argon 500 mg (3.3 mmol) of methyl 3-hydroxybenzoate, 339 µl (3.6 mmol) of 2-bromoethyl methyl ether and 1.6 g (4.93 mmol) of cesium carbonate. The mixture is stirred at ambient temperature overnight. The mixture is then diluted with diethyl ether, filtered on celite and the celite is washed several times with diethyl ether. The combined filtrates are evaporated under reduced pressure to give 682 mg of a colorless oil. Crude product is used in the next step without further purification.

Yield: 98%.

(M-OMe)+: 179.2.

Step 2: (3-(2-Methoxyethoxy)phenyl)methanol

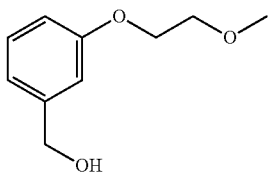

To a solution of 682 mg (3.24 mmol) of methyl 3-(2-methoxyethoxy)benzoate (described in the previous step) in 7 ml of anhydrous THF, are slowly added 123 mg (3.24 mmol) of lithium aluminum hydride at 0° C. and under argon. The solution is stirred at room temperature for 1 h then cooled to 0° C. and 200 ml of a solution of aqueous 2M NaHCO$_3$ are slowly added. The aqueous layer is then extracted 3 times with ethyl acetate, dried over sodium sulfate, filtered and evaporated under reduced pressure. 601 mg of a colorless oil are obtained. Crude product is used in the next step without purification.
Yield: Quantitative.
(M-OH)+: 165.2.

Step 3: 1-(Bromomethyl)-3-(2-methoxyethoxy)benzene

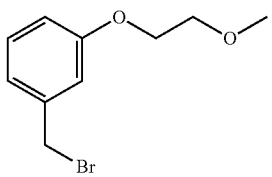

601 mg (3.3 mmol) of (3-(2-methoxyethoxy)phenyl)methanol (described in the previous step) and 464 µl (4.95 mmol) of phosphorus tribromide are dissolved in 6 ml of anhydrous THF under argon, and the mixture is stirred at ambient temperature overnight. Then the solution is diluted with diethyl ether, washed 3 times with water, dried over sodium sulfate, filtered and evaporated under reduced pressure. Crude product is purified by flash chromatography on a 10 g silica gel column with an diethyl ether/hexane mixture as eluent. 555 mg of the title compound are obtained.
Yield: 69%.
(M-Br)+: 165.1.

Step 4: 4-Bromo-1-(3-(2-methoxyethoxy)benzyl)pyridin-2(1H)-one

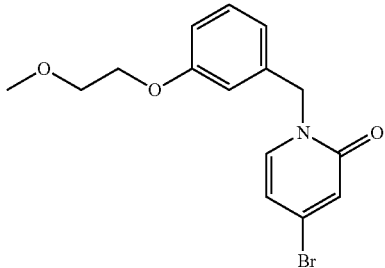 [SMILES: COCCOc1cccc(Cn2ccc(Br)cc2=O)c1]

The compound is obtained by the procedure described in example 203 step 1, using 80 mg (0.459 mmol) of 4-bromopyridin-2-(1H)-one, 135 mg (0.551 mmol) of 1-(bromomethyl)-3-(2-methoxyethoxy)benzene (described in previous step) instead of 1-(bromomethyl)naphthalene and 224 mg (0.690 mmol) of cesium carbonate. 135 mg of the title compound are obtained.
Yield: 73%.
MH+: 338.4; 340.4.

Step 5: 1-(3-(2-Methoxyethoxy)benzyl)-4-(4,4,5,5-tetramethyl-1,3,2-dioxaborolan-2-yl)pyridin-2(1H)-one

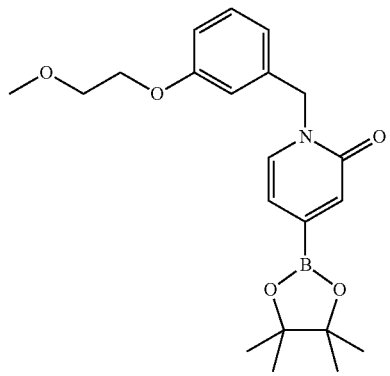 [SMILES: COCCOc1cccc(Cn2ccc(B3OC(C)(C)C(C)(C)O3)cc2=O)c1]

The compound is obtained by the procedure described in example 203 step 2, using 135 mg (0.399 mmol) of 4-bromo-1-(3-(2-methoxyethoxy)benzyl)pyridin-2(1H)-one (described in previous step), 111 mg (0.440 mmol) of bis(pinacolato)diboron, 78 mg (0.799 mmol) of potassium acetate and 28 mg of PdCl$_2$ (PPh$_3$)$_2$. 75 mg of the title compound are obtained.
Yield: 61%.
MH+: 304.4 (boronic acid).

Step 6: 1-(3-(2-Methoxyethoxy)benzyl)-4-(5-morpholino-1-tosyl-1H-pyrrolo[2,3-b]pyridin-3-yl)pyridin-2(1H)-one

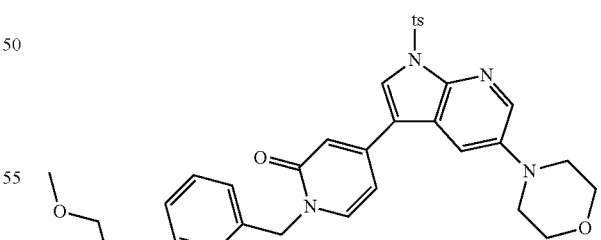

The compound is obtained by the procedure described in example 210 step 2, using 50 mg (0.103 mmol) of 3-iodo-5-morpholin-1-yl-1-tosyl-1H-pyrrolo[2,3-b]pyridine (described in example 17 step 3), 75 mg (0.247 mmol) of 1-(3-(2-methoxyethoxy)benzyl)-4-(4,4,5,5-tetramethyl-1,3,2-dioxaborolan-2-yl)pyridin-2(1H)-one (described in previous step) instead of 1-(4-chlorobenzyl)-2-oxo-1,2-dihydropyridin-4-ylboronic acid and 10 mg of PdCl$_2$(PPh$_3$)$_2$. 44 mg of the title compound are obtained.

Yield: 70%.
MH+: 615.6.

Step 7: 1-(3-(2-Methoxyethoxy)benzyl)-4-(5-morpholino-1H-pyrrolo[2,3-b]pyridin-3-yl)pyridin-2(1H)-one

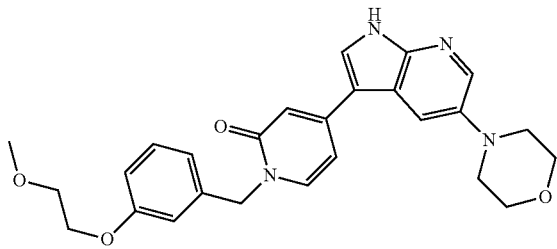 [SMILES: COCCOc1cccc(Cn2ccc(-c3c[nH]c4ncc(N5CCOCC5)cc34)cc2=O)c1]

The compound is obtained by the procedure described in example 110 step 6, using 44 mg (0.071 mmol) of 1-(3-(2-methoxyethoxy)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 10.1 mg of the title compound are obtained.

Yield: 31%.
MH+: 461.6.
$^1$H NMR (DMSO-d6, 300 MHz): δ 12.04 (br s, 1H); 8.17 (d, J=2.5 Hz, 1H); 8.08 (s, 1H); 7.73 (d, J=7.8 Hz, 1H); 7.71 (d, J=2.5 Hz, 1H); 7.27 (t, J=8.0 Hz, 1H); 6.94-6.82 (m, 3H); 6.74-6.67 (m, 2H); 5.07 (s, 2H); 4.09-4.02 (m, 2H); 3.82-3.74 (m, 4H); 3.67-3.60 (m, 2H); 3.29 (s, 3H); 3.18-3.09 (m, 4H).

Example 222: 4-(5-Morpholino-1H-pyrrolo[2,3-b]pyridin-3-yl)-1-(3-(trifluoromethoxy)benzyl)pyridin-2(1H)-one Step 1: 2-Oxo-1-(3-(trifluoromethoxy)benzyl)-1,2-dihydropyridin-4-ylboronic Acid

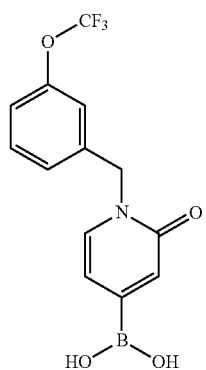 [SMILES: O=c1cc(B(O)O)ccn1Cc1cccc(OC(F)(F)F)c1]

The compound is obtained by the procedure described in example 25 step 1, using 55 µl (0.339 mmol) of 3-(trifluoromethoxy)benzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 25 mg of the title compound are obtained.

Yield: Quantitative.
MH+: 314.3.

Step 2: 4-(5-Morpholino-1-tosyl-1H-pyrrolo[2,3-b]pyridin-3-yl)-1-(3-(trifluoromethoxy)benzyl)pyridin-2(1H)-one

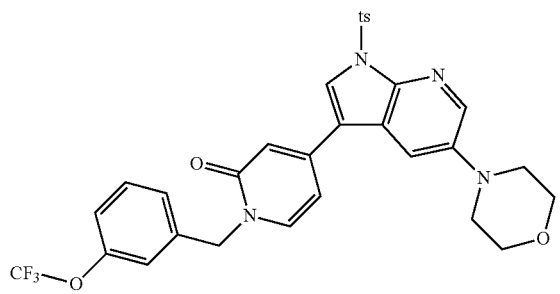

The compound is obtained by the procedure described in example 210 step 2, using 35 mg (0.073 mmol) of 3-iodo-5-morpholin-1-yl-1-tosyl-1H-pyrrolo[2,3-b]pyridine (described in example 17 step 3), 25 mg (0.79 mmol) of 2-oxo-1-(3-(trifluoromethoxy)benzyl)-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 25 mg of the title compound are obtained.

Yield: 55%.
MH+: 625.5.

Step 3: 4-(5-Morpholino-1H-pyrrolo[2,3-b]pyridin-3-yl)-1-(3-(trifluoromethoxy)benzyl)pyridin-2(1H)-one

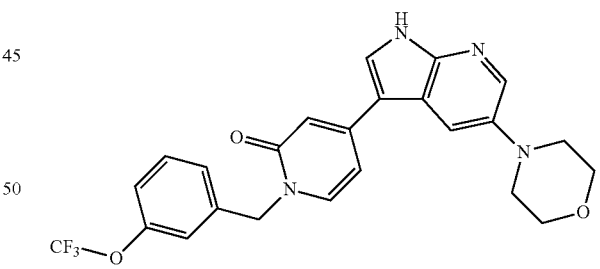

The compound is obtained by the procedure described in example 110 step 6, using 24 mg (0.039 mmol) of 4-(5-morpholino-1-tosyl-1H-pyrrolo[2,3-b]pyridin-3-yl)-1-(3-(trifluoromethoxy)benzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 11.2 mg of the title compound are obtained.

Yield: 62%.
MH+: 471.4.
$^1$H NMR (DMSO-d6, 300 MHz): δ 12.06 (br s, 1H); 8.17 (d, J=2.5 Hz, 1H); 8.10 (s, 1H); 7.81 (d, J=7.8 Hz, 1H); 7.71 (d, J=2.6 Hz, 1H); 7.51 (t, J=8.1 Hz, 1H); 7.39-7.32 (m, 2H);

7.32-7.26 (m, 1H); 6.77-6.70 (m, 2H); 5.15 (s, 2H); 3.83-3.74 (m, 4H); 3.20-3.10 (m, 4H).

Example 223: 1-(3-Fluoro-5-(trifluoromethoxy)benzyl)-4-(5-morpholino-1H-pyrrolo[2,3-b]pyridin-3-yl)pyridin-2(1H)-one Step 1: 1-(3-Fluoro-5-(trifluoromethoxy)benzyl)-2-oxo-1,2-dihydropyridin-4-ylboronic Acid

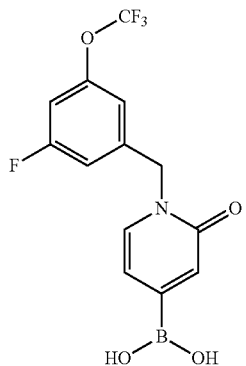

The compound is obtained by the procedure described in example 25 step 1, using 92 mg (0.339 mmol) of 1-(bromomethyl)-3-fluoro-5-(trifluoromethoxy)benzene instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 71 mg of the title compound are obtained.
Yield: Quantitative.
MH+: 332.4.

Step 2: 1-(3-Fluoro-5-(trifluoromethoxy)benzyl)-4-(5-morpholino-1-tosyl-1H-pyrrolo[2,3-b]pyridin-3-yl)pyridin-2(1H)-one

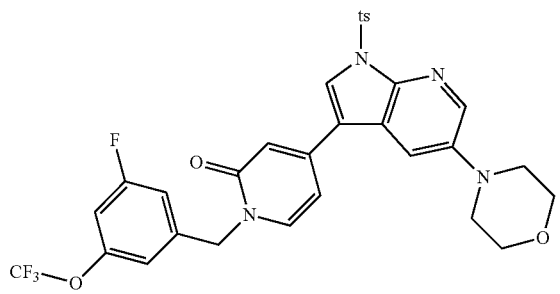

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 71 mg (0.214 mmol) of 1-(3-fluoro-5-(trifluoromethoxy)benzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 33 mg of the title compound are obtained.
Yield: 62%.
MH+: 643.4.

Step 3: 1-(3-Fluoro-5-(trifluoromethoxy)benzyl)-4-(5-morpholino-1H-pyrrolo[2,3-b]pyridin-3-yl)pyridin-2(1H)-one

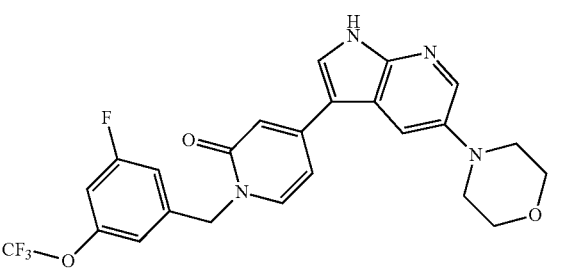 [SMILES: O=c1cc(-c2c[nH]c3ncc(N4CCOCC4)cc23)ccn1Cc1cc(F)cc(OC(F)(F)F)c1]

The compound is obtained by the procedure described in example 110 step 6, using 33 mg (0.051 mmol) of 1-(3-fluoro-5-(trifluoromethoxy)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 7.4 mg of the title compound are obtained.
Yield: 30%.
MH+: 489.4.
$^1$H NMR (DMSO-d6, 300 MHz): δ 12.07 (br s, 1H); 8.17 (d, J=2.5 Hz, 1H); 8.11 (s, 1H); 7.82 (d, J=7.0 Hz, 1H); 7.72 (d, J=2.5 Hz, 1H); 7.37-7.27 (m, 1H); 7.27-7.20 (m, 2H); 6.80-6.71 (m, 2H); 5.15 (s, 2H); 3.84-3.73 (m, 4H); 3.20-3.09 (m, 4H).

Example 224: 1-(2,3-Difluorobenzyl)-4-(5-morpholino-1H-pyrrolo[2,3-b]pyridin-3-yl)pyridin-2(1H)-one Step 1: 1-(2,3-Difluorobenzyl)-2-oxo-1,2-dihydropyridin-4-ylboronic Acid

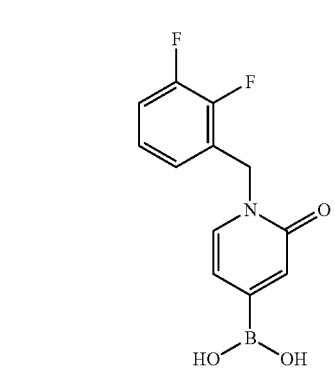

The compound is obtained by the procedure described in example 25 step 1, using 56 mg (0.271 mmol) of 2,3-difluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 28 mg of the title compound are obtained.
Yield: 46%.
MH+: 266.3.

Step 2: 1-(2,3-Difluorobenzyl)-4-(5-morpholino-1-tosyl-1H-pyrrolo[2,3-b]pyridin-3-yl)pyridin-2(1H)-one

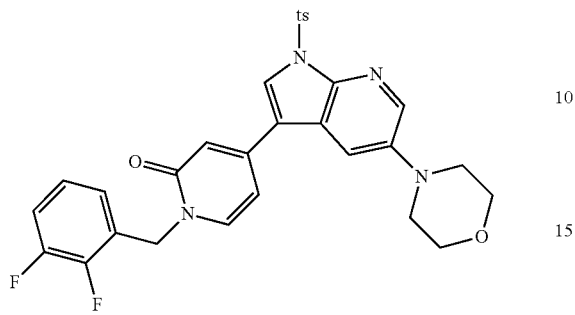

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 38 mg (0.135 mmol) of 1-(2,3-difluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$(PPh$_3$)$_2$. 30 mg of the title compound are obtained.

Yield: 65%.

MH+: 577.6.

Step 3: 1-(2,3-Difluorobenzyl)-4-(5-morpholino-1H-pyrrolo[2,3-b]pyridin-3-yl)pyridin-2(1H)-one

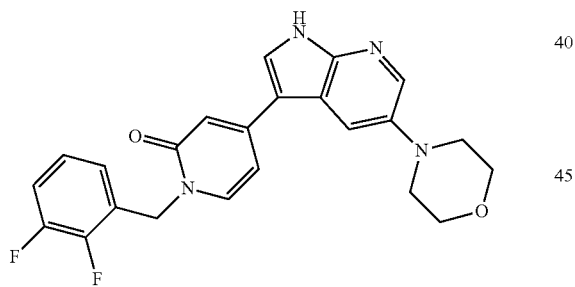

The compound is obtained by the procedure described in example 110 step 6, using 30 mg (0.059 mmol) of 1-(2,3-difluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 7.0 mg of the title compound are obtained.

Yield: 32%.

MH+: 423.4.

$^1$H NMR (DMSO-d6, 300 MHz): δ 12.06 (br s, 1H); 8.17 (d, J=2.5 Hz, 1H); 8.10 (s, 1H); 7.77-7.69 (m, 2H); 7.45-7.31 (m, 1H); 7.25-7.13 (m, 1H); 7.04-6.95 (m, 1H); 6.75 (dd, J=7.2 and 2.0 Hz, 1H); 6.71 (d, J=1.9 Hz, 1H); 5.19 (s, 2H); 3.84-3.73 (m, 4H); 3.19-3.09 (m, 4H).

Example 225: 4-(5-Morpholino-1H-pyrrolo[2,3-b]pyridin-3-yl)-1-(2,3,4-trifluorobenzyl)pyridin-2(1H)-one

Step 1: 2-Oxo-1-(2,3,4-trifluorobenzyl)-1,2-dihydropyridin-4-ylboronic Acid

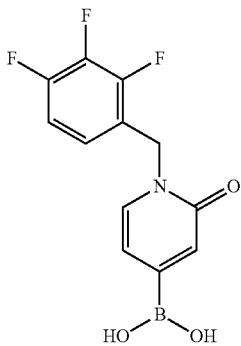 [SMILES: O=c1cc(B(O)O)ccn1Cc1ccc(F)c(F)c1F]

The compound is obtained by the procedure described in example 25 step 1, using 112 mg (0.497 mmol) of 2,3,4-trifluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 61 mg of the title compound are obtained.

Yield: Quantitative.

MH+: 284.3.

Step 2: 4-(5-Morpholino-1-tosyl-1H-pyrrolo[2,3-b]pyridin-3-yl)-1-(2,3,4-trifluorobenzyl)pyridin-2(1H)-one

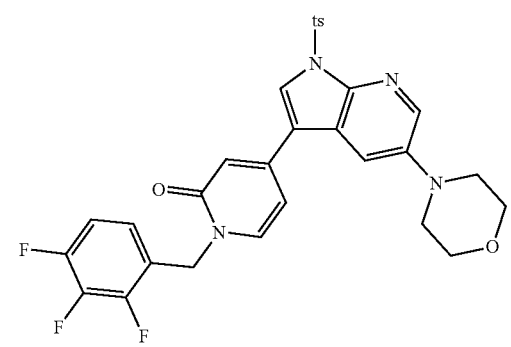

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 61 mg (0.135 mmol) of 2-oxo-1-(2,3,4-trifluorobenzyl)-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$(PPh$_3$)$_2$. 34 mg of the title compound are obtained.

Yield: 69%.

MH+: 595.4.

Step 3: 4-(5-Morpholino-1H-pyrrolo[2,3-b]pyridin-3-yl)-1-(2,3,4-trifluorobenzyl)pyridin-2(1H)-one

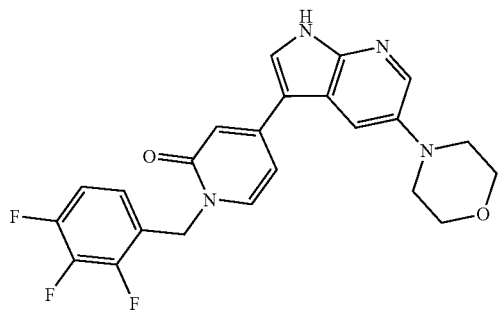 [SMILES: O=c1cc(-c2c[nH]c3ncc(N4CCOCC4)cc23)ccn1Cc1ccc(F)c(F)c1F]

The compound is obtained by the procedure described in example 110 step 6, using 34 mg (0.057 mmol) of 4-(5-morpholino-1-tosyl-1H-pyrrolo[2,3-b]pyridin-3-yl)-1-(2,3,4-trifluorobenzyl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 6.8 mg of the title compound are obtained.
Yield: 27%.
MH+: 441.3.
$^1$H NMR (DMSO-d6, 300 MHz): δ 12.07 (br s, 1H); 8.17 (d, J=2.5 Hz, 1H); 8.10 (s, 1H); 7.74 (d, J=7.2 Hz, 1H); 7.70 (d, J=2.6 Hz, 1H); 7.38-7.25 (m, 1H); 7.16-7.05 (m, 1H); 6.75 (dd, J=7.2 and 2.0 Hz, 1H); 6.70 (d, J=1.9 Hz, 1H); 5.16 (s, 2H); 3.84-3.75 (m, 4H); 3.19-3.10 (m, 4H).

Example 226: 1-(2-Chloro-3-fluorobenzyl)-4-(5-morpholino-1H-pyrrolo[2,3-b]pyridin-3-yl)pyridin-2(1H)-one

Step 1: 1-(2-Chloro-3-fluorobenzyl)-2-oxo-1,2-dihydropyridin-4-ylboronic Acid

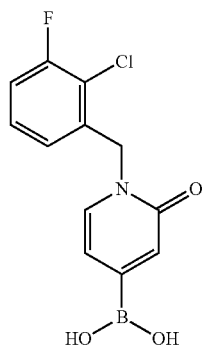 [SMILES: O=c1cc(B(O)O)ccn1Cc1cccc(F)c1Cl]

The compound is obtained by the procedure described in example 25 step 1, using 61 mg (0.271 mmol) of 2-chloro-3-fluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 39 mg of the title compound are obtained.
Yield: 61%.
MH+: 282.3; 284.3.

Step 2: 1-(2-Chloro-3-fluorobenzyl)-4-(5-morpholino-1-tosyl-1H-pyrrolo[2,3-b]pyridin-3-yl)pyridin-2(1H)-one

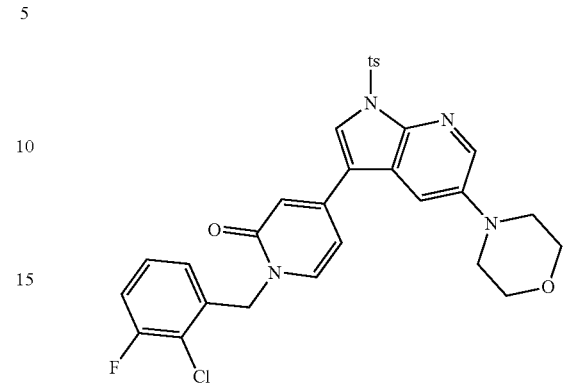

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 38 mg (0.135 mmol) of 1-(2-chloro-3-fluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 32 mg of the title compound are obtained.
Yield: 65%.
MH+: 593.5; 595.5.

Step 3: 1-(2-Chloro-3-fluorobenzyl)-4-(5-morpholino-1H-pyrrolo[2,3-b]pyridin-3-yl)pyridin-2(1H)-one

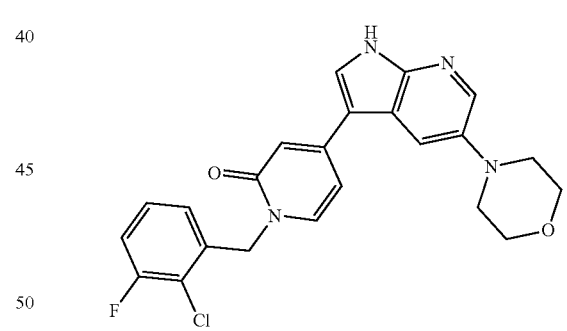

The compound is obtained by the procedure described in example 110 step 6, using 32 mg (0.054 mmol) of 1-(2-chloro-3-fluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 7.7 mg of the title compound are obtained.
Yield: 32%.
MH+: 439.4; 441.4.
$^1$H NMR (DMSO-d6, 300 MHz): δ 12.08 (br s, 1H); 8.18 (d, J=2.5 Hz, 1H); 8.13 (s, 1H); 7.73 (d, J=2.6 Hz, 1H); 7.71 (d, J=7.2 Hz, 1H); 7.42-7.34 (m, 2H); 6.84-6.74 (m, 3H); 5.21 (s, 2H); 3.84-3.74 (m, 4H); 3.21-3.11 (m, 4H).

Example 227: 1-(3-Chloro-5-fluorobenzyl)-4-(5-morpholino-1H-pyrrolo[2,3-b]pyridin-3-yl)pyridin-2(1H)-one

Step 1: 1-(3-Chloro-5-fluorobenzyl)-2-oxo-1,2-dihydropyridin-4-ylboronic Acid

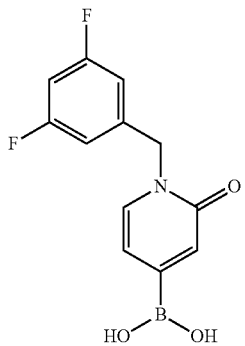 [SMILES: O=c1cc(B(O)O)ccn1Cc1cc(F)cc(F)c1]

The compound is obtained by the procedure described in example 25 step 1, using 61 mg (0.271 mmol) of 3-chloro-5-fluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 57 mg of the title compound are obtained.

Yield: Quantitative.

MH+: 282.3; 284.3.

Step 2: 1-(3-Chloro-5-fluorobenzyl)-4-(5-morpholino-1-tosyl-1H-pyrrolo[2,3-b]pyridin-3-yl)pyridin-2(1H)-one

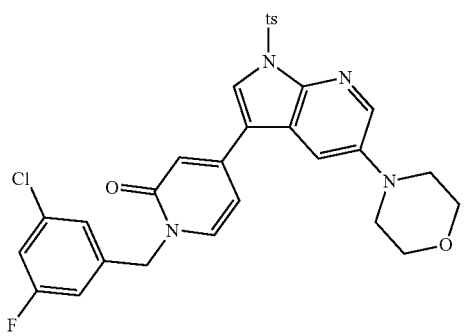

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 57 mg (0.202 mmol) of 1-(3-chloro-5-fluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$(PPh$_3$)$_2$. 24 mg of the title compound are obtained.

Yield: 62%.

MH+: 593.5; 595.5.

Step 3: 1-(3-Chloro-5-fluorobenzyl)-4-(5-morpholino-1H-pyrrolo[2,3-b]pyridin-3-yl)pyridin-2(1H)-one

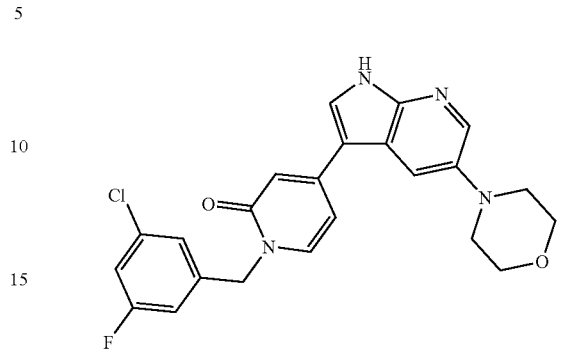

The compound is obtained by the procedure described in example 110 step 6, using 24 mg (0.040 mmol) of 1-(3-chloro-5-fluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 8.3 mg of the title compound are obtained.

Yield: 46%.

MH+: 439.4; 441.4.

$^1$H NMR (DMSO-d6, 300 MHz): δ 12.07 (br s, 1H); 8.17 (d, J=2.5 Hz, 1H); 8.10 (s, 1H); 7.81 (d, J=7.1 Hz, 1H); 7.72 (d, J=2.6 Hz, 1H); 7.42-7.35 (m, 1H); 7.27 (s, 1H); 7.22-7.16 (m, 1H); 6.79-6.71 (m, 2H); 5.11 (s, 2H); 3.84-3.74 (m, 4H); 3.20-3.10 (m, 4H).

Example 228: 1-(5-Chloro-2-fluorobenzyl)-4-(5-morpholino-1H-pyrrolo[2,3-b]pyridin-3-yl)pyridin-2(1H)-one

Step 1: 1-(5-Chloro-2-fluorobenzyl)-2-oxo-1,2-dihydropyridin-4-ylboronic Acid

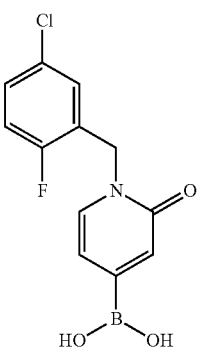 [SMILES: O=c1cc(B(O)O)ccn1Cc1cc(Cl)ccc1F]

The compound is obtained by the procedure described in example 25 step 1, using 40 μl (0.294 mmol) of 5-chloro-2-fluorobenzyl bromide instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 78 mg of the title compound are obtained.

Yield: Quantitative.

MH+: 282.3; 284.3.

Step 2: 1-(5-Chloro-2-fluorobenzyl)-4-(5-morpholino-1-tosyl-1H-pyrrolo[2,3-b]pyridin-3-yl)pyridin-2(1H)-one

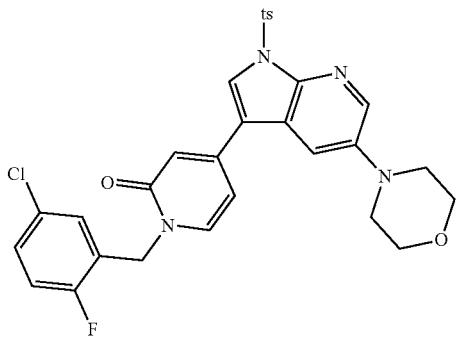

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 78 mg (0.277 mmol) of 1-(5-chloro-2-fluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 23 mg of the title compound are obtained.

Yield: 47%.
MH+: 593.5; 595.5.

Step 3: 1-(5-Chloro-2-fluorobenzyl)-4-(5-morpholino-1H-pyrrolo[2,3-b]pyridin-3-yl)pyridin-2(1H)-one

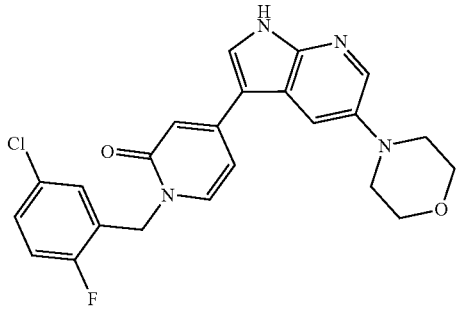 [SMILES: O=c1cc(-c2c[nH]c3ncc(N4CCOCC4)cc23)ccn1Cc1cc(Cl)ccc1F]

The compound is obtained by the procedure described in example 110 step 6, using 23 mg (0.039 mmol) of 1-(5-chloro-2-fluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 6.6 mg of the title compound are obtained.

Yield: 39%.
MH+: 439.4; 441.4.
$^1$H NMR (DMSO-d6, 300 MHz): δ 12.07 (br s, 1H); 8.17 (d, J=2.5 Hz, 1H); 8.11 (s, 1H); 7.77-7.71 (m, 2H); 7.48-7.39 (m, 1H); 7.31 (t, J=8.9 Hz, 1H); 7.23 (dd, J=6.4 and 2.7 Hz, 1H); 6.76 (dd, J=7.2 and 2.0 Hz, 1H); 6.72 (d, J=1.9 Hz, 1H); 5.13 (s, 2H); 3.83-3.73 (m, 4H); 3.20-3.09 (m, 4H).

Example 229: 1-(3-Chloro-2,4-difluorobenzyl)-4-(5-morpholino-1H-pyrrolo[2,3-b]pyridin-3-yl)pyridin-2(1H)-one

Step 1: (3-Chloro-2,4-difluorophenyl)methanol

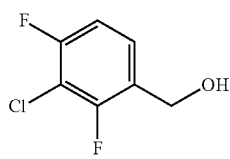 [SMILES: OCc1ccc(F)c(Cl)c1F]

1 ml (1 mmol) of a solution of BH$_3$ (1M in THF) is added slowly to a solution of 150 mg (0.85 mmol) of 3-chloro-2,4-difluorobenzaldehyde in 2 ml of anhydrous THF under argon at 0° C. The solution is stirred at 0° C. for 1 h. LC/MS shows complete conversion of the substrate. Then pieces of ice are slowly added until the end of gas evolution. NaHCO$_3$ in powder is added until pH 8-9. The solution is then diluted with water, extracted 3 times with DCM, dried over sodium sulfate, filtered and evaporated under reduced pressure. Crude product is purified by flash chromatography on a 30 g silica gel column with an ethyl acetate/hexane mixture as eluent. 126 mg of the title compound are obtained.

Yield: 83%.
(M-OH)+: 161.0; 163.0.

Step 2: 3-Chloro-2,4-difluorobenzyl Bromide

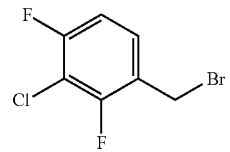 [SMILES: Fc1ccc(CBr)c(F)c1Cl]

126 mg (0.71 mmol) of (3-chloro-2,4-difluorophenyl)methanol (described in the previous step) and 99 µl (1.06 mmol) of phosphorus tribromide are dissolved in 3 ml of anhydrous THF under argon, and the mixture is stirred at ambient temperature for 16 h. Then the solution is diluted with Et$_2$O. The organic layer is washed 3 times with water, dried over sodium sulfate, filtered and evaporated under reduced pressure. Crude product is purified by flash chromatography on a 30 g silica gel column with an ethyl acetate/hexane mixture as eluent. 159 mg of the title compound are obtained.

Yield: 93%.
(M-Br)+: 161.0; 163.0.

Step 3: 1-(3-Chloro-2,4-difluorobenzyl)-2-oxo-1,2-dihydropyridin-4-ylboronic Acid

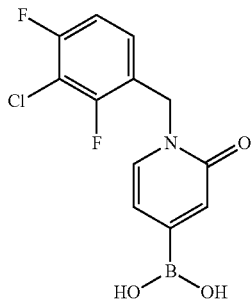 [SMILES: O=c1cc(B(O)O)ccn1Cc1ccc(F)c(Cl)c1F]

The compound is obtained by the procedure described in example 25 step 1, using 158 mg (0.654 mmol) of 3-chloro-2,4-difluorobenzyl bromide (described in the previous step) instead of benzyl bromide, 100 mg (0.452 mmol) of 4-(4,4,5,5-tetramethyl-[1,3,2]dioxaborolan-2-yl)-1H-pyridin-2-one and 220 mg (0.678 mmol) of cesium carbonate. 43 mg of the title compound are obtained.

Yield: 30%.
MH+: 300.3; 302.3.

Step 4: 1-(3-Chloro-2,4-difluorobenzyl)-4-(5-morpholino-1-tosyl-1H-pyrrolo[2,3-b]pyridin-3-yl)pyridin-2(1H)-one

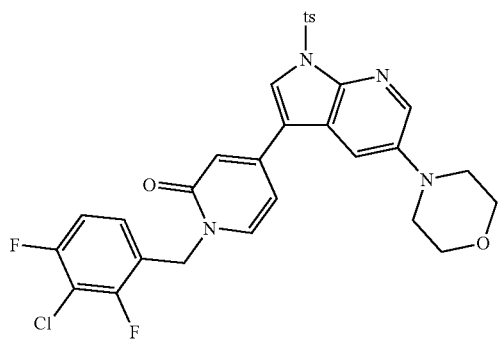

The compound is obtained by the procedure described in example 210 step 2, using 58 mg (0.120 mmol) of 3-iodo-5-morpholin-1-yl-1-tosyl-1H-pyrrolo[2,3-b]pyridine (described in example 17 step 3), 43 mg (0.143 mmol) of 1-(3-chloro-2,4-difluorobenzyl)-2-oxo-1,2-dihydropyridin-4-ylboronic acid (described in previous step) instead of 1-(4-chlorobenzyl)-2-oxo-1,2-dihydropyridin-4-ylboronic acid and 6 mg of PdCl$_2$(PPh$_3$)$_2$. 38 mg of the title compound are obtained.

Yield: 52%.
MH+: 611.3; 613.3.

Step 5: 1-(3-Chloro-2,4-difluorobenzyl)-4-(5-morpholino-1H-pyrrolo[2,3-b]pyridin-3-yl)pyridin-2(1H)-one

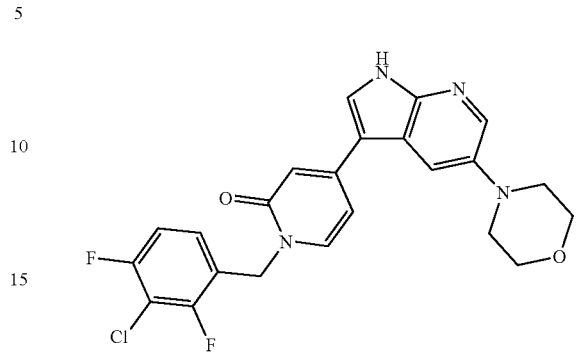

The compound is obtained by the procedure described in example 110 step 6, using 38 mg (0.062 mmol) of 1-(3-chloro-2,4-difluorobenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 6.4 mg of the title compound are obtained.

Yield: 22%.
MH+: 457.4; 459.3.
$^1$H NMR (DMSO-d6, 300 MHz): δ 12.07 (br s, 1H); 8.17 (d, J=2.5 Hz, 1H); 8.10 (s, 1H); 7.75 (d, J=7.1 Hz, 1H); 7.70 (d, J=2.6 Hz, 1H); 7.37-7.22 (m, 2H); 6.75 (dd, J=7.2 and 2.0 Hz, 1H); 6.70 (d, J=1.9 Hz, 1H); 5.15 (s, 2H); 3.84-3.74 (m, 4H); 3.20-3.10 (m, 4H).

Example 230: 1-(3-Fluoro-4-(trifluoromethyl)benzyl)-4-(5-morpholino-1H-pyrrolo[2,3-b]pyridin-3-yl)pyridin-2(1H)-one

Step 1: 1-(3-Fluoro-4-(trifluoromethyl)benzyl)-2-oxo-1,2-dihydropyridin-4-ylboronic Acid

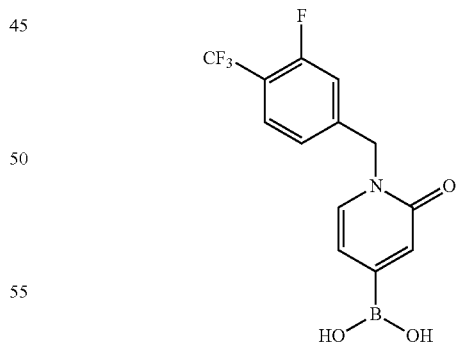

The compound is obtained by the procedure described in example 25 step 1, using 43 µl (0.272 mmol) of 4-(bromomethyl)-2-fluoro-1-(trifluoromethyl)benzene instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 92 mg of the title compound are obtained.

Yield: Quantitative.
MH+: 316.4.

Step 2: 1-(3-Fluoro-4-(trifluoromethyl)benzyl)-4-(5-morpholino-1-tosyl-1H-pyrrolo[2,3-b]pyridin-3-yl)pyridin-2(1H)-one

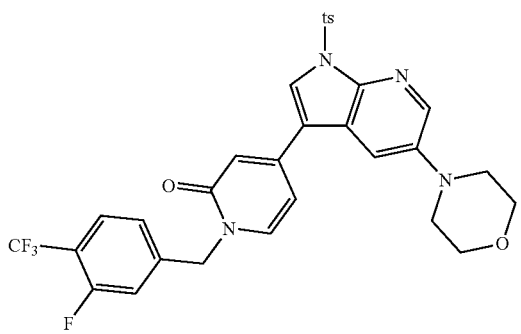

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 92 mg (0.226 mmol) of 1-(3-fluoro-4-(trifluoromethyl)benzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of $PdCl_2$ $(PPh_3)_2$. 36 mg of the title compound are obtained.

Yield: 70%.
MH+: 627.6.

Step 3: 1-(3-Fluoro-4-(trifluoromethyl)benzyl)-4-(5-morpholino-1H-pyrrolo[2,3-b]pyridin-3-yl)pyridin-2(1H)-one

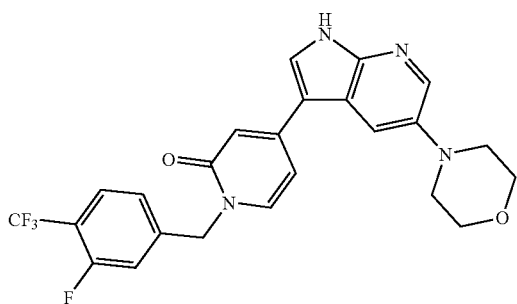 [SMILES: O=c1cc(-c2c[nH]c3ncc(N4CCOCC4)cc23)ccn1Cc1ccc(C(F)(F)F)c(F)c1]

The compound is obtained by the procedure described in example 110 step 6, using 36 mg (0.057 mmol) of 1-(3-fluoro-4-(trifluoromethyl)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 12.4 mg of the title compound are obtained.

Yield: 45%.
MH+: 473.5.

$^1$H NMR (DMSO-d6, 300 MHz): δ 12.07 (br s, 1H); 8.17 (d, J=2.5 Hz, 1H); 8.11 (s, 1H); 7.85-7.74 (m, 2H); 7.71 (d, J=2.5 Hz, 1H); 7.45 (d, J=11.6 Hz, 1H); 7.31 (d, J=8.3 Hz, 1H); 6.80-6.72 (m, 2H); 5.20 (s, 2H); 3.84-3.74 (m, 4H); 3.19-3.09 (m, 4H).

Example 231: 1-(2-Fluoro-3-(trifluoromethyl)benzyl)-4-(5-morpholino-1H-pyrrolo[2,3-b]pyridin-3-yl)pyridin-2(1H)-one

Step 1: 1-(2-Fluoro-3-(trifluoromethyl)benzyl)-2-oxo-1,2-dihydropyridin-4-ylboronic Acid

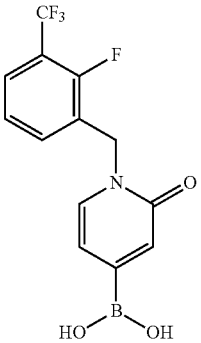 [SMILES: O=c1cc(B(O)O)ccn1Cc1cccc(C(F)(F)F)c1F]

The compound is obtained by the procedure described in example 25 step 1, using 70 mg (0.271 mmol) of 1-(bromomethyl)-2-fluoro-3-(trifluoromethyl)benzene instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 32 mg of the title compound are obtained.

Yield: 45%.
MH+: 316.4.

Step 2: 1-(2-Fluoro-3-(trifluoromethyl)benzyl)-4-(5-morpholino-1-tosyl-1H-pyrrolo[2,3-b]pyridin-3-yl)pyridin-2(1H)-one

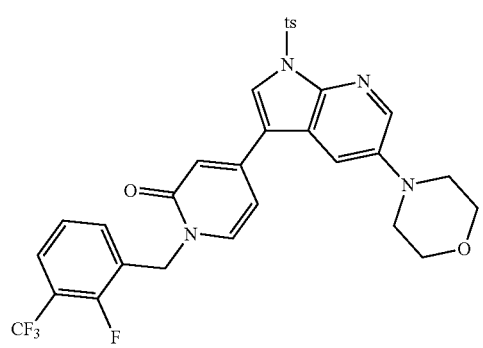

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 32 mg (0.102 mmol) of 1-(2-fluoro-3-(trifluoromethyl)benzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of $PdCl_2$ $(PPh_3)_2$. 34 mg of the title compound are obtained.

Yield: 66%.
MH+: 627.5.

Step 3: 1-(2-Fluoro-3-(trifluoromethyl)benzyl)-4-(5-morpholino-1H-pyrrolo[2,3-b]pyridin-3-yl)pyridin-2(1H)-one

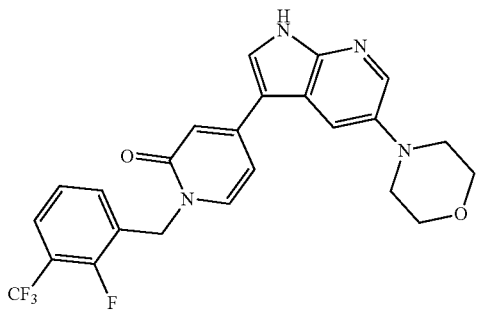 [SMILES: O=c1cc(-c2c[nH]c3ncc(N4CCOCC4)cc23)ccn1Cc1cccc(C(F)(F)F)c1F]

The compound is obtained by the procedure described in example 110 step 6, using 34 mg (0.059 mmol) of 1-(2-fluoro-3-(trifluoromethyl)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 10.2 mg of the title compound are obtained.

Yield: 37%.

MH+: 473.5.

$^1$H NMR (DMSO-d6, 300 MHz): δ 12.08 (br s, 1H); 8.17 (d, J=2.5 Hz, 1H); 8.11 (s, 1H); 7.78 (d, J=7.1 Hz, 1H); 7.75-7.68 (m, 2H); 7.55-7.45 (m, 1H); 7.40 (t, J=7.5 Hz, 1H); 6.78 (dd, J=7.2 and 1.9 Hz, 1H); 6.72 (d, J=1. Hz, 1H); 5.22 (s, 2H); 3.83-3.73 (m, 4H); 3.19-3.10 (m, 4H).

Example 232: 1-(3-Chloro-4-(trifluoromethyl)benzyl)-4-(5-morpholino-1H-pyrrolo[2,3-b]pyridin-3-yl)pyridin-2(1H)-one

Step 1: (3-Chloro-4-(trifluoromethyl)phenyl)methanol

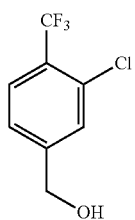

To a solution of 300 mg (1.34 mmol) of 3-chloro-4-(trifluoromethyl)benzoic acid in 3 ml of anhydrous THF, are slowly added 4.7 ml (4.69 mmol) of a solution of BH$_3$ (1M in THF) at 0° C. and under argon. The solution is stirred at room temperature for 3 h then cooled to 0° C. Pieces of ice are slowly added until the end of gas evolution. NaHCO$_3$ in powder is added until pH 8-9. The solution is then diluted with water, extracted 3 times with DCM, dried over sodium sulfate, filtered and evaporated under reduced pressure. Crude product is used in the next step without further purification. 251 mg of the title compound are obtained.

Yield: 89%.

(M-OH)+: 193.2; 195.2.

Step 2: 4-(Bromomethyl)-2-chloro-1-(trifluoromethyl)benzene

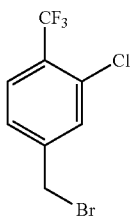 [SMILES: FC(F)(F)c1ccc(CBr)cc1Cl]

251 mg (1.19 mmol) of (3-chloro-4-(trifluoromethyl)phenyl)methanol (described in the previous step) and 168 μl (1.79 mmol) of phosphorus tribromide are dissolved in 3 ml of anhydrous THF under argon, and the mixture is stirred at ambient temperature overnight. Then the solution is diluted with diethyl ether, washed 3 times with water, dried over sodium sulfate, filtered and evaporated under reduced pressure. Crude product is used in the next step without further purification. 400 mg of the title compound are obtained.

Yield: Quantitative.

Step 3: 4-Bromo-1-(3-chloro-4-(trifluoromethyl)benzyl)pyridin-2(1H)-one

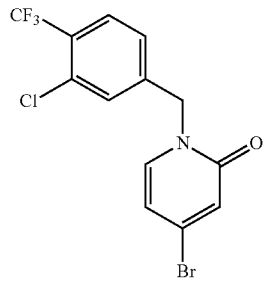 [SMILES: O=c1cc(Br)ccn1Cc1ccc(C(F)(F)F)c(Cl)c1]

The compound is obtained by the procedure described in example 203 step 1, using 218 mg (1.25 mmol) of 4-bromopyridin-2-(1H)-one, 325 mg (1.19 mmol) of 4-(bromomethyl)-2-chloro-1-(trifluoromethyl)benzene (described in previous step) instead of 1-(bromomethyl)naphthalene and 583 mg (1.79 mmol) of cesium carbonate. 266 mg of the title compound are obtained.

Yield: 61%.

MH+: 366.3; 368.3; 370.4.

Step 4: 1-(3-Chloro-4-(trifluoromethyl)benzyl)-4-(4,4,5,5-tetramethyl-1,3,2-dioxaborolan-2-yl)pyridin-2(1H)-one

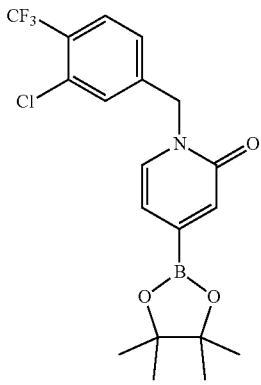 [SMILES: CC1(C)OB(c2ccn(Cc3ccc(C(F)(F)F)c(Cl)c3)c(=O)c2)OC1(C)C]

The compound is obtained by the procedure described in example 203 step 2, using 266 mg (0.726 mmol) of 4-bromo-1-(3-chloro-4-(trifluoromethyl)benzyl)pyridin-2(1H)-one (described in previous step), 203 mg (0.799 mmol) of bis(pinacolato)diboron, 142 mg (1.45 mmol) of potassium acetate and 25 mg of PdCl$_2$(PPh$_3$)$_2$. 140 mg of the title compound are obtained.

Yield: 58%.

MH+: 332.4; 334.4 (boronic acid).

Step 5: 1-(3-Chloro-4-(trifluoromethyl)benzyl)-4-(5-morpholino-1-tosyl-1H-pyrrolo[2,3-b]pyridin-3-yl)pyridin-2(1H)-one

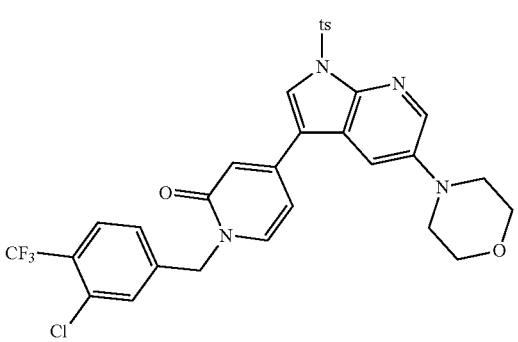

The compound is obtained by the procedure described in example 210 step 2, using 52 mg (0.108 mmol) of 3-iodo-5-morpholin-1-yl-1-tosyl-1H-pyrrolo[2,3-b]pyridine (described in example 17 step 3), 38 mg (0.113 mmol) of 1-(3-chloro-4-(trifluoromethyl)benzyl)-4-(4,4,5,5-tetramethyl-1,3,2-dioxaborolan-2-yl)pyridin-2(1H)-one (described in previous step) instead of 1-(4-chlorobenzyl)-2-oxo-1,2-dihydropyridin-4-ylboronic acid and 8 mg of PdCl$_2$ (PPh$_3$)$_2$. 29 mg of the title compound are obtained.

Yield: 42%.

MH+: 643.5; 645.5.

Step 6: 1-(3-Chloro-4-(trifluoromethyl)benzyl)-4-(5-morpholino-1H-pyrrolo[2,3-b]pyridin-3-yl)pyridin-2(1H)-one

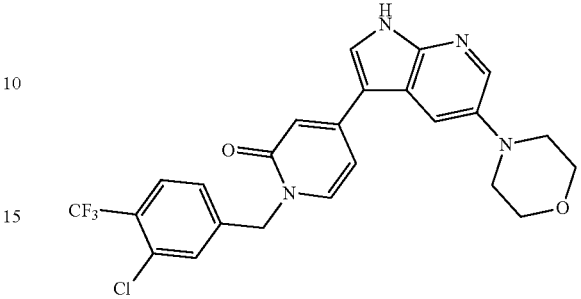

The compound is obtained by the procedure described in example 110 step 6, using 29 mg (0.045 mmol) of 1-(3-chloro-4-(trifluoromethyl)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 12 mg of the title compound are obtained.

Yield: 55%.

MH+: 489.5; 491.5.

$^1$H NMR (DMSO-d6, 300 MHz): δ 12.08 (br s, 1H); 8.17 (d, J=2.5 Hz, 1H); 8.12 (d, J=2.9 Hz, 1H); 7.90-7.79 (m, 2H); 7.72 (d, J=2.3 Hz, 1H); 7.68 (s, 1H); 7.45 (d, J=7.9 Hz, 1H); 6.80-6.71 (m, 2H); 5.19 (s, 2H); 3.84-3.74 (m, 4H); 3.20-3.09 (m, 4H).

Example 233: 1-(5-Chloro-2-methoxybenzyl)-4-(5-morpholino-1H-pyrrolo[2,3-b]pyridin-3-yl)pyridin-2(1H)-one

Step 1: (5-Chloro-2-methoxyphenyl)methanol

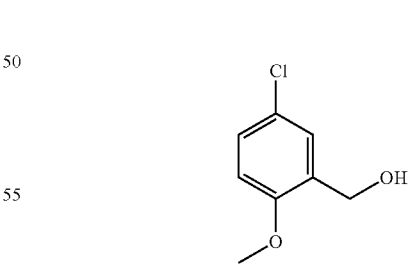

The compound is obtained by the procedure described in example 229 step 1, using 1.35 ml (1.35 mmol) of a solution of BH$_3$ (1M in THF) and 200 mg (1.18 mmol) of 5-chloro-2-methoxybenzaldehyde instead of 3-chloro-2,4-difluorobenzaldehyde. 181 mg of the title compound are obtained.

Yield: 90%.

(M-OH)+: 154.9; 157.0.

Step 2: 2-(Bromomethyl)-4-chloro-1-methoxybenzene

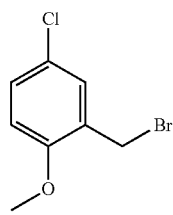

The compound is obtained by the procedure described in example 229 step 2, using 181 mg (1.04 mmol) of (5-chloro-2-methoxyphenyl)methanol (described in previous step) instead of (3-chloro-2,4-difluorophenyl)methanol and 146 μl (1.56 mmol) of phosphorus tribromide. 244 mg of the title compound are obtained.

Yield: Quantitative.

(M-Br)+: 154.9; 156.9.

Step 3: 1-(5-Chloro-2-methoxybenzyl)-2-oxo-1,2-dihydropyridin-4-ylboronic Acid

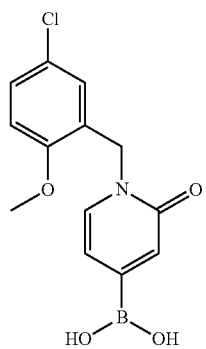 [SMILES: COc1ccc(Cl)cc1Cn1ccc(B(O)O)cc1=O]

The compound is obtained by the procedure described in example 25 step 1, using 127 mg (0.542 mmol) of 2-(bromomethyl)-4-chloro-1-methoxybenzene (described in the previous step) instead of benzyl bromide, 100 mg (0.452 mmol) of 4-(4,4,5,5-tetramethyl-[1,3,2]dioxaborolan-2-yl)-1H-pyridin-2-one and 220 mg (0.678 mmol) of cesium carbonate. 49 mg of the title compound are obtained.

Yield: 37%.

MH+: 294.3; 296.3.

Step 4: 1-(5-Chloro-2-methoxybenzyl)-4-(5-morpholino-1-tosyl-1H-pyrrolo[2,3-b]pyridin-3-yl)pyridin-2(1H)-one

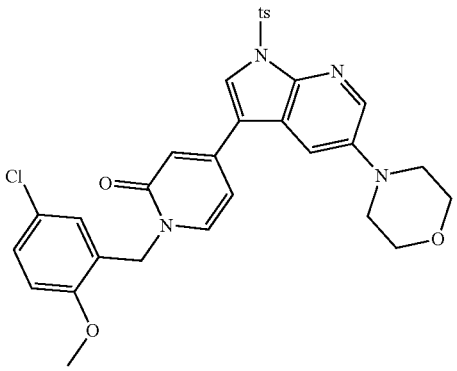

The compound is obtained by the procedure described in example 210 step 2, using 67 mg (0.140 mmol) of 3-iodo-5-morpholin-1-yl-1-tosyl-1H-pyrrolo[2,3-b]pyridine (described in example 17 step 3), 49 mg (0.166 mmol) of 1-(5-chloro-2-methoxybenzyl)-2-oxo-1,2-dihydropyridin-4-ylboronic acid (described in previous step) instead of 1-(4-chlorobenzyl)-2-oxo-1,2-dihydropyridin-4-ylboronic acid and 13 mg of PdCl$_2$(PPh$_3$)$_2$. 50 mg of the title compound are obtained.

Yield: 60%.

MH+: 605.4; 607.4.

Step 5: 1-(5-Chloro-2-methoxybenzyl)-4-(5-morpholino-1H-pyrrolo[2,3-b]pyridin-3-yl)pyridin-2(1H)-one

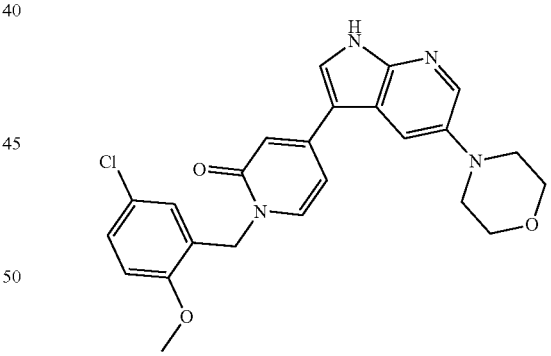

The compound is obtained by the procedure described in example 110 step 6, using 50 mg (0.082 mmol) of 1-(5-chloro-2-methoxybenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 12.3 mg of the title compound are obtained.

Yield: 33%.

MH+: 451.4; 453.3.

$^1$H NMR (DMSO-d6, 300 MHz): δ 12.06 (br s, 1H); 8.17 (d, J=2.5 Hz, 1H); 8.10 (s, 1H); 7.72 (d, J=2.6 Hz, 1H); 7.66 (d, J=7.8 Hz, 1H); 7.34 (dd, J=8.8 and 2. Hz, 1H); 7.08 (d, J=8.8 Hz, 1H); 6.95 (d, J=2. Hz, 1H); 6.77-6.69 (m, 2H); 5.01 (s, 2H); 3.86 (s, 3H); 3.83-3.73 (m, 4H); 3.19-3.10 (m, 4H).

Example 234: 1-(4-Chloro-2-methoxybenzyl)-4-(5-morpholino-1H-pyrrolo[2,3-b]pyridin-3-yl)pyridin-2(1H)-one Step 1: 1-(Bromomethyl)-4-chloro-2-methoxybenzene

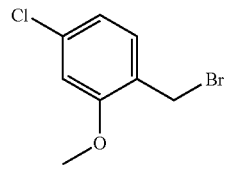

The compound is obtained by the procedure described in example 229 step 2, using 180 mg (1.04 mmol) of (4-chloro-2-methoxyphenyl)methanol instead of (3-chloro-2,4-difluorophenyl)methanol and 146 µl (1.56 mmol) of phosphorus tribromide. 310 mg of the title compound are obtained.

Yield: Quantitative.

(M-Br)+: 154.9; 157.0.

Step 2: 1-(4-Chloro-2-methoxybenzyl)-2-oxo-1,2-dihydropyridin-4-ylboronic Acid

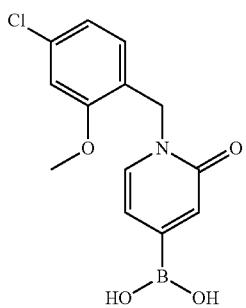 [SMILES: COc1cc(Cl)ccc1Cn1ccc(B(O)O)cc1=O]

The compound is obtained by the procedure described in example 25 step 1, using 127 mg (0.542 mmol) of 1-(bromomethyl)-4-chloro-2-methoxybenzene (described in the previous step) instead of benzyl bromide, 100 mg (0.452 mmol) of 4-(4,4,5,5-tetramethyl-[1,3,2]dioxaborolan-2-yl)-1H-pyridin-2-one and 220 mg (0.678 mmol) of cesium carbonate. 38 mg of the title compound are obtained.

Yield: 29%.

MH+: 294.3; 296.3.

Step 3: 1-(4-Chloro-2-methoxybenzyl)-4-(5-morpholino-1-tosyl-1H-pyrrolo[2,3-b]pyridin-3-yl)pyridin-2(1H)-one

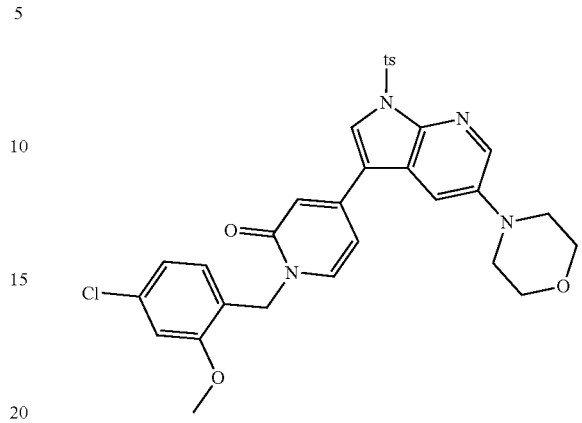

The compound is obtained by the procedure described in example 210 step 2, using 52 mg (0.108 mmol) of 3-iodo-5-morpholin-1-yl-1-tosyl-1H-pyrrolo[2,3-b]pyridine (described in example 17 step 3), 38 mg (0.129 mmol) of 1-(4-chloro-2-methoxybenzyl)-2-oxo-1,2-dihydropyridin-4-ylboronic acid (described in previous step) instead of 1-(4-chlorobenzyl)-2-oxo-1,2-dihydropyridin-4-ylboronic acid and 10 mg of PdCl$_2$ (PPh$_3$)$_2$. 35 mg of the title compound are obtained.

Yield: 53%.

MH+: 605.4; 607.4.

Step 4: 1-(4-Chloro-2-methoxybenzyl)-4-(5-morpholino-1H-pyrrolo[2,3-b]pyridin-3-yl)pyridin-2(1H)-one

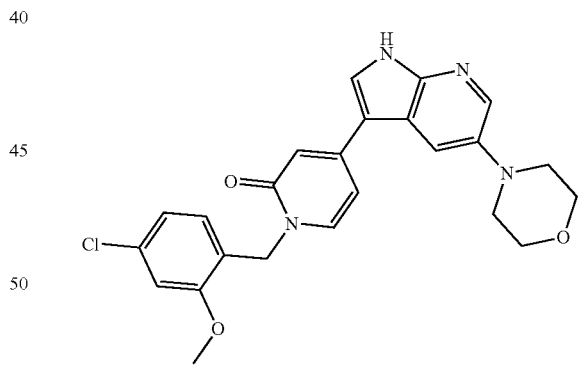

The compound is obtained by the procedure described in example 110 step 6, using 35 mg (0.058 mmol) of 1-(4-chloro-2-methoxybenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 14.9 mg of the title compound are obtained.

Yield: 73%.

MH+: 451.4; 453.4.

$^1$H NMR (DMSO-d6, 300 MHz): δ 12.04 (br s, 1H); 8.17 (d, J=2.5 Hz, 1H); 8.08 (s, 1H); 7.71 (d, J=2.6 Hz, 1H);

7.67-7.60 (m, 1H); 7.13 (d, J=1.0 Hz, 1H); 7.00-6.96 (m, 2H); 6.74-6.68 (m, 2H); 5.00 (s, 2H); 3.88 (s, 3H); 3.83-3.72 (m, 4H); 3.20-3.09 (m, 4H).

Example 235: 1-(3-Chloro-5-methoxybenzyl)-4-(5-morpholino-1H-pyrrolo[2,3-b]pyridin-3-yl)pyridin-2(1H)-one Step 1: 1-(3-Chloro-5-methoxybenzyl)-2-oxo-1,2-dihydropyridin-4-ylboronic Acid

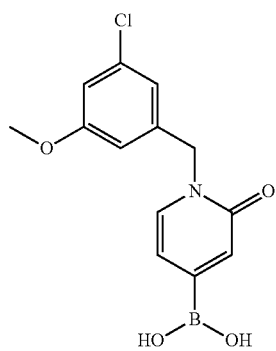 [SMILES: COc1cc(Cl)cc(Cn2ccc(B(O)O)cc2=O)c1]

The compound is obtained by the procedure described in example 25 step 1, using 91 mg (0.339 mmol) of 1-(bromomethyl)-3-chloro-5-methoxybenzene instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 91 mg of the title compound are obtained.
Yield: Quantitative.
MH+: 294.4; 296.5.

Step 2: 1-(3-Chloro-5-methoxybenzyl)-4-(5-morpholino-1-tosyl-1H-pyrrolo[2,3-b]pyridin-3-yl)pyridin-2(1H)-one

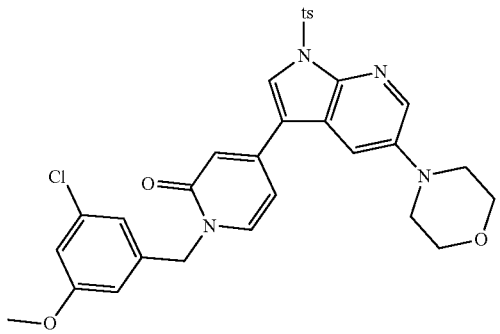

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 55 mg (0.187 mmol) of 1-(3-chloro-5-methoxybenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 19 mg of the title compound are obtained.
Yield: 38%.
MH+: 605.6; 607.7.

Step 3: 1-(3-Chloro-5-methoxybenzyl)-4-(5-morpholino-1H-pyrrolo[2,3-b]pyridin-3-yl)pyridin-2(1H)-one

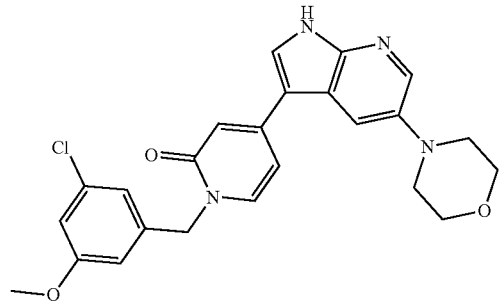 [SMILES: COc1cc(Cl)cc(Cn2ccc(-c3c[nH]c4ncc(N5CCOCC5)cc34)cc2=O)c1]

The compound is obtained by the procedure described in example 110 step 6, using 19 mg (0.031 mmol) of 1-(3-chloro-5-methoxybenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 6.0 mg of the title compound are obtained.
Yield: 40%.
MH+: 451.5; 453.5.
$^1$H NMR (DMSO-d6, 300 MHz): δ 12.06 (br s, 1H); 8.17 (d, J=2.5 Hz, 1H); 8.10 (s, 1H); 7.77 (d, J=7.9 Hz, 1H); 7.71 (d, J=2.5 Hz, 1H); 6.99-6.93 (m, 2H); 6.93-6.88 (m, 1H); 6.77-6.69 (m, 2H); 5.06 (s, 2H); 3.85-3.70 (m, 7H); 3.20-3.09 (m, 4H).

Example 236: 1-(3-Chloro-5-isopropoxybenzyl)-4-(5-morpholino-1H-pyrrolo[2,3-b]pyridin-3-yl)pyridin-2(1H)-one Step 1: 4-Bromo-1-(3-chloro-5-hydroxybenzyl)pyridin-2(1H)-one

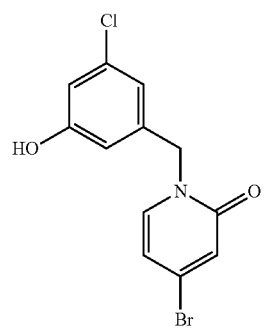

The compound is obtained by the procedure described in example 203 step 1, using 139 mg (0.804 mmol) of 4-bromopyridin-2-(1H)-one, 196 mg (0.885 mmol) of 3-(bromomethyl)-5-chlorophenol (described in example 36 step 3) instead of 1-(bromomethyl)naphthalene and 392 mg (1.2 mmol) of cesium carbonate. 280 mg of the title compound are obtained.
Yield: Quantitative.
MH+: 314.3; 316.3; 318.3.

Step 2: 4-Bromo-1-(3-chloro-5-isopropoxybenzyl) pyridin-2(1H)-one

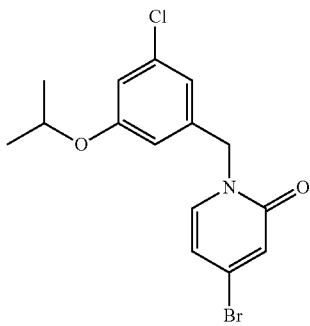 [SMILES: CC(C)Oc1cc(Cl)cc(Cn2ccc(Br)cc2=O)c1]

In 1 ml of anhydrous DMF, are added 90 mg (0.284 mmol) of 4-bromo-1-(3-chloro-5-hydroxybenzyl)pyridin-2 (1H)-one (described in previous step), 31 μl (0.312 mmol) of 2-iodopropane and 47 mg (0.341 mmol) of potassium carbonate under argon. The mixture is stirred at ambient temperature for 16 h, then 31 μl (0.312 mmol) of 2-iodopropane are added, and the mixture is stirred for 16 h more at room temperature. The mixture is then diluted with water, extracted 3 times with ethyl acetate. The combined organic layers are dried over sodium sulfate and evaporated under reduced pressure. Crude product is purified by flash chromatography on a 10 g silica gel column with an ethyl acetate/hexane mixture as eluent. 72 mg of the title compound are obtained.

Yield: 71%.
MH+: 356.4; 358.4; 360.4.

Step 3: 1-(3-Chloro-5-isopropoxybenzyl)-4-(4,4,5,5-tetramethyl-1,3,2-dioxaborolan-2-yl)pyridin-2(1H)-one

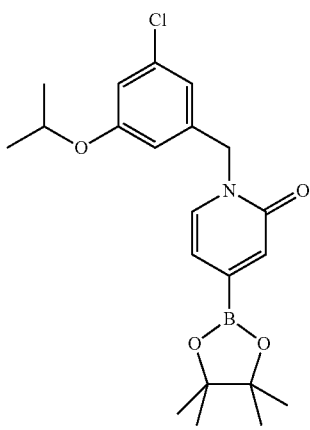 [SMILES: CC(C)Oc1cc(Cl)cc(Cn2ccc(B3OC(C)(C)C(C)(C)O3)cc2=O)c1]

The compound is obtained by the procedure described in example 203 step 2, using 70 mg (0.196 mmol) of 4-bromo-1-(3-chloro-5-isopropoxybenzyl)pyridin-2(1H)-one (described in previous step), 55 mg (0.216 mmol) of bis(pinacolato)diboron, 38 mg (0.392 mmol) of potassium acetate and 14 mg of PdCl$_2$ (PPh$_3$)$_2$. 74 mg of the title compound are obtained.

Yield: Quantitative.
MH+: 322.5; 324.5.

Step 4: 1-(3-Chloro-5-isopropoxybenzyl)-4-(5-morpholino-1-tosyl-1H-pyrrolo[2,3-b]pyridin-3-yl)pyridin-2(1H)-one

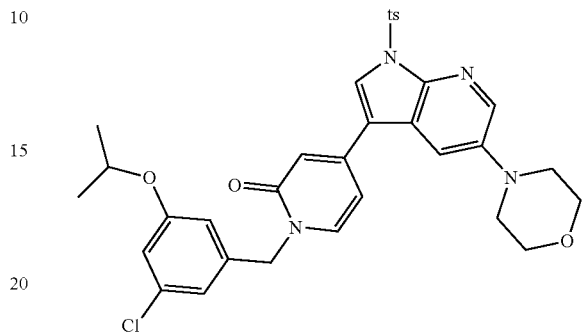

The compound is obtained by the procedure described in example 210 step 2, using 101 mg (0.208 mmol) of 3-iodo-5-morpholin-1-yl-1-tosyl-1H-pyrrolo[2,3-b]pyridine (described in example 17 step 3), 70 mg (0.218 mmol) of 1-(3-chloro-5-isopropoxybenzyl)-4-(4,4,5,5-tetramethyl-1,3,2-dioxaborolan-2-yl)pyridin-2(1H)-one (described in previous step) instead of 1-(4-chlorobenzyl)-2-oxo-1,2-dihydropyridin-4-ylboronic acid and 31 mg of PdCl$_2$ (PPh$_3$)$_2$. 101 mg of the title compound are obtained.

Yield: 73%.
MH+: 633.5; 635.5.

Step 5: 1-(3-Chloro-5-isopropoxybenzyl)-4-(5-morpholino-1H-pyrrolo[2,3-b]pyridin-3-yl)pyridin-2(1H)-one

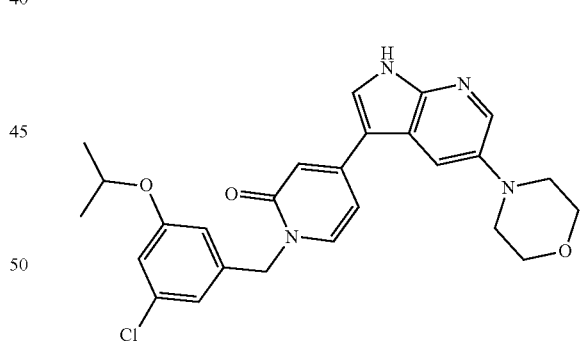

The compound is obtained by the procedure described in example 110 step 6, using 101 mg (0.160 mmol) of 1-(3-chloro-5-isopropoxybenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 22 mg of the title compound are obtained.

Yield: 29%.
MH+: 479.6; 481.6.
$^1$H NMR (DMSO-d6, 300 MHz): δ 12.05 (br s, 1H); 8.17 (d, J=2.5 Hz, 1H); 8.09 (s, 1H); 7.77 (d, J=7.8 Hz, 1H); 7.71 (d, J=2.5 Hz, 1H); 6.93 (d, J=1.6 Hz, 2H); 6.74 (d, J=1.6 Hz, 1H); 6.77-6.69 (m, 2H); 5.04 (s, 2H); 4.63 (sept, J=6.0 Hz, 1H); 3.84-3.73 (m, 4H); 3.20-3.07 (m, 4H); 1.24 (d, J=6.0 Hz, 6H).

Example 237: 1-(3-Chloro-5-(2-hydroxyethoxy)benzyl)-4-(5-morpholino-1H-pyrrolo[2,3-b]pyridin-3-yl)pyridin-2(1H)-one Step 1: 4-Bromo-1-(3-chloro-5-(2-hydroxyethoxy)benzyl)pyridin-2(1H)-one

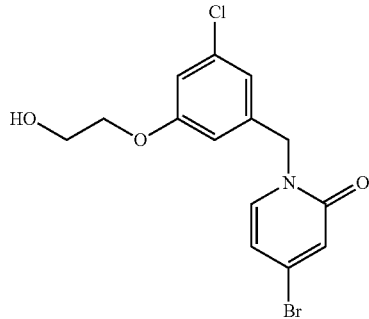 [SMILES: O=c1cc(Br)ccn1Cc1cc(Cl)cc(OCCO)c1]

In 2 ml of anhydrous DMF, are added 211 mg (0.670 mmol) of 4-bromo-1-(3-chloro-5-hydroxybenzyl)pyridin-2(1H)-one (described in example 236 step 1), 146 µl (2 mmol) of 2-bromoethanol and 655 mg (2 mmol) of cesium carbonate under argon. The mixture is heated at 70° C. for 2 h, then 146 µl (2 mmol) of 2-bromoethanol are added and the mixture is stirred for another 2 h at 70° C. The mixture is then diluted with ethyl acetate, washed 5 times with water, dried over sodium sulfate and evaporated under reduced pressure. Crude product is purified by flash chromatography on a 10 g silica gel column with an ethyl acetate/hexane mixture as eluent. 103 mg of the title compound are obtained.
Yield: 43%.
MH+: 358.3; 360.3; 362.2.

Step 2: 1-(3-Chloro-5-(2-hydroxyethoxy)benzyl)-4-(4,4,5,5-tetramethyl-1,3,2-dioxaborolan-2-yl)pyridin-2(1H)-one

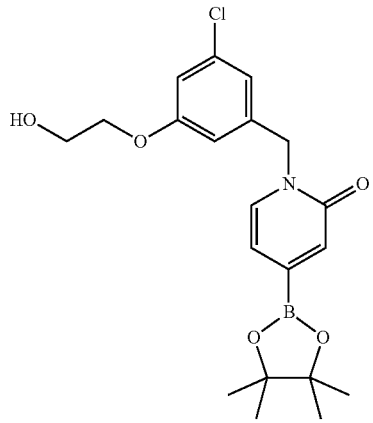 [SMILES: CC1(C)OB(c2ccn(Cc3cc(Cl)cc(OCCO)c3)c(=O)c2)OC1(C)C]

The compound is obtained by the procedure described in example 203 step 2, using 103 mg (0.287 mmol) of 4-bromo-1-(3-chloro-5-(2-hydroxyethoxy)benzyl)pyridin-2(1H)-one (described in previous step), 145 mg (0.574 mmol) of bis(pinacolato)diboron, 56 mg (0.574 mmol) of potassium acetate and 20 mg of PdCl$_2$(PPh$_3$)$_2$. 100 mg of the title compound are obtained.
Yield: Quantitative.
MH+: 324.4; 326.4 (boronic acid).

Step 3: 1-(3-Chloro-5-(2-hydroxyethoxy)benzyl)-4-(5-morpholino-1-tosyl-1H-pyrrolo[2,3-b]pyridin-3-yl)pyridin-2(1H)-one

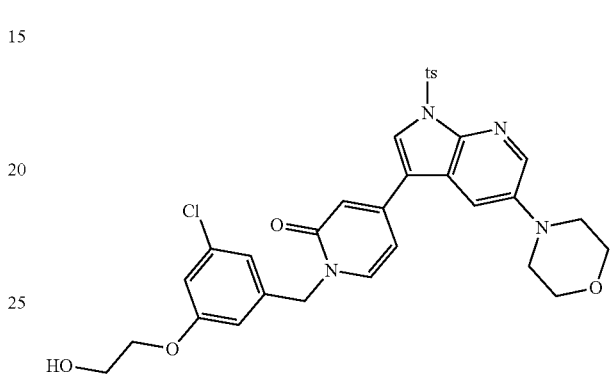

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 80 mg (0.247 mmol) of 1-(3-chloro-5-(2-hydroxyethoxy)benzyl)-4-(4,4,5,5-tetramethyl-1,3,2-dioxaborolan-2-yl)pyridin-2(1H)-one (described in previous step) instead of 1-(4-chlorobenzyl)-2-oxo-1,2-dihydropyridin-4-ylboronic acid and 8 mg of PdCl$_2$(PPh$_3$)$_2$. 8 mg of the title compound are obtained.
Yield: 15%.
MH+: 635.4; 637.4.

Step 4: 1-(3-Chloro-5-(2-hydroxyethoxy)benzyl)-4-(5-morpholino-1H-pyrrolo[2,3-b]pyridin-3-yl)pyridin-2(1H)-one

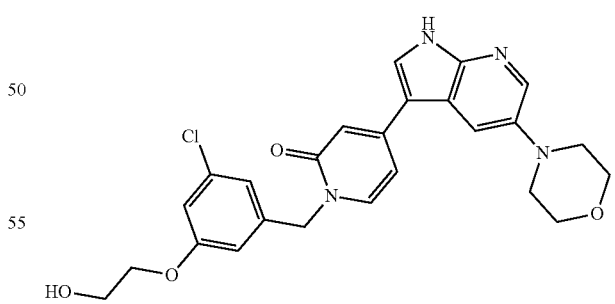

The compound is obtained by the procedure described in example 110 step 6, using 8 mg (0.013 mmol) of 1-(3-chloro-5-(2-hydroxyethoxy)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 4.1 mg of the title compound are obtained.

Yield: 68%.

MH+: 481.5; 483.5.

Example 238: 1-(3-Chloro-5-methylbenzyl)-4-(5-morpholino-1H-pyrrolo[2,3-b]pyridin-3-yl)pyridin-2(1H)-one Step 1: (3-Chloro-5-methylphenyl)methanol

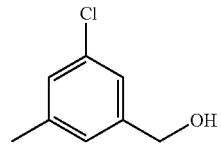

2.18 ml (2.18 mmol) of a solution of BH$_3$ (1M in THF) are added slowly to a solution of 200 mg (1.17 mmol) of 3-chloro-5-methylbenzoic acid in 3 ml of anhydrous THF under argon at 0° C. The solution is stirred at 0° C. for 2 h and 2.2 ml (2.2 mmol) of a solution of BH$_3$ (1M in THF) are added. The solution is allowed to reach room temperature during the night. LC/MS shows complete conversion of the substrate. Then pieces of ice are slowly added until the end of gas evolution. NaHCO$_3$ in powder is added until pH 8-9. The solution is then diluted with water, extracted 3 times with DCM, dried over sodium sulfate, filtered and evaporated under reduced pressure. Crude product is purified by flash chromatography on a 30 g silica gel column with an ethyl acetate/hexane mixture as eluent. 170 mg of the title compound are obtained.

Yield: 93%.

(M-OH)+: 138.9; 140.9.

Step 2: 1-(Bromomethyl)-3-chloro-5-methylbenzene

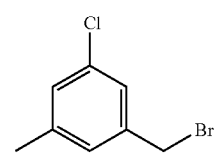

The compound is obtained by the procedure described in example 229 step 2, using 170 mg (1.08 mmol) of (3-chloro-5-methylphenyl)methanol (described in previous step) instead of (3-chloro-2,4-difluorophenyl)methanol and 152 µl (1.63 mmol) of phosphorus tribromide. 153 mg of the title compound are obtained.

Yield: 65%.

(M-Br)+: 138.9; 140.9.

Step 3: 1-(3-Chloro-5-methylbenzyl)-2-oxo-1,2-dihydropyridin-4-ylboronic Acid

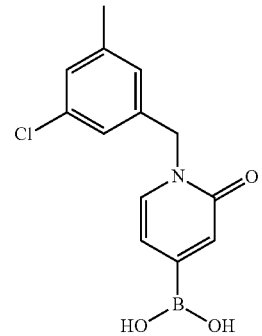 [SMILES: Cc1cc(Cl)cc(Cn2ccc(B(O)O)cc2=O)c1]

The compound is obtained by the procedure described in example 25 step 1, using 75 mg (0.339 mmol) of 1-(bromomethyl)-3-chloro-5-methylbenzene (described in the previous step) instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 57 mg of the title compound are obtained.

Yield: 91%.

MH+: 278.3; 280.3.

Step 4: 1-(3-Chloro-5-methylbenzyl)-4-(5-morpholino-1-tosyl-1H-pyrrolo[2,3-b]pyridin-3-yl)pyridin-2(1H)-one

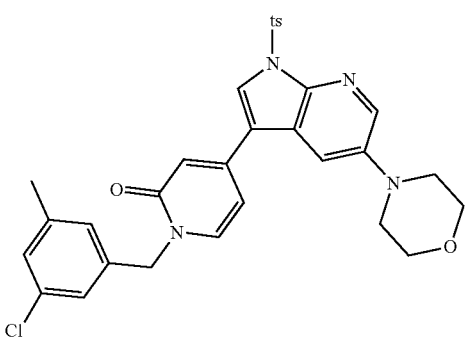

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 57 mg (0.206 mmol) of 1-(3-chloro-5-methylbenzyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 29 mg of the title compound are obtained.

Yield: 59%.

MH+: 589.5; 591.4.

Step 5: 1-(3-Chloro-5-methylbenzyl)-4-(5-morpholino-1H-pyrrolo[2,3-b]pyridin-3-yl)pyridin-2(1H)-one

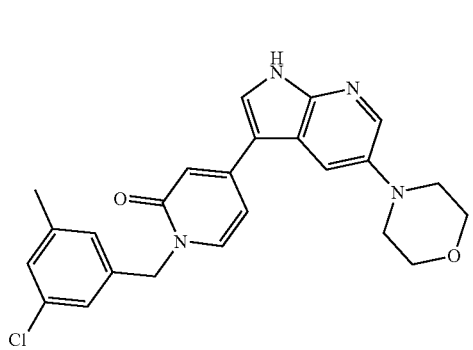 [SMILES: Cc1cc(Cl)cc(Cn2ccc(-c3c[nH]c4ncc(N5CCOCC5)cc34)cc2=O)c1]

The compound is obtained by the procedure described in example 110 step 6, using 25 mg (0.042 mmol) of 1-(3-chloro-5-methylbenzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 2.0 mg of the title compound are obtained.

Yield: 11%.

MH+: 435.4; 437.4.

$^1$H NMR (DMSO-d6, 300 MHz): δ 12.06 (br s, 1H); 8.17 (d, J=2.5 Hz, 1H); 8.09 (s, 1H); 7.77 (d, J=7.9 Hz, 1H); 7.71 (d, J=2.6 Hz, 1H); 7.20 (s, 2H); 7.13 (s, 1H); 6.75-6.69 (m, 2H); 5.06 (s, 2H); 3.85-3.73 (m, 4H); 3.20-3.10 (m, 4H); 2.29 (s, 3H).

Example 239: 1-((5-Chloropyridin-3-yl)methyl)-4-(5-morpholino-1H-pyrrolo[2,3-b]pyridin-3-yl)pyridin-2(1H)-one Step 1: 3-(Bromomethyl)-5-chloropyridine

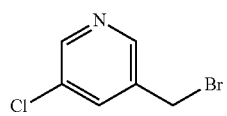

The compound is obtained by the procedure described in example 229 step 2, using 80 mg (0.557 mmol) of (5-chloro-3-pyridinyl)methanol instead of (3-chloro-2,4-difluorophenyl)methanol and 78 μl (0.225 mmol) of phosphorus tribromide. 202 mg of the title compound are obtained. Yield: Quantitative.

MH+: 206.1; 208.1; 210.1.

Step 2: 1-((5-Chloropyridin-3-yl)methyl)-2-oxo-1,2-dihydropyridin-4-ylboronic Acid

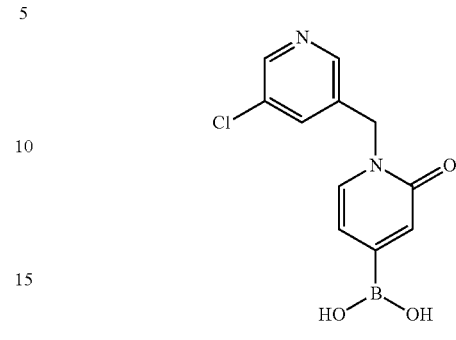

The compound is obtained by the procedure described in example 25 step 1, using 115 mg (0.558 mmol) of 3-(bromomethyl)-5-chloropyridine (described in the previous step) instead of benzyl bromide, 50 mg (0.226 mmol) of 4-(4,4,5,5-tetramethyl-[1,3,2]dioxaborolan-2-yl)-1H-pyridin-2-one and 110 mg (0.339 mmol) of cesium carbonate. 102 mg of the title compound are obtained.

Yield: Quantitative.

MH+: 265.3; 267.3.

Step 3: 1-((5-Chloropyridin-3-yl)methyl)-4-(5-morpholino-1-tosyl-1H-pyrrolo[2,3-b]pyridin-3-yl)pyridin-2(1H)-one

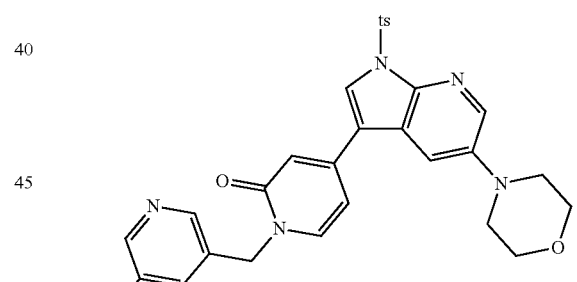

The compound is obtained by the procedure described in example 210 step 2, using 40 mg (0.083 mmol) of 3-iodo-5-morpholin-1-yl-1-tosyl-1H-pyrrolo[2,3-b]pyridine (described in example 17 step 3), 102 mg (0.226 mmol) of 1-((5-chloropyridin-3-yl)methyl)-2-oxo-1,2-dihydropyridin-4-ylboronic acid (described in previous step) instead of 1-(4-chlorobenzyl)-2-oxo-1,2-dihydropyridin-4-ylboronic acid and 8 mg of PdCl$_2$ (PPh$_3$)$_2$. 17 mg of the title compound are obtained.

Yield: 36%.

MH+: 576.6; 578.6.

193

Step 4: 1-((5-Chloropyridin-3-yl)methyl)-4-(5-morpholino-1H-pyrrolo[2,3-b]pyridin-3-yl)pyridin-2(1H)-one

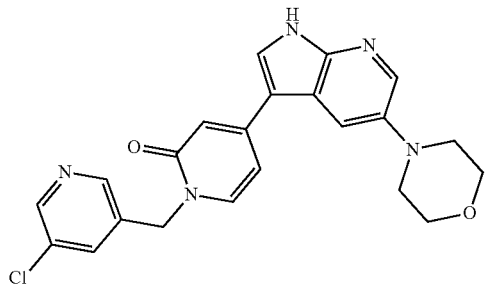 [SMILES: O=c1cc(-c2c[nH]c3ncc(N4CCOCC4)cc23)ccn1Cc1cncc(Cl)c1]

The compound is obtained by the procedure described in example 110 step 6, using 17 mg (0.030 mmol) of 1-((5-chloropyridin-3-yl)methyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 2.6 mg of the title compound are obtained.

Yield: 20%.

MH+: 422.5; 424.6.

$^1$H NMR (DMSO-d6, 300 MHz): δ 12.00 (br s, 1H); 8.67 (d, J=1.4 Hz, 1H); 8.60 (d, J=2.4 Hz, 1H); 8.18-8.08 (m, 3H); 8.08-8.02 (m, 1H); 7.78 (d, J=2.4 Hz, 1H); 7.43 (dd, J=5.3 and 1.4 Hz, 1H); 7.21 (s, 1H); 5.45 (s, 2H); 3.84-3.74 (m, 4H); 3.20-3.10 (m, 4H).

Example 240: 1-(3-Chloro-5-(hydroxymethyl)benzyl)-4-(5-morpholino-1H-pyrrolo[2,3-b]pyridin-3-yl)pyridin-2(1H)-one Step 1: 3-(Bromomethyl)-5-chlorobenzonitrile

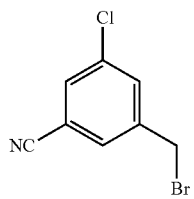

The compound is obtained by the procedure described in example 229 step 2, using 250 mg (1.49 mmol) of 3-chloro-5-(hydroxymethyl)benzonitrile instead of (3-chloro-2,4-difluorophenyl)methanol and 210 µl (2.20 mmol) of phosphorus tribromide. 350 mg of the title compound are obtained.

Yield: Quantitative.

194

Step 2: 3-((4-Bromo-2-oxopyridin-1(2H)-yl)methyl)-5-chlorobenzonitrile

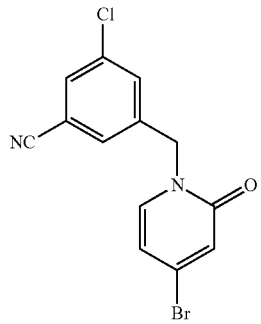 [SMILES: N#Cc1cc(Cl)cc(Cn2ccc(Br)cc2=O)c1]

The compound is obtained by the procedure described in example 203 step 1, using 56 mg (0.319 mmol) of 4-bromopyridin-2-(1H)-one, 81 mg (0.351 mmol) of 3-(bromomethyl)-5-chlorobenzonitrile (described in previous step) instead of 1-(bromomethyl)naphthalene and 156 mg (0.479 mmol) of cesium carbonate. 55 mg of the title compound are obtained.

Yield: 53%.

MH+: 322.9; 324.9; 326.9.

Step 3: 4-Bromo-1-(3-chloro-5-(hydroxymethyl)benzyl)pyridin-2(1H)-one

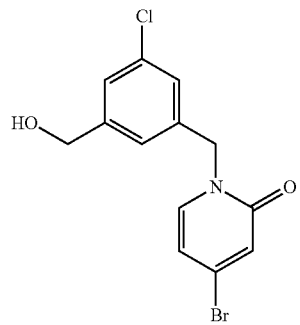 [SMILES: O=c1cc(Br)ccn1Cc1cc(Cl)cc(CO)c1]

256 mg (0.791 mmol) of 3-((4-bromo-2-oxopyridin-1(2H)-yl)methyl)-5-chlorobenzonitrile (described in previous step) are dissolved in a mixture of 4 ml of pyridine/acetic acid/water (2/1/1). 168 mg (1.50 mmol) of sodium hypophosphite monohydrate are added, followed by several drops of Raney nickel in water, and the mixture is stirred at 50° C. for 1 hour under argon. After cooling to ambient temperature, the mixture is filtered carefully on celite and the celite is washed several times with ethyl acetate. The combined filtrates are evaporated under reduced pressure to give the crude product which is directly purified by flash chromatography on a 60 g silica gel column with an ethyl acetate/hexane mixture as eluent. 100 mg of the titled compound are obtained.

Yield: 40%.

MH+: 328.3; 330.4; 332.3.

Step 4: 1-(3-Chloro-5-(hydroxymethyl)benzyl)-4-(4,4,5,5-tetramethyl-1,3,2-dioxaborolan-2-yl)pyridin-2(1H)-one

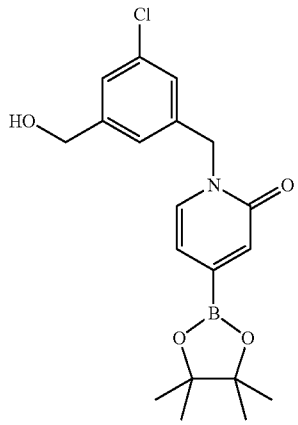 [SMILES: CC1(C)OB(c2ccn(Cc3cc(Cl)cc(CO)c3)c(=O)c2)OC1(C)C]

The compound is obtained by the procedure described in example 203 step 2, using 17 mg (0.052 mmol) of 4-bromo-1-(3-chloro-5-(hydroxymethyl)benzyl)pyridin-2(1H)-one (described in previous step), 13.1 mg (0.052 mmol) of bis(pinacolato)diboron, 10.2 mg (0.103 mmol) of potassium acetate and 2 mg of PdCl$_2$(PPh$_3$)$_2$. 20 mg of the title compound are obtained.

Yield: Quantitative.

MH+: 294.1; 296.1 (boronic acid).

Step 5: 1-(3-Chloro-5-(hydroxymethyl)benzyl)-4-(5-morpholino-1-tosyl-1H-pyrrolo[2,3-b]pyridin-3-yl)pyridin-2(1H)-one

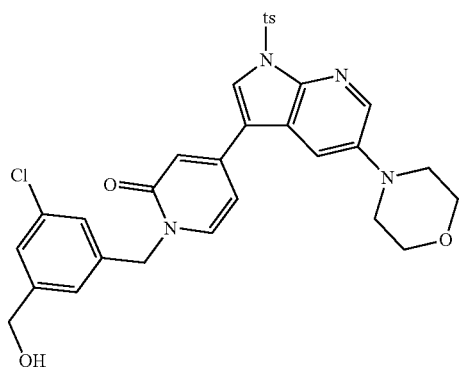

The compound is obtained by the procedure described in example 210 step 2, using 38 mg (0.078 mmol) of 3-iodo-5-morpholin-1-yl-1-tosyl-1H-pyrrolo[2,3-b]pyridine (described in example 17 step 3), 20 mg (0.068 mmol) of 1-(3-chloro-5-(hydroxymethyl)benzyl)-4-(4,4,5,5-tetramethyl-1,3,2-dioxaborolan-2-yl)pyridin-2(1H)-one (described in previous step) instead of 1-(4-chlorobenzyl)-2-oxo-1,2-dihydropyridin-4-ylboronic acid and 5 mg of PdCl$_2$ (PPh$_3$)$_2$. 13.2 mg of the title compound are obtained.

Yield: 28%.

MH+: 605.1; 607.1.

Step 6: 1-(3-Chloro-5-(hydroxymethyl)benzyl)-4-(5-morpholino-1H-pyrrolo[2,3-b]pyridin-3-yl)pyridin-2(1H)-one

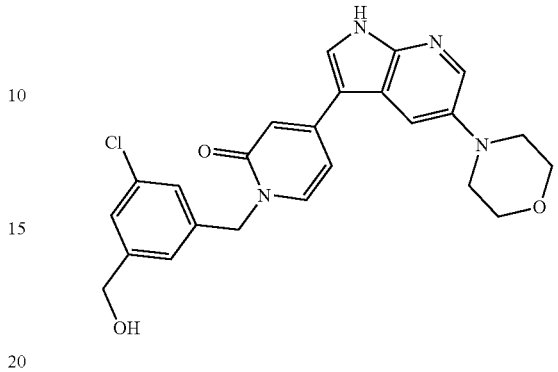

The compound is obtained by the procedure described in example 110 step 6, using 13.2 mg (0.022 mmol) of 1-(3-chloro-5-(hydroxymethyl)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 5.5 mg of the title compound are obtained.

Yield: 55%.

MH+: 451.0; 453.0.

$^1$H NMR (DMSO-d6, 300 MHz): δ 12.04 (br s, 1H); 8.16 (d, J=2.5 Hz, 1H); 8.09 (s, 1H); 7.77 (d, J=7.9 Hz, 1H); 7.70 (d, J=2.5 Hz, 1H); 7.31-7.22 (m, 3H); 6.76-6.68 (m, 2H); 5.41-5.26 (m, 1H); 5.09 (s, 2H); 4.47 (s, 2H); 3.84-3.72 (m, 4H); 3.20-3.08 (m, 4H).

Example 241: 1-(3-Chloro-5-(methoxymethyl)benzyl)-4-(5-morpholino-1H-pyrrolo[2,3-b]pyridin-3-yl)pyridin-2(1H)-one

Step 1: 4-Bromo-1-(3-chloro-5-(methoxymethyl)benzyl)pyridin-2(1H)-one

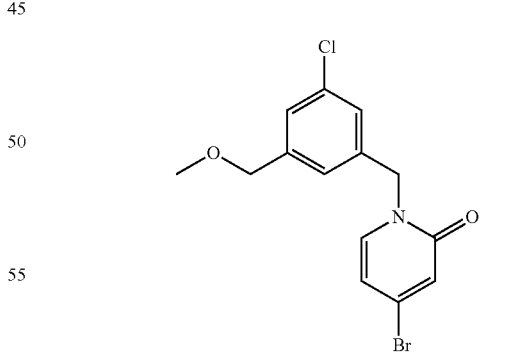

To a mixture of 100 mg (0.306 mmol) of 4-bromo-1-(3-chloro-5-(hydroxymethyl)benzyl)pyridin-2(1H)-one (described in example 240 step 3) and 18 mg (0.459 mmol) of sodium hydride (60% in paraffin oil) in 3 ml of anhydrous DMF is added 48 mg (0.336 mmol) of methyl iodide under argon at 0° C. The mixture is stirred at room temperature for the night. Mixture is diluted in ethyl acetate and washed 3 times with water, dried over sodium sulfate and evaporated under reduced pressure. Crude product is purified by flash chromatography on a 10 g silica gel column with a dichloromethane/methanol mixture as eluent. 15.6 mg of the title compound are obtained.

Yield: 15%.
MH+: 342.3; 344.3; 346.3.

Step 2: 1-(3-Chloro-5-(methoxymethyl)benzyl)-4-(4,4,5,5-tetramethyl-1,3,2-dioxaborolan-2-yl)pyridin-2(1H)-one

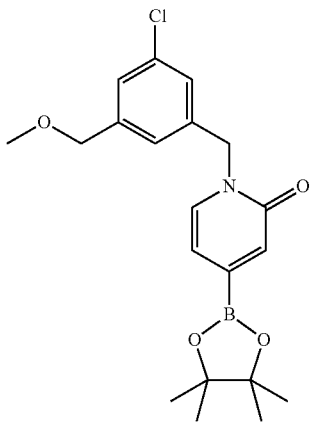 [SMILES: COCc1cc(Cl)cc(Cn2ccc(B3OC(C)(C)C(C)(C)O3)cc2=O)c1]

The compound is obtained by the procedure described in example 203 step 2, using 15.6 mg (0.046 mmol) of 4-bromo-1-(3-chloro-5-(methoxymethyl)benzyl)pyridin-2(1H)-one (described in previous step), 12.7 mg (0.050 mmol) of bis(pinacolato)diboron, 9 mg (0.091 mmol) of potassium acetate and 2 mg of PdCl$_2$ (PPh$_3$)$_2$. 17 mg of the title compound are obtained.
Yield: Quantitative.
MH+: 308.4; 310.4 (boronic acid).

Step 3: 1-(3-Chloro-5-(methoxymethyl)benzyl)-4-(5-morpholino-1-tosyl-1H-pyrrolo[2,3-b]pyridin-3-yl)pyridin-2(1H)-one

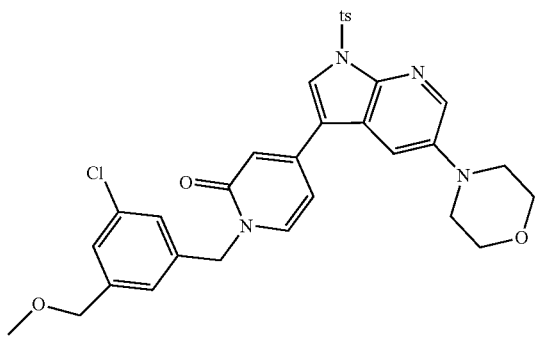

The compound is obtained by the procedure described in example 210 step 2, using 14 mg (0.028 mmol) of 3-iodo-5-morpholin-1-yl-1-tosyl-1H-pyrrolo[2,3-b]pyridine (described in example 17 step 3), 17 mg (0.055 mmol) of 1-(3-chloro-5-(methoxymethyl)benzyl)-4-(4,4,5,5-tetramethyl-1,3,2-dioxaborolan-2-yl)pyridin-2(1H)-one (described in previous step) instead of 1-(4-chlorobenzyl)-2-oxo-1,2-dihydropyridin-4-ylboronic acid and 3 mg of PdCl$_2$ (PPh$_3$)$_2$. 10 mg of the title compound are obtained.
Yield: 55%.
MH+: 619.7; 621.6.

Step 4: 1-(3-Chloro-5-(methoxymethyl)benzyl)-4-(5-morpholino-1H-pyrrolo[2,3-b]pyridin-3-yl)pyridin-2(1H)-one

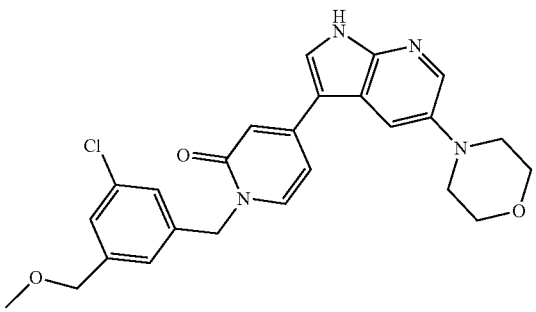 [SMILES: COCc1cc(Cl)cc(Cn2ccc(-c3c[nH]c4ncc(N5CCOCC5)cc34)cc2=O)c1]

The compound is obtained by the procedure described in example 110 step 6, using 10 mg (0.016 mmol) of 1-(3-chloro-5-(methoxymethyl)benzyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 3.0 mg of the title compound are obtained.
Yield: 40%.
MH+: 465.5; 467.5.
$^1$H NMR (DMSO-d6, 300 MHz): δ 12.06 (br s, 1H); 8.16 (d, J=2. Hz, 1H); 8.09 (s, 1H); 7.79 (d, J=7.8 Hz, 1H); 7.71 (d, J=2.2 Hz, 1H); 7.35-7.25 (m, 3H); 6.77-6.69 (m, 2H); 5.10 (s, 2H); 4.40 (s, 2H); 3.85-3.72 (m, 4H); 3.29 (s, 3H); 3.21-3.08 (m, 4H).

Example 303: 1-(1-(3-Chlorophenyl)ethyl)-4-(5-morpholino-1H-pyrrolo[2,3-b]pyridin-3-yl)pyridin-2(1H)-one Step 1: 4-Bromo-1-(1-(3-chlorophenyl)ethyl)pyridin-2(1H)-one

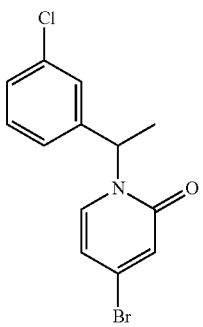 [SMILES: CC(c1cccc(Cl)c1)n1ccc(Br)cc1=O]

The compound is obtained by the procedure described in example 203 step 1, using 390 mg (2.24 mmol) of 4-bromopyridin-2-(1H)-one, 410 mg (1.87 mmol) of 3-(1-bromoethyl)-1-chlorobenzene instead of 1-(bromomethyl)naphthalene and 1.21 g (3.74 mmol) of cesium carbonate. 135 mg of the title compound are obtained.

Yield: 23%.

MH+: 311.9; 313.9; 315.9.

Step 2: 1-(1-(3-Chlorophenyl)ethyl)-4-(4,4,5,5-tetramethyl-1,3,2-dioxaborolan-2-yl)pyridin-2(1H)-one

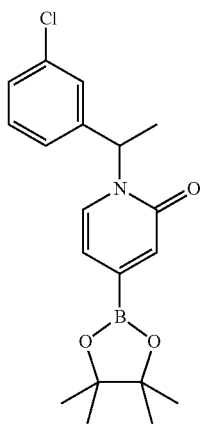 [SMILES: CC(c1cccc(Cl)c1)n1ccc(B2OC(C)(C)C(C)(C)O2)cc1=O]

The compound is obtained by the procedure described in example 203 step 2, using 110 mg (0.352 mmol) of 4-bromo-1-(1-(3-chlorophenyl)ethyl)pyridin-2(1H)-one (described in previous step), 188 mg (0.739 mmol) of bis(pinacolato)diboron, 69 mg (0.704 mmol) of potassium acetate and 12 mg of $PdCl_2$ $(PPh_3)_2$. 130 mg of the title compound are obtained.

Yield: Quantitative.

Step 3: 1-(1-(3-Chlorophenyl)ethyl)-4-(5-morpholino-1-tosyl-1H-pyrrolo[2,3-b]pyridin-3-yl)pyridin-2(1H)-one

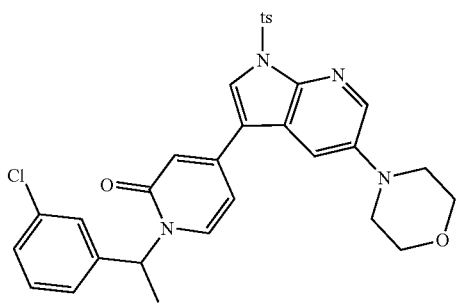

The compound is obtained by the procedure described in example 203 step 3, using 67 mg (0.139 mmol) of 3-iodo-5-morpholin-1-yl-1-tosyl-1H-pyrrolo[2,3-b]pyridine (described in example 17 step 3), 60 mg (0.167 mmol) of 1-(1-(3-chlorophenyl)ethyl)-4-(4,4,5,5-tetramethyl-1,3,2-dioxaborolan-2-yl)pyridin-2(1H)-one (described in previous step) instead of 1-(naphthalen-1-ylmethyl)-4-(4,4,5,5-tetramethyl-1,3,2-dioxaborolan-2-yl)pyridin-2(1H)-one and 5 mg of $PdCl_2$ $(PPh_3)_2$. 60 mg of the title compound are obtained.

Yield: 61%.

MH+: 588.8; 590.9.

Step 4: 1-(1-(3-Chlorophenyl)ethyl)-4-(5-morpholino-1H-pyrrolo[2,3-b]pyridin-3-yl)pyridin-2(1H)-one

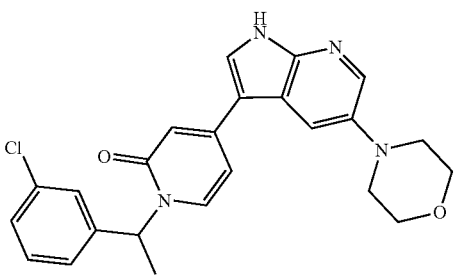 [SMILES: CC(c1cccc(Cl)c1)n1ccc(-c2c[nH]c3ncc(N4CCOCC4)cc23)cc1=O]

The compound is obtained by the procedure described in example 110 step 6, using 60 mg (0.051 mmol) of 1-(1-(3-chlorophenyl)ethyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 8.0 mg of the title compound are obtained.

Yield: 36%.

MH+: 435.4; 437.4.

$^1$H NMR (DMSO-d6, 300 MHz): δ 12.06 (br s, 1H); 8.17 (d, J=2.5 Hz, 1H); 8.08 (s, 1H); 7.70 (d, J=2.5 Hz, 1H); 7.65 (d, J=8.0 Hz, 1H); 7.45-7.33 (m, 3H); 7.33-7.26 (m, 1H); 6.75-6.67 (m, 2H); 6.16 (q, J=7.2 Hz, 1H); 3.85-3.72 (m, 4H); 3.19-3.08 (m, 4H); 1.72 (d, J=7.2 Hz, 3H).

Step 5: (+)-1-(1-(3-Chlorophenyl)ethyl)-4-(5-morpholino-1H-pyrrolo[2,3-b]pyridin-3-yl)pyridin-2(1H)-one and (−)-1-(1-(3-chlorophenyl)ethyl)-4-(5-morpholino-1H-pyrrolo[2,3-b]pyridin-3-yl)pyridin-2(1H)-one Enantiomers are obtained by semi-preparative chiral chromatography starting from 16 mg of racemate compound described in the previous step using a Chiralpak IE column and a mixture of heptane/ethanol/chloroform (50/30/20) as the mobile phase. First fraction to be eluted is the (−)-enantiomer (7.8 mg with an ee=98.4%), followed by the (+)-enantiomer (8.5 mg with an ee=98.3%).

Example 305: 1-(1-(3-Chlorophenyl)-2-methoxyethyl)-4-(5-morpholino-1H-pyrrolo[2,3-b]pyridin-3-yl)pyridin-2(1H)-one

Step 1: 4-Bromo-1-(1-(3-chlorophenyl)-2-methoxyethyl)pyridin-2(1H)-one

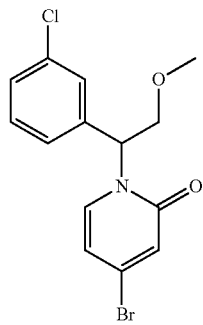 [SMILES: COCC(c1cccc(Cl)c1)n1ccc(Br)cc1=O]

To a mixture of 93 mg (0.283 mmol) of 4-bromo-1-(1-(3-chlorophenyl)-2-hydroxyethyl)pyridin-2(1H)-one (described in example 42 step 2) and 17 mg (0.425 mmol) of sodium hydride (60% in paraffin oil) in 3 ml of anhydrous DMF is added 20 µl (0.311 mmol) of methyl iodide under argon at 0° C. The mixture is stirred at room temperature for the night. Mixture is diluted in ethyl acetate and washed 3 times with water, dried over sodium sulfate and evaporated under reduced pressure. Crude product is purified by flash chromatography on a 10 g silica gel column with a dichloromethane/methanol mixture as eluent. 68 mg of the title compound are obtained.

Yield: 70%.
MH+: 342.3; 344.2; 346.2.

Step 2: 1-(1-(3-Chlorophenyl)-2-methoxyethyl)-4-(4,4,5,5-tetramethyl-1,3,2-dioxaborolan-2-yl)pyridin-2(1H)-one

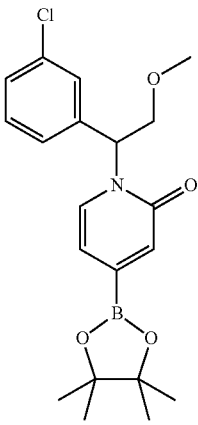 [SMILES: COCC(c1cccc(Cl)c1)n1ccc(B2OC(C)(C)C(C)(C)O2)cc1=O]

The compound is obtained by the procedure described in example 203 step 2, using 68 mg (0.198 mmol) of 4-bromo-1-(1-(3-chlorophenyl)-2-methoxyethyl)pyridin-2(1H)-one (described in previous step), 101 mg (0.397 mmol) of bis(pinacolato)diboron, 39 mg (0.397 mmol) of potassium acetate and 7 mg of PdCl$_2$(PPh$_3$)$_2$. 86 mg of the title compound are obtained.

Yield: Quantitative.
MH+: 308.4; 310.4 (boronic acid).

Step 3: 1-(1-(3-Chlorophenyl)-2-methoxyethyl)-4-(5-morpholino-1-tosyl-1H-pyrrolo[2,3-b]pyridin-3-yl)pyridin-2(1H)-one

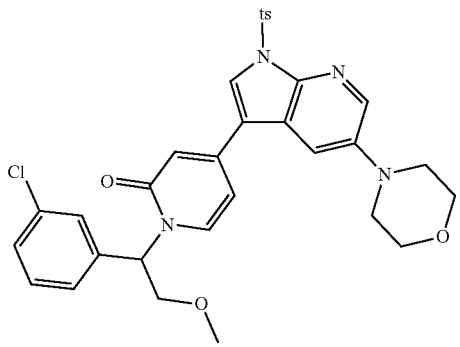

The compound is obtained by the procedure described in example 203 step 3, using 71 mg (0.147 mmol) of 3-iodo-5-morpholin-1-yl-1-tosyl-1H-pyrrolo[2,3-b]pyridine (described in example 17 step 3), 86 mg (0.221 mmol) of 1-(1-(3-chlorophenyl)-2-methoxyethyl)-4-(4,4,5,5-tetramethyl-1,3,2-dioxaborolan-2-yl)pyridin-2(1H)-one (described in previous step) instead of 1-(naphthalen-1-ylmethyl)-4-(4,4,5,5-tetramethyl-1,3,2-dioxaborolan-2-yl)pyridin-2(1H)-one and 7 mg of PdCl$_2$ (PPh$_3$)$_2$. 100 mg of the title compound are obtained.

Yield: Quantitative.
MH+: 619.5; 621.5.

Step 4: 1-(1-(3-Chlorophenyl)-2-methoxyethyl)-4-(5-morpholino-1H-pyrrolo[2,3-b]pyridin-3-yl)pyridin-2(1H)-one

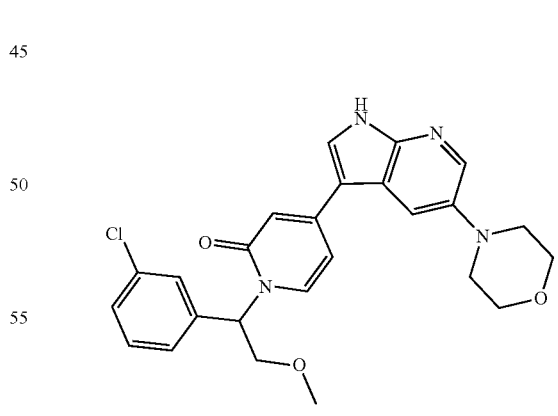

The compound is obtained by the procedure described in example 110 step 6, using 100 mg (0.162 mmol) of 1-(1-(3-chlorophenyl)-2-methoxyethyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]octan-8-yl)-1-tosyl-1H-pyrrolo[2,3-b]pyridin-3-yl)-1-(3,4-dichlorobenzyl)pyridin-2(1H)-one. 20 mg of the title compound are obtained.

Yield: 27%.

MH+: 465.4; 467.4.

$^1$H NMR (DMSO-d6, 300 MHz): δ 12.06 (br s, 1H); 8.17 (d, J=2.5 Hz, 1H); 8.10 (s, 1H); 7.77-7.69 (m, 2H); 7.45-7.35 (m, 3H); 7.33-7.25 (m, 1H); 6.76-6.68 (m, 2H); 6.23-6.12 (m, 1H); 4.25-4.13 (m, 1H); 4.02-3.90 (m, 1H); 3.85-3.73 (m, 4H); 3.32 (s, 3H); 3.19-3.09 (m, 4H).

Step 5: (+)-1-(1-(3-Chlorophenyl)-2-methoxyethyl)-4-(5-morpholino-1H-pyrrolo[2,3-b]pyridin-3-yl)pyridin-2(1H)-one and (−)-1-(1-(3-chlorophenyl)-2-methoxyethyl)-4-(5-morpholino-1H-pyrrolo[2,3-b]pyridin-3-yl)pyridin-2(1H)-one Enantiomers are obtained by semi-preparative chiral chromatography starting from 8 mg of racemate compound described in the previous step using a Chiralpak IC column and a mixture of heptane/ethanol (50/50) as the mobile phase. First fraction to be eluted is the (+)-enantiomer (4.1 mg with an ee=99.5%), followed by the (−)-enantiomer (3.3 mg with an ee=98.9%).

Example 308: 1-(1-(3,4-Dichlorophenyl)ethyl)-4-(5-morpholino-1H-pyrrolo[2,3-b]pyridin-3-yl)pyridin-2(1H)-one Step 1: 4-bromo-1-(1-(3,4-Dichlorophenyl)ethyl)pyridin-2(1H)-one

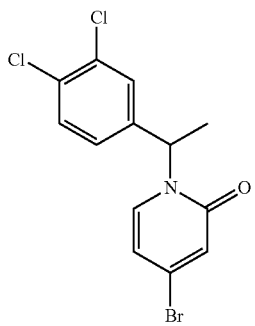 [SMILES: CC(c1ccc(Cl)c(Cl)c1)n1ccc(Br)cc1=O]

The compound is obtained by the procedure described in example 203 step 1, using 327 mg (1.88 mmol) of 4-bromopyridin-2-(1H)-one, 400 mg (1.57 mmol) of 4-(1-bromoethyl)-1,2-dichlorobenzene instead of 1-(bromomethyl)naphthalene and 1.02 g (3.14 mmol) of cesium carbonate. 90 mg of the title compound are obtained.

Yield: 18%.

MH+: 939.

Step 2: 1-(1-(3,4-Dichlorophenyl)ethyl)-4-(4,4,5,5-tetramethyl-1,3,2-dioxaborolan-2-yl)pyridin-2(1H)-one

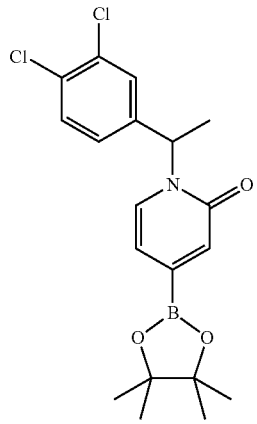 [SMILES: CC(c1ccc(Cl)c(Cl)c1)n1ccc(B2OC(C)(C)C(C)(C)O2)cc1=O]

The compound is obtained by the procedure described in example 203 step 2, using 90 mg (0.259 mmol) of 4-bromo-1-(1-(3,4-dichlorophenyl)ethyl)pyridin-2(1H)-one (described in previous step), 145 mg (0.570 mmol) of bis(pinacolato)diboron, 51 mg (0.518 mmol) of potassium acetate and 9 mg of PdCl$_2$ (PPh$_3$)$_2$. 120 mg of the title compound are obtained.

Yield: Quantitative.

MH+: 311.9; 313.9; 315.9 (boronic acid).

Step 3: 1-(1-(3,4-Dichlorophenyl)ethyl)-4-(5-morpholino-1-tosyl-1H-pyrrolo[2,3-b]pyridin-3-yl)pyridin-2(1H)-one

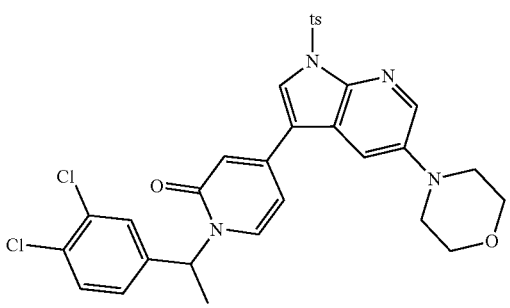

The compound is obtained by the procedure described in example 203 step 3, using 51 mg (0.106 mmol) of 3-iodo-5-morpholin-1-yl-1-tosyl-1H-pyrrolo[2,3-b]pyridine (described in example 17 step 3), 50 mg (0.127 mmol) of 1-(1-(3,4-dichlorophenyl)ethyl)-4-(4,4,5,5-tetramethyl-1,3,2-dioxaborolan-2-yl)pyridin-2(1H)-one (described in previous step) instead of 1-(naphthalen-1-ylmethyl)-4-(4,4,5,5-tetramethyl-1,3,2-dioxaborolan-2-yl)pyridin-2(1H)-one and 4 mg of PdCl$_2$ (PPh$_3$)$_2$. 45 mg of the title compound are obtained.

Yield: 57%.

MH+: 622.8; 624.8; 626.8.

Step 4: 1-(1-(3,4-Dichlorophenyl)ethyl)-4-(5-morpholino-1H-pyrrolo[2,3-b]pyridin-3-yl)pyridin-2(1H)-one

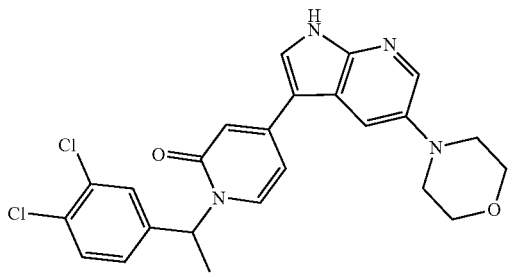 [SMILES: CC(c1ccc(Cl)c(Cl)c1)n1ccc(-c2c[nH]c3ncc(N4CCOCC4)cc23)cc1=O]

The compound is obtained by the procedure described in example 110 step 6, using 45 mg (0.072 mmol) of 1-(1-(3,4-dichlorophenyl)ethyl)-4-(5-morpholino-1-tosyl-1H-pyrrolo[2,3-b]pyridin-3-yl)pyridin-2(1H)-one (described in previous step) instead of 4-(5-(3-oxa-8-azabicyclo[3.2.1]oct-8-yl)-1-tosyl-1H-pyrrolo[2,3-b]pyridin-3-yl)-1-(3,4-dichlorobenzyl)pyridin-2(1H)-one. 8.0 mg of the title compound are obtained.

Yield: 24%.
MH+: 468.9; 470.9; 472.9.
$^1$H NMR (DMSO-d6, 300 MHz): δ 12.07 (br s, 1H); 8.17 (d, J=2.5 Hz, 1H); 8.09 (s, 1H); 7.72-7.60 (m, 4H); 7.30 (dd, J=8.3 and 2.2 Hz, 1H); 6.76-6.68 (m, 2H); 6.13 (q, J=7.2 Hz, 1H); 3.83-3.74 (m, 4H); 3.18-3.09 (m, 4H); 1.73 (d, J=7.2 Hz, 3H).

Example 400: (3-(1-(3-Chloro-2-fluorobenzyl)-2-oxo-1,2-dihydropyridin-4-yl)-5-morpholino-1H-pyrrolo[2,3-b]pyridin-1-yl)methyl Isobutyrate

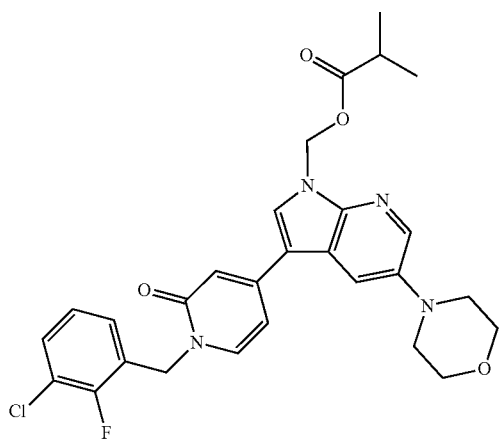 [SMILES: CC(C)C(=O)OCn1cc(-c2ccn(Cc3cccc(Cl)c3F)c(=O)c2)c2cc(N3CCOCC3)cnc21]

To a solution of 83 mg (0.189 mmol) of 1-(3-chloro-2-fluorobenzyl)-4-(5-morpholino-1H-pyrrolo[2,3-b]pyridin-3-yl)pyridin-2(1H)-one (described in example 32 step 2) in 2 ml of anhydrous DMF are added 15 mg (0.378 mmol) of sodium hydride (60% in paraffin oil) under argon at 0° C. The mixture is stirred at 0° C. for 15 min, then 39 mg (0.284 mmol) of chloromethyl isobutyrate are added and the mixture is stirred at room temperature for the night. Reaction mixture is diluted with ethyl acetate, washed 5 times with water, dried over sodium sulfate and evaporated under reduced pressure. Crude product is first purified by flash chromatography on a 10 g silica gel column with a dichloromethane/methanol mixture as eluent, and then by flash chromatography with a 30 g C18 column and a water/acetonitrile mixture as eluent. 75 mg of the title compound are obtained.

Yield: 74%.
MH+: 539.5; 541.5.
$^1$H NMR (DMSO-d6, 300 MHz): δ 8.25 (d, J=2.3 Hz, 1H); 8.21 (s, 1H); 7.80 (d, J=6.8 Hz, 1H); 7.74 (d, J=2.2 Hz, 1H); 7.54 (dt, J=6.7 and 2.4 Hz, 1H); 7.28-7.12 (m, 2H); 6.80-6.67 (m, 2H); 6.22 (s, 2H); 5.19 (s, 2H); 3.88-3.74 (m, 4H); 3.24-3.10 (m, 4H); 1.04 (d, J=7.0 Hz, 6H).

Example 401: (3-(1-(3-Chloro-2-fluorobenzyl)-2-oxo-1,2-dihydropyridin-4-yl)-5-morpholino-1H-pyrrolo[2,3-b]pyridin-1-yl)methyl Pivalate

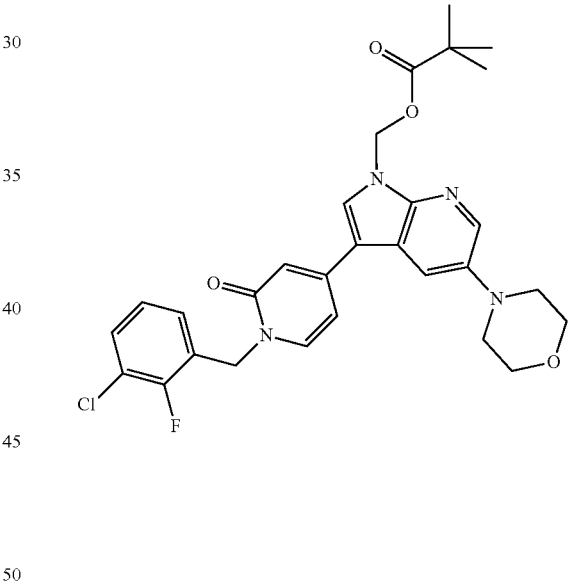

The compound is obtained by the procedure described in example 400, using 83 mg (0.189 mmol) of 1-(3-chloro-2-fluorobenzyl)-4-(5-morpholino-1H-pyrrolo[2,3-b]pyridin-3-yl)pyridin-2(1H)-one (described in example 32 step 2), 15 mg (0.378 mmol) of sodium hydride (60% in paraffin oil) and 41 μl (0.284 mmol) of chloromethyl pivalate instead of chloromethyl isobutyrate. 60 mg of the title compound are obtained.

Yield: 57%.
MH+: 553.5; 555.6.
$^1$H NMR (DMSO-d6, 300 MHz): δ 8.26 (d, J=2.4 Hz, 1H); 8.22 (s, 1H); 7.79 (d, J=6.9 Hz, 1H); 7.74 (d, J=2.4 Hz, 1H); 7.54 (dt, J=6.8 and 2.3 Hz, 1H); 7.26-7.11 (m, 2H); 6.77-6.67 (m, 2H); 6.22 (s, 2H); 5.19 (s, 2H); 3.83-3.73 (m, 4H); 3.22-3.13 (m, 4H); 1.08 (s, 9H).

Example 402: (3-(1-(3-Chloro-2-fluorobenzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl Phosphate (402a)

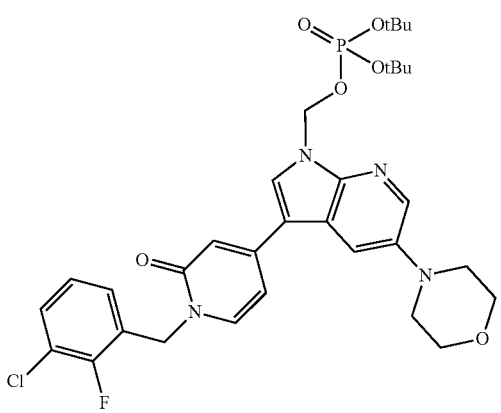 [SMILES: CC(C)(C)OP(=O)(OCn1cc(-c2ccn(Cc3cccc(Cl)c3F)c(=O)c2)c2cc(N3CCOCC3)cnc21)OC(C)(C)C]

To a solution of 100 mg (0.228 mmol) of 1-(3-chloro-2-fluorobenzyl)-4-(5-morpholino-1H-pyrrolo[2,3-b]pyridin-3-yl)pyridin-2(1H)-one (described in example 32 step 2) in 2 ml of anhydrous DMF are added 18 mg (0.456 mmol) of sodium hydride (60% in paraffin oil) under argon at 0° C. The mixture is stirred at 0° C. for 15 min, then 89 mg (0.342 mmol) of di-tert-butyl chloromethyl phosphate are added and the mixture is stirred at room temperature for the night. Reaction mixture is diluted with 60 ml of ethyl acetate, washed 3 times with 30 ml of water, dried over sodium sulfate and evaporated under reduced pressure. Crude product is purified by flash chromatography on a 30 g silica gel column with a dichloromethane/methanol mixture as eluent. 46 mg of the title compound are obtained.
Yield: 30%.
MH+: 661.6; 663.6.

Step 2: (3-(1-(3-Chloro-2-fluorobenzyl)-2-oxo-1,2-dihydropyridin-4-yl)-5-morpholino-1H-pyrrolo[2,3-b]pyridin-1-yl)methyl Dihydrogen Phosphate

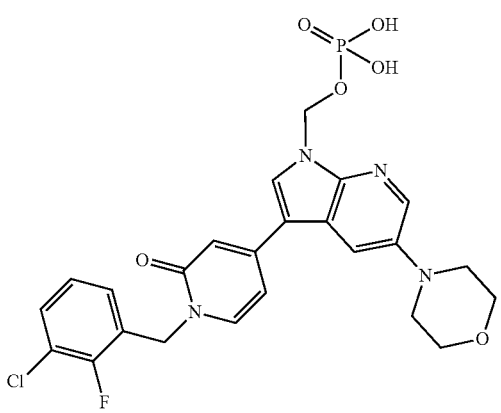 [SMILES: O=c1cc(-c2cn(COP(=O)(O)O)c3ncc(N4CCOCC4)cc23)ccn1Cc1cccc(Cl)c1F]

To a solution of 46 mg (0.070 mmol) of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate (described in previous step) in 2 ml of anhydrous DCM, 0.6 ml of trifluoroacetic acid are slowly added at 0° C. The solution is stirred at room temperature for 10 min. LCMS shows complete conversion. Then the solution is evaporated under reduced pressure at room temperature. Crude product is directly purified by flash chromatography with a 30 g C18 column and a water/acetonitrile mixture as eluent. Fractions are collected and lyophilized to give 10.7 mg of the title compound.
Yield: 28%.
MH+: 549.4; 551.4.
$^1$H NMR (DMSO-d6, 300 MHz): δ 12.06 (br s, 1H); 8.17 (d, J=2.5 Hz, 1H); 8.10 (s, 1H); 7.77-7.69 (m, 2H); 7.45-7.35 (m, 3H); 7.33-7.25 (m, 1H); 6.76-6.68 (m, 2H); 6.23-6.12 (m, 1H); 4.25-4.13 (m, 1H); 4.02-3.90 (m, 1H); 3.85-3.73 (m, 4H); 3.32 (s, 3H); 3.19-3.09 (m, 4H).
$^{31}$P NMR (DMSO-d6, 300 MHz): δ 12.06 (s).

Example 403: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl Phosphate (403a)

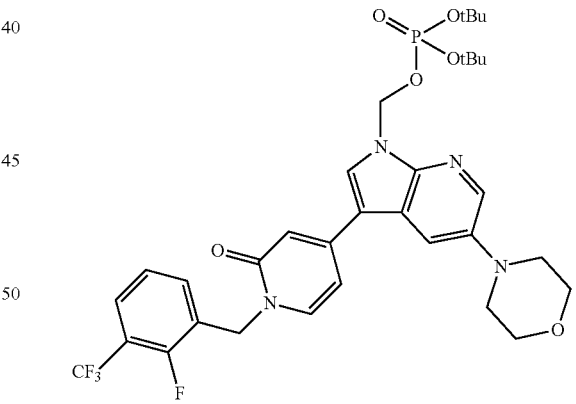

The compound is obtained by the procedure described in example 402 step 1, using 392 mg (0.831 mmol) of 1-(2-fluoro-3-(trifluoromethyl)benzyl)-4-(5-morpholino-1H-pyrrolo[2,3-b]pyridin-3-yl)pyridin-2(1H)-one (described in example 231) instead of 1-(3-chloro-2-fluorobenzyl)-4-(5-morpholino-1H-pyrrolo[2,3-b]pyridin-3-yl)pyridin-2(1H)-one, 66 mg (1.66 mmol) of sodium hydride (60% in paraffin oil) and 322 mg (1.25 mmol) of di-tert-butyl chloromethyl phosphate. 222 mg of the title compound are obtained.
Yield: 38%.
MH+: 695.7.

Step 2: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl Dihydrogen Phosphate

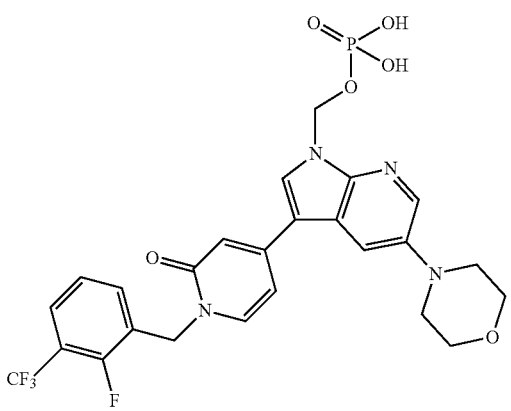 [SMILES: O=c1cc(-c2cn(COP(=O)(O)O)c3ncc(N4CCOCC4)cc23)ccn1Cc1cccc(C(F)(F)F)c1F]

The compound is obtained by the procedure described in example 402 step 2, using 222 mg (0.320 mmol) of di-tert-butyl(3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 54 mg of the title compound are obtained.

Yield: 29%.
MH+: 583.6.
$^1$H NMR (DMSO-d6, 300 MHz): δ 8.24 (d, J=2.4 Hz, 1H); 8.18 (s, 1H); 7.83 (d, J=6.9 Hz, 1H); 7.78-7.68 (m, 2H); 7.56-7.46 (m, 1H); 7.45-7.35 (m, 1H); 6.76-6.68 (m, 2H); 5.99 (d, J=9.3 Hz, 2H); 5.23 (s, 2H); 3.84-3.74 (m, 4H); 3.21-3.11 (m, 4H).
$^{31}$P NMR (DMSO-d6, 300 MHz): δ −2.40 (s).

Example 404: (3-(1-(3-Chlorobenzyl)-2-oxo-1,2-dihydropyridin-4-yl)-5-morpholino-1H-pyrrolo[2,3-b]pyridin-1-yl)methyl dihydrogen phosphate

Step 1: Di-tert-butyl(3-(1-(3-chlorobenzyl)-2-oxo-1,2-dihydropyridin-4-yl)-5-morpholino-1H-pyrrolo[2,3-b]pyridin-1-yl)methyl Phosphate (404a)

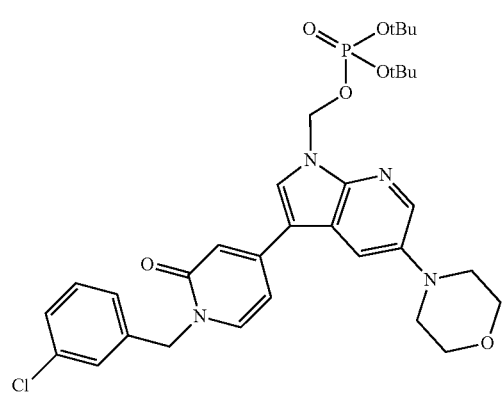 [SMILES: CC(C)(C)OP(=O)(OCn1cc(-c2ccn(Cc3cccc(Cl)c3)c(=O)c2)c2cc(N3CCOCC3)cnc21)OC(C)(C)C]

The compound is obtained by the procedure described in example 402 step 1, using 104 mg (0.247 mmol) of 1-(3-chlorobenzyl)-4-(5-morpholino-1H-pyrrolo[2,3-b]pyridin-3-yl)pyridin-2(1H)-one (described in example 17 step 4) instead of 1-(3-chloro-2-fluorobenzyl)-4-(5-morpholino-1H-pyrrolo[2,3-b]pyridin-3-yl)pyridin-2(1H)-one, 15 mg (0.371 mmol) of sodium hydride (60% in paraffin oil) and 96 mg (1.25 mmol) of di-tert-butyl chloromethyl phosphate in 2 ml of anhydrous DMF. 54 mg of the title compound are obtained.

Yield: 37%.
MH+: 643.6; 645.6.

Step 2: (3-(1-(3-Chlorobenzyl)-2-oxo-1,2-dihydropyridin-4-yl)-5-morpholino-1H-pyrrolo[2,3-b]pyridin-1-yl)methyl Dihydrogen Phosphate

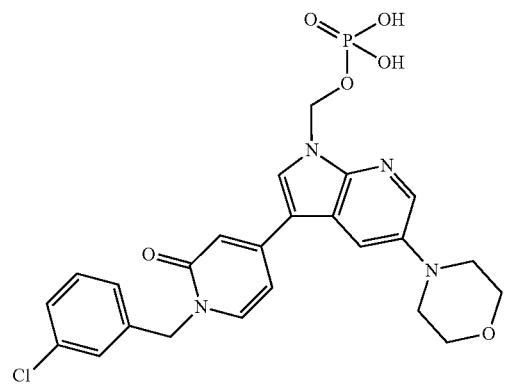 [SMILES: O=c1cc(-c2cn(COP(=O)(O)O)c3ncc(N4CCOCC4)cc23)ccn1Cc1cccc(Cl)c1]

The compound is obtained by the procedure described in example 402 step 2, using 54 mg (0.092 mmol) of di-tert-butyl(3-(1-(3-chlorobenzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 13.5 mg of the title compound are obtained.

Yield: 28%.
MH+: 531.6; 533.5.
$^1$H NMR (DMSO-d6, 300 MHz): δ 8.23 (d, J=2.3 Hz, 1H); 8.16 (s, 1H); 7.84 (d, J=7.2 Hz, 1H); 7.73 (d, J=2.3 Hz, 1H); 7.45-7.26 (m, 4H); 6.73 (d, J=1.6 Hz, 1H); 6.66 (dd, J=7.0 and 2.0 Hz, 1H); 5.97 (d, J=9.3 Hz, 2H); 5.12 (s, 2H); 3.85-3.72 (m, 4H); 3.21-3.11 (m, 4H).
$^{31}$P NMR (DMSO-d6, 300 MHz): δ −2.42 (s).

Example 405: (3-(1-(3-Bromobenzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(3-bromobenzyl)-2-oxo-1,2-dihydropyridin-4-yl)-5-morpholino-1H-pyrrolo[2,3-b]pyridin-1-yl)methyl Phosphate (405a)

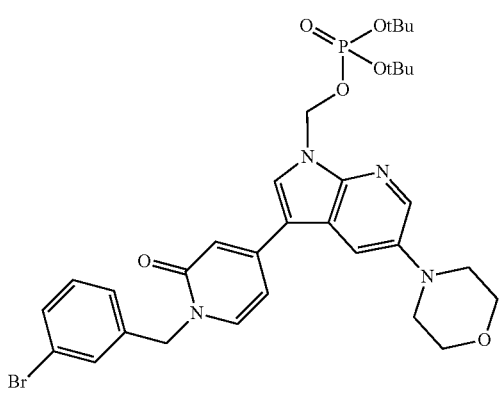

The compound is obtained by the procedure described in example 402 step 1, using 100 mg (0.215 mmol) of 1-(3-bromobenzyl)-4-(5-morpholino-1H-pyrrolo[2,3-b]pyridin-3-yl)pyridin-2(1H)-one (described in example 211 step 3) instead of 1-(3-chloro-2-fluorobenzyl)-4-(5-morpholino-1H-pyrrolo[2,3-b]pyridin-3-yl)pyridin-2(1H)-one, 14 mg (0.323 mmol) of sodium hydride (60% in paraffin oil) and 84 mg (0.323 mmol) of di-tert-butyl chloromethyl phosphate in 2 ml of anhydrous DMF. 98 mg of the title compound are obtained.

Yield: 72%.
MH+: 687.6; 689.6.

Step 2: (3-(1-(3-Bromobenzyl)-2-oxo-1,2-dihydropyridin-4-yl)-5-morpholino-1H-pyrrolo[2,3-b]pyridin-1-yl)methyl Dihydrogen Phosphate

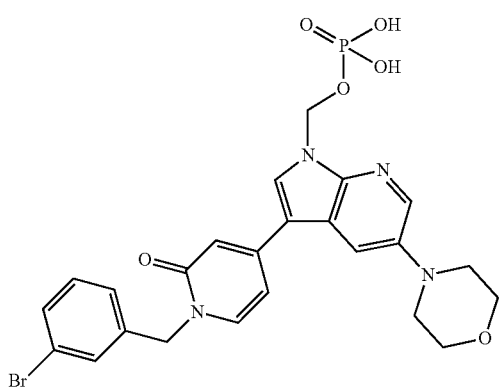

The compound is obtained by the procedure described in example 402 step 2, using 98 mg (0.155 mmol) of di-tert-butyl(3-(1-(3-bromobenzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl) methyl phosphate. 25.6 mg of the title compound are obtained.

Yield: 29%.
MH+: 575.5; 577.5.

$^1$H NMR (DMSO-d6, 300 MHz): δ 8.24 (d, J=2.5 Hz, 1H); 8.17 (s, 1H); 7.85 (d, J=7.2 Hz, 1H); 7.74 (d, J=2.4 Hz, 1H); 7.57 (s, 1H); 7.54-7.46 (m, 1H); 7.39-7.28 (m, 2H); 6.74 (d, J=1. Hz, 1H); 6.67 (dd, J=6.9 and 1.9 Hz, 1H); 5.99 (d, J=9.4 Hz, 2H); 5.11 (s, 2H); 3.85-3.73 (m, 4H); 3.23-3.10 (m, 4H).

$^{31}$P NMR (DMSO-d6, 300 MHz): δ −2.49 (s).

Example 406: (3-(1-(3-Bromo-5-fluorobenzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(3-bromo-5-fluorobenzyl)-2-oxo-1,2-dihydropyridin-4-yl)-5-morpholino-1H-pyrrolo[2,3-b]pyridin-1-yl)methyl Phosphate (406a)

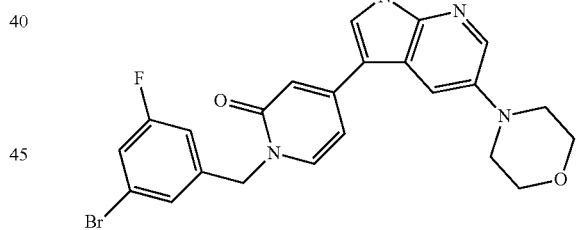

The compound is obtained by the procedure described in example 402 step 1, using 181 mg (0.374 mmol) of 1-(3-bromo-5-fluorobenzyl)-4-(5-morpholino-1H-pyrrolo[2,3-b]pyridin-3-yl)pyridin-2(1H)-one (described in example 213 step 3) instead of 1-(3-chloro-2-fluorobenzyl)-4-(5-morpholino-1H-pyrrolo[2,3-b]pyridin-3-yl)pyridin-2(1H)-one, 23 mg (0.561 mmol) of sodium hydride (60% in paraffin oil) and 145 mg (0.561 mmol) of di-tert-butyl chloromethyl phosphate in 3 ml of anhydrous DMF. 150 mg of the title compound are obtained.

Yield: 57%.
MH+: 705.5; 707.5.

Step 2: (3-(1-(3-Bromo-5-fluorobenzyl)-2-oxo-1,2-dihydropyridin-4-yl)-5-morpholino-1H-pyrrolo[2,3-b]pyridin-1-yl)methyl Dihydrogen Phosphate

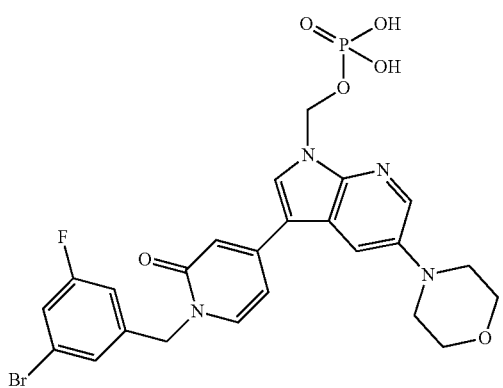

The compound is obtained by the procedure described in example 402 step 2, using 150 mg (0.212 mmol) of di-tert-butyl(3-(1-(3-bromo-5-fluorobenzyl)-2-oxo-1,2-dihydropyridin-4-yl)-5-morpholino-1H-pyrrolo[2,3-b]pyridin-1-yl) methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 39.2 mg of the title compound are obtained.
Yield: 31%.
MH+: 593.5; 595.5.
$^1$H NMR (DMSO-d6, 300 MHz): δ 8.24 (d, J=2.2 Hz, 1H); 8.18 (s, 1H); 7.86 (d, J=7.3 Hz, 1H); 7.75 (d, J=2.5 Hz, 1H); 7.54-7.47 (m, 1H); 7.42 (s, 1H); 7.27-7.20 (m, 1H); 6.75 (d, J=1. Hz, 1H); 6.69 (dd, J=7.5 and 1.4 Hz, 1H); 5.98 (d, J=9.4 Hz, 2H); 5.12 (s, 2H); 3.84-3.75 (m, 4H); 3.21-3.12 (m, 4H).
$^{31}$P NMR (DMSO-d6, 300 MHz): δ −2.46 (s).

Example 407: (3-(1-(3-Bromo-2-fluorobenzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(3-bromo-2-fluorobenzyl)-2-oxo-1,2-dihydropyridin-4-yl)-5-morpholino-1H-pyrrolo[2,3-b]pyridin-1-yl)methyl phosphate (407a)

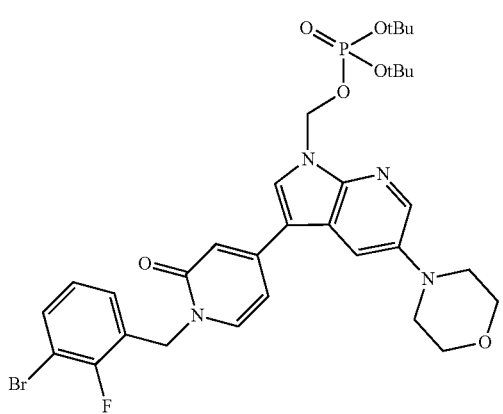

The compound is obtained by the procedure described in example 402 step 1, using 178 mg (0.368 mmol) of 1-(3-bromo-2-fluorobenzyl)-4-(5-morpholino-1H-pyrrolo[2,3-b]pyridin-3-yl)pyridin-2(1H)-one (described in example 214 step 3) instead of 1-(3-chloro-2-fluorobenzyl)-4-(5-morpholino-1H-pyrrolo[2,3-b]pyridin-3-yl)pyridin-2(1H)-one, 22 mg (0.552 mmol) of sodium hydride (60% in paraffin oil) and 143 mg (0.552 mmol) of di-tert-butyl chloromethyl phosphate in 3 ml of anhydrous DMF. 165 mg of the title compound are obtained.
Yield: 63%.
MH+: 705.6; 707.7.

Step 2: (3-(1-(3-Bromo-2-fluorobenzyl)-2-oxo-1,2-dihydropyridin-4-yl)-5-morpholino-1H-pyrrolo[2,3-b]pyridin-1-yl)methyl Dihydrogen Phosphate

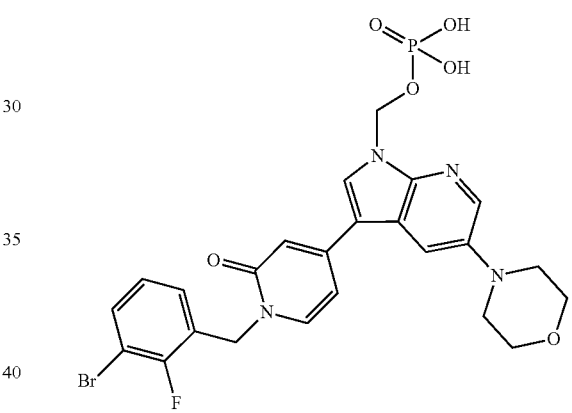

The compound is obtained by the procedure described in example 402 step 2, using 165 mg (0.234 mmol) of di-tert-butyl(3-(1-(3-bromo-2-fluorobenzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 25.8 mg of the title compound are obtained.
Yield: 19%.
MH+: 593.5; 595.5.
$^1$H NMR (DMSO-d6, 300 MHz): δ 8.25 (d, J=2.3 Hz, 1H); 8.18 (s, 1H); 7.80 (d, J=6. Hz, 1H); 7.74 (d, J=2.4 Hz, 1H); 7.69-7.61 (m, 1H); 7.24-7.11 (m, 2H); 6.76-6.66 (m, 2H); 5.99 (d, J=9.3 Hz, 2H); 5.19 (s, 2H); 3.84-3.74 (m, 4H); 3.22-3.11 (m, 4H).
$^{31}$P NMR (DMSO-d6, 300 MHz): δ −2.48 (s).

Example 408: (3-(1-(3-Chloro-5-fluorobenzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(3-chloro-5-fluorobenzyl)-2-oxo-1,2-dihydropyridin-4-yl)-5-morpholino-1H-pyrrolo[2,3-b]pyridin-1-yl)methyl Phosphate (408a)

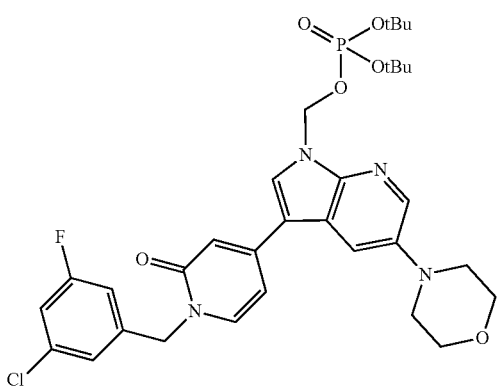 [SMILES: CC(C)(C)OP(=O)(OCn1cc(-c2ccn(Cc3cc(F)cc(Cl)c3)c(=O)c2)c2cc(N3CCOCC3)cnc21)OC(C)(C)C]

The compound is obtained by the procedure described in example 402 step 1, using 297 mg (0.678 mmol) of 1-(3-chloro-5-fluorobenzyl)-4-(5-morpholino-1H-pyrrolo[2,3-b]pyridin-3-yl)pyridin-2(1H)-one (described in example 227 step 3) instead of 1-(3-chloro-2-fluorobenzyl)-4-(5-morpholino-1H-pyrrolo[2,3-b]pyridin-3-yl)pyridin-2(1H)-one, 40 mg (1.02 mmol) of sodium hydride (60% in paraffin oil) and 263 mg (1.02 mmol) of di-tert-butyl chloromethyl phosphate in 4 ml of anhydrous DMF. 282 mg of the title compound are obtained.

Yield: 63%.
MH+: 661.7; 663.6.

Step 2: (3-(1-(3-Chloro-5-fluorobenzyl)-2-oxo-1,2-dihydropyridin-4-yl)-5-morpholino-1H-pyrrolo[2,3-b]pyridin-1-yl)methyl Dihydrogen Phosphate

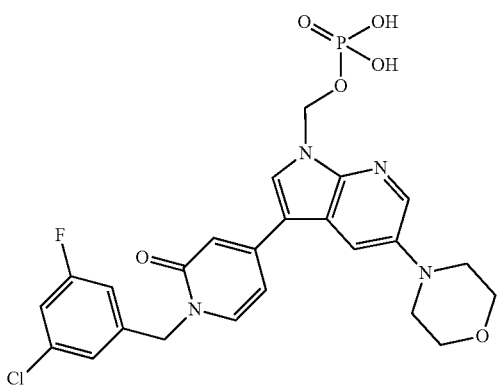 [SMILES: O=c1cc(-c2cn(COP(=O)(O)O)c3ncc(N4CCOCC4)cc23)ccn1Cc1cc(F)cc(Cl)c1]

The compound is obtained by the procedure described in example 402 step 2, using 282 mg (0.426 mmol) of di-tert-butyl(3-(1-(3-chloro-5-fluorobenzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 48 mg of the title compound are obtained.

Yield: 16%.
MH+: 549.6; 551.5.

$^1$H NMR (DMSO-d6, 300 MHz): δ 8.24 (d, J=2.4 Hz, 1H); 8.18 (s, 1H); 7.86 (d, J=7.0 Hz, 1H); 7.74 (d, J=2.3 Hz, 1H); 7.42-7.35 (m, 1H); 7.29 (s, 1H); 7.24-7.15 (m, 1H); 6.79-6.65 (m, 2H); 5.98 (d, J=9.2 Hz, 2H); 5.12 (s, 2H); 3.88-3.75 (m, 4H); 3.22-3.11 (m, 4H).
$^{31}$P NMR (DMSO-d6, 300 MHz): δ −2.45 (s).

Example 409: (3-(1-(3-Fluoro-5-iodobenzyl)-2-oxo-1,2-dihydropyridin-4-yl)-5-morpholino-1H-pyrrolo[2,3-b]pyridin-1-yl)methyl Dihydrogen Phosphate Step 1: Di-tert-butyl(3-(1-(3-fluoro-5-iodobenzyl)-2-oxo-1,2-dihydropyridin-4-yl)-5-morpholino-1H-pyrrolo[2,3-b]pyridin-1-yl)methyl Phosphate (409a)

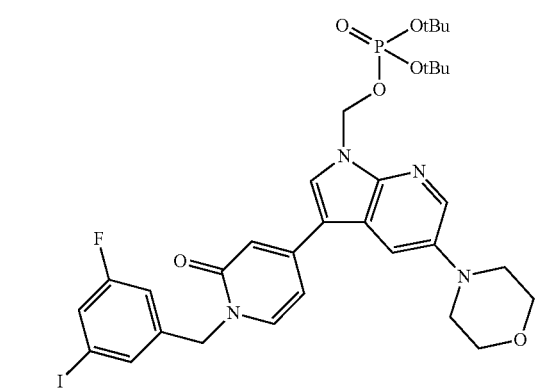 [SMILES: CC(C)(C)OP(=O)(OCn1cc(-c2ccn(Cc3cc(F)cc(I)c3)c(=O)c2)c2cc(N3CCOCC3)cnc21)OC(C)(C)C]

The compound is obtained by the procedure described in example 402 step 1, using 230 mg (0.434 mmol) of 1-(3-fluoro-5-iodobenzyl)-4-(5-morpholino-1H-pyrrolo[2,3-b]pyridin-3-yl)pyridin-2(1H)-one (described in example 218 step 3) instead of 1-(3-chloro-2-fluorobenzyl)-4-(5-morpholino-1H-pyrrolo[2,3-b]pyridin-3-yl)pyridin-2(1H)-one, 35 mg (0.867 mmol) of sodium hydride (60% in paraffin oil) and 168 mg (0.651 mmol) of di-tert-butyl chloromethyl phosphate in 10 ml of anhydrous DMF. 210 mg of the title compound are obtained.

Yield: 64%.
MH+: 753.7.

Step 2: (3-(1-(3-Fluoro-5-iodobenzyl)-2-oxo-1,2-dihydropyridin-4-yl)-5-morpholino-1H-pyrrolo[2,3-b]pyridin-1-yl)methyl Dihydrogen Phosphate

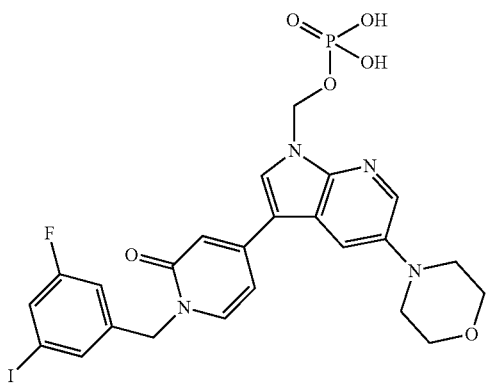 [SMILES: O=c1cc(-c2cn(COP(=O)(O)O)c3ncc(N4CCOCC4)cc23)ccn1Cc1cc(F)cc(I)c1]

The compound is obtained by the procedure described in example 402 step 2, using 210 mg (0.279 mmol) of di-tert-butyl(3-(1-(3-fluoro-5-iodobenzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 49.8 mg of the title compound are obtained.

Yield: 28%.
MH+: 641.5.
$^1$H NMR (DMSO-d6, 300 MHz): δ 8.24 (d, J=2.4 Hz, 1H); 8.18 (s, 1H); 7.85 (d, J=7.2 Hz, 1H); 7.74 (d, J=2.2 Hz, 1H); 7.63-7.56 (m, 2H); 7.26-7.18 (m, 1H); 6.74 (d, J=1.5 Hz, 1H); 6.68 (dd, J=7.2 and 1. Hz, 1H); 5.98 (d, J=9.3 Hz, 2H); 5.08 (s, 2H); 3.85-3.73 (m, 4H); 3.22-3.11 (m, 4H).
$^{31}$P NMR (DMSO-d6, 300 MHz): δ -2.44 (s).

Example 415: (3-(1-(4-Chlorobenzyl)-2-oxo-1,2-dihydropyridin-4-yl)-5-morpholino-1H-pyrrolo[2,3-b]pyridin-1-yl)methyl Dihydrogen Phosphate

Step 1: Di-tert-butyl(3-(1-(4-chlorobenzyl)-2-oxo-1,2-dihydropyridin-4-yl)-5-morpholino-1H-pyrrolo[2,3-b]pyridin-1-yl)methyl Phosphate (415a)

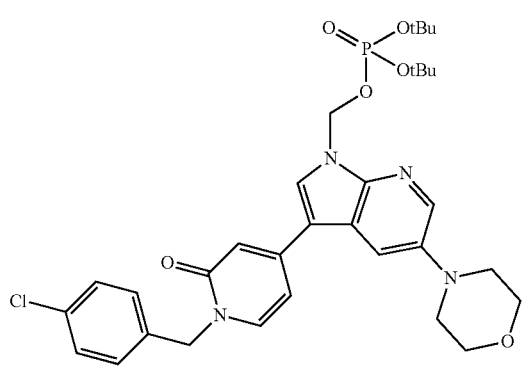 [SMILES: CC(C)(C)OP(=O)(OCn1cc(-c2ccn(Cc3ccc(Cl)cc3)c(=O)c2)c2cc(N3CCOCC3)cnc21)OC(C)(C)C]

The compound is obtained by the procedure described in example 402 step 1, using 324 mg (0.770 mmol) of 1-(4-chlorobenzyl)-4-(5-morpholino-1H-pyrrolo[2,3-b]pyridin-3-yl)pyridin-2(1H)-one (described in example 210) instead of 1-(3-chloro-2-fluorobenzyl)-4-(5-morpholino-1H-pyrrolo[2,3-b]pyridin-3-yl)pyridin-2(1H)-one, 46 mg (1.15 mmol) of sodium hydride (60% in paraffin oil) and 298 mg (1.15 mmol) of di-tert-butyl chloromethyl phosphate in 4 ml of anhydrous DMF. 364 mg of the title compound are obtained.

Yield: 75%.
MH+: 643.9; 645.9.

Step 2: (3-(1-(4-Chlorobenzyl)-2-oxo-1,2-dihydropyridin-4-yl)-5-morpholino-1H-pyrrolo[2,3-b]pyridin-1-yl)methyl Dihydrogen Phosphate

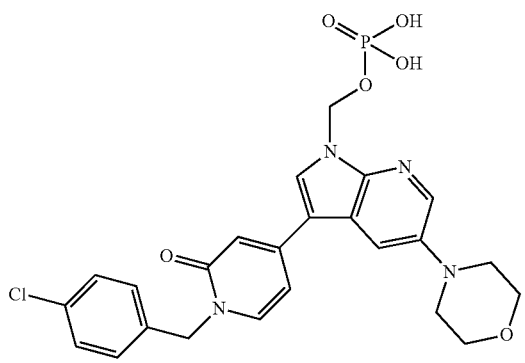 [SMILES: O=c1cc(-c2cn(COP(=O)(O)O)c3ncc(N4CCOCC4)cc23)ccn1Cc1ccc(Cl)cc1]

The compound is obtained by the procedure described in example 402 step 2, using 364 mg (0.566 mmol) of di-tert-butyl(3-(1-(4-chlorobenzyl)-2-oxo-1,2-dihydropyridin-4-yl)-5-morpholino-1H-pyrrolo[2,3-b]pyridin-1-yl)methyl phosphate (described in previous step) instead of di-tert-butyl(3-(1-(3-chloro-2-fluorobenzyl)-2-oxo-1,2-dihydropyridin-4-yl)-5-morpholino-1H-pyrrolo[2,3-b]pyridin-1-yl)methyl phosphate. 69 mg of the title compound are obtained.

Yield: 23%.
MH+: 531.4; 533.4.
$^1$H NMR (DMSO-d6, 300 MHz): δ 8.23 (d, J=2.3 Hz, 1H); 8.15 (s, 1H); 7.81 (d, J=7.1 Hz, 1H); 7.71 (d, J=2.3 Hz, 1H); 7.46-7.33 (m, 4H); 6.72 (d, J=1. Hz, 1H); 6.65 (dd, J=7.9 and 1.2 Hz, 1H); 5.97 (d, J=9.3 Hz, 2H); 5.10 (s, 2H); 3.84-3.74 (m, 4H); 3.22-3.12 (m, 4H).
$^{31}$P NMR (DMSO-d6, 300 MHz): δ -2.35 (s).

Example 416: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl Sodium Hydrogen Phosphate

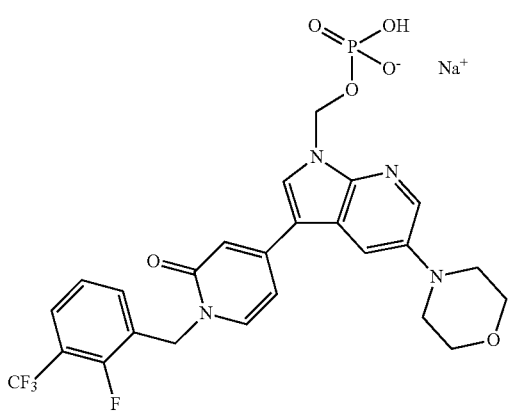 [SMILES: O=c1cc(-c2cn(COP(=O)([O-])O)c3ncc(N4CCOCC4)cc23)ccn1Cc1cccc(C(F)(F)F)c1F ; [Na+]]

To a solution of 10 mg (0.017 mmol) of (3-(1-(2-fluoro-3-(trifluoromethyl)benzyl)-2-oxo-1,2-dihydropyridin-4-yl)-5-morpholino-1H-pyrrolo[2,3-b]pyridin-1-yl)methyl dihydrogen phosphate (described in example 403) in 400 µl of water is added 1.5 mg (0.018 mmol) of sodium hydrogen carbonate. The solution is stirred at room temperature for 2 h then directly lyophilized for the night. 10 mg of the title compound are obtained.

Yield: Quantitative.
MH+: 583.6.
$^1$H NMR (D$_2$O, 300 MHz): δ 8.03 (d, J=1. Hz, 1H); 7.97 (s, 1H); 7.69-7.59 (m, 2H); 7.59-7.51 (m, 1H); 7.51-7.41 (m, 1H); 7.33-7.23 (m, 1H); 6.71-6.61 (m, 2H); 5.82 (d, J=7.4 Hz, 2H); 5.15 (s, 2H); 3.95-3.82 (m, 4H); 3.19-3.01 (m, 4H).
$^{31}$P NMR (D$_2$O, 300 MHz): δ −0.83 (s).

Example 417: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl Disodium Phosphate

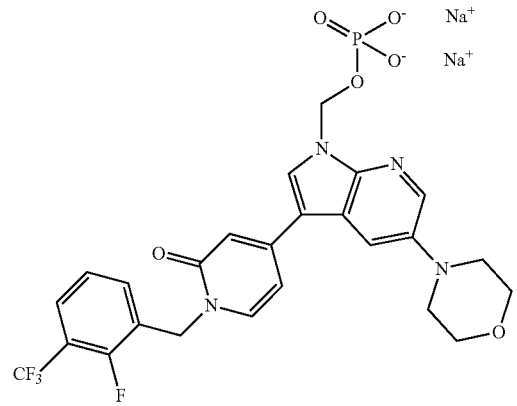 [SMILES: [Na+] ; O=c1cc(-c2cn(COP(=O)([O-])[O-])c3ncc(N4CCOCC4)cc23)ccn1Cc1cccc(C(F)(F)F)c1F ; [Na+]]

To a solution of 10 mg (0.017 mmol) of (3-(1-(2-fluoro-3-(trifluoromethyl)benzyl)-2-oxo-1,2-dihydropyridin-4-yl)-5-morpholino-1H-pyrrolo[2,3-b]pyridin-1-yl)methyl dihydrogen phosphate (described in example 403) in 400 µl of water is added 3 mg (0.036 mmol) of sodium hydrogen carbonate. The solution is stirred at room temperature for 2 h then directly lyophilized for the night. 10 mg of the title compound are obtained.

Yield: Quantitative.
MH+: 583.4.
$^1$H NMR (D$_2$O, 300 MHz): δ 8.15 (d, J=1.8 Hz, 1H); 8.11 (s, 1H); 7.83 (d, J=1.8 Hz, 1H); 7.70-7.60 (m, 2H); 7.48-7.39 (m, 1H); 7.33-7.24 (m, 1H); 6.86-6.78 (m, 2H); 5.86 (d, J=6.4 Hz, 2H); 5.22 (s, 2H); 3.99-3.86 (m, 4H); 3.26-3.12 (m, 4H).
$^{31}$P NMR (D$_2$O, 300 MHz): δ2.40 (s).

The following table illustrates the chemical structures of the compounds according to the invention:

TABLE 1

Chemical structure of the invention compounds

| No | Structures |
|----|------------|
| 1 | (structure image) |

TABLE 1-continued
Chemical structure of the invention compounds
| No | Structures |
|----|------------|
| 2 | 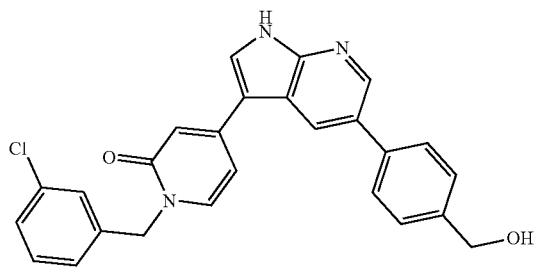 [SMILES: O=c1cc(-c2c[nH]c3ncc(-c4ccc(CO)cc4)cc23)ccn1Cc1cccc(Cl)c1] |
| 3 | 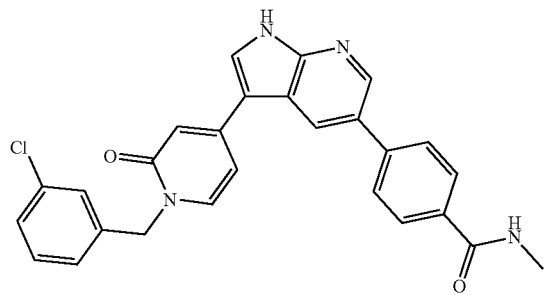 [SMILES: CNC(=O)c1ccc(-c2cnc3[nH]cc(-c4ccn(Cc5cccc(Cl)c5)c(=O)c4)c3c2)cc1] |
| 4 | 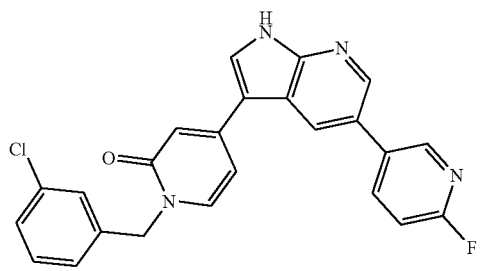 [SMILES: O=c1cc(-c2c[nH]c3ncc(-c4ccc(F)nc4)cc23)ccn1Cc1cccc(Cl)c1] |
| 5 | 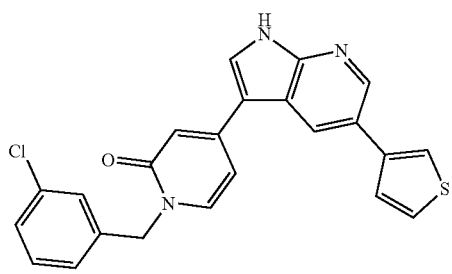 [SMILES: O=c1cc(-c2c[nH]c3ncc(-c4ccsc4)cc23)ccn1Cc1cccc(Cl)c1] |
| 6 | 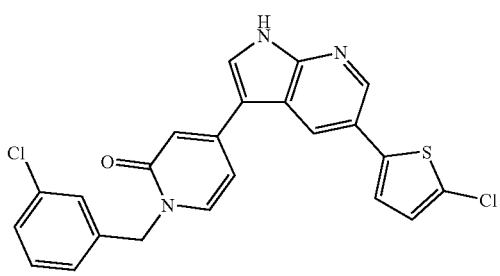 [SMILES: O=c1cc(-c2c[nH]c3ncc(-c4ccc(Cl)s4)cc23)ccn1Cc1cccc(Cl)c1] |

TABLE 1-continued

Chemical structure of the invention compounds

| No | Structures |
|----|------------|
| 7  | 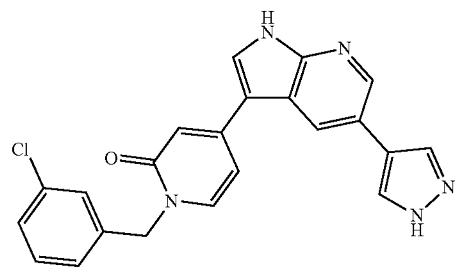 [SMILES: O=c1cc(-c2c[nH]c3ncc(-c4cn[nH]c4)cc23)ccn1Cc1cccc(Cl)c1] |
| 8  | 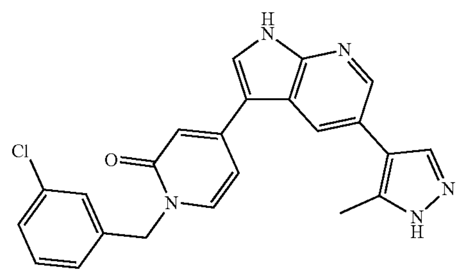 [SMILES: Cc1[nH]ncc1-c1cnc2[nH]cc(-c3ccn(Cc4cccc(Cl)c4)c(=O)c3)c2c1] |
| 9  | 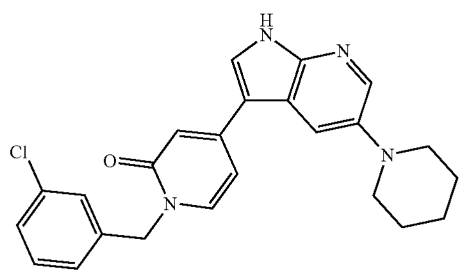 |
| 10 | 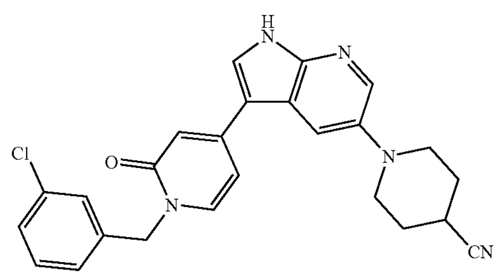 [SMILES: N#CC1CCN(c2cnc3[nH]cc(-c4ccn(Cc5cccc(Cl)c5)c(=O)c4)c3c2)CC1] |
| 11 | 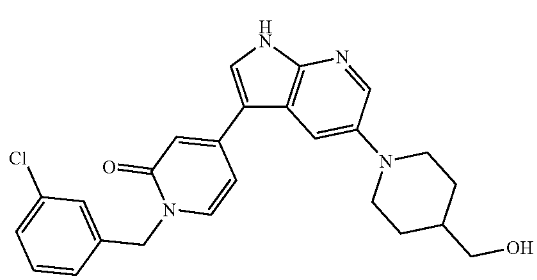 [SMILES: O=c1cc(-c2c[nH]c3ncc(N4CCC(CO)CC4)cc23)ccn1Cc1cccc(Cl)c1] |

TABLE 1-continued
Chemical structure of the invention compounds
| No | Structures |
|----|------------|
| 12 | 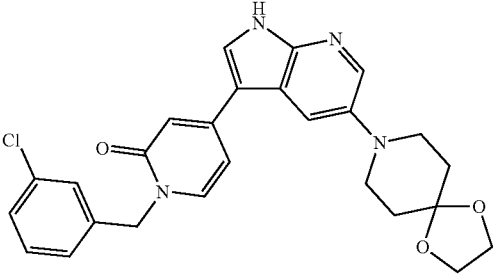 [SMILES: O=c1cc(-c2c[nH]c3ncc(N4CCC5(CC4)OCCO5)cc23)ccn1Cc1cccc(Cl)c1] |
| 13 | 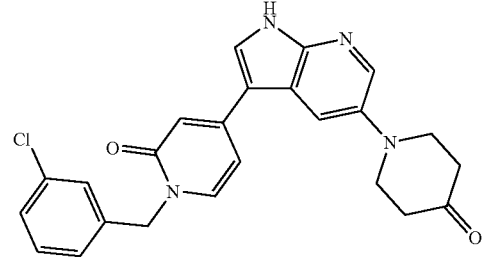 [SMILES: O=C1CCN(c2cnc3[nH]cc(-c4ccn(Cc5cccc(Cl)c5)c(=O)c4)c3c2)CC1] |
| 14 | 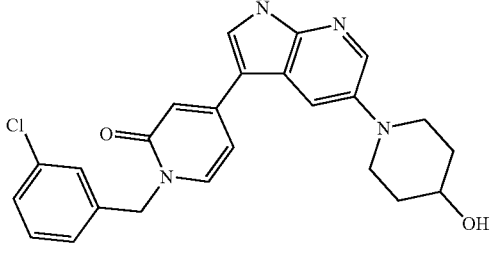 |
| 15 | 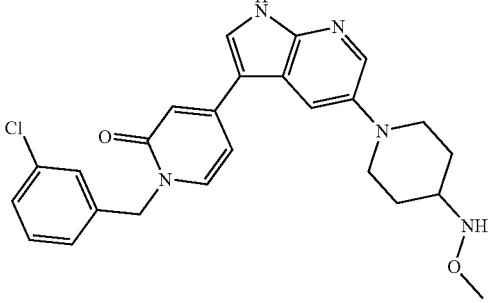 |
| 16 | 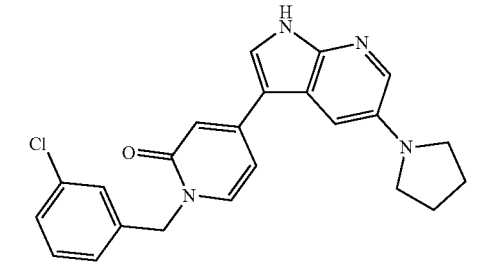 [SMILES: O=c1cc(-c2c[nH]c3ncc(N4CCCC4)cc23)ccn1Cc1cccc(Cl)c1] |

TABLE 1-continued

Chemical structure of the invention compounds

| No | Structures |
|---|---|
| 17 | 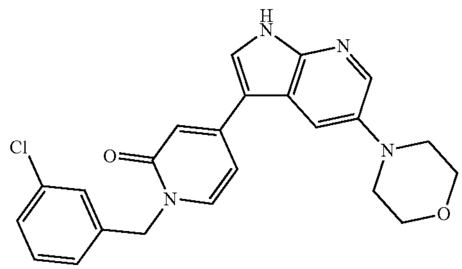 [SMILES: O=c1cc(-c2c[nH]c3ncc(N4CCOCC4)cc23)ccn1Cc1cccc(Cl)c1] |
| 18 | 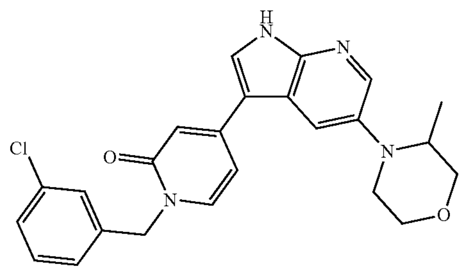 [SMILES: CC1COCCN1c1cnc2[nH]cc(-c3ccn(Cc4cccc(Cl)c4)c(=O)c3)c2c1] |
| 19 | 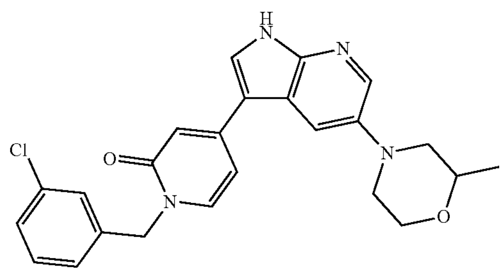 [SMILES: CC1CN(c2cnc3[nH]cc(-c4ccn(Cc5cccc(Cl)c5)c(=O)c4)c3c2)CCO1] |
| 20 | 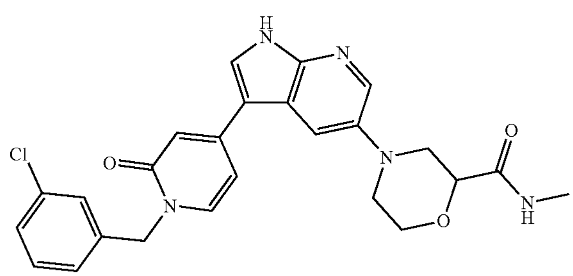 [SMILES: CNC(=O)C1CN(c2cnc3[nH]cc(-c4ccn(Cc5cccc(Cl)c5)c(=O)c4)c3c2)CCO1] |
| 21 | 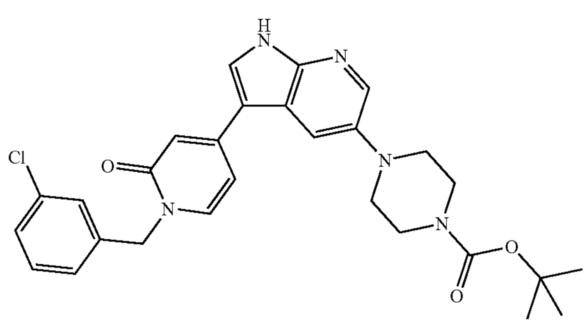 [SMILES: CC(C)(C)OC(=O)N1CCN(c2cnc3[nH]cc(-c4ccn(Cc5cccc(Cl)c5)c(=O)c4)c3c2)CC1] |

229
230
TABLE 1-continued
Chemical structure of the invention compounds
| No | Structures |
|---|---|
| 22 | 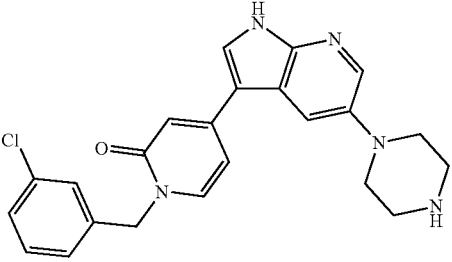 |
| 23 | 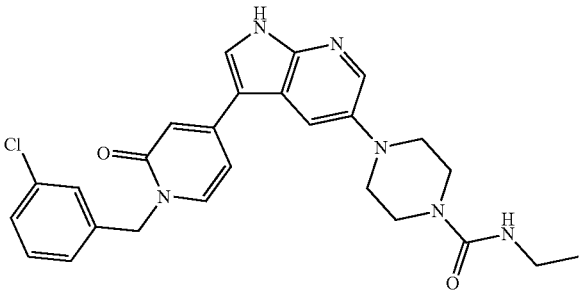 [SMILES: CCNC(=O)N1CCN(c2cnc3[nH]cc(-c4ccn(Cc5cccc(Cl)c5)c(=O)c4)c3c2)CC1] |
| 24 | 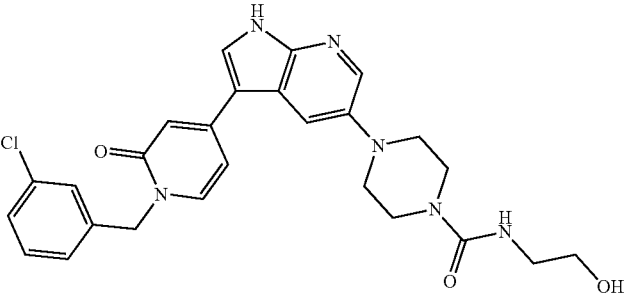 [SMILES: O=C(NCCO)N1CCN(c2cnc3[nH]cc(-c4ccn(Cc5cccc(Cl)c5)c(=O)c4)c3c2)CC1] |
| 25 | 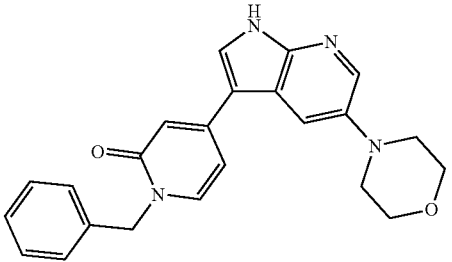 [SMILES: O=c1cc(-c2c[nH]c3ncc(N4CCOCC4)cc23)ccn1Cc1ccccc1] |
| 26 | 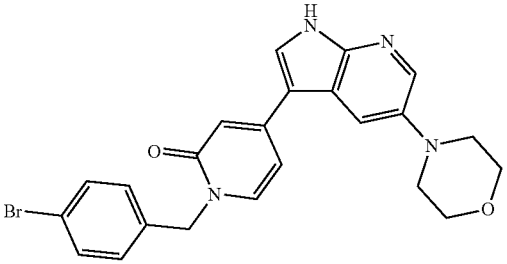 |

TABLE 1-continued

Chemical structure of the invention compounds

| No | Structures |
|---|---|
| 27 | 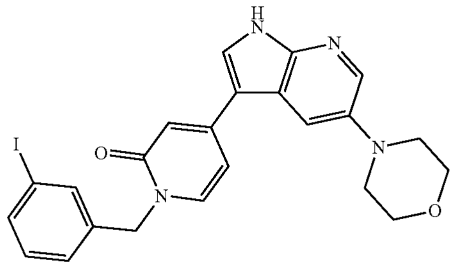 [SMILES: O=c1cc(-c2c[nH]c3ncc(N4CCOCC4)cc23)ccn1Cc1cccc(I)c1] |
| 28 | 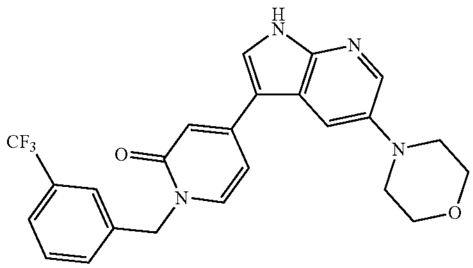 [SMILES: O=c1cc(-c2c[nH]c3ncc(N4CCOCC4)cc23)ccn1Cc1cccc(C(F)(F)F)c1] |
| 29 | 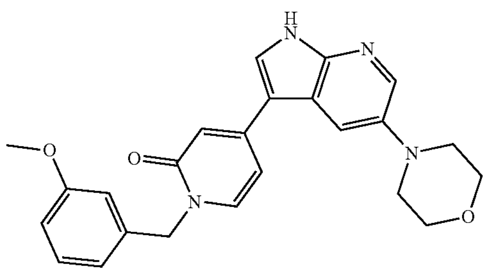 [SMILES: COc1cccc(Cn2ccc(-c3c[nH]c4ncc(N5CCOCC5)cc34)cc2=O)c1] |
| 30 | 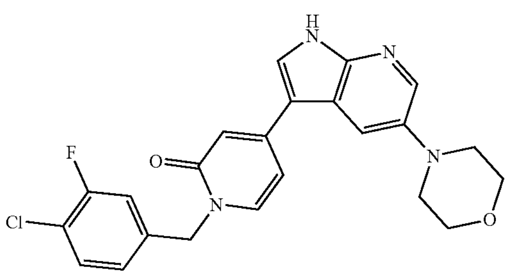 [SMILES: O=c1cc(-c2c[nH]c3ncc(N4CCOCC4)cc23)ccn1Cc1ccc(Cl)c(F)c1] |
| 31 | 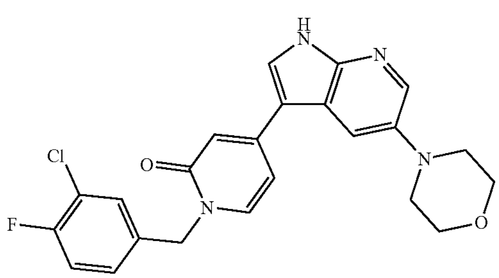 [SMILES: O=c1cc(-c2c[nH]c3ncc(N4CCOCC4)cc23)ccn1Cc1ccc(F)c(Cl)c1] |

TABLE 1-continued
Chemical structure of the invention compounds
| No | Structures |
|---|---|
| 32 | 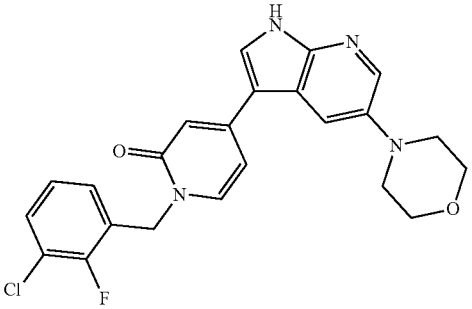 [SMILES: O=c1cc(-c2c[nH]c3ncc(N4CCOCC4)cc23)ccn1Cc1cccc(Cl)c1F] |
| 33 | 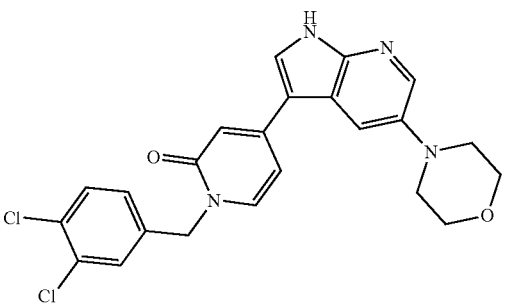 [SMILES: O=c1cc(-c2c[nH]c3ncc(N4CCOCC4)cc23)ccn1Cc1ccc(Cl)c(Cl)c1] |
| 34 | 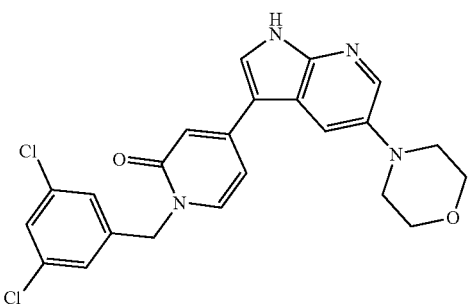 |
| 35 | 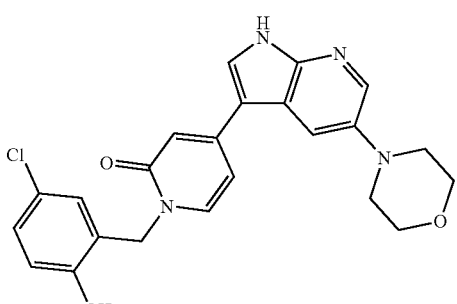 |
| 36 | 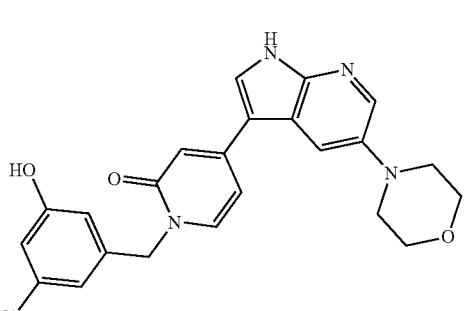 |

TABLE 1-continued
Chemical structure of the invention compounds
| No | Structures |
|---|---|
| 37 | 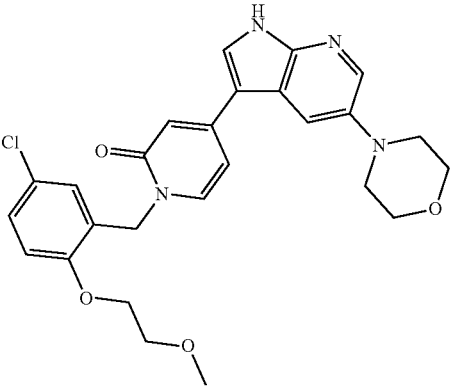 [SMILES: COCCOc1ccc(Cl)cc1Cn1ccc(-c2c[nH]c3ncc(N4CCOCC4)cc23)cc1=O] |
| 38 | 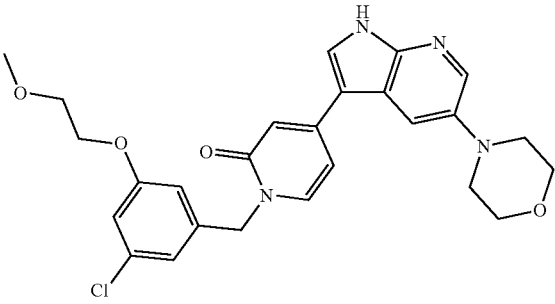 [SMILES: COCCOc1cc(Cl)cc(Cn2ccc(-c3c[nH]c4ncc(N5CCOCC5)cc34)cc2=O)c1] |
| 39 | 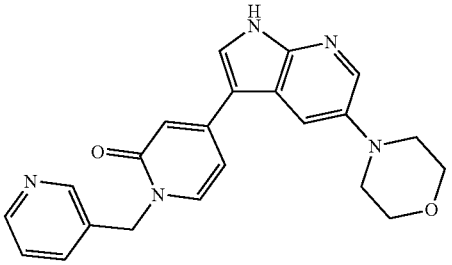 [SMILES: O=c1cc(-c2c[nH]c3ncc(N4CCOCC4)cc23)ccn1Cc1cccnc1] |
| 40 | 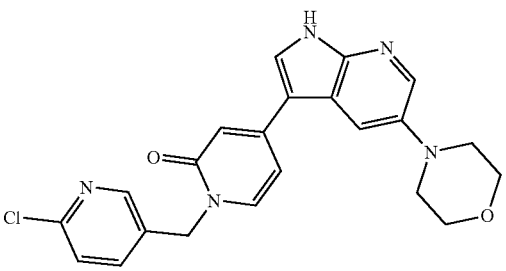 [SMILES: O=c1cc(-c2c[nH]c3ncc(N4CCOCC4)cc23)ccn1Cc1ccc(Cl)nc1] |
| 41 | 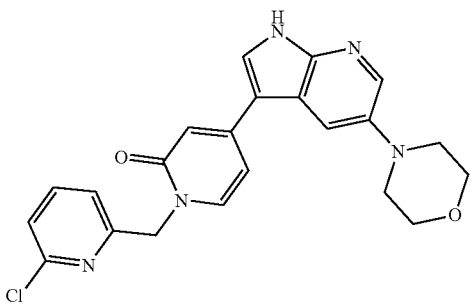 [SMILES: O=c1cc(-c2c[nH]c3ncc(N4CCOCC4)cc23)ccn1Cc1cccc(Cl)n1] |

TABLE 1-continued
Chemical structure of the invention compounds
| No | Structures |
|---|---|
| 42 | 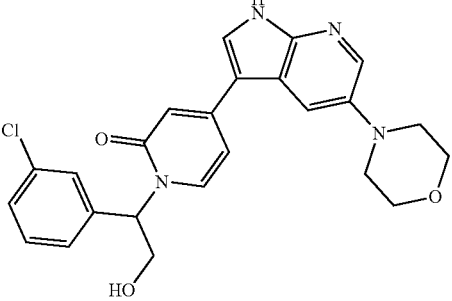 |
| 43 | 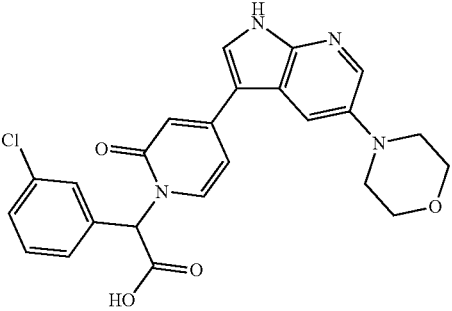 [SMILES: O=C(O)C(c1cccc(Cl)c1)n1ccc(-c2c[nH]c3ncc(N4CCOCC4)cc23)cc1=O] |
| 44 | 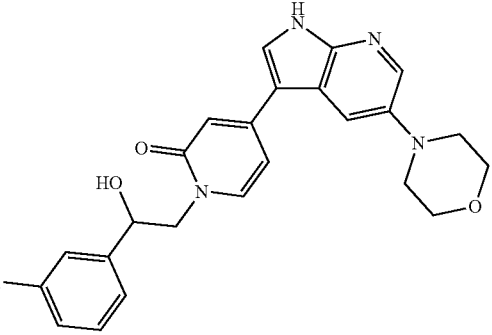 |
| 100 | 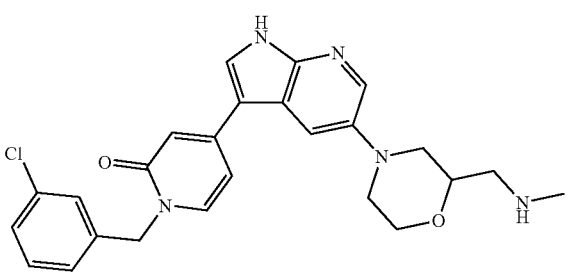 [SMILES: CNCC1CN(c2cnc3[nH]cc(-c4ccn(Cc5cccc(Cl)c5)c(=O)c4)c3c2)CCO1] |
| 101 | 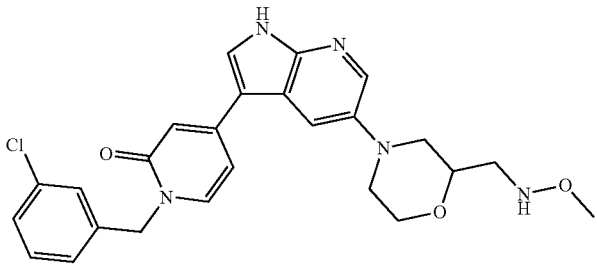 [SMILES: CONCC1CN(c2cnc3[nH]cc(-c4ccn(Cc5cccc(Cl)c5)c(=O)c4)c3c2)CCO1] |

TABLE 1-continued
Chemical structure of the invention compounds
| No | Structures |
|---|---|
| 102 | 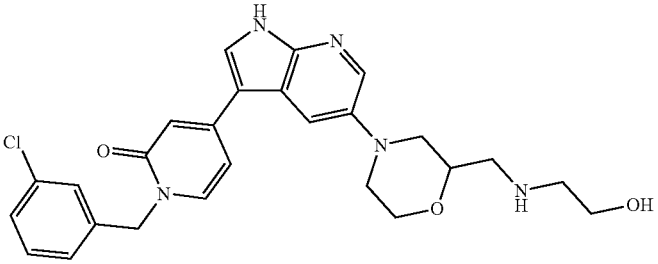 [SMILES: O=c1cc(-c2c[nH]c3ncc(N4CCOC(CNCCO)C4)cc23)ccn1Cc1cccc(Cl)c1] |
| 103 | 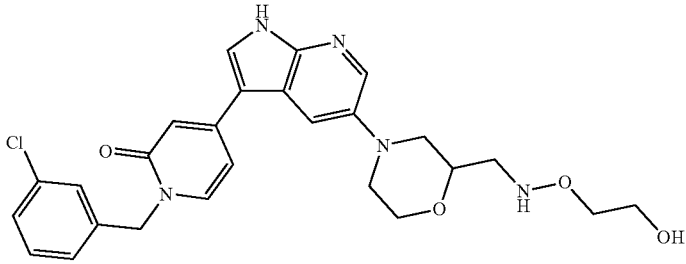 [SMILES: O=c1cc(-c2c[nH]c3ncc(N4CCOC(CNOCCO)C4)cc23)ccn1Cc1cccc(Cl)c1] |
| 104 | 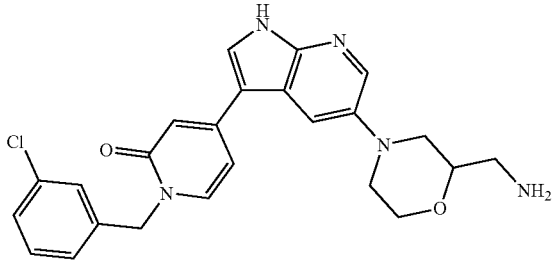 [SMILES: NCC1CN(c2cnc3[nH]cc(-c4ccn(Cc5cccc(Cl)c5)c(=O)c4)c3c2)CCO1] |
| 105 | 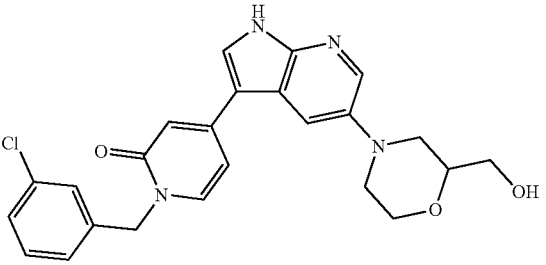 [SMILES: O=c1cc(-c2c[nH]c3ncc(N4CCOC(CO)C4)cc23)ccn1Cc1cccc(Cl)c1] |
| 106 | 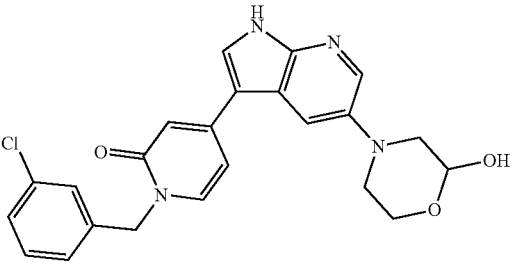 [SMILES: O=c1cc(-c2c[nH]c3ncc(N4CCOC(O)C4)cc23)ccn1Cc1cccc(Cl)c1] |

TABLE 1-continued

Chemical structure of the invention compounds

| No | Structures |
|---|---|
| 107 | 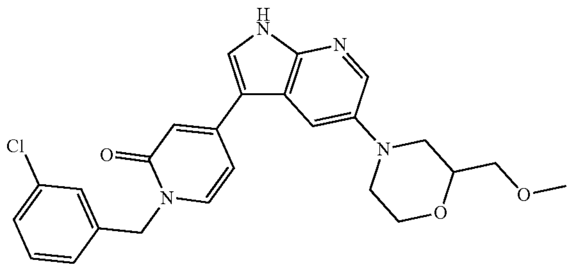 [SMILES: COCC1CN(c2cnc3[nH]cc(-c4ccn(Cc5cccc(Cl)c5)c(=O)c4)c3c2)CCO1] |
| 108 | 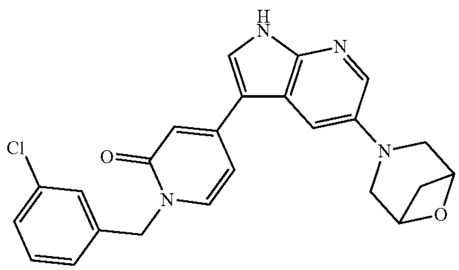 [SMILES: O=c1cc(-c2c[nH]c3ncc(N4CC5CC(C4)O5)cc23)ccn1Cc1cccc(Cl)c1] |
| 109 | 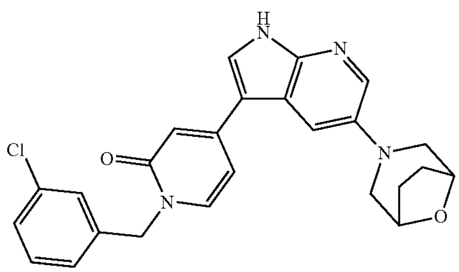 [SMILES: O=c1cc(-c2c[nH]c3ncc(N4CC5CCC(C4)O5)cc23)ccn1Cc1cccc(Cl)c1] |
| 110 | 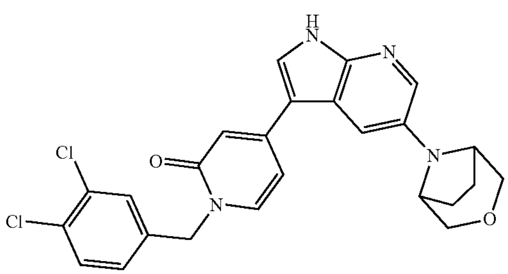 [SMILES: O=c1cc(-c2c[nH]c3ncc(N4C5CCC4COC5)cc23)ccn1Cc1ccc(Cl)c(Cl)c1] |
| 111 | 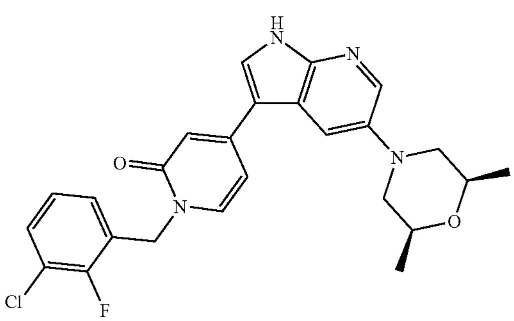 [SMILES: C[C@@H]1CN(c2cnc3[nH]cc(-c4ccn(Cc5cccc(Cl)c5F)c(=O)c4)c3c2)C[C@H](C)O1] |

TABLE 1-continued
Chemical structure of the invention compounds
| No | Structures |
|---|---|
| 112 | 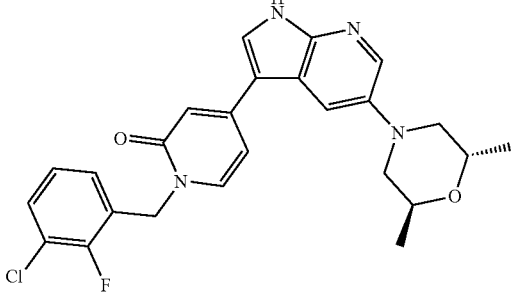 |
| 113 | 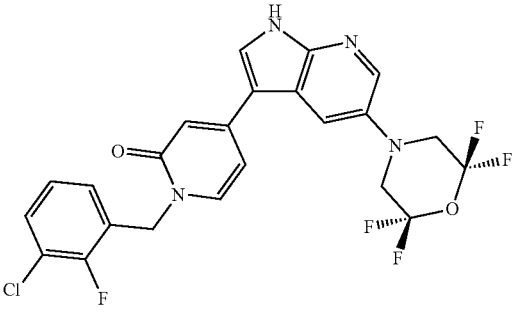 |
| 114 | 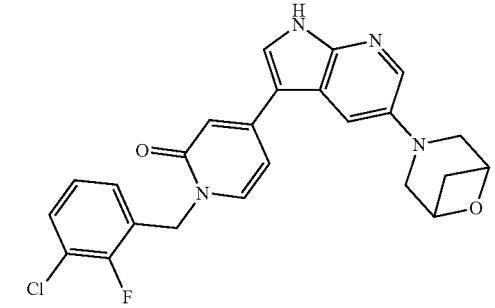 [SMILES: O=c1cc(-c2c[nH]c3ncc(N4CC5CC(C4)O5)cc23)ccn1Cc1cccc(Cl)c1F] |
| 115 | 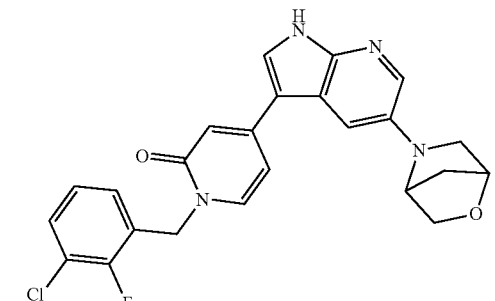 |
| 116 | 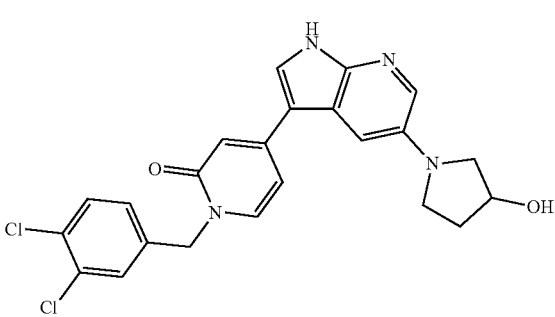 [SMILES: O=c1cc(-c2c[nH]c3ncc(N4CCC(O)C4)cc23)ccn1Cc1ccc(Cl)c(Cl)c1] |

TABLE 1-continued

Chemical structure of the invention compounds

| No | Structures |
|---|---|
| 117 | 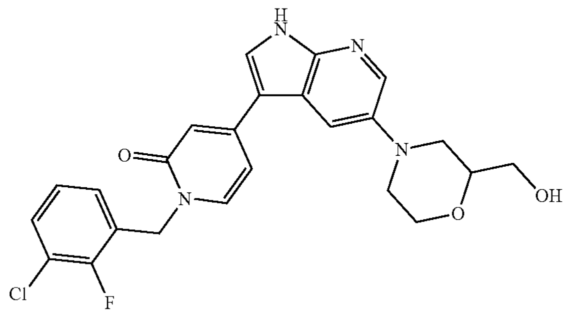 [SMILES: O=c1cc(-c2c[nH]c3ncc(N4CCOC(CO)C4)cc23)ccn1Cc1cccc(Cl)c1F] |
| 118 | 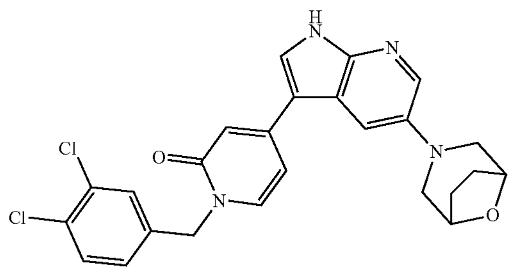 [SMILES: O=c1cc(-c2c[nH]c3ncc(N4CC5CCC(C4)O5)cc23)ccn1Cc1ccc(Cl)c(Cl)c1] |
| 119 | 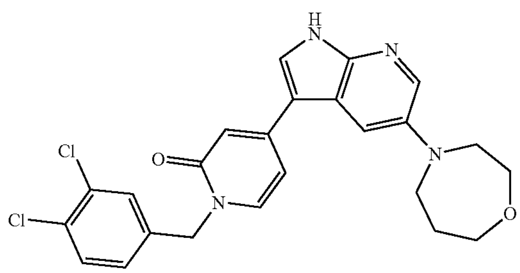 [SMILES: O=c1cc(-c2c[nH]c3ncc(N4CCCOCC4)cc23)ccn1Cc1ccc(Cl)c(Cl)c1] |
| 120 | 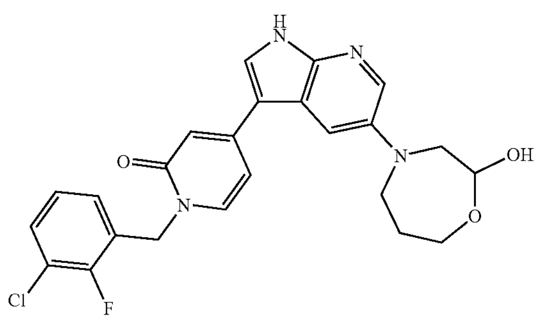 [SMILES: O=c1cc(-c2c[nH]c3ncc(N4CCCOC(O)C4)cc23)ccn1Cc1cccc(Cl)c1F] |
| 121 | 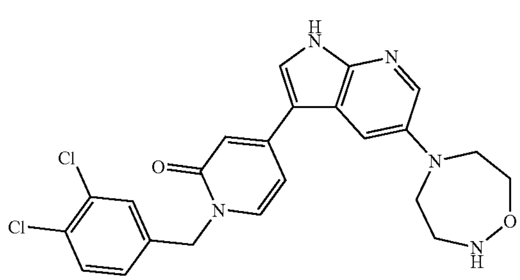 [SMILES: O=c1cc(-c2c[nH]c3ncc(N4CCNOCC4)cc23)ccn1Cc1ccc(Cl)c(Cl)c1] |

TABLE 1-continued

Chemical structure of the invention compounds

| No | Structures |
|---|---|
| 122 | 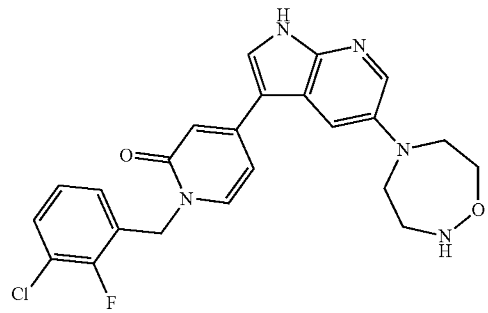 [SMILES: O=c1cc(-c2c[nH]c3ncc(N4CCNOCC4)cc23)ccn1Cc1cccc(Cl)c1F] |
| 123 | 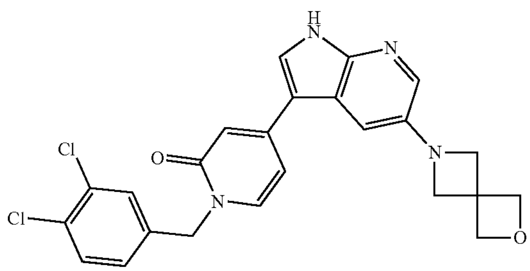 [SMILES: O=c1cc(-c2c[nH]c3ncc(N4CC5(COC5)C4)cc23)ccn1Cc1ccc(Cl)c(Cl)c1] |
| 124 | 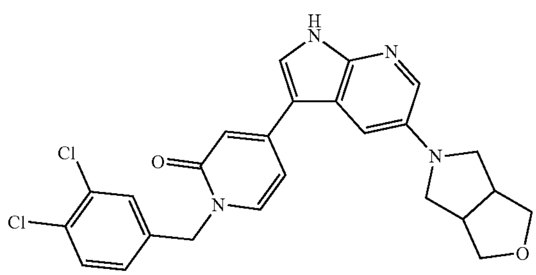 [SMILES: O=c1cc(-c2c[nH]c3ncc(N4CC5COCC5C4)cc23)ccn1Cc1ccc(Cl)c(Cl)c1] |
| 125 | 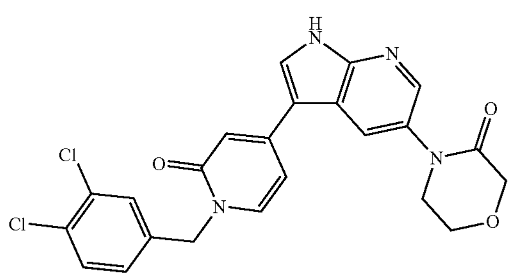 [SMILES: O=C1COCCN1c1cnc2[nH]cc(-c3ccn(Cc4ccc(Cl)c(Cl)c4)c(=O)c3)c2c1] |
| 126 | 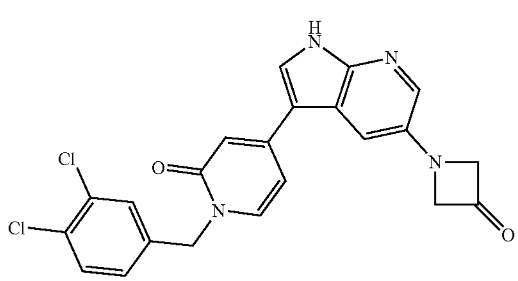 [SMILES: O=C1CN(c2cnc3[nH]cc(-c4ccn(Cc5ccc(Cl)c(Cl)c5)c(=O)c4)c3c2)C1] |

TABLE 1-continued
Chemical structure of the invention compounds
| No | Structures |
|---|---|
| 127 | 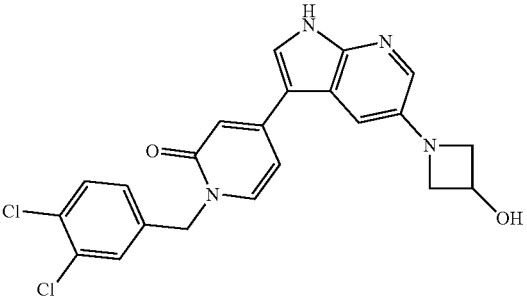 [SMILES: O=c1cc(-c2c[nH]c3ncc(N4CC(O)C4)cc23)ccn1Cc1ccc(Cl)c(Cl)c1] |
| 128 | 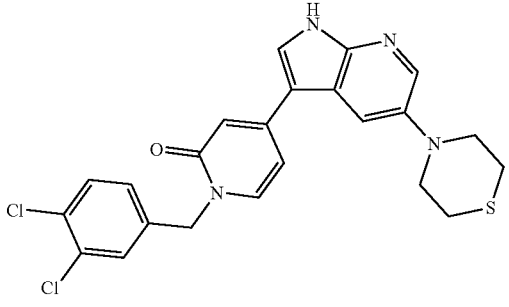 |
| 129 | 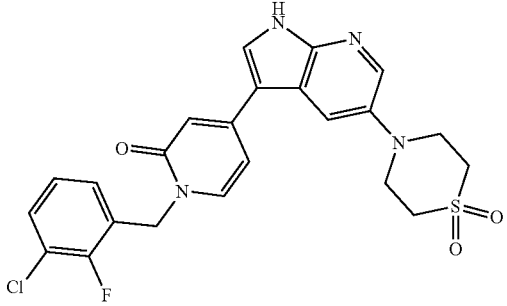 [SMILES: O=c1cc(-c2c[nH]c3ncc(N4CCS(=O)(=O)CC4)cc23)ccn1Cc1cccc(Cl)c1F] |
| 130 | 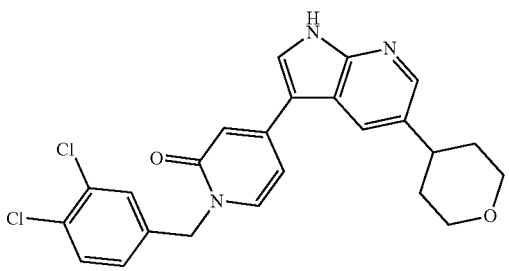 [SMILES: O=c1cc(-c2c[nH]c3ncc(C4CCOCC4)cc23)ccn1Cc1ccc(Cl)c(Cl)c1] |
| 201 | 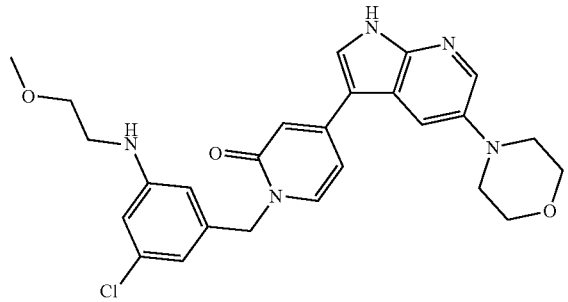 [SMILES: COCCNc1cc(Cl)cc(Cn2ccc(-c3c[nH]c4ncc(N5CCOCC5)cc34)cc2=O)c1] |

TABLE 1-continued
Chemical structure of the invention compounds
| No | Structures |
|---|---|
| 202 | 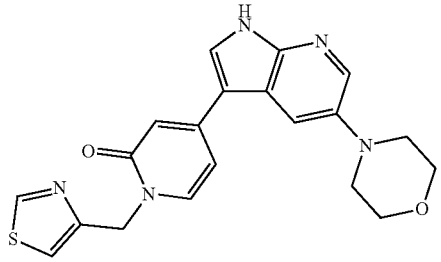 [SMILES: O=c1cc(-c2c[nH]c3ncc(N4CCOCC4)cc23)ccn1Cc1cscn1] |
| 203 | 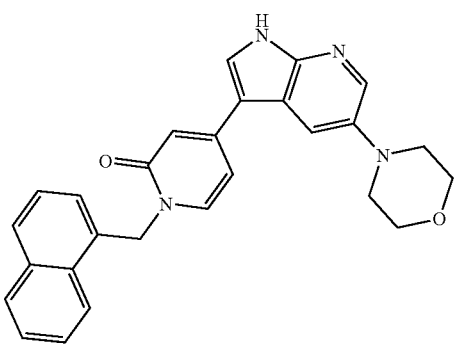 [SMILES: O=c1cc(-c2c[nH]c3ncc(N4CCOCC4)cc23)ccn1Cc1cccc2ccccc12] |
| 204 | 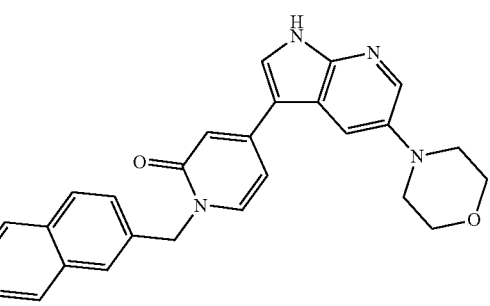 |
| 205 | 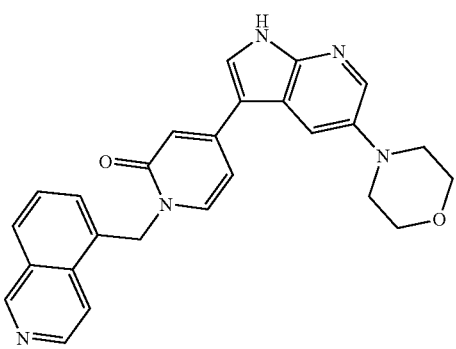 [SMILES: O=c1cc(-c2c[nH]c3ncc(N4CCOCC4)cc23)ccn1Cc1cccc2cnccc12] |
| 206 | 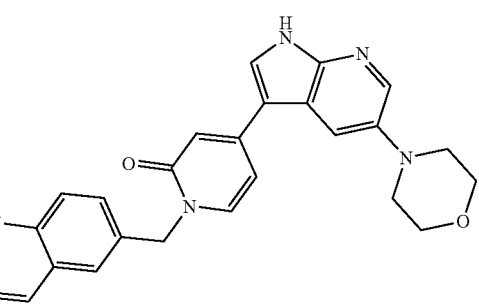 |

TABLE 1-continued
Chemical structure of the invention compounds
| No | Structures |
|---|---|
| 207 | 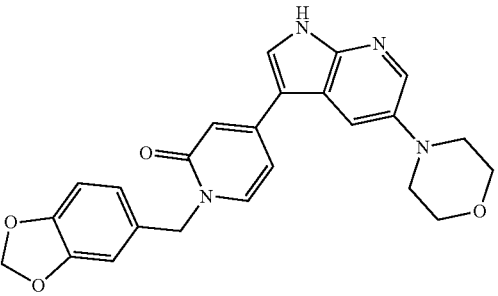 [SMILES: O=c1cc(-c2c[nH]c3ncc(N4CCOCC4)cc23)ccn1Cc1ccc2c(c1)OCO2] |
| 208 | 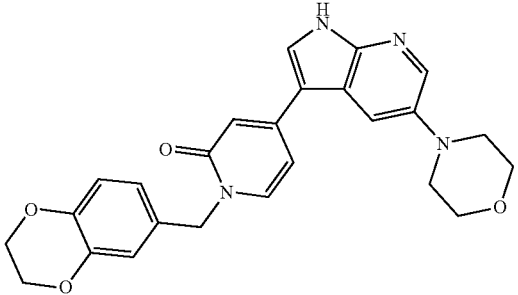 [SMILES: O=c1cc(-c2c[nH]c3ncc(N4CCOCC4)cc23)ccn1Cc1ccc2c(c1)OCCO2] |
| 209 | 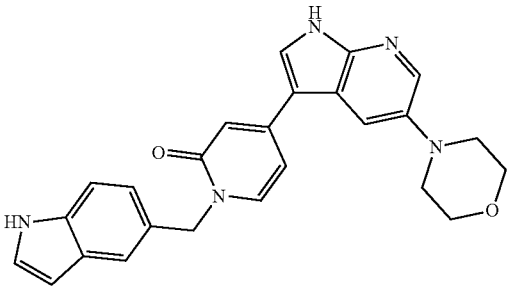 [SMILES: O=c1cc(-c2c[nH]c3ncc(N4CCOCC4)cc23)ccn1Cc1ccc2[nH]ccc2c1] |
| 210 | 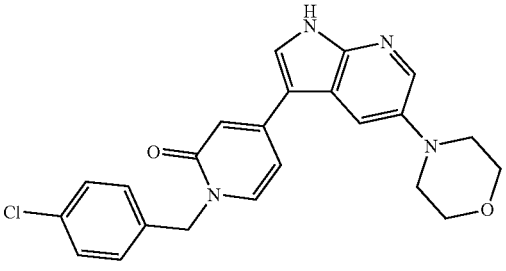 [SMILES: O=c1cc(-c2c[nH]c3ncc(N4CCOCC4)cc23)ccn1Cc1ccc(Cl)cc1] |
| 211 | 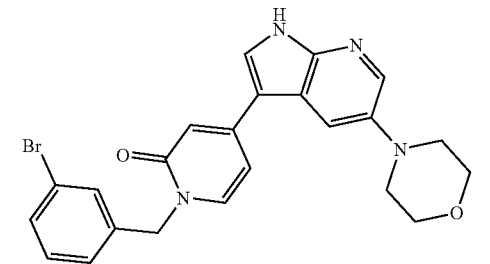 |

TABLE 1-continued

Chemical structure of the invention compounds

| No | Structures |
|----|------------|
| 212 | 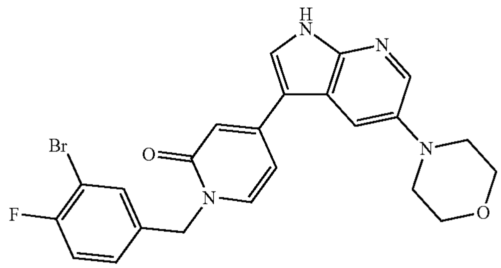 |
| 213 | 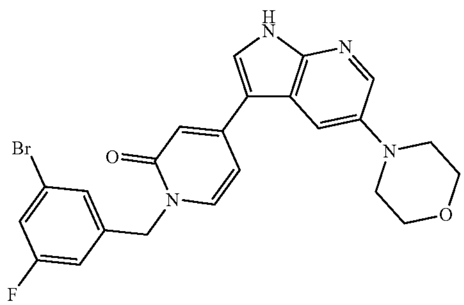 |
| 214 | 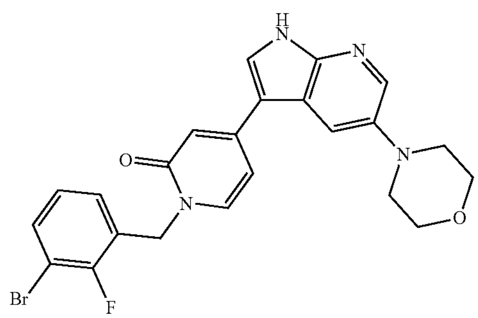 |
| 215 | 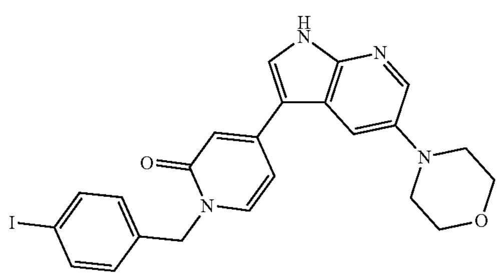 [SMILES: O=c1cc(-c2c[nH]c3ncc(N4CCOCC4)cc23)ccn1Cc1ccc(I)cc1] |
| 216 | 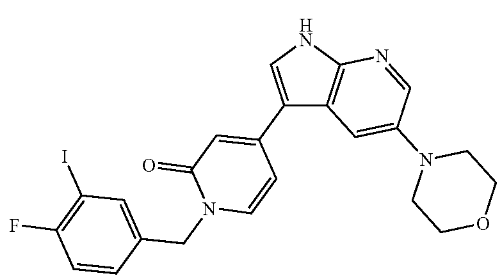 [SMILES: O=c1cc(-c2c[nH]c3ncc(N4CCOCC4)cc23)ccn1Cc1ccc(F)c(I)c1] |

TABLE 1-continued
Chemical structure of the invention compounds
| No | Structures |
|---|---|
| 217 | 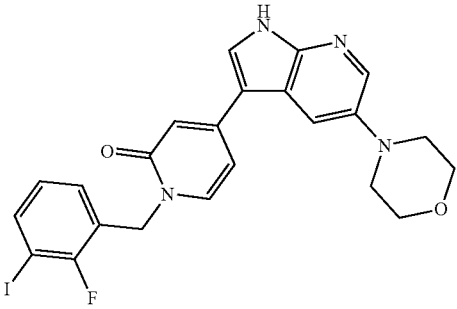 [SMILES: O=c1cc(-c2c[nH]c3ncc(N4CCOCC4)cc23)ccn1Cc1cccc(I)c1F] |
| 218 | 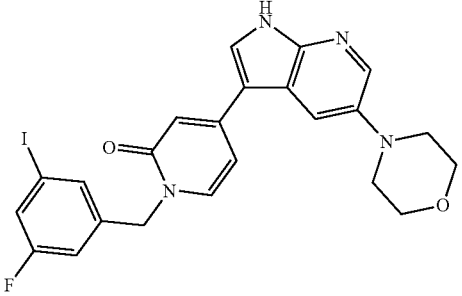 [SMILES: O=c1cc(-c2c[nH]c3ncc(N4CCOCC4)cc23)ccn1Cc1cc(F)cc(I)c1] |
| 219 | 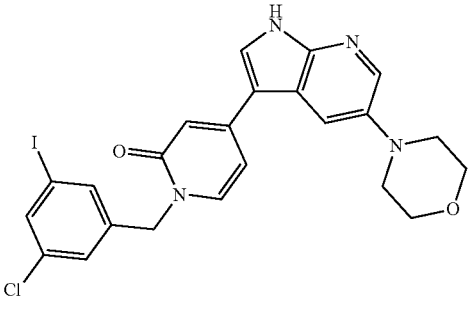 [SMILES: O=c1cc(-c2c[nH]c3ncc(N4CCOCC4)cc23)ccn1Cc1cc(Cl)cc(I)c1] |
| 220 | 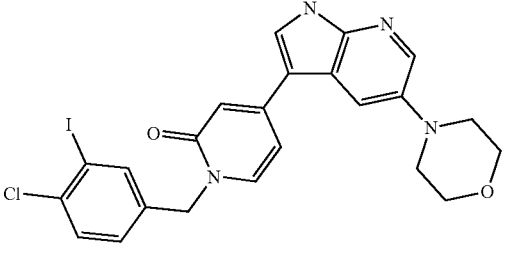 |
| 221 | 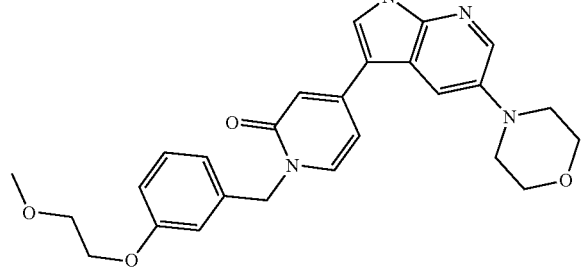 |

TABLE 1-continued
Chemical structure of the invention compounds
| No | Structures |
|---|---|
| 222 | 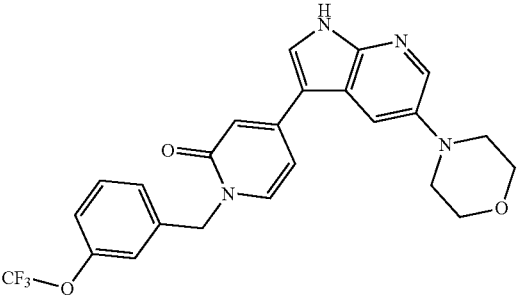 [SMILES: O=c1cc(-c2c[nH]c3ncc(N4CCOCC4)cc23)ccn1Cc1cccc(OC(F)(F)F)c1] |
| 223 | 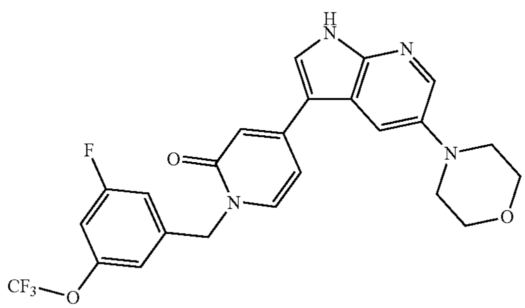 [SMILES: O=c1cc(-c2c[nH]c3ncc(N4CCOCC4)cc23)ccn1Cc1cc(F)cc(OC(F)(F)F)c1] |
| 224 | 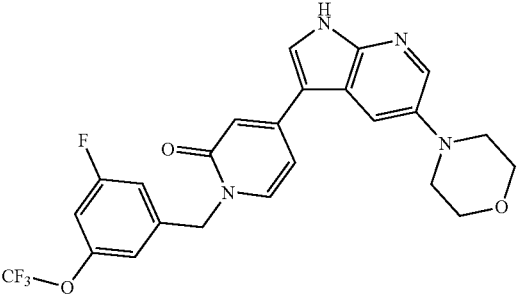 |
| 225 | 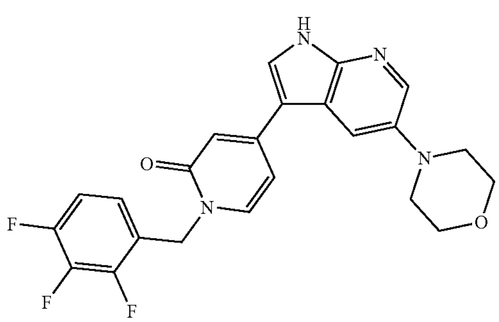 [SMILES: O=c1cc(-c2c[nH]c3ncc(N4CCOCC4)cc23)ccn1Cc1ccc(F)c(F)c1F] |
| 226 | 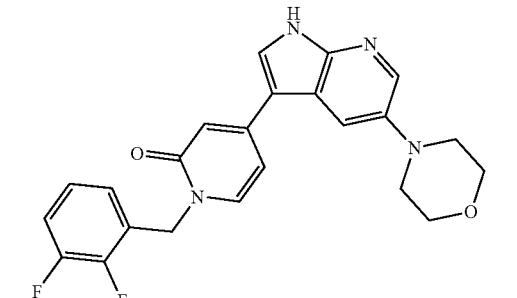 |

TABLE 1-continued
Chemical structure of the invention compounds
| No | Structures |
|---|---|
| 227 | 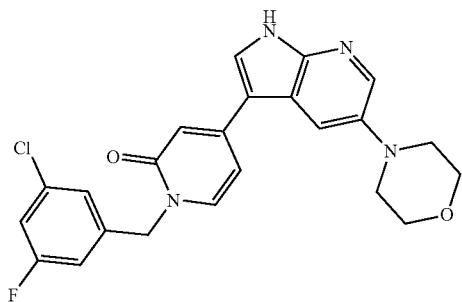 [SMILES: O=c1cc(-c2c[nH]c3ncc(N4CCOCC4)cc23)ccn1Cc1cc(F)cc(Cl)c1] |
| 228 | 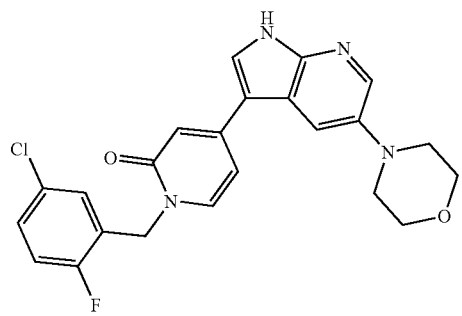 [SMILES: O=c1cc(-c2c[nH]c3ncc(N4CCOCC4)cc23)ccn1Cc1cc(Cl)ccc1F] |
| 229 | 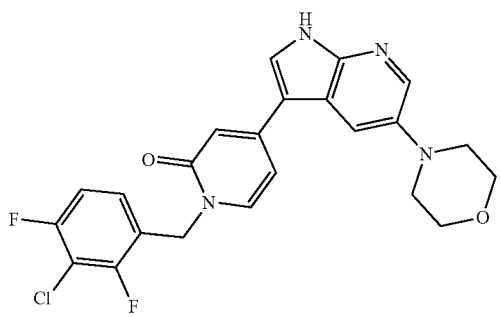 |
| 230 | 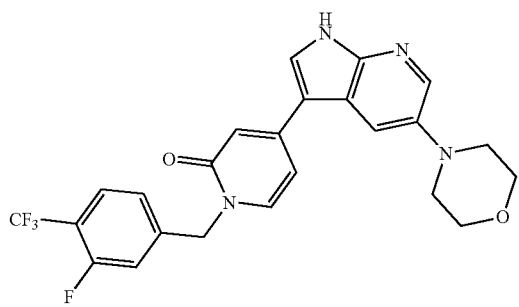 [SMILES: O=c1cc(-c2c[nH]c3ncc(N4CCOCC4)cc23)ccn1Cc1ccc(C(F)(F)F)c(F)c1] |

TABLE 1-continued

Chemical structure of the invention compounds

| No | Structures |
|---|---|
| 231 | 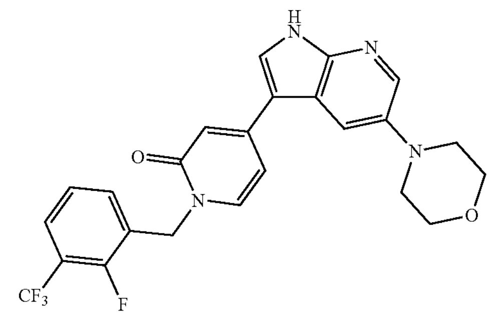 [SMILES: O=c1cc(-c2c[nH]c3ncc(N4CCOCC4)cc23)ccn1Cc1cccc(C(F)(F)F)c1F] |
| 232 | 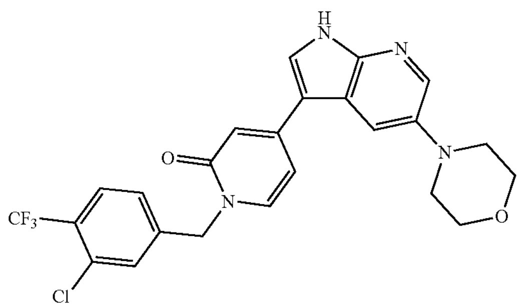 |
| 233 | 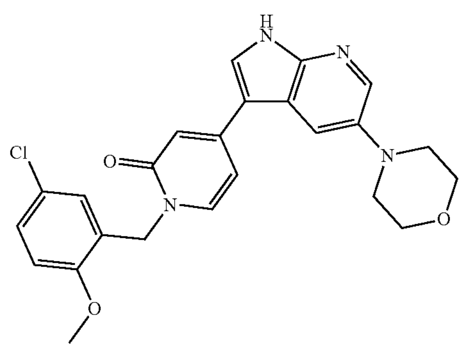 [SMILES: COc1ccc(Cl)cc1Cn1ccc(-c2c[nH]c3ncc(N4CCOCC4)cc23)cc1=O] |
| 234 | 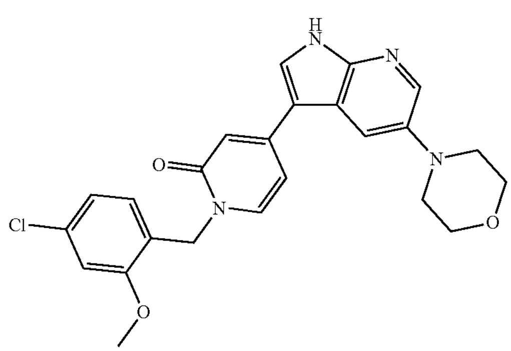 [SMILES: COc1cc(Cl)ccc1Cn1ccc(-c2c[nH]c3ncc(N4CCOCC4)cc23)cc1=O] |

TABLE 1-continued
Chemical structure of the invention compounds
| No | Structures |
|---|---|
| 235 | 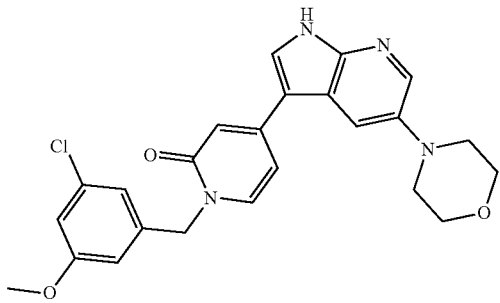 [SMILES: COc1cc(Cl)cc(Cn2ccc(-c3c[nH]c4ncc(N5CCOCC5)cc34)cc2=O)c1] |
| 236 | 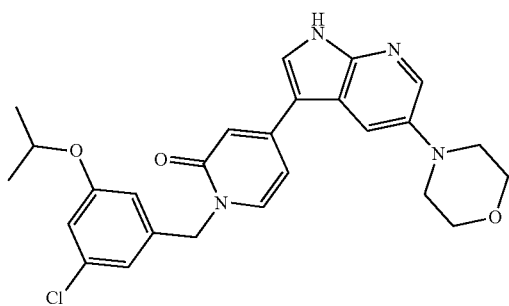 [SMILES: CC(C)Oc1cc(Cl)cc(Cn2ccc(-c3c[nH]c4ncc(N5CCOCC5)cc34)cc2=O)c1] |
| 237 | 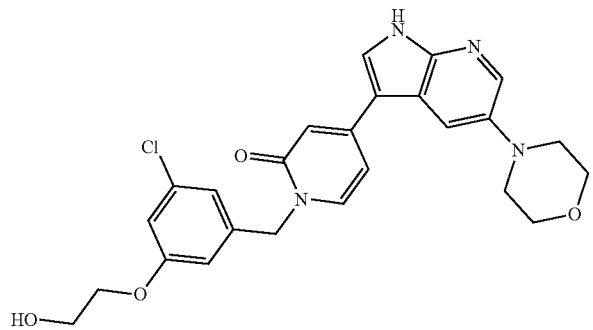 [SMILES: O=c1cc(-c2c[nH]c3ncc(N4CCOCC4)cc23)ccn1Cc1cc(Cl)cc(OCCO)c1] |
| 238 | 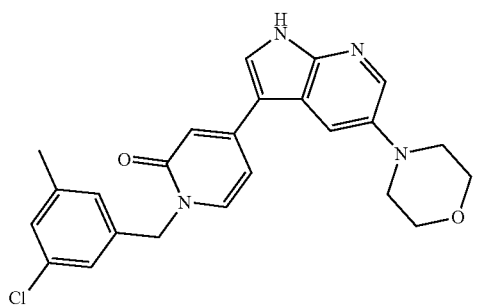 |
| 239 | 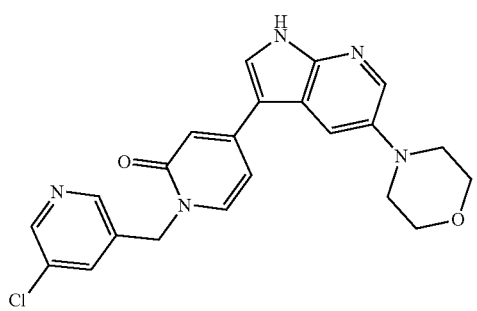 [SMILES: O=c1cc(-c2c[nH]c3ncc(N4CCOCC4)cc23)ccn1Cc1cncc(Cl)c1] |

TABLE 1-continued
Chemical structure of the invention compounds
| No | Structures |
|---|---|
| 240 | 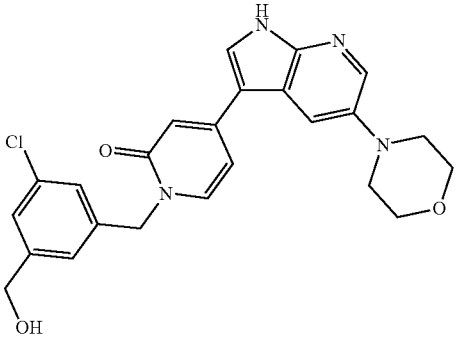 [SMILES: O=c1cc(-c2c[nH]c3ncc(N4CCOCC4)cc23)ccn1Cc1cc(Cl)cc(CO)c1] |
| 241 | 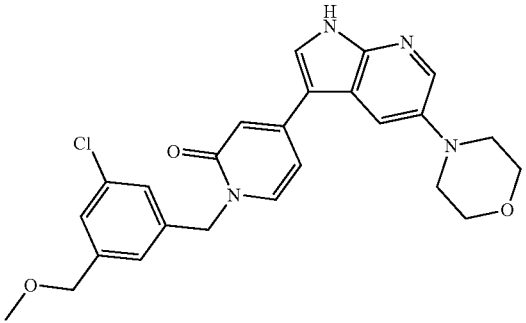 [SMILES: COCc1cc(Cl)cc(Cn2ccc(-c3c[nH]c4ncc(N5CCOCC5)cc34)cc2=O)c1] |
| 301 | 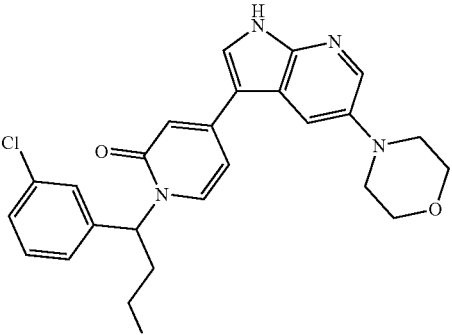 |
| 302 | 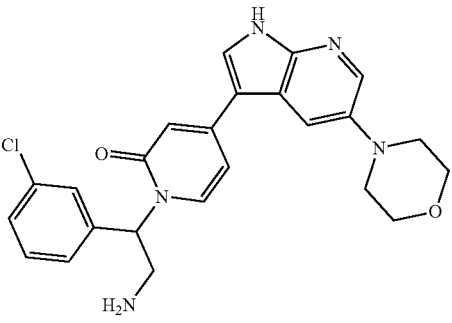 [SMILES: NCC(c1cccc(Cl)c1)n1ccc(-c2c[nH]c3ncc(N4CCOCC4)cc23)cc1=O] |

US 10,995,089 B2
269                                                                                                                           270
TABLE 1-continued
Chemical structure of the invention compounds
| No | Structures |
|---|---|
| 303 | 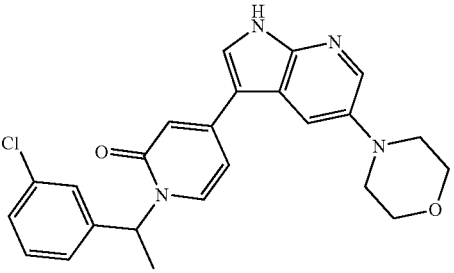 [SMILES: CC(c1cccc(Cl)c1)n1ccc(-c2c[nH]c3ncc(N4CCOCC4)cc23)cc1=O] |
| 304 | 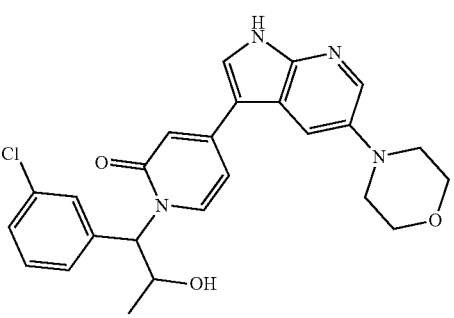 [SMILES: CC(O)C(c1cccc(Cl)c1)n1ccc(-c2c[nH]c3ncc(N4CCOCC4)cc23)cc1=O] |
| 305 | 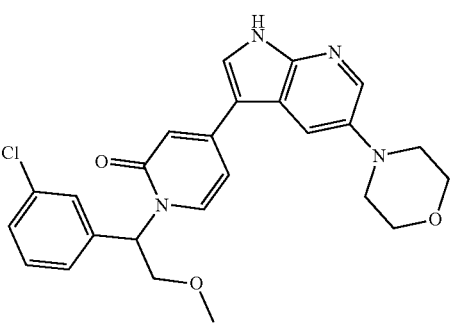 [SMILES: COCC(c1cccc(Cl)c1)n1ccc(-c2c[nH]c3ncc(N4CCOCC4)cc23)cc1=O] |
| 306 | 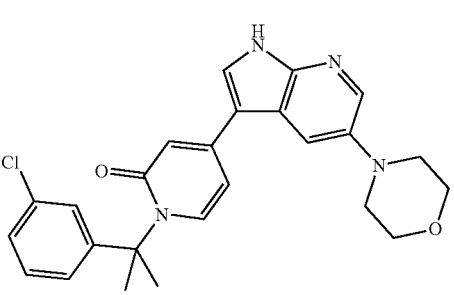 [SMILES: CC(C)(c1cccc(Cl)c1)n1ccc(-c2c[nH]c3ncc(N4CCOCC4)cc23)cc1=O] |
| 307 | 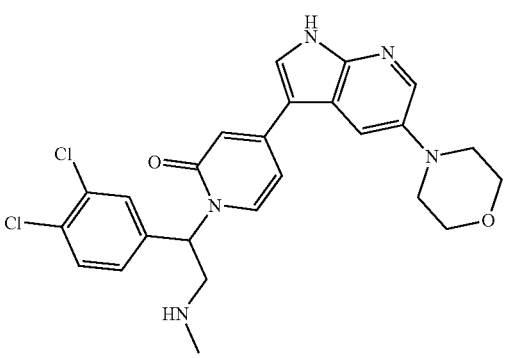 [SMILES: CNCC(c1ccc(Cl)c(Cl)c1)n1ccc(-c2c[nH]c3ncc(N4CCOCC4)cc23)cc1=O] |

TABLE 1-continued
Chemical structure of the invention compounds
| No | Structures |
|---|---|
| 308 | 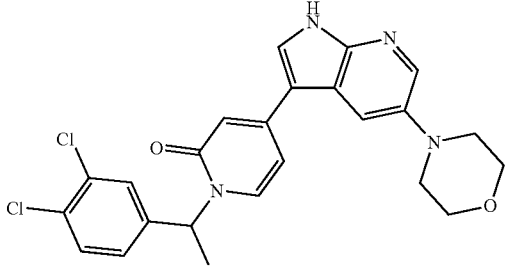 [SMILES: CC(c1ccc(Cl)c(Cl)c1)n1ccc(-c2c[nH]c3ncc(N4CCOCC4)cc23)cc1=O] |
| 400 | 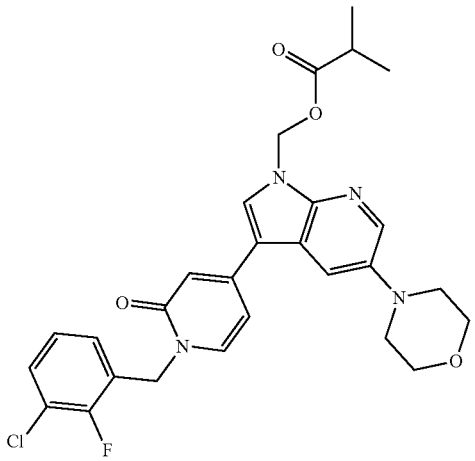 [SMILES: CC(C)C(=O)OCn1cc(-c2ccn(Cc3cccc(Cl)c3F)c(=O)c2)c2cc(N3CCOCC3)cnc21] |
| 401 | 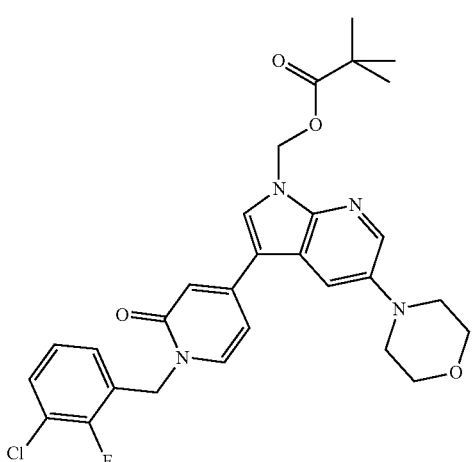 |

TABLE 1-continued
Chemical structure of the invention compounds
| No | Structures |
|---|---|
| 402 | 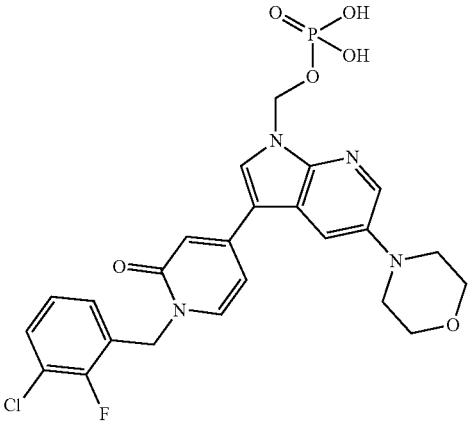 [SMILES: O=c1cc(-c2cn(COP(=O)(O)O)c3ncc(N4CCOCC4)cc23)ccn1Cc1cccc(Cl)c1F] |
| 403 | 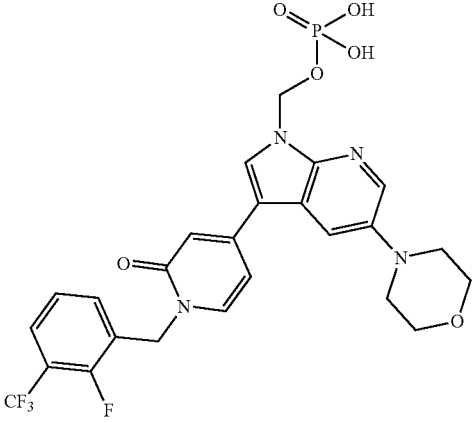 [SMILES: O=c1cc(-c2cn(COP(=O)(O)O)c3ncc(N4CCOCC4)cc23)ccn1Cc1cccc(C(F)(F)F)c1F] |
| 404 | 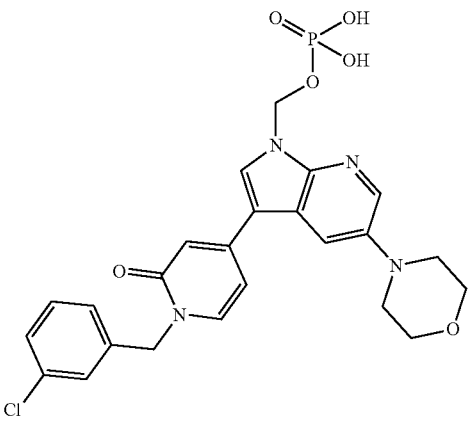 |

TABLE 1-continued
Chemical structure of the invention compounds
| No | Structures |
|---|---|
| 405 | 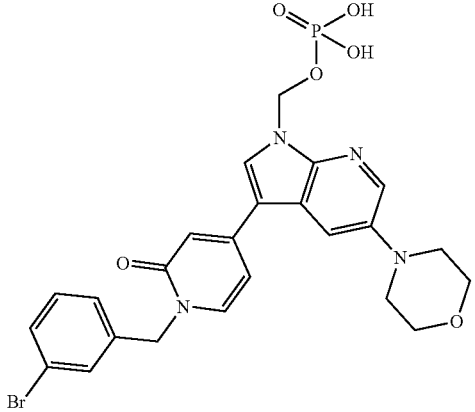 [SMILES: O=c1cc(-c2cn(COP(=O)(O)O)c3ncc(N4CCOCC4)cc23)ccn1Cc1cccc(Cl)c1] |
| 406 | 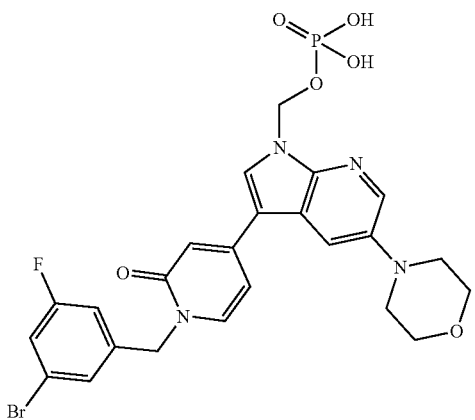 |
| 407 | 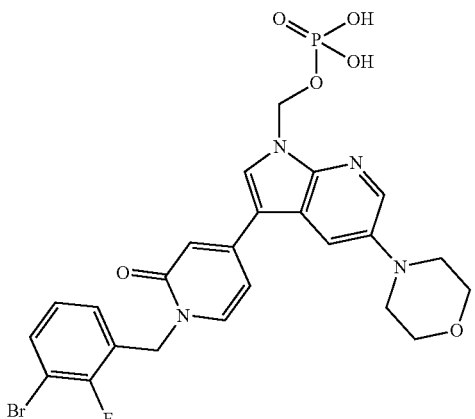 |

TABLE 1-continued
Chemical structure of the invention compounds
| No | Structures |
|---|---|
| 408 | 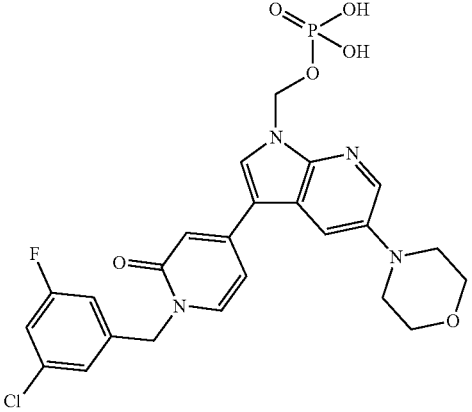 [SMILES: O=c1cc(-c2cn(COP(=O)(O)O)c3ncc(N4CCOCC4)cc23)ccn1Cc1cc(F)cc(Cl)c1] |
| 409 | 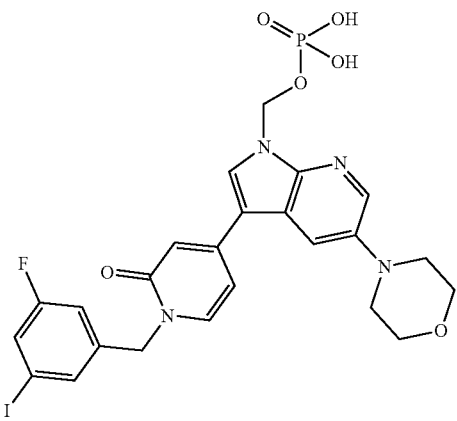 [SMILES: O=c1cc(-c2cn(COP(=O)(O)O)c3ncc(N4CCOCC4)cc23)ccn1Cc1cc(F)cc(I)c1] |
| 410 | 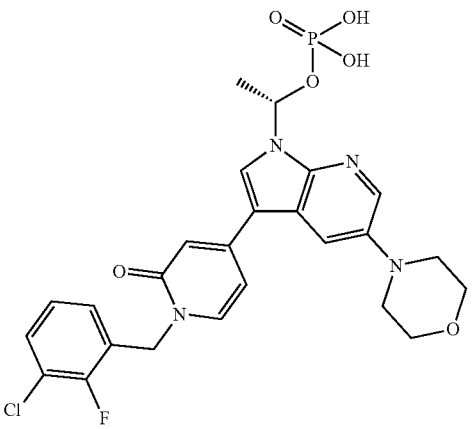 [SMILES: C[C@H](OP(=O)(O)O)n1cc(-c2ccn(Cc3cccc(Cl)c3F)c(=O)c2)c2cc(N3CCOCC3)cnc21] |

TABLE 1-continued
Chemical structure of the invention compounds
| No | Structures |
|---|---|
| 411 | 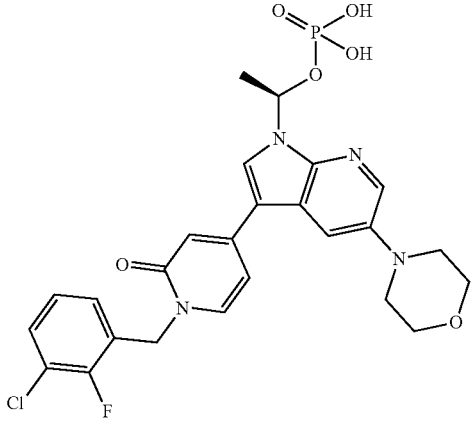 [SMILES: C[C@@H](OP(=O)(O)O)n1cc(-c2ccn(Cc3cccc(Cl)c3F)c(=O)c2)c2cc(N3CCOCC3)cnc21] |
| 412 | 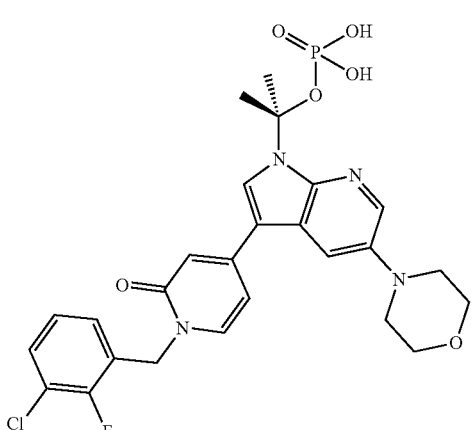 |
| 413 | 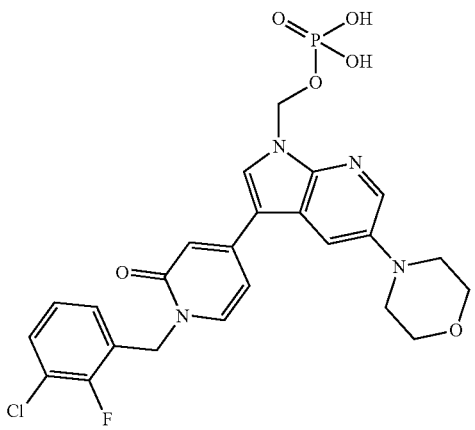<br>Lysinate |

TABLE 1-continued
Chemical structure of the invention compounds
| No | Structures |
|---|---|
| 414 | 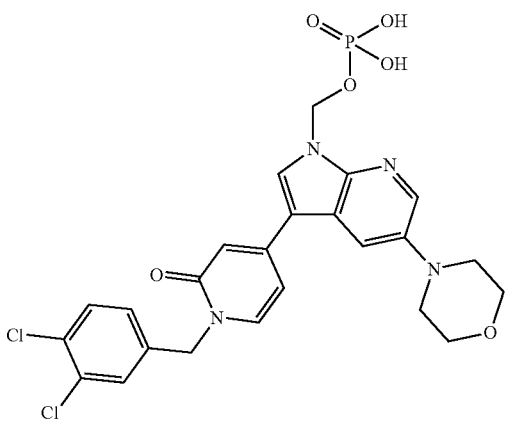 [SMILES: O=c1cc(-c2cn(COP(=O)(O)O)c3ncc(N4CCOCC4)cc23)ccn1Cc1ccc(Cl)c(Cl)c1] |
| 415 | 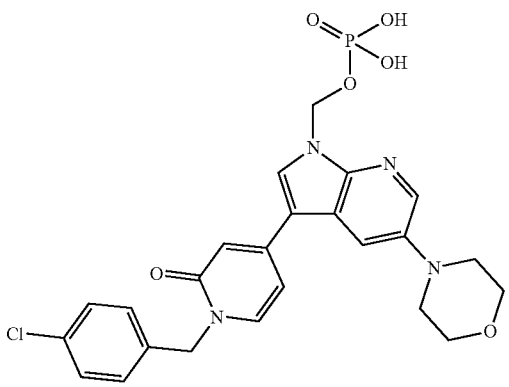 [SMILES: O=c1cc(-c2cn(COP(=O)(O)O)c3ncc(N4CCOCC4)cc23)ccn1Cc1ccc(Cl)cc1] |
| 416 | 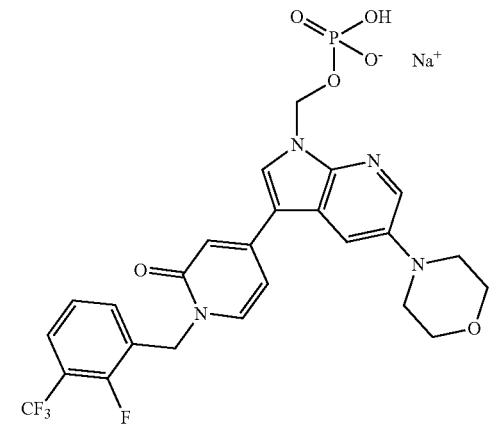 [SMILES: O=c1cc(-c2cn(COP(=O)([O-])O)c3ncc(N4CCOCC4)cc23)ccn1Cc1cccc(C(F)(F)F)c1F ; [Na+]] |

TABLE 1-continued

Chemical structure of the invention compounds

| No | Structures |
|---|---|
| 417 | 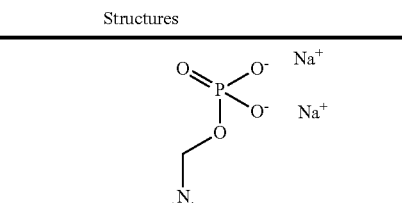 |

Example 45: ERK2 Enzymatic Assay

To assess compounds capacity to inhibit ERK2 enzymatic activity, Z'-Lyte biochemical assay from Life technologies was used according to manufacturer's instructions. Briefly, black 384-well plates containing 100 nl of 100× compound solution in 100% DMSO, 2.4 µl kinase buffer, 5 µl 2×MAPK1 (ERK2)/Ser/Thr 03 mixture and 2.5 µl 4×ATP solution were used. Plates were shaken for 30 seconds and incubated for 60 minutes at room temperature. Then, 5 µl of a 1:1024 dilution of Development Reagent A was added. Plates were shaken for 30 seconds and incubated for 60 minutes at room temperature. A plate reader was used to read fluorescence. In this assay, ERK2 enzyme was used at a concentration of 0.4 µg/ml (5.74 nM) at ATP Km (100 µM). Kinase buffer consisted of 50 mM HEPES pH 7.5, 0.01% BRIJ-35, 10 mM MgCl2, 1 mM EGTA. Compounds $IC_{50}$ were determined with a 3-fold serial dilution (10 point titrations in duplicate).

ERK2 inhibitory activity of selected compounds ("ERK2 $IC_{50}$") is reported in table 2 as followed:

All tested compounds exhibit a capacity to inhibit ERK2 enzymatic activity.

In particular, compounds having an activity designated as "A" provided an $IC_{50}$ value <10 nM. Compounds having an activity designated as "B" provided an $IC_{50}$ value between 10 nM and 25 nM. Compounds having an activity designated as "C" provided an $IC_{50}$ value between 25 nM and 50 nM. Compounds having an activity designated as "D" provided an $IC_{50}$ value between 50 nM and 100 nM. Compounds having an activity designated as "E" provided an $IC_{50}$ value >100 nM.

Example 46: Cell Line Proliferation Assay

A cell line assay was used to determine compounds capacity to inhibit cell proliferation. A375 cells (malignant melanoma) were grown to near 80% confluence and seeded at 4000 cells per 100 µl per well in DMEM with 10% FBS in 96-well flat bottom plates. Cells were incubated for 24 hours at 37° C. under 5% $CO_2$. 100 µl compound solutions were added to cells and incubated for 72 hours at 37° C. Total volume of media was 200 µl per well. Compounds were screened in 0.15% DMSO (final) using 6 point titrations in duplicate. Negative control wells consisted of vehicle only (0.15% DMSO in 10% FBS DMEM). After 72 hours of compound treatment, SDS 1% (final) was added to positive control wells for 15 minutes at 37° C. Then, medium was discarded and replaced by 100 µl per well of a MTT solution (3-[4.5-dimethylthiazol-2-yl]-2.5-diphenyltetrazolium bromide) (Sigma, Cat#M5655) at 0.5 mg/ml in 10% FBS DMEM. Cells were incubated for 4 hours at 37° C. MTT reaction was stopped and homogenized by the addition of 100 µl per well of SDS 10% 0.01M HCl. After 2 hours at 37° C., absorbance was measured at 570 nm in a Bio-Tek plate reader (PowerWave HT). Percent of proliferation inhibition was calculated using negative controls (0.15% DMSO) as 0% growth inhibition and positive controls (1% SDS) as 100% growth inhibition. $IC_{50}$ values (concentration inducing a half-maximal growth inhibition) were determined by non-linear regression analysis of the inhibition curve generated by mean replicate values (using a sigmoid dose-response with variable Hill Slope and constraining the top to a constant value of 100 and the bottom to a value between 0 and 50). Analysis was performed using GraphPad Prism software.

Cell proliferation inhibitory activity of selected compounds ("A375 $IC_{50}$") is reported in table 2 as followed:

Compounds having an activity designated as "A'" provided an $IC_{50}$ value <150 nM. Compounds having an activity designated as "B'" provided an $IC_{50}$ value between 150 nM and 300 nM. Compounds having an activity designated as "C'" provided an $IC_{50}$ value between 300 nM and 500 nM. Compounds having an activity designated as "D'" provided an $IC_{50}$ value between 500 nM and 1000 nM. Compounds having an activity designated as "E'" provided an $IC_{50}$ value >1000 nM.

TABLE 2

ERK2 activity inhibition of selected compounds

| Ex. | ERK2 IC$_{50}$ | A375 IC$_{50}$ | Ex. | ERK2 IC$_{50}$ | A375 IC$_{50}$ |
|---|---|---|---|---|---|
| 1 | B | B' | 11 |  | E' |
| 2 | A | B' | 12 | C | E' |
| 3 | B | C' | 13 | C | E' |
| 4 | B | B' | 14 | C | E' |
| 5 | B | D' | 15 | D | E' |
| 6 | C | E' | 16 |  | E' |
| 7 | A | B' | 17 | A | A' |
| 8 | A | C' | 18 | B | D' |
| 9 |  | E' | 19 | A | D' |
| 10 |  | E' | 20 | A | E' |
| 21 | D | E' | 31 | A | A' |
| 22 | D | E' | 32 | A | A' |
| 23 | B | E' | 33 | A | A' |
| 24 | C | E' | 34 | A | B' |
| 25 | A | C' | 35 |  | C' |
| 26 | A | B' | 36 |  | D' |
| 27 | A | A' | 37 | A | B' |
| 28 | A | B' | 38 | A | A' |
| 29 | A | D' | 39 | B | E' |
| 30 | A | A' | 40 | C | E' |
| 41 | A | B' | 116 | D | C' |
| 42 | A(+, −), A(+), D(−) | C'(+, −), A'(+), E'(−) | 117 | A | C' |
| 43 | E | E' | 118 | B | B' |
| 44 | B | C' | 119 | B | A' |
| 110 | C | D' | 120 | A | A' |
| 111 |  | E' | 122 | B | D' |
| 112 | A | C' | 123 | B | D' |
| 113 | C | E' | 124 | C | D' |
| 114 | A | D' | 127 | D | E' |
| 115 | D | C' | 128 | B | B' |
| 129 |  | E' | 215 | A | B' |
| 130 | A | B' | 216 | A | A' |
| 203 | B | E' | 217 | A | A' |
| 204 | A | B' | 218 | A | A' |
| 208 | B | D' | 219 | A | B' |
| 210 | A | B' | 220 | A | A' |
| 211 | A | A' | 221 | A | D' |
| 212 | A | A' | 222 | A | C' |
| 213 | A | A' | 223 | A | C' |
| 214 | A | A' | 224 | A | C' |
| 225 | A | E' | 236 | A | B' |
| 226 | A | C' | 237 | A | C' |
| 227 | A | A' | 238 | A | A' |
| 228 | A | C' | 239 | E | E' |
| 229 | A | B' | 240 | A | D' |
| 230 | A | A' | 241 | A | A' |
| 231 | B | A' | 303 | A(+, −), A(+), C(−) | A'(+, −), A'(+), D'(−) |
| 232 | A | A' | 305 | A(+, −), A(+), E(−) | B'(+, −), A'(+), E'(−) |
| 233 | A | B' | 400 |  | A' |
| 234 | A | B' | 401 |  | B' |
| 235 | A | B' | 402 | A | A' |

Example 47: Solubility Assay for Parent Drugs and Methylphosphate Prodrugs

Kinetic solubility in aqueous solutions was determined using turbidimetry method. To this aim, compound solutions were prepared in DMSO and diluted in H$_2$O or PBS (1% DMSO final) in 96-well plate. Each compound was tested in triplicate. Plate was shaken for 90 min at room temperature and absorbance was measured at 620 nm. Solubility range was estimated from the highest concentration with no increase in absorbance and the lower concentration that produces an increase in absorbance above vehicle.

TABLE 3

Solubility of parent drug and methylphosphate prodrugs

| Examples | Chemical structure | Solubility range in water (µg/ml) | Solubility range in PBS (µg/ml) |
|---|---|---|---|
| 32 | 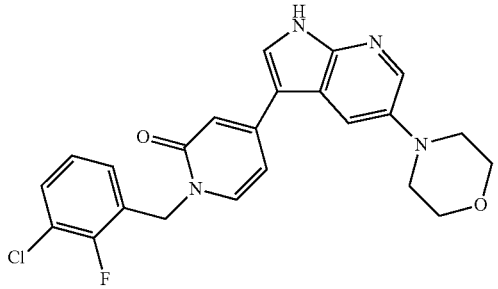 [SMILES: O=c1cc(-c2c[nH]c3ncc(N4CCOCC4)cc23)ccn1Cc1cccc(Cl)c1F] | [13-29] | [0-4] |
| 402 | 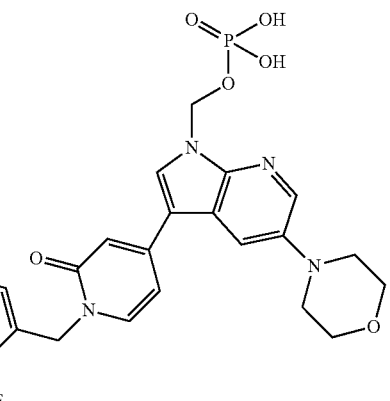 | [36-54] | [316-474] |

Example 48: Solubility Assay for Methylphosphate Prodrug Salts

To assess solubility of prodrug salts, 2.0 mg of compounds were weighed in a transparent vial. Water was then added by 10 µl increment until a limpid solution was obtained. After each addition, compounds were quickly vortexed and centrifuged. Solubility range was estimated from the lowest concentration with an apparent precipitate and the highest concentration that produces a clear solution.

TABLE 4

Solubility of methylphosphate prodrug salt

| Examples | Chemical structure | Solubility range in water (µg/ml) |
|---|---|---|
| 416 | 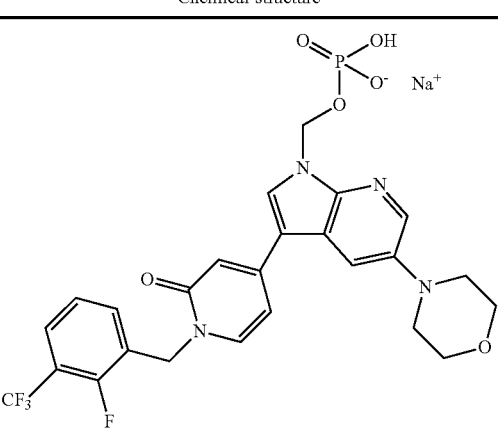 | [26600-35400] |

TABLE 4-continued

Solubility of methylphosphate prodrug salt

| Examples | Chemical structure | Solubility range in water (μg/ml) |
|---|---|---|
| 417 | 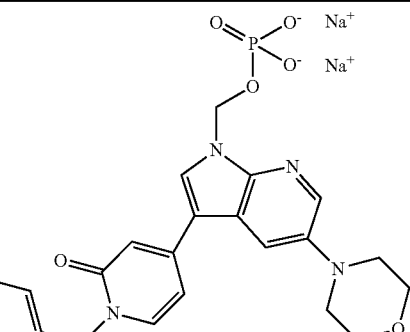 | [55400-73800] |

Example 48: Pharmacokinetics Studies

To determine their absolute oral bioavailability, compounds were dissolved in 80% PEG-400, 20% DMSO and administered to a group of 5-6 weeks old male BalbC mice. For intraveinous injection, a single 2 mg/kg dose was injected in tail vein and blood was collected at 0.12, 0.25, 0.5, 1, 2, 4, 8 and 24 h after injection. For oral route, a single 20 mg/kg dose was administered and blood was collected at 0.25, 0.5, 1, 2, 4, 8, 10 and 24 h after gavage. Plasma separated from blood samples was stored at −20° C. until analysis. Vials containing the study samples were retrieved and thawed to room temperature. A volume of 50 μl of sample was added to 200 μl of acetonitrile containing internal standard (tolbutamide; 25 ng/mL) and vortexed for 5 min and centrifuged at 14000 rpm for 5 min at 4° C. 200 μl of supernatant was separated and transferred to HPLC vial for analysis. For prodrug pharmacokinetics, only parent drug was dosed by HPLC.

FIG. 1 presents the pharmacokinetics profile of a parent drug (example 32) and corresponding prodrug (compound 402) after an intraveinous dose of 2 mg/kg: the mean of concentration in plasma for both compounds of examples 32 and 402 is represented as a function of time (in hours).

FIG. 2 presents the pharmacokinetics profile of parent drug (example 32) and corresponding prodrug (compound 402) after an oral dose of 20 mg/kg: the mean of concentration in plasma for both compounds of examples 32 and 402 is represented as a function of time (in hours).

TABLE 5

Pharmacokinetic parameters of parent drug alone and parent drug released from prodrug after an intraveinous dose of 2 mg/kg

| IV Parameters | Unit | Ex. 32 | Ex. 402 |
|---|---|---|---|
| $t_{1/2}$ | (h) | 0.85 | 1.71 |
| $AUC_{0-\infty}$ | (μg · h/mL) | 1.2 | 8.1 |
| $C_0$ | (μg/mL) | 2.5 | 26.9 |
| CL | (mL/min/kg) | 28.8 | 3.3 |
| $V_d$ | L/kg | 2.1 | 0.5 |
| $V_{dss}$ | L/kg | 0.9 | 0.1 |

$t_{1/2}$: terminal half-life;
$AUC_{0-\infty}$: area under the plasma concentration-time curve from time zero to infinity;
$C_0$: extrapolated concentration at zero time point;
CL: clearance;
$V_d$: volume of distribution;
$V_{dss}$: volume of distribution at steady state.

TABLE 6

Pharmacokinetic parameters of parent drug alone and parent drug released from prodrug after an oral dose of 20 mg/kg

| PO Parameters | Unit | Ex. 32 | Ex. 402 |
|---|---|---|---|
| $t_{1/2}$ | (h) | 0.98 | 1.31 |
| $AUC_{0-\infty}$ | (μg · h/mL) | 4.0 | 37.8 |
| $C_{max}$ | (μg/mL) | 2.4 | 22.8 |
| $t_{max}$ | (h) | 0.25 | 0.25 |
| Oral bioavailability (F %) | | 34.5 | 46.8 |

The invention claimed is:
1. A compound of formula (I):

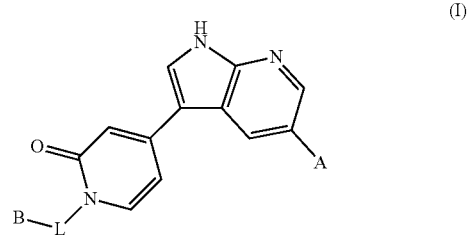

(I)

wherein:
- -A represents a 6- to 10-membered aryl group; a 5- to 12-membered heteroaryl group or a 4- to 12-membered heterocyclic group, A being non-substituted or being substituted with one or more substituents chosen among halogen atoms, hydroxyl, $(C_1-C_6)$alkyl, cyano, oxo, tert-butyloxycarbonyl, 1,3-dioxolanyl, 1,4-dioxolanyl, $(C_1-C_6)$alkoxy, —$COOR_1$, —$CONR_1R_2$ and $NR_1R_2$,
  with said $(C_1-C_6)$alkyl being non-substituted or being itself optionally substituted with a hydroxyl, $NR_1R_2$, $(C_1-C_6)$alkoxy, or —$S(C_1-C_6)$alkyl group, and
  said 4- to 12-membered heterocyclic group optionally comprising two fused cycles wherein the two cycles share at least two atoms;
- —L represents a linker chosen among linear or branched $(C_1-C_6)$alkylene group, said alkylene group being non-substituted or being substituted with at least one halogen, hydroxyl, $(C_1-C_6)$alkoxy, —$COOR_1$ or $NR_1R_2$ groups;
- —B represents a 6- to 10-membered aryl or a 5- to 12-membered heteroaryl group with B being non-substituted or being substituted with one or more substituents chosen among halogen atoms, trifluoromethyl, trifluoromethoxy, hydroxyl, $(C_1-C_6)$alkyl, $(C_1-C_6)$alkoxy, —$CONR_1R_2$, $NR_1R_2$, hydroxy($C_1$-$C_6$)alkyl, hydroxy($C_1$-$C_6$)alkoxy, $(C_1$-$C_6)$alkoxy($C_1$-$C_6)$alkyl, $(C_1$-$C_6)$alkoxy($C_1$-$C_6)$alkoxy and $(C_1$-$C_6)$ alkyl $NR_1R_2$ groups;
  with two adjacent carbon atoms of said 6- to 10-membered aryl group being non-substituted or being substituted by two oxygen atoms linked together by a $(C_1-C_6)$alkylene group, and
    $R_1$ and $R_2$ represent, independently of each other, a hydrogen atom, a $(C_1-C_6)$alkyl group, a $(C_1-C_6)$ alkoxy group, a hydroxy($C_1-C_6$)alkyl group or a hydroxy($C_1-C_6$)alkoxy group,
  or a pharmaceutically acceptable salt thereof.

2. The compound according to claim 1, wherein L represents a linker chosen among linear or branched $(C_1-C_6)$ alkylene group, said alkylene group being non-substituted or being substituted with one group chosen from a hydroxyl group and a $(C_1-C_6)$alkoxy group.

3. The compound according to claim 1, wherein B represents a 6- to 10-membered aryl group, non-substituted or being substituted with one or two substituents chosen among trifluoromethyl, trifluoromethoxy, hydroxyl, $(C_1-C_6)$alkyl, $(C_1-C_6)$alkoxy, hydroxy($C_1-C_6$)alkoxy, $(C_1-C_6)$alkoxy($C_1-C_6)$alkyl, $(C_1-C_6)$alkoxy($C_1-C_6)$alkoxy groups or halogen atoms.

4. The compound according to claim 1, wherein B is a phenyl group substituted by one or two halogen atoms.

5. The compound according to claim 1, wherein A is a 4- to 7-membered heterocyclic group non-substituted or being substituted with one or more substituents chosen among hydroxyl, $(C_1-C_6)$alkyl, cyano, oxo, tert-butyloxycarbonyl, 1,3-dioxolanyl, 1,4-dioxolanyl, $(C_1-C_6)$alkoxy, —$COOR_1$, —$CONR_1R_2$ $NR_1R_2$, or halogen atoms, said alkyl group being non-substituted or being substituted with a hydroxyl, $NR_1R_2$, $(C_1-C_6)$alkoxy or —$S(C_1-C_6)$alkyl group.

6. The compound according to claim 1, wherein A is a morpholinyl or 1,4-oxazepanyl group non-substituted or being substituted with one or two substituents chosen among hydroxyl, $(C_1-C_6)$alkyl, cyano, 1,3-dioxolanyl, 1,4-dioxolanyl, $(C_1-C_6)$alkoxy, —$COOR_1$, —$CONR_1R_2$, and $NR_1R_2$, said alkyl group being non-substituted or being substituted with at least one hydroxyl, $NR_1R_2$, or $(C_1-C_6)$alkoxy groups or A being a morpholinyl group fused with an oxetanyl or oxolanyl group.

7. The compound according to claim 1, chosen among:
1: 1-(3-Chlorobenzyl)-4-[5-(4-fluorophenyl)-1H-pyrrolo[2,3-b]pyridin-3-yl]-1H-pyridin-2-one;
2: 1-(3-Chlorobenzyl)-4-[5-(4-hydroxymethylphenyl)-1H-pyrrolo[2,3-b]pyridin-3-yl]-1H-pyridin-2-one;
3: 4-{3-[1-(3-Chlorobenzyl)-2-oxo-1,2-dihydropyridin-4-yl]-1H-pyrrolo[2,3-b]pyridin-5-yl}-N-methylbenzamide;
4: 1-(3-Chlorobenzyl)-4-[5-(6-fluoropyridin-3-yl)-1H-pyrrolo[2,3-b]pyridin-3-yl]-1H-pyridin-2-one;
5: 1-(3-Chlorobenzyl)-4-(5-thiophen-3-yl-1H-pyrrolo[2,3-b]pyridin-3-yl)-1H-pyridin-2-one;
6: 1-(3-Chlorobenzyl)-4-[5-(5-chlorothiophen-2-yl)-1H-pyrrolo[2,3-b]pyridin-3-yl]-1H-pyridin-2-one;
7: 1-(3-Chlorobenzyl)-4-[5-(1H-pyrazol-4-yl)-1H-pyrrolo[2,3-b]pyridin-3-yl]-1H-pyridin-2-one;
8: 1-(3-Chlorobenzyl)-4-[5-(5-methyl-1H-pyrazol-4-yl)-1H-pyrrolo[2,3-b]pyridin-3-yl]-1H-pyridin-2-one;
9: 1-(3-Chlorobenzyl)-4-(5-piperidin-1-yl-1H-pyrrolo[2,3-b]pyridin-3-yl)-1H-pyridin-2-one;
10: 1-(3-Chlorobenzyl)-4-(5-(4-cyanopiperidin-1-yl)-1H-pyrrolo[2,3-b]pyridin-3-yl)-1H-pyridin-2-one;
11: 1-(3-Chlorobenzyl)-4-[5-(4-hydroxymethylpiperidin-1-yl)-1H-pyrrolo[2,3-b]pyridin-3-yl]-1H-pyridin-2-one;
12: 1-(3-Chlorobenzyl)-4-[5-(1,4-dioxa-8-azaspiro[4.5]dec-8-yl)-1H-pyrrolo[2,3-]pyridin-3-yl]-1H-pyridin-2-one;
13: 1-(3-Chlorobenzyl)-4-[5-(4-oxopiperidin-1-yl)-1H-pyrrolo[2,3-b]pyridin-3-yl]-1H-pyridin-2-one;
14: 1-(3-Chlorobenzyl)-4-[5-(4-hydroxypiperidin-1-yl)-1H-pyrrolo[2,3-b]pyridin-3-yl]-1H-pyridin-2-one;
15: 1-(3-Chlorobenzyl)-4-[5-(4-methoxyaminopiperidin-1-yl)-1H-pyrrolo[2,3-b]pyridin-3-yl]-1H-pyridin-2-one;
16: 1-(3-Chlorobenzyl)-4-(5-pyrrolidin-1-yl-1H-pyrrolo[2,3-b]pyridin-3-yl)-1H-pyridin-2-one;
17: 1-(3-Chlorobenzyl)-4-(5-morpholin-4-yl-1H-pyrrolo[2,3-b]pyridin-3-yl)-1H-pyridin-2-one;
18: 1-(3-Chlorobenzyl)-4-[5-(3-methylmorpholin-4-yl)-1H-pyrrolo[2,3-b]pyridin-3-yl]-1H-pyridin-2-one;
19: 1-(3-Chlorobenzyl)-4-[5-(2-methylmorpholin-4-yl)-1H-pyrrolo[2,3-b]pyridin-3-yl]-1H-pyridin-2-one;
20: 4-(3-(1-(3-Chlorobenzyl)-2-oxo-1,2-dihydropyridin-4-yl)-1H-pyrrolo[2,3-b]pyridin-5-yl)-N-methylmorpholine-2-carboxamide;
21: Tert-butyl 4-(3-(1-(3-chlorobenzyl)-2-oxo-1,2-dihydropyridin-4-yl)-1H-pyrrolo[2,3-b]pyridin-5-yl)piperazine-1-carboxylate;
22: 1-(3-Chlorobenzyl)-4-(5-(piperazin-1-yl)-1H-pyrrolo[2,3-b]pyridin-3-yl)pyridin-2(1H)-one;
23: 4-(3-(1-(3-Chlorobenzyl)-2-oxo-1,2-dihydropyridin-4-yl)-1H-pyrrolo[2,3-b]pyridin-5-yl)-N-ethylpiperazine-1-carboxamide;
24: 4-(3-(1-(3-Chlorobenzyl)-2-oxo-1,2-dihydropyridin-4-yl)-1H-pyrrolo[2,3-b]pyridin-5-yl)-N-(2-hydroxyethyl)piperazine-1-carboxamide;
25: 1-Benzyl-4-(5-morpholino-1H-pyrrolo[2,3-b]pyridin-3-yl)pyridin-2(1H)-one;
26: 1-(4-Bromobenzyl)-4-(5-morpholino-1H-pyrrolo[2,3-b]pyridin-3-yl)pyridin-2(1H)-one;
27: 1-(3-Iodobenzyl)-4-(5-morpholino-1H-pyrrolo[2,3-b]pyridin-3-yl)pyridin-2(1H)-one;

28: 4-(5-Morpholino-1H-pyrrolo[2,3-b]pyridin-3-yl)-1-(3-(trifluoromethyl)benzyl)pyridin-2(1H)-one;
29: 1-(3-Methoxybenzyl)-4-(5-morpholino-1H-pyrrolo[2,3-b]pyridin-3-yl)pyridin-2(1H)-one;
30: 1-(4-Chloro-3-fluorobenzyl)-4-(5-morpholino-1H-pyrrolo[2,3-b]pyridin-3-yl)pyridin-2(1H)-one;
31: 1-(3-Chloro-4-fluorobenzyl)-4-(5-morpholino-1H-pyrrolo[2,3-b]pyridin-3-yl)pyridin-2(1H)-one;
32: 1-(3-Chloro-2-fluorobenzyl)-4-(5-morpholino-1H-pyrrolo[2,3-b]pyridin-3-yl)pyridin-2(1H)-one;
33: 1-(3,4-Dichlorobenzyl)-4-(5-morpholino-1H-pyrrolo[2,3-b]pyridin-3-yl)pyridin-2(1H)-one;
34: 1-(2,4-Dichlorobenzyl)-4-(5-morpholino-1H-pyrrolo[2,3-b]pyridin-3-yl)pyridin-2(1H)-one;
35: 1-(5-Chloro-2-hydroxybenzyl)-4-(5-morpholino-1H-pyrrolo[2,3-b]pyridin-3-yl)pyridin-2(1H)-one;
36: 1-(5-Chloro-3-hydroxybenzyl)-4-(5-morpholino-1H-pyrrolo[2,3-b]pyridin-3-yl)pyridin-2(1H)-one;
37: 1-(5-Chloro-2-(2-methoxyethoxy)benzyl)-4-(5-morpholino-1H-pyrrolo[2,3-b]pyridin-3-yl)pyridin-2(1H)-one;
38: 1-(3-Chloro-5-(2-methoxyethoxy)benzyl)-4-(5-morpholino-1H-pyrrolo[2,3-b]pyridin-3-yl)pyridin-2(1H)-one;
39: 4-(5-Morpholino-1H-pyrrolo[2,3-b]pyridin-3-yl)-1-(pyridin-3-ylmethyl)pyridin-2(1H)-one;
40: 1-((6-Chloropyridin-3-yl)methyl)-4-(5-morpholino-1H-pyrrolo[2,3-b]pyridin-3-yl)pyridin-2(1H)-one;
41: 1-((6-Chloropyridin-2-yl)methyl)-4-(5-morpholino-1H-pyrrolo[2,3-b]pyridin-3-yl)pyridin-2(1H)-one;
42: 1-(1-(3-Chlorophenyl)-2-hydroxyethyl)-4-(5-morpholino-1H-pyrrolo[2,3-b]pyridin-3-yl)pyridin-2(1H)-one;
43: 2-(3-Chlorophenyl)-2-(4-(5-morpholino-1H-pyrrolo[2,3-b]pyridin-3-yl)-2-oxopyridin-1(2H)-yl)acetic acid;
44: 1-(2-(3-Chlorophenyl)-2-hydroxyethyl)-4-(5-morpholino-1H-pyrrolo[2,3-b]pyridin-3-yl)pyridin-2(1H)-one;
210: 1-(4-Chlorobenzyl)-4-(5-morpholino-1H-pyrrolo[2,3-b]pyridin-3-yl)pyridin-2(1H)-one;
211: 1-(3-Bromobenzyl)-4-(5-morpholino-1H-pyrrolo[2,3-b]pyridin-3-yl)pyridin-2(1H)-one;
212: 1-(3-Bromo-4-fluorobenzyl)-4-(5-morpholino-1H-pyrrolo[2,3-b]pyridin-3-yl)pyridin-2(1H)-one;
213: 1-(3-Bromo-5-fluorobenzyl)-4-(5-morpholino-1H-pyrrolo[2,3-b]pyridin-3-yl)pyridin-2(1H)-one;
214: 1-(3-Bromo-2-fluorobenzyl)-4-(5-morpholino-1H-pyrrolo[2,3-b]pyridin-3-yl)pyridin-2(1H)-one;
215: 1-(4-Iodobenzyl)-4-(5-morpholino-1H-pyrrolo[2,3-b]pyridin-3-yl)pyridin-2(1H)-one;
216: 1-(4-Fluoro-3-iodobenzyl)-4-(5-morpholino-1H-pyrrolo[2,3-b]pyridin-3-yl)pyridin-2(1H)-one;
217: 1-(2-Fluoro-3-iodobenzyl)-4-(5-morpholino-1H-pyrrolo[2,3-b]pyridin-3-yl)pyridin-2(1H)-one;
218: 1-(3-Fluoro-5-iodobenzyl)-4-(5-morpholino-1H-pyrrolo[2,3-b]pyridin-3-yl)pyridin-2(1H)-one;
219: 1-(3-Chloro-5-iodobenzyl)-4-(5-morpholino-1H-pyrrolo[2,3-b]pyridin-3-yl)pyridin-2(1H)-one;
220: 1-(4-Chloro-3-iodobenzyl)-4-(5-morpholino-1H-pyrrolo[2,3-b]pyridin-3-yl)pyridin-2(1H)-one;
226: 1-(2-Chloro-3-fluorobenzyl)-4-(5-morpholino-1H-pyrrolo[2,3-b]pyridin-3-yl)pyridin-2(1H)-one;
227: 1-(3-Chloro-5-fluorobenzyl)-4-(5-morpholino-1H-pyrrolo[2,3-b]pyridin-3-yl)pyridin-2(1H)-one;
228: 1-(5-Chloro-2-fluorobenzyl)-4-(5-morpholino-1H-pyrrolo[2,3-b]pyridin-3-yl)pyridin-2(1H)-one;
230: 1-(3-Fluoro-4-(trifluoromethyl)benzyl)-4-(5-morpholino-1H-pyrrolo[2,3-b]pyridin-3-yl)pyridin-2(1H)-one;
231: 1-(2-Fluoro-3-(trifluoromethyl)benzyl)-4-(5-morpholino-1H-pyrrolo[2,3-b]pyridin-3-yl)pyridin-2(1H)-one;
232: 1-(3-Chloro-4-(trifluoromethyl)benzyl)-4-(5-morpholino-1H-pyrrolo[2,3-b]pyridin-3-yl)pyridin-2(1H)-one;
238: 1-(3-Chloro-5-methylbenzyl)-4-(5-morpholino-1H-pyrrolo[2,3-b]pyridin-3-yl)pyridin-2(1H)-one;
241: 1-(3-Chloro-5-(methoxymethyl)benzyl)-4-(5-morpholino-1H-pyrrolo[2,3-b]pyridin-3-yl)pyridin-2(1H)-one;
303: 1-(1-(3-Chlorophenyl)ethyl)-4-(5-morpholino-1H-pyrrolo[2,3-b]pyridin-3-yl)pyridin-2(1H)-one;
305: 1-(1-(3-Chlorophenyl)-2-methoxyethyl)-4-(5-morpholino-1H-pyrrolo[2,3-b]pyridin-3-yl)pyridin-2(1H)-one; and
308: 1-(1-(3,4-Dichlorophenyl)ethyl)-4-(5-morpholino-1H-pyrrolo[2,3-b]pyridin-3-yl)pyridin-2(1H)-one,
or a pharmaceutically acceptable salt thereof.

8. A process for preparing a compound of formula (I) according to claim 1 wherein A represents a 6- to 10-membered aryl or a 5- to 12-membered heteroaryl group, said aryl or heteroaryl being substituted or non-substituted as defined in claim 1, wherein the following steps are carried out in that order, starting from a 5-bromo-7-azaindole:
  a) Iodinating said 5-bromo-7-azaindole for obtaining a 5-bromo-3-iodo-7-azaindole,
  b) protecting the nitrogen atom of the pyrrolyl moiety of the azaindole,
  c) carrying out a first Suzuki coupling reaction of the compound obtained at step b) with a 2-oxo-1,2-dihydropyridin-4-ylboronic acid or ester derivative at a temperature within the range from 50 to 100° C.;
  d) carrying out a second Suzuki coupling reaction of the compound obtained at step c) with an aryl or heteroarylboronic acid under microwave irradiation at a temperature within the range from 120 to 180° C.

9. A process for preparing a compound of formula (I) according to claim 1 wherein A represents 4- to 7-membered heterocyclic group, substituted or non-substituted as defined in claim 1, wherein the following steps are carried out in that order, starting from a 5-bromo-7-azaindole:
  a) carrying out a Buchwald-Hartwig coupling with a compound comprising a 4- to 7-membered heterocyclic group on said 5-bromo-7-azaindole for obtaining a 5-substituted 7-azaindole,
  b) iodinating the 5-substituted 7-azaindole for obtaining a -5-substituted-3-iodo 7-azaindole,
  c) protecting the nitrogen atom of the pyrrolyl moiety of the azaindole,
  d) carrying out a Suzuki coupling reaction of the compound obtained at step c) with a 2-oxo-1,2-dihydropyridin-4-ylboronic acid or ester derivative at a temperature within the range from 50 to 100° C.,
  e) optionally performing a microwave irradiation at a temperature within the range from 120 to 180° C.

10. A medicament comprising at least one compound as defined in claim 1, or a pharmaceutically acceptable salt thereof.

11. A pharmaceutical composition comprising at least one compound as defined in claim 1, or a pharmaceutically acceptable salt thereof, and at least one pharmaceutically acceptable excipient.

12. A prodrug (P)

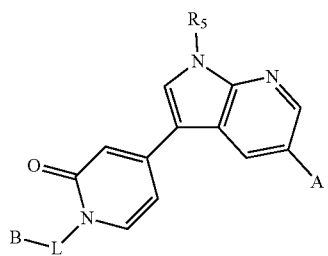

wherein R$_5$ represents a group chosen among —CH$_2$—O—COR$_6$ and —CR$_6$R$_7$—O—PO$_3$R$_8$R$_9$, with R$_6$, R$_7$, R$_8$ and R$_9$, identical or different, being chosen among H and (C$_1$-C$_6$) alkyl groups,
-A represents a 6- to 10-membered aryl group; a 5- to 12-membered heteroaryl group or a 4- to 12-membered heterocyclic group, A being non-substituted or being substituted with one or more substituents chosen among halogen atoms, hydroxyl, (C$_1$-C$_6$)alkyl, cyano, oxo, tert-butyloxycarbonyl, 1,3-dioxolanyl, 1,4-dioxolanyl, (C$_1$-C$_6$)alkoxy, —COOR$_1$, —CONR$_1$R$_2$ and NR$_1$R$_2$,
with said (C$_1$-C$_6$)alkyl being itself non-substituted or being substituted with a hydroxyl, NR$_1$R$_2$, (C$_1$-C$_6$) alkoxy, or —S(C$_1$-C$_6$)alkyl group, and
said 4- to 12-membered heterocyclic group optionally comprising two fused cycles wherein the two cycles share at least two atoms;
-L represents a linker chosen among linear or branched (C$_1$-C$_6$)alkylene group, said alkylene group being non-substituted or being substituted with at least one halogen, hydroxyl, (C$_1$-C$_6$)alkoxy, —COOR$_1$ or NR$_1$R$_2$ groups;
—B represents a 6- to 10-membered aryl or a 5- to 12-membered heteroaryl group with B being non-substituted or being substituted with one or more substituents chosen among halogen atoms, trifluoromethyl, trifluoromethoxy, hydroxyl, (C$_1$-C$_6$)alkyl, (C$_1$-C$_6$)alkoxy, —CONR$_1$R$_2$, NR$_1$R$_2$, hydroxy(C$_1$-C$_6$)alkyl, hydroxy(C$_1$-C$_6$)alkoxy, (C$_1$-C$_6$)alkoxy(C$_1$-C$_6$) alkyl, (C$_1$-C$_6$)alkoxy(C$_1$-C$_6$)alkoxy and (C$_1$-C$_6$)alkyl NR$_1$R$_2$ groups;
with two adjacent carbon atoms of said aryl group being non-substituted or being substituted by two oxygen atoms linked together by a (C$_1$-C$_6$)alkylene group, and
R$_1$ and R$_2$ represent, independently of each other, a hydrogen atom, a (C$_1$-C$_6$)alkyl group, a (C$_1$-C$_6$)alkoxy group, a hydroxy(C$_1$-C$_6$)alkyl group or a hydroxy(C$_1$-C$_6$)alkoxy group,
or a pharmaceutically acceptable salt thereof.
13. The prodrug according to claim 12 chosen among:
400: (3-(1-(3-Chloro-2-fluorobenzyl)-2-oxo-1,2-dihydropyridin-4-yl)-5-morpholino-1H-pyrrolo[2,3-b]pyridin-1-yl)methyl isobutyrate;
401: (3-(1-(3-Chloro-2-fluorobenzyl)-2-oxo-1,2-dihydropyridin-4-yl)-5-morpholino-1H-pyrrolo[2,3-b]pyridin-1-yl)methyl pivalate;
402: (3-(1-(3-Chloro-2-fluorobenzyl)-2-oxo-1,2-dihydropyridin-4-yl)-5-morpholino-1H-pyrrolo[2,3-b]pyridin-1-yl)methyl dihydrogen phosphate;
403: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl dihydrogen phosphate;
404: (3-(1-(3-Chlorobenzyl)-2-oxo-1,2-dihydropyridin-4-yl)-5-morpholino-1H-pyrrolo[2,3-b]pyridin-1-yl) methyl dihydrogen phosphate;
405: (3-(1-(3-Bromobenzyl)-2-oxo-1,2-dihydropyridin-4-yl)-5-morpholino-1H-pyrrolo[2,3-b]pyridin-1-yl) methyl dihydrogen phosphate;
406: (3-(1-(3-Bromo-5-fluorobenzyl)-2-oxo-1,2-dihydropyridin-4-yl)-5-morpholino-1H-pyrrolo[2,3-b]pyridin-1-yl)methyl dihydrogen phosphate;
407: (3-(1-(3-Bromo-2-fluorobenzyl)-2-oxo-1,2-dihydropyridin-4-yl)-5-morpholino-1H-pyrrolo[2,3-b]pyridin-1-yl)methyl dihydrogen phosphate;
408: (3-(1-(3-Chloro-5-fluorobenzyl)-2-oxo-1,2-dihydropyridin-4-yl)-5-morpholino-1H-pyrrolo[2,3-b]pyridin-1-yl)methyl dihydrogen phosphate;
409: (3-(1-(3-Fluoro-5-iodobenzyl)-2-oxo-1,2-dihydropyridin-4-yl)-5-morpholino-1H-pyrrolo[2,3-b]pyridin-1-yl)methyl dihydrogen phosphate;
415: (3-(1-(4-Chlorobenzyl)-2-oxo-1,2-dihydropyridin-4-yl)-5-morpholino-1H-pyrrolo[2,3-b]pyridin-1-yl) methyl dihydrogen phosphate;
416: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl sodium hydrogen phosphate;
417: (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl disodium phosphate;
402 a: Di-tert-butyl (3-(1-(3-chloro-2-fluorobenzyl)-2-oxo-1,2-dihydropyridin-4-yl)-5-morpholino-1H-pyrrolo[2,3-b]pyridin-1-yl)methyl phosphate;
403 a: Di-tert-butyl (3-(1-(2-Fluoro-3-(trifluoromethyl)benzyl)-2-oxo-1,2-dihydropyridin-4-yl)-5-morpholino-1H-pyrrolo[2,3-b]pyridin-1-yl)methyl phosphate;
404 a: Di-tert-butyl (3-(1-(3-chlorobenzyl)-2-oxo-1,2-dihydropyridin-4-yl)-5-morpholino-1H-pyrrolo[2,3-b] pyridin-1-yl)methyl phosphate;
405 a: Di-tert-butyl (3-(1-(3-bromobenzyl)-2-oxo-1,2-dihydropyridin-4-yl)-5-morpholino-1H-pyrrolo[2,3-b] pyridin-1-yl)methyl phosphate;
406 a: Di-tert-butyl (3-(1-(3-bromo-5-fluorobenzyl)-2-oxo-1,2-dihydropyridin-4-yl)-5-morpholino-1H-pyrrolo[2,3-b]pyridin-1-yl)methyl phosphate;
407 a: Di-tert-butyl (3-(1-(3-bromo-2-fluorobenzyl)-2-oxo-1,2-dihydropyridin-4-yl)-5-morpholino-1H-pyrrolo[2,3-b]pyridin-1-yl)methyl phosphate;
408 a: Di-tert-butyl (3-(1-(3-chloro-5-fluorobenzyl)-2-oxo-1,2-dihydropyridin-4-yl)-5-morpholino-1H-pyrrolo[2,3-b]pyridin-1-yl)methyl phosphate;
409 a: Di-tert-butyl (3-(1-(3-fluoro-5-iodobenzyl)-2-oxo-1,2-dihydropyridin-4-yl)-5-morpholino-1H-pyrrolo[2,3-b]pyridin-1-yl)methyl phosphate; and
415 a: Di-tert-butyl (3-(1-(4-chlorobenzyl)-2-oxo-1,2-dihydropyridin-4-yl)-5-morpholino-1H-pyrrolo[2,3-b] pyridin-1-yl)methyl phosphate,
or a pharmaceutically acceptable salt thereof.
14. The compound according to claim 1, wherein said 4- to 12-membered heterocyclic group comprises two fused cycles wherein the two cycles share at least two atoms.
15. The prodrug (P) according to claim 12, wherein said 4- to 12-membered heterocyclic group comprises two fused cycles wherein the two cycles share at least two atoms.

* * * * *

UNITED STATES PATENT AND TRADEMARK OFFICE
CERTIFICATE OF CORRECTION

PATENT NO. : 10,995,089 B2  
APPLICATION NO. : 15/777386  
DATED : May 4, 2021  
INVENTOR(S) : Jean-François Guichou et al.

It is certified that error appears in the above-identified patent and that said Letters Patent is hereby corrected as shown below:

On the Title Page

Item (54) "ZAINDOLE DERIVATIVES AND THEIR USE AS ERK KINASE INHIBITORS" should read --AZAINDOLE DERIVATIVES AND THEIR USE AS ERK KINASE INHIBITORS--

In the Specification

Column 1, Lines 1 and 2, "ZAINDOLE DERIVATIVES AND THEIR USE AS ERK KINASE INHIBITORS" should read --AZAINDOLE DERIVATIVES AND THEIR USE AS ERK KINASE INHIBITORS--

Signed and Sealed this  
Tenth Day of August, 2021

Drew Hirshfeld  
*Performing the Functions and Duties of the  
Under Secretary of Commerce for Intellectual Property and  
Director of the United States Patent and Trademark Office*